(12) United States Patent
van Rooyen et al.

US010622096B2

(10) Patent No.: US 10,622,096 B2
(45) Date of Patent: Apr. 14, 2020

(54) BIOINFORMATICS SYSTEMS, APPARATUSES, AND METHODS EXECUTED ON AN INTEGRATED CIRCUIT PROCESSING PLATFORM

(71) Applicant: Edico Genome Corporation, La Jolla, CA (US)

(72) Inventors: Pieter van Rooyen, La Jolla, CA (US); Michael Ruehle, Dallas, TX (US); Rami Mehio, San Diego, CA (US)

(73) Assignee: Edico Genome Corporation, La Jolla, CA (US)

( * ) Notice: Subject to any disclaimer, the term of this patent is extended or adjusted under 35 U.S.C. 154(b) by 0 days.

(21) Appl. No.: 15/700,018

(22) Filed: Sep. 8, 2017

(65) Prior Publication Data
US 2018/0181708 A1 Jun. 28, 2018

Related U.S. Application Data

(63) Continuation of application No. 15/094,939, filed on Apr. 8, 2016, now Pat. No. 9,792,405, which is a continuation-in-part of application No. 15/059,221, filed on Mar. 2, 2016, now Pat. No. 10,068,054, which is a continuation-in-part of application No. 15/048,935, filed on Feb. 19, 2016, which is a continuation-in-part of application No. 14/284,307, filed on May 21, 2014, now Pat. No. 9,235,680, which is a continuation of application No. 14/279,063, filed on May 15, 2014, now Pat. No. 9,679,104, which is a continuation-in-part of application No. 14/180,248, filed on Feb. 13, 2014, now Pat. No. 9,014,989, which is a continuation of application No. 14/158,758, filed on Jan. 17, 2014, now Pat. No. 9,483,610, and a continuation-in-part of application No. 14/179,513, filed on Feb. 12, 2014, now abandoned, which is a continuation of application No. 14/158,758, filed on Jan. 17, 2014, now Pat. No. 9,483,610, and a continuation-in-part of application No. 14/158,758, filed on Jan. 17, 2014, now Pat. No. 9,483,610.

(60) Provisional application No. 62/144,941, filed on Apr. 9, 2015, provisional application No. 62/127,232, filed on Mar. 2, 2015, provisional application No. 62/119,059, filed on Feb. 20, 2015, provisional application No. 61/988,128, filed on May 2, 2014, provisional application No. 61/984,663, filed on Apr. 25, 2014, provisional application No. 61/943,870, filed on Feb. 24, 2014, provisional application No. 61/910,868, filed on Dec. 2, 2013, provisional application No. 61/826,381, filed on May 22, 2013, provisional application No. 61/823,824, filed on May 15, 2013, provisional application No. 61/822,101, (Continued)

(51) Int. Cl.
  G16B 40/00 (2019.01)
  G06F 12/0877 (2016.01)
  G16B 30/00 (2019.01)
  G16B 50/00 (2019.01)
  H03K 19/17736 (2020.01)
  G06N 3/00 (2006.01)
  G06N 7/00 (2006.01)

(52) U.S. Cl.
  CPC ......... G16B 40/00 (2019.02); G06F 12/0877 (2013.01); G06N 3/002 (2013.01); G16B 30/00 (2019.02); G16B 50/00 (2019.02); H03K 19/17736 (2013.01); G06F 2212/6042 (2013.01); G06N 7/005 (2013.01)

(58) Field of Classification Search
  CPC ..................................................... G16B 40/00
  USPC ............................................................ 702/19
  See application file for complete search history.

(56) References Cited

U.S. PATENT DOCUMENTS

| 5,859,972 A | 1/1999 | Subramaniam et al. |
|---|---|---|
| 5,964,072 A | 10/1999 | Rasmussen |
| 6,112,288 A | 8/2000 | Ullner |

(Continued)

FOREIGN PATENT DOCUMENTS

| CN | 103293209 A | 9/2013 |
|---|---|---|
| CN | 105051741 A | 11/2015 |
| EP | 2313523 A2 | 4/2011 |
| WO | WO-2011/149534 A2 | 12/2011 |
| WO | WO-2012/122546 A2 | 9/2012 |
| WO | WO-2013/128371 A2 | 9/2013 |
| WO | WO-2014/060305 A1 | 4/2014 |

(Continued)

OTHER PUBLICATIONS

Choi, J. , et al., "Impact of Cache Architetures and Interface on Performce nd Area of FPGA-Based Processor/Parallel-Accelerator Systems", FCCM, IEEE, Apr. 29, 2012, 17-24.

(Continued)

*Primary Examiner* — Jerry Lin
(74) *Attorney, Agent, or Firm* — Fish & Richardson P.C.

(57) ABSTRACT

A system, method and apparatus for executing a bioinformatics analysis on genetic sequence data includes an integrated circuit formed of a set of hardwired digital logic circuits that are interconnected by physical electrical interconnects. One of the physical electrical interconnects forms an input to the integrated circuit that may be connected with an electronic data source for receiving reads of genomic data. The hardwired digital logic circuits may be arranged as a set of processing engines, each processing engine being formed of a subset of the hardwired digital logic circuits to perform one or more steps in the bioinformatics analysis on the reads of genomic data. Each subset of the hardwired digital logic circuits may be formed in a wired configuration to perform the one or more steps in the bioinformatics analysis.

15 Claims, 45 Drawing Sheets

Specification includes a Sequence Listing.

Related U.S. Application Data filed on May 10, 2013, provisional application No. 61/753,775, filed on Jan. 17, 2013.

(56) References Cited

U.S. PATENT DOCUMENTS

| | | |
|---|---|---|
| 6,253,529 B1 | 7/2001 | De Boer |
| 6,681,186 B1 | 1/2004 | Denisov et al. |
| 7,135,701 B2 | 11/2006 | Amin et al. |
| 7,533,068 B2 | 5/2009 | Maassen van den Brink et al. |
| 7,680,790 B2 | 3/2010 | Indeck et al. |
| 7,917,299 B2 | 3/2011 | Buhler et al. |
| 7,917,302 B2 | 3/2011 | Rognes |
| 7,948,015 B2 | 5/2011 | Rothberg et al. |
| 7,969,805 B2 | 6/2011 | Thom et al. |
| 8,190,548 B2 | 5/2012 | Choi |
| 8,195,596 B2 | 6/2012 | Rose et al. |
| 8,209,130 B1 | 6/2012 | Kennedy et al. |
| 8,217,433 B1 | 7/2012 | Fife |
| 8,280,640 B2 | 10/2012 | Levin et al. |
| 8,445,945 B2 | 5/2013 | Rothberg et al. |
| 8,524,487 B2 | 9/2013 | Fife |
| 8,558,288 B2 | 10/2013 | Rothberg et al. |
| 8,560,282 B2 | 10/2013 | Macready et al. |
| 8,594,951 B2 | 11/2013 | Homer |
| 8,620,923 B1 | 12/2013 | Wormley et al. |
| 8,700,689 B2 | 4/2014 | Macready et al. |
| 8,738,105 B2 | 5/2014 | Berkley et al. |
| 8,751,166 B2 | 6/2014 | Friedlander et al. |
| 8,936,763 B2 | 1/2015 | Rothberg et al. |
| 9,014,989 B2 | 4/2015 | McMillen et al. |
| 9,026,574 B2 | 5/2015 | Macready et al. |
| 9,235,680 B2 | 1/2016 | Van Rooyen et al. |
| 9,355,365 B2 | 5/2016 | Berkley et al. |
| 9,405,876 B2 | 8/2016 | Macready et al. |
| 9,483,610 B2 | 11/2016 | McMillen et al. |
| 9,576,103 B2 | 2/2017 | McMillen et al. |
| 9,618,474 B2 | 4/2017 | van Rooyen et al. |
| 9,679,104 B2 | 6/2017 | Van Rooyen et al. |
| 9,792,405 B2 | 10/2017 | van Rooyen et al. |
| 2003/0033279 A1 | 2/2003 | Gibson et al. |
| 2003/0033501 A1 | 2/2003 | Cooke et al. |
| 2003/0039362 A1 | 2/2003 | Califano et al. |
| 2003/0104470 A1 | 6/2003 | Fors et al. |
| 2004/0024536 A1 | 2/2004 | Rognes |
| 2004/0059721 A1 | 3/2004 | Patzer |
| 2004/0098203 A1 | 5/2004 | Rognes |
| 2004/0126840 A1 | 7/2004 | Cheng et al. |
| 2005/0060195 A1 | 3/2005 | Bessette et al. |
| 2005/0131649 A1 | 6/2005 | Larsen et al. |
| 2005/0228595 A1 | 10/2005 | Cooke et al. |
| 2006/0225165 A1 | 10/2006 | Maassen van den Brink et al. |
| 2007/0038381 A1 | 2/2007 | Melchior et al. |
| 2007/0078897 A1 | 4/2007 | Hayashi et al. |
| 2007/0088510 A1 | 4/2007 | Li et al. |
| 2007/0196816 A1 | 8/2007 | Schwartz et al. |
| 2008/0005024 A1 | 1/2008 | Kirkwood |
| 2008/0086274 A1 | 4/2008 | Chamberlain et al. |
| 2008/0176750 A1 | 7/2008 | Rose et al. |
| 2008/0250016 A1 | 10/2008 | Farrar |
| 2009/0121215 A1 | 5/2009 | Choi |
| 2009/0125248 A1 | 5/2009 | Shams et al. |
| 2009/0171647 A1 | 7/2009 | Mannava et al. |
| 2009/0253130 A1 | 10/2009 | Yoo |
| 2010/0077267 A1 | 3/2010 | Perego et al. |
| 2010/0082805 A1 | 4/2010 | Orton et al. |
| 2010/0085827 A1 | 4/2010 | Thom et al. |
| 2010/0169313 A1 | 7/2010 | Kenedy et al. |
| 2010/0281401 A1 | 11/2010 | Tebbs et al. |
| 2010/0327847 A1 | 12/2010 | Leiber et al. |
| 2011/0004413 A1 | 1/2011 | Carnevali et al. |
| 2011/0093581 A1 | 4/2011 | Venkatachalam |
| 2011/0184235 A1 | 7/2011 | Schostek et al. |
| 2011/0227043 A1 | 9/2011 | Guo et al. |
| 2012/0001615 A1 | 1/2012 | Levine |
| 2012/0089339 A1 | 4/2012 | Ganeshalingam et al. |
| 2012/0102041 A1 | 4/2012 | Park et al. |
| 2012/0109849 A1 | 5/2012 | Chamberlain et al. |
| 2012/0149981 A1 | 6/2012 | Khait et al. |
| 2012/0214172 A1 | 8/2012 | Chen et al. |
| 2013/0018599 A1 | 1/2013 | Peng |
| 2013/0091121 A1 | 4/2013 | Galinsky |
| 2013/0110407 A1 | 5/2013 | Baccash et al. |
| 2013/0124100 A1 | 5/2013 | Drmanac et al. |
| 2013/0144925 A1 | 6/2013 | Macready et al. |
| 2013/0157870 A1 | 6/2013 | Pushkarev et al. |
| 2013/0194882 A1 | 8/2013 | Ishii et al. |
| 2013/0204851 A1 | 8/2013 | Bhola et al. |
| 2013/0245958 A1 | 9/2013 | Forster et al. |
| 2013/0254202 A1 | 9/2013 | Friedlander et al. |
| 2013/0296175 A1 | 11/2013 | Rafnar et al. |
| 2013/0297221 A1 | 11/2013 | Johnson et al. |
| 2013/0307029 A1 | 11/2013 | Xu et al. |
| 2013/0311106 A1 | 11/2013 | White et al. |
| 2013/0316331 A1 | 11/2013 | Isakov et al. |
| 2013/0324417 A1 | 12/2013 | Kennedy et al. |
| 2013/0332081 A1 | 12/2013 | Reese et al. |
| 2013/0338012 A1 | 12/2013 | Sulem et al. |
| 2013/0338934 A1* | 12/2013 | Asadi .................... G16B 30/00 702/20 |
| 2014/0024537 A1 | 1/2014 | Rigatti et al. |
| 2014/0033125 A1 | 1/2014 | Merel |
| 2014/0045705 A1 | 2/2014 | Bustamante et al. |
| 2014/0046926 A1 | 2/2014 | Walton |
| 2014/0051588 A9 | 2/2014 | Drmanac et al. |
| 2014/0081665 A1 | 3/2014 | Holmes |
| 2014/0114582 A1 | 4/2014 | Mittelman et al. |
| 2014/0121116 A1 | 5/2014 | Richards et al. |
| 2014/0164516 A1 | 6/2014 | Maltbie et al. |
| 2014/0200166 A1 | 7/2014 | Van Rooyen et al. |
| 2014/0236490 A1 | 8/2014 | Van Rooyen et al. |
| 2014/0297196 A1 | 10/2014 | Olson |
| 2014/0304276 A1 | 10/2014 | Boyce |
| 2014/0309944 A1 | 10/2014 | van Rooyen et al. |
| 2014/0310215 A1 | 10/2014 | Trakadis |
| 2014/0316716 A1 | 10/2014 | Jiang et al. |
| 2014/0337052 A1 | 11/2014 | Pellini et al. |
| 2014/0350968 A1 | 11/2014 | Hahn et al. |
| 2014/0368550 A1 | 12/2014 | Vaske et al. |
| 2014/0371109 A1 | 12/2014 | McMillen et al. |
| 2014/0371110 A1 | 12/2014 | Van Rooyen et al. |
| 2015/0066824 A1 | 3/2015 | Harris et al. |
| 2015/0123600 A1 | 5/2015 | Groat et al. |
| 2015/0142334 A1 | 5/2015 | Mishra |
| 2015/0154406 A1 | 6/2015 | Naehrig et al. |
| 2015/0248525 A1 | 9/2015 | Ury et al. |
| 2015/0286645 A1 | 10/2015 | Lee |
| 2015/0310163 A1 | 10/2015 | Kingsmore et al. |
| 2015/0339437 A1 | 11/2015 | McMillen et al. |
| 2016/0046986 A1 | 2/2016 | Eltoukhy et al. |
| 2016/0092631 A1 | 3/2016 | Yandell et al. |
| 2016/0140290 A1 | 5/2016 | Rooyen et al. |
| 2016/0171153 A1 | 6/2016 | Van Rooyen et al. |
| 2016/0178569 A1 | 6/2016 | Hoffman et al. |
| 2016/0283407 A1 | 9/2016 | van Rooyen et al. |
| 2016/0306923 A1 | 10/2016 | Van Rooyen et al. |
| 2017/0270245 A1 | 9/2017 | van Rooyen et al. |
| 2017/0308644 A1 | 10/2017 | van Rooyen et al. |
| 2018/0196916 A1 | 7/2018 | Van Rooyen et al. |
| 2018/0239865 A1 | 8/2018 | Van Rooyen et al. |

FOREIGN PATENT DOCUMENTS

| | | |
|---|---|---|
| WO | WO-2014/074246 A1 | 5/2014 |
| WO | WO-2014/113736 A1 | 7/2014 |
| WO | WO-2014/121091 A1 | 8/2014 |
| WO | WO-2014/186604 A1 | 11/2014 |
| WO | WO-2015/051006 A2 | 4/2015 |
| WO | WO-2015/089333 A1 | 6/2015 |

(56) References Cited

FOREIGN PATENT DOCUMENTS

| | | |
|---|---|---|
| WO | WO-2015/100427 A1 | 7/2015 |
| WO | WO-2015/123600 A1 | 8/2015 |

OTHER PUBLICATIONS

Eusse, J. F., et al., "A Protein Sequence Analysis Hardwar Accelerator Based on Divergences", INTL Journal of Reconfigurable Computing vol. 2012, Jan. 1, 2012, 1-19.
Jacob, A. , et al., "Preliminary Results in Accelerating Profile HMM search on FPGA's", IPDPS 2007, IEEE, PI, Sep. 20, 2008, 1-8.
Oliver, N. , et al., "A Reconfigurable Computing System Based on a Cache-Coherent Fabric", RCONFIG, IEEE, Nov. 30, 2011, 1-6.
Oliver, T. , et al., "Integrating FPGA acceleration into HMMer", Parallel Computing, Elisevier V. 34 (11), Nov. 1, 2008, 681-691.
Tang, W. , et al., "Accelerating Million of Short Reads Mapping on a Heterogeneous Architecture with FPGA Accelerator", FCCM, IEEE, Apr. 29, 2012, 184-187.
Chang Mau-Chung Frank et al: "The SMEM Seeding Acceleration for DNA Sequence Alignment." 2016 IEEE 24th Annual International Symposium on Field-Programmable Custom Computing Machines (FCCM), IEEE, [retrieved on Aug. 16, 2016] May 2, 2016 (May 2, 2016), pp. 32-39.
Chang, Xin, et. al. "FPGA-based Heterogeneous Architecture for Sequence Alignment." (2014) 4 pages.
International Search Report and Written Opinion issued in International Application No. PCT/US2017/058890, dated Feb. 23, 2018 (Feb. 23, 2018). 16 pages.
A. McKenna et al. The Genome Analysis Toolkit: A MapReduce framework for analyzing next-generation DNA sequencing data. Genome Research. Published in advance Jul. 19, 2010. 20: 1297-1303. http://genome.cshlp.org/ content/20/19/1297.full.html. Retrieved May 25, 2016.
Al Junid et al. "Development of Novel Data Compression Technique for Accelerate DNA Sequence Alignment Based on Smith-Waterman Algorithm." Highlighted. University Technology Mara (UiTM). 2009 Third UKSim European Symposium on Computer Modeling and Simulation. pp. 181-186.
Al Junid et al. "Optimization of DNA Sequences Data for Accelerate DNA Sequences Alignment on FPGA." University Technology MARA (UiTM). 2010 Fourth Asia International Conference on Mathematical/Analytical Modelling and Computer Simulation. pp. 231-236.
Alachiotis, et al, Accelerating Phylogeny-Aware Short DNA Read Alignment with FPGAs, The Exelixis Lab, (2011) pp. 8, Heidelberg Institute for Theoretical Studies, Heidelberg, Germany.
Altera Corp, Implementation of the Smith-Waterman Algorithm on a Reconfigurable Supercomputing Platform, White Paper, 18 pgs. Sep. 2007 Ver. 1.
Anonymous: "FPGA-accelerated Bioinformics at #ASHG-Dragen Aligner from Edico Genome." Oct. 20, 2014 (Oct. 20, 2014). XP055360856. Retrieved from the internet: URL:http://moolog.us/blogs/glob/2014/210/20/fpga-accelerated-bioinformics-at-ashg-dragen-aligner-from-edico-genome/# [retrieved on Mar. 31, 2017]. 7 pages.
B. Langmead et al. Searching for SNPs with cloud computing. Genome Biology 2009, vol. 10: Iss, II: R134, Published Nov. 20, 2009. 10 pages.
Benkrid et al, A highly parameterized and efficient FPGA-based skeleton for pairwise biological sequence alignment, IEEE Transactions on VLSI Systems, Apr. 2009, pp. 561-570 (1-12), IEEE Educational Activities Dept. Piscataway, NJ.
Benkrid, Khaled, et. al. "A High Performance Reconfigurable Core for Motif Searching Using Profile HMM." NASA ESA Conference on Adaptive Hardware and Systems, IEEE, 2008. pp. 285-292.
Buyukkurt et al, Compiler Generated Systolic Arrays for Wavefront Algorithm Acceleration on FPGAs, Sep. 2008, 4 pgs, International Conference on Field Programmable Logic and Applications, Heidelberg, Germany.

Carneiro, Mauricio. "Accelerating Variant Calling." Broad Institute, Intel Genomic Sequencing Pipeline Workshop, Powerpoint Presentation, Mount Sinai, Dec. 10, 2013. 26 pages.
Chang, et al, Exploring Sequence Alignment Algorithms on FPGA-based Heterogeneous Architectures, Proceedings IWBBIO, pp. 330-341, 2014, Granada.
Chang, Xin, et. al. "FPGA-based Heterogeneous Architecture for Sequence Alignment." 4 pages.
Choi, Young-kyu, et al. "A Quantitative Analysis of Microarchitectures of Modern CPU-FPGA Platforms." Design Automation Conference, Jun. 5-9, 2016, DAC '16, Jun. 5-9, 2016. Austin, TX. Conference Presentation. 6 pages.
Chrysanthou, Nafsika, et. al. "Parallel Accelerators for GlimmerHMM Bioinformatics Algorithm." 2011 Design, Automation & Test in Europe Conference & Exhibition, IEEE, 2011. 6 pages.
Clive Maxfield. Impulse achieves 16X speed-up of genome analysis on $2,500 FPGA module. EE Times. Jun. 15, 2012. http://www.eetimes.com/ documentasp?doc id=1317288&print=yes. Retrieved Mar. 29, 2016. 4 pages.
Corey B. Olson et al. "Hardware Acceleration of Short Read Mapping." University of Washington, Pico Computing Inc., Fred Hutchinson Cancer Research CenterSeattle, WA. 2012. 8 pages.
Deutsch, D. "Quantum theory, the Church-Turing principle and the universal quantum computer." Proceedings of the Royal Society of London A 400, pp. 97-117 (1985). Printed in Great Britain.
Dydel, Stefan and Piotr Bala. "Large Scale Protein Sequence Alignment Using FPGA Reprogrammable Logic Devices.", Faculty of Mathematics and Computer Science. N. Copernicus University, 10 pgs, 2004, Torun, Poland.J. Becker, M. Platzner, S. Vernalde (Eds.): FPL 2004, LNCS 3203, pp. 23-32, 2004.
E. Fernandez, W. Najjar, E. Harris, and S. Lonardi. Exploration of Short Reads Genome Mapping in Hardwares. Field Programmable Logic and Applications (FPL), 20th Int. Conf. Milano, Italy, Aug. 2010. 4 pages.
Edward B. Fernandez et al. "Multithreaded FPGA Acceleration of DNA Sequence Mapping." University of California Riverside, Riverside and Jacquard Computing Inc. Riverside. 2012 IEEE. 6 pages.
Edward Fernandez et al. PowerPoint presentation on "Multithreaded FPGA Acceleration of DNA Sequence Mapping." UC Riverside, Department of Computer Science and Engineering Jacquard Computing. 2012. 20 pages.
Faes, et al, Scalable Hardware Accelerator for Comparing DNA and Protein Sequences, INFOSCALE, 2006, pp. 6, ACM, Hong Kong.
Fagin, FPGA and Rapid Prototyping Technology Use in a Special Purpose Computer for Molecular Genetics, Website: http://www.faginfamily.net/barry/Papers/ICCD92.htm, Thayer School of Engineering, Dartmouth, Hanover, NH. (1992). Retrieved Jan. 11, 2017. 6 pages.
Ferraz, Samuel and Nahri Moreano. "Evaluating Optimization Strategies for HMMer Acceleration on GPU." 2013 International Conference on Parallel and Distributed Systmes, IEEE, 2013. pp. 59-68.
Feynman, Richard P. "Simulating Physics with Computers." International Journal of Theoretical Physics, vol. 21, Nos. 6/7, (1982): pp. 467-488.
G. Auwera et al. From FastQ data to high confidence variant calls: the Genome Analysis Toolkit best practices pipeline. HHS Public Access, Published online Oct. 15, 2013. http://www.ncbi.nlm.nih.gov/pmc/articles/PMC4243306/. Retrieved May 25, 2016. 27 pages.
Guccione et al, Gene Matching Using JBits, 9 pages Xilinx, Inc. San Jose CA (2002).
Guo, Xinyu et al. "A Systolic Array-Based FPGA Parallel Architecture for the Blast Algorithm." ISRN Bioinformatics, 2012, 11 pages. vol. 2012. Article ID 195658.
Hall, Adam. "Short-Read DNA Sequence Alignment with Custom Designed FPGA-based Hardware." Master of Science Thesis. The University of Cambridge, 2007. 186 pages.
Harris et al, A Banded Smith-Waterman FPGA Accelerator for Mercury BLASTP, Research Report, (2007), pp. 5, BECS Technology, Inc./NIH/NGHRI, St. Louis, Missouri.

(56) References Cited

OTHER PUBLICATIONS

Hasan et al, An Overview of Hardware-Based Acceleration of Biological Sequence Alignment, Computational Biology and Applied Bioinformatics, Sep. 2011, pp. 187-202, InTech, Rijeka, Croatia.
Herbordt, Martin et al., "Single Pass Streaming BLAST on FPGAs", NIH Public Access Author Manuscript, Nov. 2007, 25 pgs, Parallel Comput.
Herbordt, Martin, et al., "Single Pass, BLAST-like, Approximate String Matching of FPGAs", Boston University, 2006, 19 pgs, Boston.
Hoang et al., FPGA Implementation of Systolic Sequence Alignment, 1991, 4 pgs. NSF Graduate Fellowship.
Hoang, A Systolic Array for the Sequence Alignment Problem, Apr. 1992, 25 pgs, Brown University, Providence, RI.
Hoang, Searching Genetic Databases on Splash 2, FCCM20 Endorsement, 1993, pp. 185-191, Brown University, Providence, RI.
Huang, Sitao, et. al. "Hardware Acceleration of the Pair-HMM Algorithm for DNA Variant Calling." *Proceedings of the 2017 ACM/SIGDA International Symposium on Field-Programmable Gate Arrays*, Feb. 22-24, 2017, Monterey, California, USA. pp. 275-284.
Hughey, Parallel Hardware for Sequence Comparison and Alignment, Cabios, 1996, pp. 473-479, vol. 12 No. 6, Oxford University Press, CA.
International Search Report and Written Opinion issued in International Application No. PCT/US2017/013057, dated Apr. 11, 2017 (Apr. 11, 2017). 10 pages.
International Search Report and Written Opinion issued in International Application No. PCT/US2017/036424, dated Sep. 12, 2017 (Sep. 12, 2017). 12 pages.
International Search Report and Written Opinion issued in International Application No. PCT/US2017/040385, dated Oct. 27, 2017 (Oct. 27, 2017). 15 pages.
International Search Report dated Jun. 18, 2014, for PCT application No. PCT/US2014/012144. 2 pages.
Isa, Nazrin M., et. al. "A Novel Efficient FPGA Architecture for Hmmer Acceleration." *2012 International Conference on Reconfigurable Computing and FPGAs (ReConFig)*, IEEE, 2013. 6 pages.
Isaac TS Li et al. Methodology article, 160-fold acceleration of the Smith-Waterman algorithm using a field programmable gate array (FPGA).: Published Jun. 7, 2007. BMC Bioinformatics 2007, 8:185, Institute of Biomaterials and Biomedical Engineering, University of Toronto,Ontario, Canada. 7 pages.
Jacob, Arpith et al. "FPGA-Accelerated seed generation in Mercury BLASTP", Washington University in St. Louis, BECS Technology Inc. (2007). 10 pgs.
Jacob, Arpith, et. al. "Preliminary Results in Accelerating Profile HMM Search on FPGAs." *In Proceedings of 6th IEEE International Workshop on High Performance Computational Biology*, Mar. 2007. 9 pages.
Kasap, Server et al, "Design and Implementation of an FPGA-based Core for Gapped Blast Sequence Alignment with the Two-Hit Method", Engineering Letters, 16:3 EL_16_3_25, Aug. 20, 2012, 10 pgs, Scotland, UK (2008).
Khaled Benkrid et al. Review Article: "High Performance Biological Pairwise Sequence Alignment: FPGA versus GPU versus Cell BE versus GPP." Hindawi Publishing Corporation. International Journal of Reconfigurable Computing. vol. 2012. (2012). 15 pages. ; Institute of Integrated Systems, School of Engineering, The University of Edinburgh, Kings Edinburgh, UK and Electrical and Computer Engineering Department, The University of Arizona, Tucson, AZ.
Lancaster Joseph, "Design and Evaluation of a BLAST Ungapped Extension Accelerator, Master's Thesis", Washington University, Jan. 1, 2006, 79 pgs, Report No. WUCSE-20016-21, 2006 St. Louis.
Lancaster Joseph, et al. "Acceleration of Ungapped Extension in Mercury BLAST", MSP-7th Workshop on Media and Streaming Processors, Nov. 2005, 9 pgs.
Lavenier, Dominque. "SAMBA: Systolic Accelerator for Molecular Biological Applications." Research Report RR-2845, INRIA. 22 pgs, Mar. 1996, France.
Lemoine, et al, High Speed Pattern Matching in Genetic Data Base with Reconfigurable Hardware, ISMB-94 Proceedings, 1994, pp. 269-275, AAAI (www.aaai.org), France.
Lloyd, Scott and Quinn O. Snell. "Hardware Accelerated Sequence Alignment with Traceback" *International Journal of Reconfigurable Computing*, vol. 2009, 2009. 10 pages.
Lopresti, Rapid Implementation of a Genetic Sequence Comparator Using Field-Programmable Logic Arrays, Advanced Research in VLSI, 1991, pp. 138-152, UC Santa Cruz, CA.
M. Ruffalo, T. LaFramboise, and M. Koyuturk. Comparative analysis of algorithms for next-generation sequencing read alignment. Bioinformatics (2011) 27 (20): 2790-2796. First published online: Aug. 19, 2011. https://bioinformatics.oxfordjournals.org/content/27/20/2790.full. Retrieved May 25, 2016.
M. Schatz, B. Langmead, and S. Salzberg. Cloud Computing and the DNA Data Race. HHS Public Access. Published Nat Biotechnol. Jul. 2010; 28(7): 691-693. http://www.ncbi.nlm.nih.gov/pmciarticles/PMC2904649/. Retrieved May 25, 2016.
M. Schatz, C. Trapnell, A. Delcher, and A. Varshney. High-throughput sequence alignment using Graphics Processing Units. Published Dec. 10, 2007. BMC Bioinformatics. http://bmcbioinformatics.biomedcentral.com/; articles/10.1186/1471-2105-8-474. Retrieved May 25, 2016. 13 pages.
Madhavan, Advait, et. al. "Race Logic: A Hardware Acceleration for Dynamic Programming Algorithms." *2014 ACM/IEEE 41st International Symposium on Computer Architecture (ISCA)*, IEEE, 2014. 12 pages.
Mahram, FPGA Acceleration of Sequence Analysis Tools in Bioinformatics, Dissertation, 2013, 180 pages, Boston, MA.
Michael Schatz. CloudBurst: highly sensitive read mapping with MapReduce. Bioinformatics (2009) 25 (11): 1363-1369. First published online: Apr. 8, 2009. http://bioinformatics.oxfordjournals.org/content/25/11/1363.full. Retrieved May 25, 2016.
Mikami, et al, Efficient FPGA-based Hardware Algorithms for Approximate String Matching, ITC-CSCC, 2008, pp. 201-204, Hiroshima, JP.
Miller, Neil A. et al. "A 26-hour system of highly sensitive whole genome sequencing for emergency management of genetic diseases." Genome Medicine. vol. 7, No. 100, Sep. 30, 2015 (Sep. 30, 2015). 16 pages.
Moritz, et al, Implementation of a Parallel Algorithm for Protein Pairwise Alignment Using Reconfigurable Computing, Conference date 2006, Published Feb. 12, 2007. pp. 7, Brazilian National Research Council (CNPq), Brazil.
Muriki, Krishna et al., "RC-BLAST: Towards a Portable, Cost-Effective Open Source Hardware Implementation" Supported in part by NSF Grant EIA-9985986, (2005). 8 pgs.
N. Homer, B. Merriman, and S. Nelson. BFAST: An Alignment Tool for Large Scale Genome Resequencing. PLOS. Published Nov. 11, 2009. 11 pages. http://journals.plos.org/plosone/article?id=10.1371/journal.pone.0007767. Retrieved May 25, 2016.
Nawaz, et al, A Parallel FPGA Design of the Smith-Waterman Traceback, Conference date 2010. Published Jan. 6, 2011, pp. 6, ACE Associated Compiler Expert, The Netherlands.
Nawaz, et al, Fast Smith-Waterman hardware implementation, hArtes (IST-035143), (2010) pp. 4, The MORPHEUS (IST-027342) and RCOSY (DES-6392) Projects.
Nelson, et al, Shepard: A Fast Exact Match Short Read Aligner, Research Report, (2012) pp. 4, Dept. of Electrical and Computer Engineering, Iowa State University, Ames, IA.
Oliver, et al, Using Reconfigurable Hardware to Accelerate Multiple Sequence Alignment with ClustalW, BioInformatics, 2005, pp. 3431-3432, vol. 21 No. 16, Advanced Access Publication, Singapore.
Oliver, Hyper Customized Processors for Bio-Sequence Database Scanning on FPGAs, FPGA, pp. 229-237, 2005 Monterey, CA.
Olson, Corey Bruce. "An FPGA Acceleration of Short Read Human Genome Mapping." Master of Science Thesis. University of Washington, 2011. 103 pages.
Peltenburg, Johan, et. al. "Maximizing Systolic Array Efficiency to Accelerate the PairHMM Forward Algorithm." *2016 IEEE International Conference on Bioinformatics and Biomedicine (BIBM)*, IEEE, 2016. pp. 758-762.

(56) References Cited

OTHER PUBLICATIONS

Ren, Shanshan, et. al. "FPGA Acceleration of the Pair-HMMs Forward Algorithm for DNA Sequence Analysis." *2015 IEEE International Conference on Bioinformatics and Biomedicine (BIBM)*, IEEE, 2015. 6 pages.

S. Angiuoli and S. Salzberg. Mugsy: fast multiple alignment of closely related whole genomes. Bioinformatics (2011) 27 (3): 334-342. First published online: Dec. 9, 2010. http://bioinformatics.oxfordjournals.org/content/27/31334.full. Retrieved May 25, 2016.

Sakar, Souradip et al. "Network-on-Chip Hardware Accelerators for Biological Sequence Alignment." IEEE Transactions on Computers, Jan. 2010, vol. 59, No. 1, pp. 29-41, Washington State.

Settle, Sean, et. al. "High-Performance Dynamic Programming on FPGAs with OpenCL." *2013 IEEE High Performance Extreme Computing Conference (HPEC)*, IEEE, 2013. 6 pages.

Sotiriades Euripides, et al. "FPGA based Architecture for DNA Sequence Comparison and Database Search", University of Crete, 2006, 8 pgs, Crete, Greece.

Sotiriades Euripides, et al., "Some Initial Results on Hardware BLAST acceleration with a Reconfigurable Architecture", University of Crete, 2006, 8 pgs, Crete, Greece.

Sun, Yanteng, et. al. "Accelerating HMMer on FPGAs Using Systolic Array Based Architecture." *IEEE International Symposium on Parallel & Distributed Processing*, IEEE, 2009. 8 pages.

T. Derrien et al. Fast Computation and Applications of Genome Mappability. PLOS One. Published: Jan. 19, 2012. 15 pages. http://journals.plos.org/plosone/article?id=10.1371/journal.pone.0030377. Retrieved May 25, 2016.

T. Hardcastle and K. Kelly. baySeq: Empirical Bayesian methods for identifying differential expression in sequence count data. Published Aug. 10, 2010, BMC Bioinformatics. http://bmcbioinformatics.biomedcentral.com/articles/10,1186/1471-2105-11-422. Retrieved May 25, 2016. 16 pages.

Thomas D. Wu and Colin K. Watanabe. Sequence analysis: "GMAP: a genomic mapping and alignment program for mRNA and EST sequences." Publication Feb. 22, 2005. Bioinformatics Original Paper. vol. 21 No. 9 2005, pp. 1859-1875. South San Francisco, CA.

Tim Oliver et al. "Multiple Sequence Alignment on an FPGA." IEEE Computer Society. School of Computer Engineering, Nanyang Technological University, Singapore; Project Proteus, School of Engineering, Ngee Ann Polytechnic, Singapore. Proceedings of the 2005 11th International Conference on Parallel and Distributed Systems. (2005). 5 pages.

TimeLogic Division, Active Motif Inc., "Accelerated BLAST Performance with Tera-Blast: a comparison of FPGA versus GPU and CPU Blast implementations", Technical Note, May 2013, 5 pages, Version 1.0.

Van Court et al., Families of FPGA-Based Algorithms for Approximate String Matching, (2004), 11 pgs, Boston University, ECE Dept., MA.

W. Zhang et al. A Practical Comparison of De Novo Genome Assembly Software Tools for Next-Generation Sequencing Technologies. PLOS One. Published: Mar. 14, 2011. http://journals.plos.org/plosone/article?id=10.1371/journal.pone.0017915. Retrieved May 25, 2016. 10 pages.

Yamaguchi, et al., High Speed Homology Search with FPGAs, Pacific Symposium on Biocomputing 7:271-282 (2002), Japan.

Ying Liu et al. "An FPGA-Based Web Server for High Performance Biological Sequence Alignment." The University of Edinburgh, Edinburgh, UK and the Queen's University of Belfast, Northern Ireland, UK. 2009 NASA/ESA Conference on Adaptive Hardware and Systems. pp. 361-368.

Yu, et al, A Smith-Waterman Systolic Cell, (2003), 10 pgs. Dept. of Computer Science, The Chinese University of Hong Kong.

PCT/US2016/020480, "International Search Report", dated May 17, 2016.

PCT/US2016/026796, "International Search Report", dated Jul. 18, 2016.

PCT/US2016/040842, "International Search Report", dated Oct. 4, 2016.

PCT/US2016/18765, "International Search Report", dated May 6, 2016.

Abbas, N., et al., "Combining Executin Pipelines to Improve Parallel Implementation of HMMER on FPGA", Microprocessors and Microsystems 39(7), Jun. 25, 2015, 457-470.

Derrien, S., et al., "Hardware Acceleration of HMMER on FPGAs", J Sign Process Syst 58, 2010, 53-67.

EP Extended European Search Report in EP Appln. No. 19199685.9, dated Jan. 3, 2020, 13 pages.

Giraldo, J., et al., "A HMMER Hardware Accelerator using Divergences", 2010 Design, Automation & Test in Europe Conference and Exhibition, Mar. 12, 2010, 405-410.

Jiang, K., et al., "An Efficient Parallel Implementation of the Hidden Markov Methods for Genomic Sequence Search on a Massively Parallel System", IEEE Transaction on Parallel and Distributed Systems 19(1), Jan. 2008, 1-9.

\* cited by examiner

HMM data flow and HW/SW interaction overview.

HMM Cluster Collar connections.

HMM Engine HMEM organization example.

FIG. 14 Somewhat high-level view of the major functional blocks within the HMM hardware accelerator.

Enlarged view of a portion of Figure 8 showing the data flow and dependencies between nearby cells in the HMM M, I, and D state computations.

Computations required for M, I, D state updates.

M, I, and D state update circuits, including effects of simplifying assumptions related to transition probabilities and the effect of sharing some M, I, D adder resources with the final sum operations.

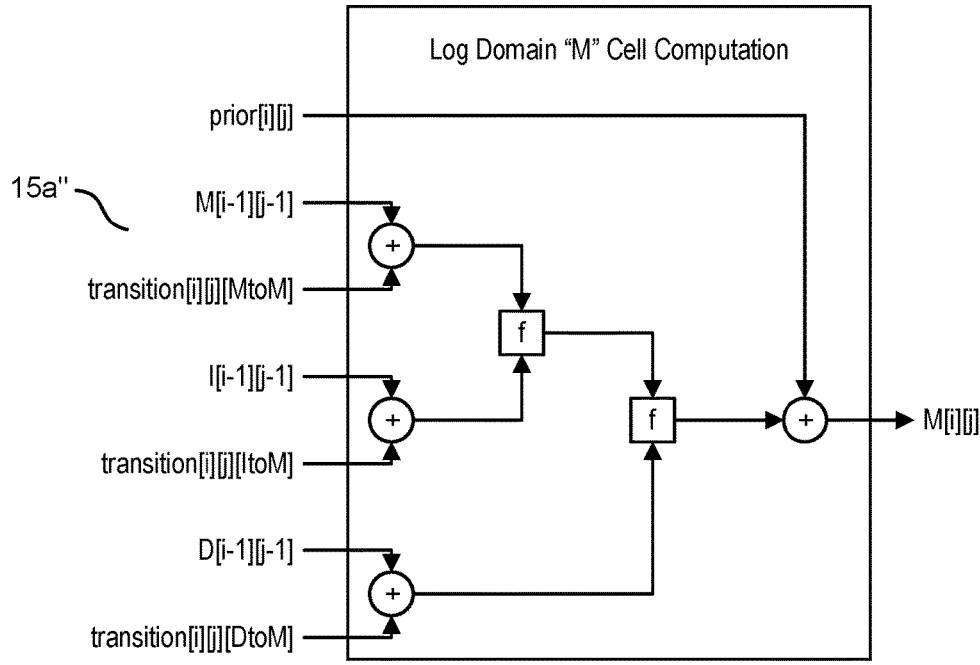
Note: The "f" function is the approximation to log of addition. I.e., f(a,b) @ max(a,b) − log₂(1+2^(-|a-b|))
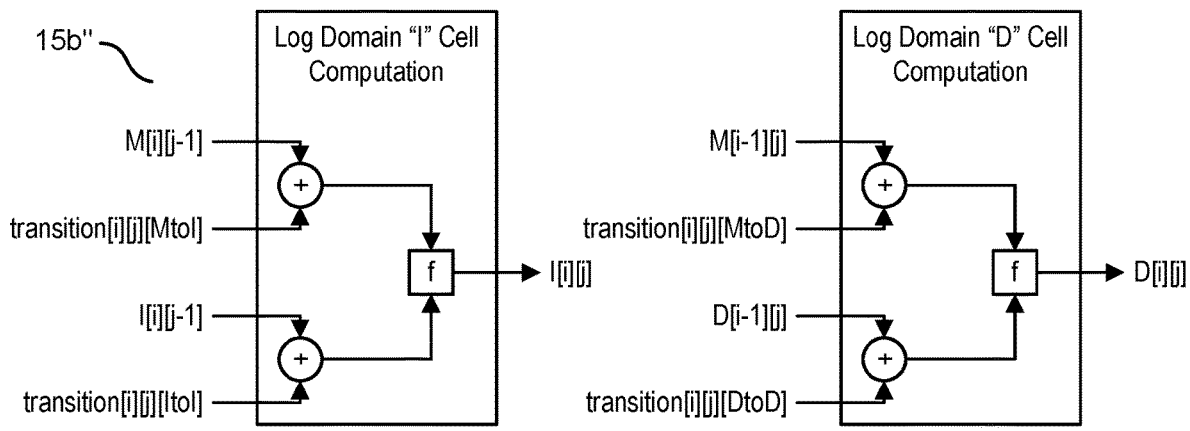
Log domain M, I, D state calculation details.
FIG. 19

HMM state transition diagram showing relation between GOP, GCP and transition probabilities.

HMM Transprobs and priors generation circuit to support the general state transaction diagram of Figure 17.

Simplified HMM state transition diagram showing relation between GOP, GCP and transition probabilities.

HMM transprobs and priors generation circuit to support the simplified state transition diagram of Figure 19.

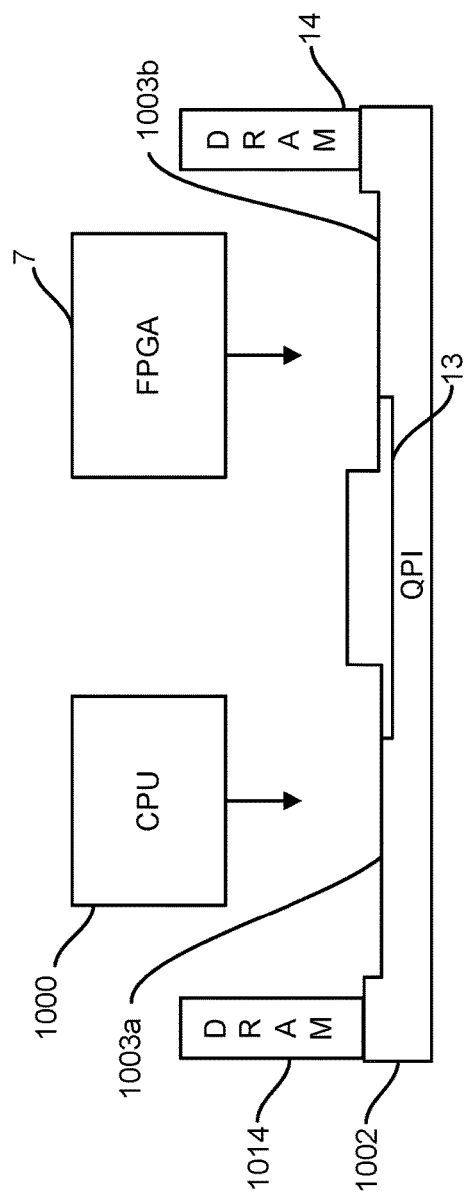
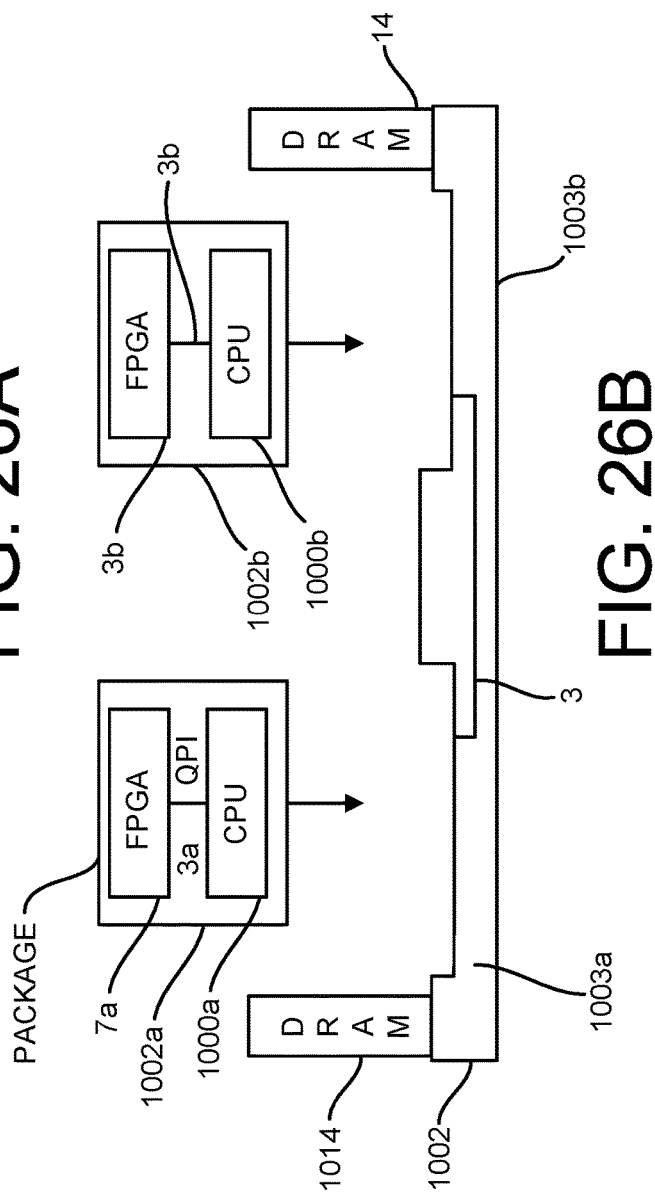
FIG. 26A
FIG. 26B

BIOINFORMATICS SYSTEMS, APPARATUSES, AND METHODS EXECUTED ON AN INTEGRATED CIRCUIT PROCESSING PLATFORM

CROSS REFERENCE TO RELATED APPLICATIONS

This application is a continuation of application Ser. No. 15/094,939, entitled "Bioinformatics Systems, Apparatuses, and Methods Executed on an Integrated Circuit Processing Platform," filed on Apr. 8, 2016, which claims the benefit of U.S. Provisional Application Ser. No. 62/144,941, entitled "Hybrid CPU and FPGA Platform for Genomic Analysis," filed on Apr. 9, 2015. This application is a continuation in part of U.S. patent application Ser. No. 15/059,221, entitled "Bioinformatics Systems, Apparatuses, and Methods Executed on an Integrated Circuit Processing Platform," Mar. 2, 2016 which in turn claims the benefit of U.S. Provisional Application Ser. No. 62/127,232, entitled "Bioinformatics Systems, Apparatuses, And Methods Executed On An Integrated Circuit Processing Platform," filed on Mar. 2, 2015. U.S. patent application Ser. No. 15/059,221, is a continuation in part of U.S. patent application Ser. No. 15/048,935, entitled "Bioinformatics Systems, Apparatuses, and Methods Executed on an Integrated Circuit Processing Platform," Feb. 19, 2016; a continuation in part of U.S. patent application Ser. No. 14/284,307, entitled "Bioinformatics Systems, Apparatuses, and Methods Executed on an Integrated Circuit Processing Platform," filed May 21, 2014, now patented as U.S. Pat. No. 9,235,680; and a continuation in part of U.S. patent application Ser. No. 14/180,248, entitled "Bioinformatics Systems, Apparatuses, and Methods Executed on an Integrated Circuit Processing Platform," filed Feb. 13, 2014, now patented as U.S. Pat. No. 9,014,989. U.S. patent application Ser. No. 15/048,935 claims the benefit of priority to U.S. Provisional Application Ser. No. 62/119,059, entitled "Bioinformatics Systems, Apparatuses, And Methods Executed On An Integrated Circuit Processing Platform," filed on Feb. 20, 2015 and U.S. Provisional Application Ser. No. 62/127,232, entitled "Bioinformatics Systems, Apparatuses, And Methods Executed On An Integrated Circuit Processing Platform," filed on Mar. 2, 2015. U.S. patent application Ser. No. 14/284,307 is a continuation of U.S. patent application Ser. No. 14/279,063, entitled "Bioinformatics Systems, Apparatuses, and Methods Executed on an Integrated Circuit Processing Platform," filed May 15, 2014, a continuation in part of: U.S. patent application Ser. No. 14/180,248, entitled "Bioinformatics Systems, Apparatuses, and Methods Executed on an Integrated Circuit Processing Platform," filed Feb. 13, 2014, now patented as U.S. Pat. No. 9,014,989, and a continuation of U.S. patent application Ser. No. 14/158,758, entitled "Bioinformatics Systems, Apparatuses, and Methods Executed on an Integrated Circuit Processing Platform," filed Jan. 17, 2014; U.S. patent application Ser. No. 14/180,248, now patented as U.S. Pat. No. 9,014,989, a continuation in part of U.S. patent application Ser. No. 14/179,513, entitled "Bioinformatics Systems, Apparatuses, and Methods Executed on an Integrated Circuit Processing Platform," filed Feb. 12, 2014, now abandoned, a continuation of U.S. patent application Ser. No. 14/158,758, and claims the benefit of and priority to under 35 U.S.C. 119(e) of U.S. Provisional Application Ser. No. 61/753,775, titled, "System and Method for Bioinformatics Processor," filed Jan. 17, 2013, U.S. Provisional Application Ser. No. 61/822,101, titled, "Bioinformatics Processor Pipeline Based on Population Inference," filed May 10, 2013, U.S. Provisional Application Ser. No. 61/823,824, titled, "Bioinformatics Processing System," filed May 15, 2013, U.S. Provisional Application Ser. No. 61/826,381 titled, "System and Method for Computation Genomics Pipeline," filed May 22, 2013; U.S. Provisional Application Ser. No. 61/910,868, titled, "Bio-Informatics Systems and Methods Executed On a Hardware Processing Platform," filed Dec. 2, 2013; U.S. Provisional Application Ser. No. 61/988,128 titled, "Bioinformatics Systems, Apparatuses, and Methods Executed on an Integrated Circuit Processing Platform," filed May 2, 2014; U.S. Provisional Application Ser. No. 61/984,663 titled, "Bioinformatics Systems, Apparatuses, and Methods Executed on an Integrated Circuit Processing Platform" filed Apr. 25, 2014; and, U.S. Provisional Application Ser. No. 61/943,870 titled, "Dynamic Genome Reference Generation for Improved NGS Accuracy and Reproducibility" filed Feb. 24, 2014. U.S. patent application Ser. No. 14/158,758 claims the benefit of and priority under 35 U.S.C. 119(e) of: U.S. Provisional Application Ser. No. 61/753,775; U.S. Provisional Application Ser. No. 61/822,101; U.S. Provisional Application Ser. No. 61/823,824; U.S. Provisional Application Ser. No. 61/826,381; U.S. Provisional Application Ser. No. 61/910,868; U.S. Provisional Application Ser. No. 61/988,128; U.S. Provisional Application Ser. No. 61/984,663; and, U.S. Provisional Application Ser. No. 61/943,870. U.S. patent application Ser. No. 14/180,248, entitled "Bioinformatics Systems, Apparatuses, and Methods Executed on an Integrated Circuit Processing Platform," filed Feb. 13, 2014, now patented as U.S. Pat. No. 9,014,989 is a continuation in part of Ser. No. 14/158,758, entitled "Bioinformatics Systems, Apparatuses, and Methods Executed on an Integrated Circuit Processing Platform," filed Jan. 17, 2014. The disclosures of the above-identified patent applications are hereby incorporated by reference in their entirety. The disclosures of the above-identified patent applications are hereby incorporated by reference in their entirety.

REFERENCE TO A "SEQUENCE LISTING," A TABLE, OR A COMPUTER PROGRAM LISTING APPENDIX SUBMITTED AS AN ASCII FILE

The Sequence Listing written in file 49927-510001US_ST25, created Jun. 22, 2016, 1,591 bytes, machine format IBM-PC, MS Windows operating system, is hereby incorporated by reference.

FIELD OF THE DISCLOSURE

The subject matter described herein relates to bioinformatics, and more particularly to systems, apparatuses, and methods for implementing bioinformatic protocols, such as performing one or more functions for analyzing genomic data on an integrated circuit, such as on a hardware processing platform.

BACKGROUND TO THE DISCLOSURE

As described in detail herein, some major computational challenges for high-throughput DNA sequencing analysis is to address the explosive growth in available genomic data, the need for increased accuracy and sensitivity when gathering that data, and the need for fast, efficient, and accurate computational tools when performing analysis on a wide range of sequencing data sets derived from such genomic data.

Keeping pace with such increased sequencing throughput generated by Next Gen Sequencers has typically been manifested as multithreaded software tools that have been executed on ever greater numbers of faster processors in computer clusters with expensive high availability storage that requires substantial power and significant IT support costs. Importantly, future increases in sequencing throughput rates will translate into accelerating real dollar costs for these secondary processing solutions.

The devices, systems, and methods of their use described herein are provided, at least in part, so as to address these and other such challenges.

SUMMARY OF THE DISCLOSURE

The present disclosure is directed to devices, systems, and methods for employing the same in the performance of one or more genomics and/or bioinformatics protocols on data generated through a primary processing procedure, such as on genetic sequence data. For instance, in various aspects, the devices, systems, and methods herein provided are configured for performing secondary analysis protocols on genetic data, such as data generated by the sequencing of RNA and/or DNA, e.g., by a Next Gen Sequencer ("NGS"). In particular embodiments, one or more secondary processing pipelines for processing genetic sequence data is provided. In other embodiments, one or more tertiary processing pipelines for processing genetic sequence data is provided, such as where the pipelines, and/or individual elements thereof, deliver superior sensitivity and improved accuracy on a wider range of sequence derived data than is currently available in the art.

For example, provided herein is a system, such as for executing a sequence analysis pipeline on genetic sequence data. In various embodiments, the system may include one or more of an electronic data source that provides digital signals representing a plurality of reads of genomic data, such as where each of the plurality of reads of genomic data include a sequence of nucleotides. The system may further include a memory, e.g., a DRAM, or a cache, such as for storing one or more of the sequenced reads, one or a plurality of genetic reference sequences, and one or more indices of the one or more genetic reference sequences. The system may additionally include an integrated circuit, such as a FPGA, ASIC, or sASIC, which integrated circuit may be formed of a set of hardwired digital logic circuits that are interconnected by a plurality of physical electrical interconnects.

In various embodiments, one or more of the plurality of physical electrical interconnects may include an input to the integrated circuit which may be connected or connectable, e.g., directly or indirectly such as via a wireless network connection (for instance, a cloud or hybrid cloud), with the electronic data source. Regardless of a connection with the sequencer, the integrated circuit may be configured for receiving the plurality of reads of genomic data, e.g., directly from the sequencer or from an associated memory. Accordingly, one or more of the plurality of physical electrical interconnects may include a memory interface so as to allow the integrated circuit to access the memory.

In particular embodiments, the hardwired digital logic circuits may be arranged as a set of processing engines, such as where each processing engine may be formed of a subset of the hardwired digital logic circuits so as to perform one or more steps in the sequence analysis pipeline, as described herein below, on the plurality of reads of genomic data. For instance, each subset of the hardwired digital logic circuits may be in a wired configuration to perform the one or more steps in the sequence analysis pipeline. Particularly, the set of processing engines may include a mapping module in the wired configuration to access, according to at least some of the sequence of nucleotides in a read of the plurality of reads, the index of the one or more genetic reference sequences from the memory via the memory interface to map the read to one or more segments of the one or more genetic reference sequences based on the index. Additionally, the set of processing engines may include an alignment module in the wired configuration to access the one or more genetic reference sequences from the memory via the memory interface to align the read, e.g., the mapped read, to one or more positions in the one or more segments of the one or more genetic reference sequences, e.g., as received from the mapping module and/or stored in the memory. Further, the set of processing engines may include a sorting module so as to sort each aligned read according to the one or more positions in the one or more genetic reference sequences. Furthermore, the set of processing engines may include a variant call module, such as for processing the mapped, aligned, and/or sorted reads, such as with respect to a reference genome, to thereby produce a variant call file detailing the variations between the sequenced genetic data and the reference genomic reference data. In various instances, one or more of the plurality of physical electrical interconnects may include an output from the integrated circuit for communicating result data from the mapping module and/or the alignment and/or sorting and/or variant call modules.

Particularly, with respect to the mapping module, in various embodiments, a system for executing a sequence analysis pipeline on a plurality of reads of genomic data using an index of genetic reference data stored in a memory is provided, such as where each read of genomic data represents a sequence of nucleotides, and the genetic reference data represents one or more genetic reference sequences. In various embodiments, the system may include an integrated circuit that is formed of a set of pre-configured hardwired digital logic circuits that are interconnected by a plurality of physical electrical interconnects. The one or more of the plurality of physical electrical interconnects may include a memory interface for the integrated circuit to access the memory. In certain embodiments, the hardwired digital logic circuits may be arranged as a set of processing engines, such as where each processing engine is formed of a subset of the hardwired digital logic circuits to perform one or more steps in the sequence analysis pipeline on the plurality of reads of genomic data.

For instance, in one embodiment, the set of processing engines may include a mapping module in a pre-configured hardwired configuration to: receive a read of genomic data via one or more of the plurality of physical electrical interconnects; extract a portion of the read to generate a seed, the seed representing a subset of the sequence of nucleotides represented by the read; calculate an address within the index based on the seed; access the address in the index in the memory; receive a record from the address, the record representing position information in the genetic reference sequence; determine one or more matching positions from the read to the genetic reference sequence based on the record; and output at least one of the matching positions to the memory via the memory interface. In another embodiment, the set of processing engines may include an alignment module in a pre-configured hardwired configuration to: receive one or more mapped positions for the read data via one or more of the plurality of physical electrical interconnects; for each mapped position, accesses the (internal or external) memory to retrieve a segment of the reference sequence/genome corresponding to the mapped position; calculate an alignment of the read to each retrieved reference segment, along with a score for the alignment, select at least one best-scoring alignment of the read, and output the at least one best-scoring alignment. In various instances, the alignment module may also implement a dynamic programming algorithm when calculating the alignment, such as a Smith-Waterman algorithm, with linear or affine gap scoring, a gapped alignment algorithm, and/or a gapless alignment algorithm. In particular instances, the calculating of the alignment may include first performing a gapless alignment to each reference segment, and based on the gapless alignment results, selecting reference segments with which to further perform gapped alignments.

More particularly, a system for mapping a plurality of reads of genomic data to a genetic reference sequence may be provided such as where the system uses an index of genetic reference data, which may be accessed directly form a sequencer or an associated memory, e.g., stored in a memory of a CPU. In such an instance, each read of the genomic data may represent a sequence of nucleotides, which sequence may have been converted into a digital and/or binary format, and likewise the genetic reference data may represent at least a portion of the genetic reference sequence that has been rendered into a digital and/or binary format.

In such instances, the system may include a mapping module formed of a set of pre-configured hardwired digital logic circuits that are interconnected by a plurality of physical electrical interconnects, such as where one or more of the plurality of physical electrical interconnects includes a memory interface for the mapping module to access the memory. In particular instances, the integrated circuit may include a set of pre-configured hardwired digital logic circuits that are interconnected by a plurality of physical electrical interconnects, and may additionally include one or more subsets of digital logic circuits that are configured to perform one or more functions in a mapping pipeline, such as: a first subset of the pre-configured hardwired digital logic circuits being configured to receive a read of genomic data via one or more of the plurality of physical electrical interconnects; a second subset of the pre-configured hardwired digital logic circuits being configured to extract a portion of the read to generate a seed, the seed representing a subset of the sequence of nucleotides represented by the read; a third subset of the pre-configured hardwired digital logic circuits being configured to calculate an address within the index based on the seed; a fourth subset of the pre-configured hardwired digital logic circuits being configured to access the address in the index in the memory; a fifth subset of the pre-configured hardwired digital logic circuits being configured to receive a record from the address, the record representing position information in the genetic reference sequence; and a sixth subset of the pre-configured hardwired digital logic circuits being configured to determine one or more matching positions from the read to the genetic reference sequence based on the record. In various embodiments, a set of memory blocks may be provided wherein the memory block(s) may be connected with the set of pre-configured hardwired digital logic circuits for temporarily storing the seed, the record, and the one or more matching positions. An output formed of a second subset of the plurality of physical electrical interconnects for outputting at least one of the matching positions may also be provided.

In other instances the system may include an alignment module formed of a set of pre-configured hardwired digital logic circuits that are interconnected by a plurality of physical electrical interconnects, such as where one or more of the plurality of physical electrical interconnects includes a memory interface for the alignment module to access the memory. In particular instances, the integrated circuit may include a set of pre-configured hardwired digital logic circuits that are interconnected by a plurality of physical electrical interconnects, and may additionally include one or more subsets of digital logic circuits that are configured to perform one or more functions in an alignment pipeline, such as: a first subset of the pre-configured hardwired digital logic circuits being configured to receives one or more mapped positions for the read, such as from the mapper and/or a memory associated therewith; a second subset of the pre-configured hardwired digital logic circuits being configured to accesses the memory so to retrieve a segment of the reference sequence/genome corresponding to the mapped position, such as for each mapped position; a third subset of the pre-configured hardwired digital logic circuits being configured to calculates an alignment of the read to each retrieved reference segment, along with a score for the alignment; and a fourth subset of the pre-configured hardwired digital logic circuits being configured to select at least one best-scoring alignment of the read. An output, may also be included, such as where the output is formed of a second subset of the plurality of physical electrical interconnects for outputting at least one best scoring alignment. In various instances, one or more additional subsets of the pre-configured hardwired digital logic circuits may be included such as where the logic circuit is configured to perform a dynamic programming algorithm, such as Smith-Waterman alignment, and/or a gapped and/or a gapless alignment algorithm.

With respect to the variant call module, in various embodiments, improved variant call functions are provided that when implemented in one or both of software and/or hardware generate superior processing speed, better processed result accuracy, and enhanced overall efficiency than the methods, devices, and systems currently known in the art. Specifically, in one aspect, improved methods for performing variant call operations in software, such as for performing one or more HMM operations on genetic sequence data, are provided. In another aspect, novel devices including an integrated circuit for performing such improved variant call operations, where at least a portion of the variant call operation is implemented in hardware, are provided.

For instance, in accordance with a particular aspect of the disclosure, presented herein is a compact hardware-accelerated, e.g., chip based, platform for performing secondary analyses on genomic sequencing data. Particularly, a platform or pipeline of hardwired digital logic circuits that have specifically been designed for performing secondary genetic analysis, such as on sequenced genetic data, is provided on a chip, such as on an FPGA, ASIC, and/or Structured ASIC ("sASIC"), or the like. Particularly, a set of hardwired digital logic circuits, which may be arranged as a set of processing engines, may be provided, such as where the processing engines may be present in a hardwired configuration on a processing chip of the disclosure, and may be specifically designed for performing secondary variant call related genetic analysis on DNA data. In particular instances, the present devices, systems, and methods of employing the same in the performance of one or more genomics and/or bioinformatics secondary processing protocols, have been optimized so as to deliver an improvement in processing speed that is orders of magnitude faster than standard secondary processing pipelines that are implemented in software. Additionally, the pipelines and/or components thereof as set forth herein provide better sensitivity and accuracy on a wide range of sequence derived data sets for the purposes of genomics and bioinformatics processing.

For example, genomics and bioinformatics are fields concerned with the application of information technology and computer science to the field of genetics and/or molecular biology. In particular, bioinformatics techniques can be applied to process and analyze various genomic data, such as from an individual, so as to determine qualitative and quantitative information about that data that can then be used by various practitioners in the development of prophylactic and therapeutic methods for preventing or at least ameliorating diseased states, and thus, improving the safety, quality, and effectiveness of health care on an individualized level. Hence, because of their focus on advancing personalized healthcare, genomics and bioinformatics fields promote individualized healthcare that is proactive, instead of reactive, and this gives the subject in need of treatment the opportunity to become more involved in their own wellness. An advantage of employing genomics and/or bioinformatics technologies, therefore, in these instances is that the qualitative and/or quantitative analyses of molecular biological data can be performed on a broader range of sample sets at a much higher rate of speed and often times more accurately, thus expediting the emergence of a personalized healthcare system.

Accordingly, to make use of these advantages, there exists commonly used software implementations for performing one or a series of such bioinformatics based analytical techniques. However, a common characteristic of such software based bioinformatics methods and systems is that they are labor intensive, take a long time to execute on general purpose processors, and are prone to errors. A bioinformatics system, therefore, that could perform the algorithms implemented by such software, e.g., various variant call functions, in a less labor and/or processing intensive manner with a greater percentage accuracy would be useful. However, the cost of analyzing, storing, and sharing this raw digital data has far outpaced the cost of producing it. This data analysis bottleneck is a key obstacle standing between these ever-growing raw data and the real medical insight we seek from it.

Presented herein, therefore, are systems, apparatuses, and methods for implementing genomics and/or bioinformatic protocols or portions thereof, such as for performing one or more functions for analyzing genomic data, for instance, on an integrated circuit, such as on a hardware processing platform. For example, as set forth herein below, in various implementations, an integrated circuit is provided, such as an integrated circuit that is at least partially formed as, or otherwise includes, a hardware accelerator. In various instances, the integrated circuit may be employed in performing such bioinformatics related tasks in an accelerated manner, and as such the integrated circuit may include a hardware accelerated configuration.

Specifically, the bioinformatics related tasks may be a variant call operation and the integrated circuit may include a hardware accelerator that is formed of one or more hardwired digital logic circuits that are adapted to perform one or more tasks in the variant call operation, such as for the performance of a Hidden Markov Model (HMM), in an accelerated manner. More specifically, the hardwired digital logic circuits may include one or more subsets of hardwired digital logic circuits that may be arranged as a first set of processing engines, which processing engines may be configured to perform one or more steps in a bioinformatics genetic analysis protocol, such as an HMM analysis, e.g., on a read of genomic sequence data and a haplotype sequence data.

Further, presented here in is an integrated circuit that may be configured in such as way so as to include a subset of digital logic circuits that can be arranged as a set of processing engines, wherein each processing engine is capable of being configured to perform one or more steps in a bioinformatics genetic analysis protocol, such as for executing one or more HMM operations, such as in the performance of at least a portion of a variant call function. An advantage of this arrangement is that the bioinformatics related tasks may be performed in a manner that is faster than the software typically engaged for performing such tasks. Such hardware accelerator technology, however, is currently not typically employed in the genomics and/or bioinformatics space.

The present disclosure, therefore, is related to performing a task such as in a bioinformatics protocol. In various instances, a plurality of tasks are performed, and in some instances these tasks are performed in a manner so as to form a pipeline, wherein each task and/or its substantial completion acts as a building block for each subsequent task until a desired end result is achieved. Accordingly, in various embodiments, the present disclosure is directed to performing one or more methods on one or more apparatuses wherein the apparatus has been optimized for performing those methods. In certain embodiments, the one or more methods and/or one or more apparatuses are formulated into one or more systems.

For instance, in certain aspects, the present disclosure is directed to systems, apparatuses, and methods for implementing genomics and/or bioinformatic protocols such as, in various instances, for performing one or more functions for analyzing genetic data on an integrated circuit, such as implemented in a hardware processing platform. For example, in one aspect, a bioinformatics system is provided. The system may involve the performance of various bioanalytical functions, such as a variant call function, which have been optimized so as to be performed faster and/or with increased accuracy. The methods for performing these functions may be implemented in software or hardware solutions or in a combination of the two implementations.

Accordingly, in certain instances, methods are presented where the method involves the performance of an algorithm where the algorithm has been optimized in accordance with the manner in which it is to be implemented. In particular, where the algorithm is to be implemented in a software solution, the algorithm and/or its attendant processes, has been optimized so as to be performed faster and/or with better accuracy for execution by that media. For instance, in particular embodiments, a method for performing a variant call function is provided where various of the operations of the function have been optimized so as to be performed in a software solution. In such an instance, the algorithm and/or its attendant processes for performing these operations, have been optimized so as to be performed faster and/or with better accuracy for execution by that media. Likewise, where the functions of algorithm, e.g., a variant call functions, are to be implemented in a hardware solution, the hardware, as presented herein, has been designed to perform these functions and/or their attendant processes in an optimized manner so as to be performed faster and/or with better accuracy for execution by that media.

Accordingly, in one aspect, presented herein are systems, apparatuses, and methods for implementing bioinformatic protocols, such as for performing one or more functions for analyzing genetic data, for instance, via one or more optimized algorithms and/or on one or more optimized integrated circuits, such as on one or more hardware processing platforms. Hence, in one instance, methods are provided for implementing one or more algorithms for the performance of one or more steps for analyzing genomic data in a bioinformatics protocol, such as where one or more of the steps are to be implemented within the framework of computer readable media or implemented via one or more of firmware and/or hardware.

In other instances, methods are provided for implementing the functions of one or more algorithms for the performance of one or more steps for analyzing genomic data in a bioinformatics protocol, wherein the functions are implemented on an integrated circuit formed of one or more hardwired digital logic circuits. In such an instance, the hardwired digital logic circuits may be interconnected, such as by one or a plurality of physical electrical interconnects, and may be arranged to function as one or more processing engines. In various instances, a plurality of hardwired digital logic circuits are provided, which hardwired digital logic circuits are configured as a set of processing engines, wherein each processing engine is capable of performing one or more steps in a bioinformatics genetic analysis protocol.

More particularly, in various instances, systems for executing one or more sequence analysis pipelines such as on genetic sequence data is provided. The system may include one or more of an electronic data source, a memory, and an integrated circuit. For instance, in one embodiment, an electronic data source is included, wherein the electronic data source may be configured for generating and/or providing one or more digital signals, such as a digital signal representing one or more reads of genetic data, for example, where each read of genetic data includes genomic data that further includes one or more sequences of nucleotides. Further, the memory may be configured for storing one or more genetic reference sequences, e.g., one or more haplotype or theoretical haplotype sequences, and may further be configured for storing an index, such as an index of the one or more genetic reference sequences or reads of genetic sequences.

Further still, for those hardware designed implementations, the integrated circuit may be formed of a set of hardwired digital logic circuits such as where the hardwired digital logic circuits are interconnected, e.g., by a plurality of physical electrical interconnects. In various instances, one or more of the plurality of physical electrical interconnects may include an input, such as to the integrated circuit, and may further include an input such as to a memory and/or a electronic data source, e.g., an NGS, so as to allow the integrated circuit to communicate with the memory and/or NGS, and thereby be capable of receiving genetic data therefrom, such as to receive the one or more reads or references of genomic data.

In various embodiments, the hardwired digital logic circuits may be arranged as a set of processing engines, such as where each processing engine is formed of a subset of the hardwired digital logic circuits, and is configured so as to perform one or more steps in the sequence analysis pipeline, such as on the plurality of reads of genomic data. In such instances, the one or more steps may include the performance of a mapping, aligning, sorting, and/or variant call function on genomic sequence data, and in such instances each subset of the hardwired digital logic circuits may be in a wired configuration so as to perform the one or more steps in the sequence analysis pipeline, such s in an accelerated manner.

Accordingly, in various instances, a plurality of hardwired digital logic circuits are provided wherein the hardwired digital logic circuits are arranged as a set of processing engines, wherein one or more of the processing engines may include one or more of a mapping module and/or an alignment module and/or a sorting module and/or one or more portions of a variant call function. For instance, in various embodiments, the one or more of the processing engines may include a mapping module, which mapping module may be in a wired configuration and further be configured for accessing an index of the one or more genetic reference sequences from an associated memory, such as by one or more of the plurality of physical electronic interconnects, for example, so as to map a plurality of reads, representative of the genomic data of an individual, to one or more segments of one or more genetic reference sequences. In such an instance, a set of mapped reads may be produced, where the reads have been mapped to one or more positions, e.g., one or more segments, in a reference, e.g., haplotype, sequence, which once mapped may be stored, such as on an onboard memory or in the memory of an associated CPU on computer or server.

Further, in various embodiments, the one or more of the processing engines may include an alignment module, which alignment module may be in the wired configuration, and may be configured for accessing the one or more genetic reference sequences and/or the mapped reads from the memory, such as by one or more of the plurality of physical electronic interconnects, for example, so as to align the plurality of above mapped reads to the one or more segments of the one or more genetic reference sequences. In various embodiments, the one or more of the processing engines may further include a sorting module, which sorting module may be in the wired configuration and may be configured for accessing the one or more mapped and/or aligned reads from the memory, such as by one or more of the plurality of physical electronic interconnects, for example, so as to sort each mapped and/or aligned read, such as according to its one or more positions in the one or more genetic reference sequences.

Additionally, in various embodiments, the one or more of the processing engines may include a variant call module, which variant call module may be in a wired configuration and further be configured for accessing the index of the one or more genetic reference sequences, e.g., one or more haplotype reference sequences, and one or more mapped and/or aligned and/or sorted reads from the memory, such as by one or more of the plurality of physical electronic interconnects, for example, so as to generate a variant call file with respect to how the mapped, aligned, and/or sorted reads may vary from one or more genetic reference sequences. In such instances, the one or more of the plurality of physical electrical interconnects may include an output from the integrated circuit, such as for communicating result data from the mapping module and/or the alignment module and/or the sorting module and/or variant call module.

For instance, in a particular embodiment, a system for executing a Hidden Markov Model (HMM) analysis on genetic sequence data is provided, such as where the genetic sequence data includes a read of genomic sequence and a reference haplotype sequence. In particular instances, the system may include an electron data source, such as an NGS sequencer, such as for producing the read of genomic data, and may include one or more memories for storing the read of genomic sequence data and/or the reference haplotype sequence data, such as where each of the read of genomic sequence data and the reference haplotype sequence data include a sequence of nucleotides.

The system may additionally include an integrated circuit for running the HMM analysis on the genetic sequence data, such as an integrated circuit that is formed of one or more hardwired digital logic circuits which may be interconnectable by a plurality of physical electrical interconnects. In such an instance, the one or more of the plurality of physical electrical interconnects may include a memory interface for the integrated circuit to access the memory, which memory may be configured store the read of genomic sequence and/or the reference haplotype sequence. In particular instances, the hardwired digital logic circuits may include at least a first subset of hardwired digital logic circuits, such as where the first subset of hardwired digital logic circuits are arranged as a first set of processing engines.

For instance, the first set of processing engines may be configured to perform one or more steps in the HMM analysis on the read of genomic sequence data and the haplotype sequence data. Accordingly, the first set of processing engines may include an HMM module in a first configuration of the subset of hardwired digital logic circuits to access in the memory, via the memory interface, at least some of the sequence of nucleotides in the read of genomic sequence data and the haplotype sequence data, and to perform the MINI analysis on the at least some of the sequence of nucleotides in the read of genomic sequence data and the at least some of the sequence of nucleotides in the haplotype sequence data to produce MINI result data. In various instances, one or more of the plurality of physical electrical interconnects comprising an output from the integrated circuit for communicating the HMM result data from the HMM module.

In various instances, the integrated circuit may include a master controller so as to establish the wired configuration for each subset of the hardwired digital logic circuits, for instance, for performing the one or more of mapping, aligning, sorting, and/or variant calling, which functions may be performed individually and/or may be configured as one or more steps in a sequence analysis pipeline. Further, in various embodiments, the integrated circuit may be configured as a field programmable gate array (FPGA) having hardwired digital logic circuits, such as where the wired configuration may be established upon manufacture of the integrated circuit, and thus may be non-volatile. In other various embodiments, the integrated circuit may be configured as an application specific integrated circuit (ASIC) and/or structured ASIC having hardwired digital logic circuits.

In certain instances, the integrated circuit and/or the memory and/or, in various embodiments, the DNA sequencer, may be housed on an expansion card, such as a peripheral component interconnect (PCI) card, for instance, in various embodiments, the integrated circuit may be a chip having a PCIe card. In various instances, the integrated circuit and/or chip may be a component within a sequencer, such as an automated sequencer or other genetic analysis apparatus, such as a mapper and/or aligner, and/or in other embodiments, the integrated circuit and/or expansion card may be accessible via the internet, e.g., cloud. Further, in some instances, the memory may be a volatile random access memory (RAM), e.g., a direct access memory (DRAM). Particularly, in various embodiments, the memory may include at least two memories, such as a first memory that is an HMEM, e.g., for storing the reference haplotype sequence data, and a second memory that is an RMEM, e.g., for storing the read of genomic sequence data. In particular instances, each of the two memories may include a write port and/or a read port, such as where the write port and the read port each accessing a separate clock. Additionally, each of the two memories may include a flip-flop configuration for storing a multiplicity of genetic sequence data.

Accordingly, in another aspect, the system may be configured for sharing memory resources amongst its component parts, such as in relation to performing some computational tasks via software, such as run by the CPU, and performing other computational tasks via firmware, such as via the hardware of an associated chip. This may be achieved in a number of different ways, such as by a direct loose or tight coupling between the CPU and the chip, e.g., FPGA. Such configurations may be particularly useful when distributing operations related to the processing of large data structures to be used and accessed by both the CPU and the chip. Particularly, in various embodiments, when processing data through a genomics pipeline, as herein described, such as to accelerate overall processing function, timing, and efficiency, a number of different operations may be run on the data, which operations may involve both software and hardware processing components.

Consequently, data may need to be shared and/or otherwise communicated, between the software component running on the CPU and the hardware component embodied in the chip, e.g., an FPGA. Accordingly, one or more of the various steps in the processing pipeline, or a portion thereof, may be performed by one device, e.g., the CPU, and one or more of the various steps may be performed by the other device, e.g., the FPGA. In such an instance, the CPU and the FPGA need to be communicably coupled in such a manner to allow the efficient transmission of such data, which coupling may involve the shared use of memory resources. To achieve such distribution of tasks and the sharing of information for the performance of such tasks, the CPU may be loosely or tightly coupled to the FPGA, or other chip set.

Particularly, in various embodiments, a genomics analysis platform is provided. For instance, the platform may include a motherboard, a memory, and plurality of integrated circuits, such as forming one or more of a CPU, a mapping module, an alignment module, and/or a variant call module. Specifically, in particular embodiments, the platform may include a first integrated circuit, such as an integrated circuit forming a central processing unit (CPU) that is responsive to one or more software algorithms that are configured to instruct the CPU to perform one or more sets of genomics analysis functions, as described herein, such as where the CPU includes a first set of physical electronic interconnects to connect with the motherboard. In various instances, the memory may also be attached to the motherboard and may further be electronically connected with the CPU, such as via at least a portion of the first set of physical electronic interconnects. In such instances, the memory may be configured for storing a plurality of reads of genomic data, and/or at least one or more genetic reference sequences, and/or an index of the one or more genetic reference sequences.

Additionally, the platform may include one or more of a second integrated circuits, such as where each second integrated circuit forms a field programmable gate array (FPGA) having a second set of physical electronic interconnects to connect with the CPU and the memory, such as via a point-to-point interconnect protocol. In such an instance, the FPGA may be programmable by firmware to configure a set of hardwired digital logic circuits that are interconnected by a plurality of physical interconnects to perform a second set of genomics analysis functions, e.g., mapping, aligning, variant calling, etc. Particularly, the hardwired digital logic circuits of the FPGA may be arranged as a set of processing engines to perform one or more pre-configured steps in a sequence analysis pipeline of the genomics analysis, such as where the set(s) of processing engines include one or more of a mapping and/or aligning and/or variant call module, which modules may be formed of the separate or the same subsets of processing engines.

As indicated, the system may be configured to include one or more processing engines, and in various embodiments, an included processing engine may itself be configured for determining one or more transition probabilities for the sequence of nucleotides of the read of genomic sequence going from one state to another, such as from a match state to an inset state, or match state to a delete state, and/or back again such as from an insert or delete state back to a match state. Additionally, in various instances, the integrated circuit may have a pipelined configuration and/or may include a second and/or third and/or fourth subset of hardwired digital logic circuits, such as including a second set of processing engines, where the second set of processing engines includes a mapping module configured to map the read of genomic sequence to the reference haplotype sequence to produce a mapped read. A third subset of hardwired digital logic circuits may also be included such as where the third set of processing engines includes an aligning module configured to align the mapped read to one or more positions in the reference haplotype sequence. A fourth subset of hardwired digital logic circuits may additionally be included such as where the fourth set of processing engines includes a sorting module configured to sort the mapped and/or aligned read to its relative positions in the chromosome. Like above, in various of these instances, the mapping module and/or the aligning module and/or the sorting module, e.g., along with the variant call module, may be physically integrated on the expansion card. And in certain embodiments, the expansion card may be physically integrated with a genetic sequencer, such as a next gen sequencer and the like.

Accordingly, in one aspect, an apparatus for executing one or more steps of a sequence analysis pipeline, such as on genetic data, is provided wherein the genetic data includes one or more of a genetic reference sequence(s), such as a haplotype or hypothetical haplotype sequence, an index of the one or more genetic reference sequence(s), and/or a plurality of reads, such as of genetic and/or genomic data, which data may be stored in one or more shared memory devices, and/or processed by a distributed processing resource, such as a CPU and/or FPGA, which are coupled, e.g., tightly or loosely together. Hence, in various instances, the apparatus may include an integrated circuit, which integrated circuit may include one or more, e.g., a set, of hardwired digital logic circuits, wherein the set of hardwired digital logic circuits may be interconnected, such as by one or a plurality of physical electrical interconnects.

In certain instances, the one or more of the plurality of physical electrical interconnects may include an input, such as for receiving the haplotype or hypothetical haplotype sequence, the index of the one or more genomic reference sequence(s), and/or a plurality of reads of genomic data, such as from the CPU. Additionally, the set of hardwired digital logic circuits may further be in a wired configuration, so as to access the index of the one or more genetic reference sequences, e.g., from the CPU, via one of the plurality of physical electrical interconnects, and to map the plurality of reads, e.g., via onboard firmware, to one or more segments of the one or more genetic reference sequences, such as according to the index.

In various embodiments, the index may include one or more hash tables, such as a primary and/or secondary hash table. For instance, a primary hash table may be included, wherein in such an instance, the set of hardwired digital logic circuits may be configured to do one or more of: extracting one or more seeds of genetic data from the plurality of reads of genetic data; executing a primary hash function, such as on the one or more seeds of genetic data so as to generate a lookup address for each of the one or more seeds; and accessing the primary hash table using the lookup address so as to provide a location in the one or more genetic reference sequences for each of the one or more seeds of genetic data. In various instances, the one or more seeds of genetic data may have a fixed number of nucleotides.

Further, in various embodiments, the index may include a secondary hash table, such as where the set of hardwired digital logic circuits is configured for at least one of extending at least one of the one or more seeds with additional neighboring nucleotides, so as to produce at least one extended seed of genetic data; executing a hash function, e.g., a secondary hash function, on the at least one extended seed of genetic data, so as to generate a second lookup address for the at least one extended seed; and accessing the secondary hash table, e.g., using the second lookup address, so as to provide a location in the one or more genetic reference sequences for each of the at least one extended seed of genetic data. In various instances, the secondary hash function may be executed by the set of hardwired digital logic circuits, such as when the primary hash table returns an extend record instructing the set of hardwired digital logic circuits to extend the at least one of the one or more seeds with the additional neighboring nucleotides. In certain instances, the extend record may specify the number of additional neighboring nucleotides by which the at least one or more seeds is extended, and/or the manner in which the seed is to be extended, e.g., equally by an even number of "x" nucleotides to each end of the seed.

Additionally, in one aspect, an apparatus for executing one or more steps of a sequence analysis pipeline on genetic sequence data is provided, wherein the genetic sequence data includes one or more of one or a plurality of genetic reference sequences, an index of the one or more genetic reference sequences, and a plurality of reads of genomic data, which reads may have been previously mapped to the genetic reference sequences such as in relation to the index. In various instances, the apparatus may include an integrated circuit, which integrated circuit may include one or more, e.g., a set, of hardwired digital logic circuits, wherein the set of hardwired digital logic circuits may be interconnected, such as by one or a plurality of physical electrical interconnects. In certain instances, the one or more of the plurality of physical electrical interconnects may include an input, such as from a CPU and/or a memory associated therewith, and configured for receiving the plurality of reads of genomic data, which reads may have previously been mapped, as described herein. Additionally, the set of hardwired digital logic circuits may further be in a wired configuration, so as to access the one or more genetic reference sequences, such as from a memory coupled to the hardwired digital logic circuit and/or an associated CPU, e.g., via one of the plurality of physical electrical interconnects, to receive location information specifying one or more segments of the one or more reference sequences, and to align the plurality of reads to the one or more segments of the one or more genetic reference sequences.

Particularly, in various instances, the wired configuration of the set of hardwired digital logic circuits are configured to align the plurality of reads to the one or more segments of the one or more genetic reference sequences, and consequently, may further include a wave front processor that may be formed of the wired configuration of the set of hardwired digital logic circuits. In certain embodiments, the wave front processor may be configured to process an array of cells of an alignment matrix, such as a virtual matrix defined by a subset of the set of hardwired digital logic circuits. For instance, in certain instances, the alignment matrix may define a first axis, e.g., representing one of the plurality of reads, and a second axis, e.g., representing one of the segments of the one or more genetic reference sequences. In such an instance, the wave front processor may be configured to generate a wave front pattern of cells that extend across the array of cells from the first axis to the second axis; and may further be configured to generate a score, such as for each cell in the wave front pattern of cells, which score may represent the degree of matching of the one of the plurality of reads and the one of the segments of the one or more genetic reference sequences.

In an instance such as this, and others as herein described, the wave front processor may further be configured so as to steer the wave front pattern of cells over the alignment matrix such that the highest score may be centered on the wave front pattern of cells. Additionally, in various embodiments, the wave front processor may further be configured to backtrace one or more, e.g., all, the positions in the scored wave front pattern of cells through previous positions in the alignment matrix; track one or more, e.g., all, of the backtraced paths until a convergence is generated; and generate a CIGAR string based on the backtrace from the convergence.

In certain embodiments, the wired configuration of the set of hardwired digital logic circuits to align the plurality of reads to the one or more segments of the one or more genetic reference sequences may include a wired configuration to implement a Smith-Waterman and/or Burrows-Wheeler scoring algorithm and/or a Needleman-Wunsch aligner. In such an instance, the Smith-Waterman and/or Burrows-Wheeler and/or Needleman-Wunsch scoring algorithm may be configured to implement a scoring parameter that is sensitive to base quality scores. Further, in certain embodiments, the Smith-Waterman scoring algorithm may be an affine Smith-Waterman scoring algorithm.

In various embodiments, the wired configuration of the set of hardwired digital logic circuits may be configured to perform one or more steps in a variant call operation so as to determine how the plurality of reads differ from the one or more genetic reference sequences. Particularly, in various instances, the set of hardwired digital logical circuits may include a wired configuration to implement one or more algorithms for performing a Variant Call operation, or portions thereof. Specifically, in particular embodiments, a system for executing a De Bruijn graph and/or executing a Hidden Markov Model (HMM) analysis on genetic sequence data is provided. The genetic sequence data may include a read of genomic sequence and/or a reference haplotype sequence, such as a hypothesized reference haplotype sequence.

Additionally, the system may include one or more memories for storing the read of genomic sequence data and the reference haplotype sequence data, e.g., a hypothetical haplotype sequence, such as where each of the read of genomic sequence data and the reference haplotype sequence data comprise a sequence of nucleotides. In certain instances, the one or more memories may be coupled to an associated CPU and/or may be coupled to the chip, e.g., the FPGA, containing the integrated circuit. In particular instances, the system includes both a CPU and a chip containing the integrated circuit, such as an FPGA, where each of the CPU and the FPGA is operably coupled to separate memories, e.g., DRAMs, and further coupled to one another in a loose coupling manner. In other instances, only a single memory need be provided, such as where the CPU or the FPGA may be coupled to the memory that is accessible by the other device, such as where the CPU and the FPGA are coupled to one another in a tight coupling manner such as via a low latency, high bandwidth interface, such as a quick path interconnect (QPI), or other suitably configured processor interconnect, such as such as configured for high bandwidth, low latency, and efficient data transfer between the CPU and FPGA. In such an instance, one or more of the devices may include reciprocating caches that are suitably configured so as to communicate with each other in a coherent fashion, and in this manner the shared memory may be efficiently accessed by either of the coupled devices, such as with respect to performing one or more operations, as herein described, such as in a parallel and/or distributed method.

Accordingly, the system may be configured to include an integrated circuit formed of one or more digital logic circuits that are interconnected by a plurality of physical electrical interconnects, one or more of the plurality of physical electrical interconnects having one or more of a memory interface and/or cache, for the integrated circuit to access the memory and/or data stored thereon and to retrieve the same, such as in a cache coherent manner between the CPU and associated chip, e.g., FPGA. In various instances, the digital logic circuits may include at least a first subset of digital logic circuits, such as where the first subset of digital logic circuits may be arranged as a first set of processing engines, which processing engine may be configured for accessing the data stored in the cache and/or direct or indirectly coupled memory. For instance, the first set of processing engines may be configured to perform one or more steps in a mapping and/or aligning and/or sorting analysis, as described above, and/or an HMM analysis on the read of genomic sequence data and the haplotype sequence data.

More particularly, a first set of processing engines may include an HMM module, such as in a first configuration of the subset of digital logic circuits, which is adapted to access in the memory, e.g., via the memory interface, at least some of the sequence of nucleotides in the read of genomic sequence data and the haplotype sequence data, and may also be configured to perform the HMM analysis on the at least some of the sequence of nucleotides in the read of genomic sequence data and the at least some of the sequence of nucleotides in the haplotype sequence data so as to produce HMM result data. Additionally, the one or more of the plurality of physical electrical interconnects may include an output from the integrated circuit such as for communicating the HMM result data from the HMM module, such as to a CPU of a server or server cluster.

Accordingly, in one aspect, a method for executing a sequence analysis pipeline such as on genetic sequence data is provided. The genetic data may include one or more genetic reference or haplotype sequences, one or more indexes of the one or more genetic reference and/or haplotype sequences, and/or a plurality of reads of genomic data. The method may include one or more of receiving, accessing, mapping, aligning, sorting various iterations of the genetic sequence data and/or employing the results thereof in a method for producing one or more variant call files. For instance, in certain embodiments, the method may include receiving, on an input to an integrated circuit from an electronic data source, one or more of a plurality of reads of genomic data, wherein each read of genomic data may include a sequence of nucleotides.

In various instances, the integrated circuit may be formed of a set of hardwired digital logic circuits that may be arranged as one or more processing engines. In such an instance, a processing engine may be formed of a subset of the hardwired digital logic circuits that may be in a wired configuration. In such an instance, the processing engine may be configured to perform one or more pre-configured steps such as for implementing one or more of receiving, accessing, mapping, aligning, sorting various iterations of the genetic sequence data and/or employing the results thereof in a method for producing one or more variant call files. In some embodiments, the provided digital logic circuits may be interconnected such as by a plurality of physical electrical interconnects, which may include an input.

The method may further include accessing, by the integrated circuit on one or more of the plurality of physical electrical interconnects from a memory, data for performing one or more of the operations detailed herein. In various instances, the integrated circuit may be part of a chipset such as embedded or otherwise contained as part of an FPGA, ASIC, or structured ASIC, and the memory may be directly or indirectly coupled to one or both of the chip and/or a CPU associated therewith. For instance, the memory may be a plurality of memories one of each coupled to the chip and a CPU that is itself coupled to the chip, e.g., loosely. In other instances, the memory may be a single memory that may be coupled to a CPU that is itself tightly coupled to the FPGA, e.g., via a tight processing interconnect or QPI, and thereby accessible to the FPGA, such as in a cache coherent manner. Accordingly, the integrated circuit may be directly or indirectly coupled to the memory so as to access data relevant to performing the functions herein presented, such as for accessing one or more of a plurality of reads, one or more genetic reference or theoretical reference sequences, and/or an index of the one or more genetic reference sequences, e.g., in the performance of a mapping operation.

Accordingly, in such an instance the method may include mapping, by a first subset of the hardwired digital logic circuits of the integrated circuit, the plurality of reads to one or more segments of the one or more genetic reference sequences. Additionally, the method may include accessing, by the integrated circuit on one or more of the plurality of physical electrical interconnects from the memory or a cache associated therewith, one or more of the mapped reads and/or one or more of the genetic reference sequences; and aligning, by a second subset of the hardwired digital logic circuits of the integrated circuit, the plurality of mapped reads to the one or more segments of the one or more genetic reference sequences.

In various embodiments, the method may additionally include accessing, by the integrated circuit on one or more of the plurality of physical electrical interconnects from a memory or a cache associated therewith, the aligned plurality of reads. In such an instance the method may include sorting, by a third subset of the hardwired digital logic circuits of the integrated circuit, the aligned plurality of reads according to their positions in the one or more genetic reference sequences. In certain instances, the method may further include outputting, such as on one or more of the plurality of physical electrical interconnects of the integrated circuit, result data from the mapping and/or the aligning and/or the sorting, such as where the result data includes positions of the mapped and/or aligned and/or sorted plurality of reads.

In some instances, the method may additionally include using the obtained result data, such as by a further subset of the hardwired digital logic circuits of the integrated circuit, for the purpose of determining how the mapped, aligned, and/or sorted data, derived from the subject's sequenced genetic sample, differs from a reference sequence, so as to produce a variant call file delineating the genetic differences between the two samples. Accordingly, in various embodiments, the method may further include accessing, by the integrated circuit on one or more of the plurality of physical electrical interconnects from a memory or a cache associated therewith, the mapped and/or aligned and/or sorted plurality of reads. In such an instance the method may include performing a variant call function, e.g., an HMM or paired MINI operation, on the accessed reads, by a third or fourth subset of the hardwired digital logic circuits of the integrated circuit, so as to produce a variant call file detailing how the mapped, aligned, and/or sorted reads vary from that of one or more reference, e.g., haplotype, sequences.

Hence, in various instances, implementations of various aspects of the disclosure may include, but are not limited to: apparatuses, systems, and methods including one or more features as described in detail herein, as well as articles that comprise a tangibly embodied machine-readable medium operable to cause one or more machines (e.g., computers, etc.) to result in operations described herein. Similarly, computer systems are also described that may include one or more processors and/or one or more memories coupled to the one or more processors. Accordingly, computer implemented methods consistent with one or more implementations of the current subject matter can be implemented by one or more data processors residing in a single computing system or multiple computing systems containing multiple computers, such as in a computing or super-computing bank.

Such multiple computing systems can be connected and can exchange data and/or commands or other instructions or the like via one or more connections, including but not limited to a connection over a network (e.g. the Internet, a wireless wide area network, a local area network, a wide area network, a wired network, a physical electrical interconnect, or the like), via a direct connection between one or more of the multiple computing systems, etc. A memory, which can include a computer-readable storage medium, may include, encode, store, or the like one or more programs that cause one or more processors to perform one or more of the operations associated with one or more of the algorithms described herein.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

BRIEF DESCRIPTION OF THE FIGURES

The accompanying drawings, which are incorporated in and constitute a part of this specification, show certain aspects of the subject matter disclosed herein and, together with the description, help explain some of the principles associated with the disclosed implementations.

FIG. 19 depicts Log domain M, I, D state calculation details.

FIG. 26A depicts a direct coupling of a CPU and a FPGA of the disclosure.

FIG. 26B depicts an alternative embodiment of the direct coupling of a CPU and a FPGA of FIG. 26A.

DETAILED DESCRIPTION OF THE DISCLOSURE

Figure 1:
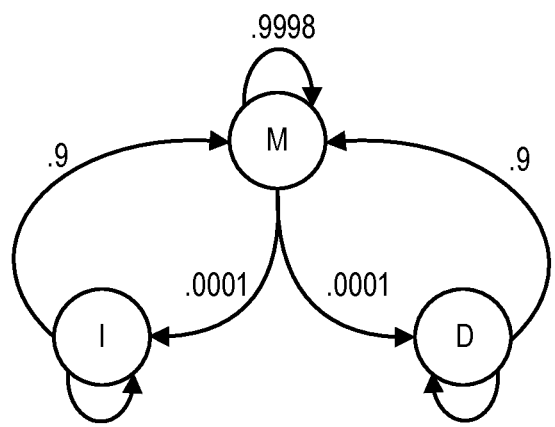
FIG. 1 depicts an HMM 3-state based model illustrating the transition probabilities of going from one state to another.

As summarized above, the present disclosure is directed to devices, systems, and methods for employing the same in the performance of one or more genomics and/or bioinformatics protocols, such as a mapping, aligning, sorting, and/or variant call protocol on data generated through a primary processing procedure, such as on genetic sequence data. For instance, in various aspects, the devices, systems, and methods herein provided are configured for performing secondary analysis protocols on genetic data, such as data generated by the sequencing of RNA and/or DNA, e.g., by a Next Gen Sequencer ("NGS") or sequencing-on-a-chip technology, as described in U.S. Ser. No. 15/065,744, incorporated herein in its entirety by reference. In particular embodiments, one or more secondary processing pipelines for processing genetic sequence data is provided, such as where the pipelines, and/or individual elements thereof, may be implemented in software, hardware, or a combination thereof in a distributed and/or an optimized fashion so as to deliver superior sensitivity and improved accuracy on a wider range of sequence derived data than is currently available in the art.

Accordingly, provided herein are software and/or hardware e.g., chip based, accelerated platform analysis technologies for performing secondary analysis of DNA/RNA sequencing data. More particularly, a platform, or pipeline, of processing engines, such as in a software implemented and/or hardwired configuration, which have specifically been designed for performing secondary genetic analysis, e.g., mapping, aligning, sorting, and/or variant calling, such as with respect to genetic based sequencing data, which in various instances may be implemented or otherwise associated with a chip, such as on an FPGA, ASIC, and/or Structured ASIC, or the like, in an optimized format that delivers an improvement in processing speed that is magnitudes faster than standard pipelines that are implemented in known software alone. Additionally, the pipelines presented herein provide better sensitivity and accuracy on a wide range of sequence derived data sets, such as on nucleic acid or protein derived sequences.

As indicated above, in various instances, it is a goal of bioinformatics processing to determine individual genomes and/or protein sequences of people, which determinations may be used in gene discovery protocols as well as for prophylaxis and/or therapeutic regimes to better enhance the livelihood of each particular person and human kind as a whole. Further, knowledge of an individual's genome and/or protein compellation may be used such as in drug discovery and/or FDA trials to better predict with particularity which, if any, drugs will be likely to work on an individual and/or which would be likely to have deleterious side effects, such as by analyzing the individual's genome and/or a protein profile derived therefrom and comparing the same with predicted biological response from such drug administration.

Such bioinformatics processing usually involves three well defined, but typically separate phases of information processing. The first phase, termed primary processing, involves DNA/RNA sequencing, where a subject's DNA and/or RNA is obtained and subjected to various processes whereby the subject's genetic code is converted to a machine-readable digital code, e.g., a FASTQ file. The second phase, termed secondary processing, involves using the subject's generated digital genetic code for the determination of the individual's genetic makeup, e.g., determining the individual's genomic nucleotide sequence. And the third phase, termed tertiary processing, involves performing one or more analyses on the subject's genetic makeup so as to determine therapeutically useful information therefrom.

Accordingly, once a subject's genetic code is sequenced, such as by a NextGen sequencer, so as to produce a machine readable digital representation of the subject's genetic code, e.g., in a FASTQ digital file format, it may be useful to further process the digitally encoded genetic sequence data obtained from the sequencer and/or sequencing protocol, such as by subjecting the digitally represented data to secondary processing. This secondary processing, for instance, can be used to map and/or align and/or otherwise assemble an entire genomic and/or protein profile of an individual, such as where the individual's entire genetic makeup is determined, for instance, where each and every nucleotide of each and every chromosome is determined in sequential order such that the composition of the individual's entire genome has been identified. In such processing, the genome of the individual may be assembled such as by comparison to a reference genome, such as a reference standard, e.g., one or more genomes obtained from the human genome project or the like, so as to determine how the individual's genetic makeup differs from that of the referent(s). This process is commonly known as variant calling. As the difference between the DNA of any one person to another is 1 in 1,000 base pairs, such a variant calling process can be very labor and time intensive, requiring many steps that may need to be performed one after the other and/or simultaneously, such as in a pipeline, so to analyze the subject's genomic data and determine how that genetic sequence differs from a given reference.

In performing a secondary analysis pipeline, such as for generating a variant call file for a given query sequence of an individual subject; a genetic sample, e.g., DNA, RNA, protein sample, or the like may be obtained, form the subject. The subject's DNA/RNA may then be sequenced, e.g., by a NextGen Sequencer (NGS) and/or a sequencer-on-a-chip technology, e.g., in a primary processing step, so as to produce a multiplicity of read sequence segments ("reads") covering all or a portion of the individual's genome, such as in an oversampled manner. The end product generated by the sequencing device may be a collection of short sequences, e.g., reads, that represent small segments of the subject's genome, e.g., short genetic sequences representing the individual's entire genome. As indicated, typically, the information represented by these reads may be in a digital format, such as in FASTQ, BCL, or other similar file format.

Particularly, in a typical secondary processing protocol, a subject's genetic makeup is assembled by comparison to a reference genome. This comparison involves the reconstruction of the individual's genome from millions upon millions of short read sequences and/or the comparison of the whole of the individual's DNA to an exemplary DNA sequence model. In a typical secondary processing protocol a FASTQ file is received from the sequencer containing the raw sequenced read data. For instance, in certain instances, there can be up to 30,000,000 reads or more covering the subject's 3 billion base pair genome, assuming no oversampling, such as where each read is about 100 nucleotides in length. Hence, in such an instance, in order to compare the subject's genome to that of the standard reference genome, it needs to be determined where each of these reads map to the reference genome, such as how each is aligned with respect to one another, and/or how each read can also be sorted by chromosome order so as to determine at what position and in which chromosome each read belongs. One or more of these functions may take place prior to performing a variant call function on the entire full-length sequence, e.g., once assembled. Specifically, once it is determined where in the genome each read belongs, the full length genetic sequence may be determined, and then the differences between the subject's genetic code and that of the referent can be assessed.

For instance, reference based assembly is a typical secondary processing assembly protocol involving the comparison of sequenced genomic DNA/RNA of a subject to that of one or more standards, e.g., known reference sequences. Various mapping, aligning, sorting, and/or variant calling algorithms have been developed to help expedite these processes. These algorithms, therefore, typically include some variation of one or more of: mapping, aligning, and/or sorting the millions of reads received from the FASTQ file communicated by the sequencer, to determine where on each chromosome each particular read is located. It is noted that these processes may be implemented in software or hardware, such as by the methods and/or devices described in U.S. Pat. Nos. 9,014,989 and 9,235,680 both assigned to Edico Genome Corporation and incorporated by reference herein in their entireties. Often a common feature behind the functioning of these various algorithms and/or hardware implementations is their use of an index and/or an array to expedite their processing function.

For example, with respect to mapping, a large quantity, e.g., all, of the sequenced reads may be processed to determine the possible locations in the reference genome to which those reads could possibly align. One methodology that can be used for this purpose is to do a direct comparison of the read to the reference genome so as to find all the positions of matching. Another methodology is to employ a prefix or suffix array, or to build out a prefix or suffix tree, for the purpose of mapping the reads to various positions in the reference genome. A typical algorithm useful in performing such a function is a Burrows-Wheeler transform, which is used to map a selection of reads to a reference using a compression formula that compresses repeating sequences of data.

A further methodology is to employ a hash table, such as where a selected subset of the reads, a k-mer of a selected length "k", e.g., a seed, are placed in a hash table as keys and the reference sequence is broken into equivalent k-mer length portions and those portions and their location are inserted by an algorithm into the hash table at those locations in the table to which they map according to a hashing function. A typical algorithm for performing this function is "BLAST", a Basic Local Alignment Search Tool. Such hash table based programs compare query nucleotide or protein sequences to one or more standard reference sequence databases and calculates the statistical significance of matches. In such manners as these, it may be determined where any given read is possibly located with respect to a reference genome. These algorithms are useful because they require less memory, fewer look ups, LUTs, and therefore require fewer processing resources and time in the performance of their functions, than would otherwise be the case, such as if the subject's genome were being assembled by direct comparison, such as without the use of these algorithms.

Additionally, an aligning function may be performed to determine out of all the possible locations a given read may map to on a genome, such as in those instances where a read may map to multiple positions in the genome, which is in fact the location from which it actually was derived, such as by being sequenced therefrom by the original sequencing protocol. This function may be performed on a number of the reads, e.g., mapped reads, of the genome and a string of ordered nucleotide bases representing a portion or the entire genetic sequence of the subject's DNA/RNA may be obtained. Along with the ordered genetic sequence a score may be given for each nucleotide in a given position, representing the likelihood that for any given nucleotide position, the nucleotide, e.g., "A", "C", "G", "T" (or "U"), predicted to be in that position is in fact the nucleotide that belongs in that assigned position. Typical algorithms for performing alignment functions include Needleman-Wunsch and Smith-Waterman algorithms. In either case, these algorithms perform sequence alignments between a string of the subject's query genomic sequence and a string of the reference genomic sequence whereby instead of comparing the entire genomic sequences, one with the other, segments of a selection of possible lengths are compared.

Once the reads have been assigned a position, such as relative to the reference genome, which may include identifying to which chromosome the read belongs and/or its offset from the beginning of that chromosome, the reads may be sorted by position. This may enable downstream analyses to take advantage of the oversampling procedures described herein. All of the reads that overlap a given position in the genome will be adjacent to each other after sorting and they can be organized into a pileup and readily examined to determine if the majority of them agree with the reference value or not. If they do not, a variant can be flagged.

Accordingly, as set forth above, bioinformatics processing procedures typically involve genetic sequencing so as to produce genetic sequencing data that may then be used to determine the nucleotide identity of a individual's genetic code. Primary processing involves generating, by a sequencer, millions and millions of reads consisting of short strings of nucleotide sequence data in a digital FASTQ file format. These reads represent a portion or the entire genome of the individual. Accordingly, mapping, in general, usually involves plotting the reads to all the locations in the reference genome to where there is a match. For example, dependent on the size of the read there may be one or a plurality of locations where the read substantially matches a corresponding sequence in the reference genome. Hence, the mapping and/or other functions disclosed herein may be configured for determining where out of all the possible locations one or more reads may match to in the reference genome is actually the true location to where they map.

For instance, such sequencing data may be obtained directly from an automated, high throughput sequencer system such as by a direct linkage with the sequencing processing unit, or the sequencing data may be obtained indirectly, e.g., remotely, such as from a database, for instance, accessible via the internet or through a wireless communications protocol, such as Wi-Fi, Bluetooth, LE Bluetooth, or the like. For instance, as is known in the art, such sequencing data may be produced by an electronic data source, such as by a Next Generation Sequencer ("NGS") or a Sequencer on a Chip technology (See U.S. Ser. No. 15/065,744 incorporated herein in its entirety by reference). Particularly, an electronic data source may be provided wherein the electronic data source may be configured for generating and/or providing one or more digital signals, such as a digital signal representing one or more sequences of nucleotides, or "reads," of genetic data, e.g., DNA and/or RNA, where each read of genetic data includes one or more sequences of nucleotides. In a manner such as this, an individual subject's DNA and/or RNA may be obtained and subjected to various processes whereby the subject's genetic code is converted to a machine-readable digital code, e.g., a FASTQ file.

However, because the processing of the DNA/RNA samples required to produce engineered read lengths of a specific size is both labor and chemistry intensive, and because the sequencing itself often depends on the functioning of the sequencing machinery, there is some possibility that errors may be made throughout the sequencing process thereby introducing an abnormality into that portion of the sequenced genome where the error occurred. Such errors can be problematic, especially where a purpose for reconstructing a subject's genome is to determine how it or at least a portion of the genome varies from a standard or model reference. For instance, a machine or chemistry error resulting in the change of one nucleotide, e.g., in a read, for another will give a false indication of a variation that is not really there. This can result in an incorrect variant call and may further result in the false indication of a diseased state and the like. Accordingly, because of the possibility of machine, chemistry, and/or even human error in the execution of a sequencing protocol, in many instances, it is desirable to distinguish true variation from that caused by error, and one method for better determining such a distinction is to build sequencing redundancy into the overall analysis system, such as by oversampling portions of or the entire sequenced genome.

More particularly, automated sequencers not only produces a FASTQ file calling out a sequence of reads having nucleotides at a given position, e.g., a base call, the FASTQ file further includes the probability that the call for a given nucleotide being at the called position might actually be incorrect. In such an instance, it is often desirable to employ methods, such as oversampling, for ensuring that such base calls made by the sequencing processes can be detected, determined, and if necessary corrected. Accordingly, in various instances, it may be useful, such as during the performance of a primary sequencing protocol, to produce oversampling for one or more regions of the subject's genome. These regions may be selected based on known areas of increased variability, suspected regions of variability, such as based on the condition of the subject, and/or on the entire genome generally.

For instance, in its basic form, based on the type of sequencing protocols performed, sequencing produces readouts, e.g., reads, that are digital representations of the subject's sequenced genetic code. The lengths of the reads are typically designed based on the type of sequencing machinery being employed. Oversampling can be used to produce a pile-up of reads of sequenced genetic material at a designated region so as to improve the accuracy in reconstructing the subject's genome with respect to that region, especially in instances where the subject's genome is to be compared against a reference genome so as to determine those instances where the subject's genetic sequence truly differs from that of the reference genetic sequence. These pile-ups represent the coverage for any particular location and may be useful for determining with better accuracy the correct sequence of the subject's genome.

For example, as indicated, sequencing results in the production of reads, and in various instances, the reads produced are over sampled, e.g., to produce pileups, such that at various positions the various generated reads for that position will overlap. This overlapping is useful for determining the actual sample genome such as with a high probability of correctness. Particularly, where the subject's genetic sequence is to be rebuilt with respect to the use of a reference genome, once the reads, e.g., a pile-up of reads, have been generated, the digital representation of the reads may be transferred, directly, e.g., via a physical electrical interconnect, or indirectly, e.g., over a network, to the secondary analysis pipeline as described herein. For instance, in various instances, a FASTQ file system, such as a RAID 0 array of SSDs, may be employed to feed the generated reads to the hardwired pipeline architecture, disclosed herein, such as at a rate that has been optimized for a maximally efficient processing of the data by the various hardwired pipeline processing engines. In certain instances, this transference may be in excess of about 200 or about 300 MB/S, such as in excess of about 400 or about 500 MB/S, or even 600 MB/S or more from uncompressed FASTQ, simultaneously with similar write bandwidth. In particular embodiments, this transfer may be in a cache coherent manner over a tightly coupled interface that couples the host CPU and/or memory to the processor running the mapping and/or other functions of the bioinformatics platform.

As the data streams into the analyzer system, such as a pipeline analyzer-on-a-chip, e.g., by onboard instructions and/or the host software, the data may be preprocessed and packed into a binary internal format, and streamed by Direct Memory Access (DMA) over a PCIe bus to the pipeline board, as described in greater detail herein below. As indicated, such transfer may be via a low-latency interconnect, such as in a tight coupling arrangement. So being, the transfer of read pairs (or single-ended reads) may be load-balanced such as to one or more map/align/sorting/variant call engines, as described herein, such as two or three, or four or more map/align/sorting/variant call engines. More particularly, the number of map/align/sorting/variant call engines, e.g., forming a processing module and/or block, may be selected so as to maximize processing power while at the same time as minimizing space on the chip. As described, within each processing block or module, custom logic may be organized into a pipeline, such as a pipeline of processing engines, about approximately 140 stages long, so as to execute all the various stages of mapping and/or alignment and/or sorting and/or variant calling, e.g., simultaneously and/or sequentially, on various reads, and/or various seeds, and/or alignments within a read.

Accordingly, once the DNA/RNA sequence has been generated, and/or streamed into the analyzer, e.g., the pipeline analyzer, the next steps may then be to map and/or align and/or sort the reads with respect to one or more reference genomes (e.g., the more exemplary reference genomes available as models the better the analysis is likely to be) so as to thereby rebuild the genome of the subject, this results in a series of reads that have been mapped and/or aligned with the reference genome(s) at all possible positions along the chain where there is a match, and at each such position they are given a probability score as to the probability that they actually belong in that position. Particularly, in various instances, once the reads have been generated, their positions mapped, e.g., the potential locations in the reference genome to which the reads may map have been determined, and their sequential order aligned, the actual genetic sequence of the subject's genome may be determined, such as by performing a sorting function on the aligned data.

Further, in various embodiments, the methods of the disclosure may include generating a variant call file (VCF) identifying one or more, e.g., all, of the genetic variants in the individual who's DNA/RNA were sequenced, e.g., relevant to one or more reference genomes. For instance, once the actual sample genome is known and compared to the reference genome, the variations between the two can be determined, and a list of all the variations/deviations between the reference genome(s) and the sample genome may be called out, e.g., a variant call file may be produced.

Particularly, in one aspect, a variant call file containing all the variations of the subject's genetic sequence to the reference sequence(s) may be generated.

As indicated above, such variations between the two genetic sequences may be due to a number of reasons. Hence, in order to generate such a file, the genome of the subject must be sequenced and rebuilt prior to determining its variants. There are, however, several problems that may occur when attempting to generate such an assembly. For example, there may be problems with the chemistry, the sequencing machine, and/or human error that occur in the sequencing process. Furthermore, there may be genetic artifacts that make such reconstructions problematic. For instance, a typical problem with performing such assemblies is that there are sometimes huge portions of the genome that repeat themselves, such as long sections of the genome that include the same strings of nucleotides. Hence, because any genetic sequence is not unique everywhere, it may be difficult to determine where in the genome an identified read actually maps and aligns. Additionally, there may be a single nucleotide polymorphism (SNP), such as wherein one base in the subject's genetic sequence has been substituted for another; there may be more extensive substitutions of a plurality of nucleotides; there may be an insertion or a deletion, such as where one or a multiplicity of bases have been added to or deleted from the subject's genetic sequence, and/or there may be a structural variant, e.g., such as caused by the crossing of legs of two chromosomes, and/or there may simply be an offset causing a shift in the sequence.

Accordingly, there are two main possibilities for variation. For one, there is an actual variation at the particular location in question, for instance, where the person's genome is in fact different at a particular location than that of the reference, e.g., there is a natural variation due to an SNP (one base substitution), an Insertion or Deletion (of one or more nucleotides in length), and/or there is a structural variant, such as where the DNA material from one chromosome gets crossed onto a different chromosome or leg, or where a certain region gets copied twice in the DNA. Alternatively, a variation may be caused by there being a problem in the read data, either through chemistry or the machine, sequencer or aligner, or other human error. The methods disclosed herein may be employed in a manner so as to compensate for these types of errors, and more particularly so as to distinguish errors in variation due to chemistry, machine or human, and real variations in the sequenced genome. More specifically, the methods, apparatuses, and systems for employing the same, as here in described, have been developed so as to clearly distinguish between these two different types of variations and therefore to better ensure the accuracy of any call files generated so as to correctly identify true variants.

Hence, in particular embodiments, a platform of technologies for performing genetic analyses are provided where the platform may include the performance of one or more of: mapping, aligning, sorting, local realignment, duplicate marking, base quality score recalibration, variant calling, compression, and/or decompression functions. For instance, in various aspects a pipeline may be provided wherein the pipeline includes performing one or more analytic functions, as described herein, on a genomic sequence of one or more individuals, such as data obtained in a digital, e.g., FASTQ, file format from an automated sequencer. A typical pipeline to be executed may include one or more of sequencing genetic material, such as a portion or an entire genome, of one or more individual subjects, which genetic material may include DNA, ssDNA, RNA, rRNA, tRNA, and the like, and/or in some instances the genetic material may represent coding or non-coding regions, such as exomes and/or episomes of the DNA. The pipeline may include one or more of performing a base calling and/or error correction operation, such as on the digitized genetic data, and/or may include one or more of performing a mapping, an alignment, and/or a sorting function on the genetic data. In certain instances, the pipeline may include performing one or more of a realignment, a deduplication, a base quality or score recalibration, a reduction and/or compression, and/or a decompression on the digitized genetic data. In certain instances the pipeline may include performing a variant calling operation on the genetic data.

Accordingly, in certain instances, the implementation of one or more of these platform functions is for the purpose of performing one or more of determining and/or reconstructing a subject's consensus genomic sequence, comparing a subject's genomic sequence to a referent sequence, e.g., a reference or model genetic sequence, determining the manner in which the subject's genomic DNA or RNA differs from a referent, e.g., variant calling, and/or for performing a tertiary analysis on the subject's genomic sequence, such as for genome-wide variation analysis, gene function analysis, protein function analysis, e.g., protein binding analysis, quantitative and/or assembly analysis of genomes and/or transcriptomes, as well as for various diagnostic, and/or a prophylactic and/or therapeutic evaluation analyses.

As indicated above, in one aspect one or more of these platform functions, e.g., mapping, aligning, sorting, realignment, duplicate marking, base quality score recalibration, variant calling, compression, and/or decompression functions is configured for implementation in software. In some aspects, one or more of these platform functions, e.g., mapping, aligning, sorting, local realignment, duplicate marking, base quality score recalibration, decompression, variant calling, compression, and/or decompression functions is configured for implementation in hardware, e.g., firmware. In certain aspects, these genetic analysis technologies may employ improved algorithms that may be implemented by software that is run in a less processing intensive and/or less time consuming manner and/or with greater percentage accuracy, e.g., the hardware implemented functionality is faster, less processing intensive, and more accurate.

For instance, in certain embodiments, improved algorithms for performing such secondary and/or tertiary processing, as disclosed herein, are provided. The improved algorithms are directed to more efficiently and/or more accurately performing one or more of mapping, aligning, and/or sorting functions, such as on a digital representation of DNA/RNA sequence data obtained from a sequencing platform, such as in a FASTQ file format obtained from an automated sequencer such as one of those set forth above. In particular embodiments, the improved algorithms may be directed to more efficiently and/or more accurately performing one or more of local realignment, duplicate marking, base quality score recalibration, variant calling, compression, and/or decompression functions. Further, as described in greater detail herein below, in certain embodiments, these genetic analysis technologies may employ one or more algorithms, such as improved algorithms, that may be implemented by hardware that is run in a less processing intensive and/or less time consuming manner and/or with greater percentage accuracy than various software implementations for doing the same.

Hence, in various aspects, presented herein are systems, apparatuses, and methods for implementing bioinformatics protocols, such as for performing one or more functions for analyzing genetic data, such as genomic data, for instance, via one or more optimized algorithms and/or on one or more optimized integrated circuits, such as on one or more hardware processing platforms. In one instance, systems and methods are provided for implementing one or more algorithms, e.g., in software and/or in firmware, for the performance of one or more steps for analyzing genomic data in a bioinformatics protocol, such as where the steps may include the performance of one or more of: mapping, aligning, sorting, local realignment, duplicate marking, base quality score recalibration, variant calling, compression, and/or decompression. Accordingly, in certain instances, methods, including software, firmware, and/or hardware for performing the methods, are presented herein where the methods involve the performance of an algorithm, such as an algorithm for implementing one or more genetic analysis functions such as mapping, aligning, sorting, realignment, duplicate marking, base quality score recalibration, variant calling, compression, and/or decompression where the algorithm, e.g., including firmware, has been optimized in accordance with the manner in which it is to be implemented.

In particular, where the algorithm is to be implemented in a software solution, the algorithm and/or its attendant processes, has been optimized so as to be performed faster and/or with better accuracy for execution by that media. Likewise, where the functions of the algorithm are to be implemented in a hardware solution, e.g., as firmware, the hardware has been designed to perform these functions and/or their attendant processes in an optimized manner so as to be performed faster and/or with better accuracy for execution by that media. These methods, for instance, can be employed such as in an iterative mapping, aligning, sorting, and/or variant calling procedure. In another instance, systems and methods are provided for implementing the functions of one or more algorithms for the performance of one or more steps for analyzing genomic data in a bioinformatics protocol, as set forth herein, wherein the functions are implemented on a hardware accelerator, which may or may not be coupled with one or more general purpose processors and/or super computers.

More specifically, in some instances, methods and/or machinery for implementing those methods, for performing secondary analytics on data pertaining to the genetic composition of a subject are provided. In one instance, the analytics to be performed may involve reference based reconstruction of the subject genome. For instance, referenced based mapping involves the use of a reference genome, which may be generated from sequencing the genome of a single or multiple individuals, or it may be an amalgamation of various people's DNA/RNA that have been combined in such a manner so as to produce a prototypical, standard reference genome to which any individual's genetic material, e.g., DNA/RNA, may be compared, for example, so as to determine and reconstruct the individual's genetic sequence and/or for determining the difference between their genetic makeup and that of the standard reference, e.g., variant calling.

Particularly, a reason for performing a secondary analysis on a subject's sequenced DNA/RNA is to determine how the subject's DNA/RNA varies from that of the reference, such as to determine one, a multiplicity, or all, of the differences in the nucleotide sequence of the subject from that of the reference. For instance, the differences between the genetic sequences of any two random persons is 1 about in 1,000 base pairs, which when taken in view of the entire genome of over 3 billion base pairs amounts to a variation of up to 3,000,000 divergent base pairs per person. Determining these differences may be useful such as in a tertiary analysis protocol, for instance, so as to predict the potential for the occurrence of a diseased state, such as because of a genetic abnormality, and/or the likelihood of success of a prophylactic or therapeutic modality, such as based on how a prophylactic or therapeutic is expected to interact with the subject's DNA or the proteins generated therefrom. In various instances, it may be useful to perform both a de novo and a reference based reconstruction of the subject's genome so as to confirm the results of one against the other, and to, where desirable, enhance the accuracy of a variant calling protocol.

Accordingly, in one aspect, in various embodiments, once the subject's genome has been reconstructed and/or a VCF has been generated, such data may then be subjected to tertiary processing so as to interpret it, such as for determining what the data means with respect to identifying what diseases this person may or may have the potential for suffer from and/or for determining what treatments or lifestyle changes this subject may want to employ so as to ameliorate and/or prevent a diseased state. For example, the subject's genetic sequence and/or their variant call file may be analyzed to determine clinically relevant genetic markers that indicate the existence or potential for a diseased state and/or the efficacy of a proposed therapeutic or prophylactic regimen may have on the subject. This data may then be used to provide the subject with one or more therapeutic or prophylactic regimens so as to better the subject's quality of life, such as treating and/or preventing a diseased state. Particularly, once one or more of an individual's genetic variations are determined, such variant call file information can be used to develop medically useful information, which in turn can be used to determine, e.g., using various known statistical analysis models, health related data and/or medical useful information, e.g., for diagnostic purposes, e.g., diagnosing a disease or potential therefore, clinical interpretation (e.g., looking for markers that represent a disease variant), whether the subject should be included or excluded in various clinical trials, and other such purposes.

As there are a finite number of diseased states that are caused by genetic malformations, in tertiary processing variants of a certain type, e.g., those known to be related to the onset of diseased states, can be queried for, such as by determining if one or more genetic based diseased markers are included in the variant call file of the subject. Consequently, in various instances, the methods herein disclosed may involve analyzing, e.g., scanning, the VCF and/or the generated sequence, against a known disease sequence variant, such as in a data base of genomic markers therefore, so as to identify the presence of the genetic marker in the VCF and/or the generated sequence, and if present to make a call as to the presence or potential for a genetically induced diseased state. Since there are a large number of known genetic variations and a large number of individual's suffering from diseases caused by such variations, in some embodiments, the methods disclosed herein may entail the generation of one or more databases linking sequenced data for an entire genome and/or a variant call file pertaining thereto, e.g., such as from an individual or a plurality of individuals, and a diseased state and/or searching the generated databases to determine if a particular subject has a genetic composition that would predispose them to having such diseased state. Such searching may involve a comparison of one entire genome with one or more others, or a fragment of a genome, such as a fragment containing only the variations, to one or more fragments of one or more other genomes such as in a database of reference genomes or fragments thereof.

Therefore, in various instances, a pipeline of the disclosure may include one or more modules, wherein the modules are configured for performing one or more functions, such as a base calling and/or error correction operation and/or a mapping and/or an alignment and/or a sorting function on genetic data, e.g., sequenced genetic data. And in various instances, the pipeline may include one or more modules, wherein the modules are configured for performing one more of a local realignment, a deduplication, a base quality score recalibration, a variant calling, a reduction and/or compression, and/or a decompression on the genetic data. Many of these modules may either be performed by software or on hardware or remotely, e.g., via software or hardware, such as on the cloud or a remote server and/or server bank. Additionally, many of these steps and/or modules of the pipeline are optional and/or can be arranged in any logical order and/or omitted entirely. For instance, the software and/or hardware disclosed herein may or may not include a base calling or sequence correction algorithm, such as where there may be concern that such functions may result in a statistical bias. Consequently the system will include or will not include the base calling and/or sequence correction function, respectively, dependent on the level of accuracy and/or efficiency desired. And as indicated above, one or more of the pipeline functions may be employed in the generation of a genomic sequence of a subject such as through a reference based genomic reconstruction. Also as indicated above, in certain instances, the output from the pipeline is a variant call file indicating a portion or all the variants in a genome or a portion thereof.

Accordingly, in a first instance, a mapping procedure may be performed, e.g., in software and/or hardware. In such an instance, an output from a sequencing protocol may be received, such as a FASTQ file, which output may include a plurality of reads, where each read includes a sequence, e.g., a string, of nucleotides where the position of every nucleotide has been called, and a quality score representing the probability that the called nucleotide is wrong. For instance, in certain instances, the raw FASTQ file data may be processed to clean up the initial base calls obtained from the sequencer/reader, such as in a primary processing stage, e.g., prior to the secondary processing described herein above. Specifically, the nucleotide and/or protein sequencer/reader typically analyzes the sequencing data, such as the fluorescent and/or electronic and/or chemical data indicating which nucleotide is at what position, and converts the image or electromagnetic data into a base call with a quality score, such as where the quality score is based on the comparative brightness or intensity of the detectable marker at each position. A specialized algorithm may be employed, such as in a primary processing stage, to correctly analyze these distinctions in intensity levels so as to more accurately make the appropriate base call. As indicated above, this step may be performed individually or may be included in a pipeline of steps and may be implemented via software or hardware or both, however, in this instance would be part of a primary processing platform.

Hence, in accordance with the aspects of the disclosure, in various instances, the methods, apparatuses, and/or systems for implementing the methods of the disclosure, may include obtaining read data, that either have or have not been preprocessed, such as by being obtained directly from a FASTQ file of a sequencing apparatus, and subjecting the obtained data to one or more of a mapping, aligning, sorting, and/or variant calling function. The performance of such functions may be useful, for instance, because, as set forth above, in various instances, the sequencing data, e.g., reads, typically generated by various automated sequencers, have lengths that are substantially shorter than the entire genomic sequence being analyzed, and since the human genome typically has a multiplicity of repetitive sections, and is known to have various repeating patterns in it, there may be therefore a multiplicity of locations that any given read sequence may correspond to a segment in the human genome.

Consequently, given all the possibilities a given read may match to the sequence of the genome, such as because of various repeating sequences in the genome, etc. the raw read data may not clearly indicate which one of the possibilities is in fact the correct location from which it was derived. Thus, for each read it may need to be determined to where in the genome the read(s)s actually map. Additionally, it may also be useful to determine the sequential alignment of the reads, so as to determine the actual sequence identity of the subject, and/or it may also be useful to determine the chromosomal location for each portion of the sequence.

Accordingly, in various instances, the methods of the disclosure may be directed to mapping, aligning, and/or sorting the raw read data of the FASTQ files so as to find all the likely places that a given read may be aligned, and/or to determine the actual sequence identity of a subject, and/or to determine the chromosome location for each portion of the sequence. For example, mapping may be employed so as to map the generated reads to the reference genome and thereby find the location where each read appears to match well to the genome, e.g., finding all the places where there might be a good score for aligning any given read to the reference genome. Mapping therefore may involve taking one or more, e.g., all, of the raw or preprocessed reads received from the FASTQ file and comparing the reads with one or more reference genomes and determining where the read may match with the reference genome(s). In its basic form, mapping involves finding the location(s) in the reference genome where one or more of the FASTQ reads obtained from the sequencer appears to match.

Likewise, alignment may be employed so as to evaluate all the candidate locations of the individual reads against a windowed portion of the reference genome to determine where and how the read sequences best align to the genome. However, performing an alignment may be difficult due to substitutions, insertions, deletions, structural variations, and the like that may prevent the read from aligning exactly to the reference. There are, therefore, several different ways to get an alignment, but to do so may require making changes in the read, where each change that needs to be made to get the appropriate alignment results in a lower confidence score. For instance, any given read may have substitutions, insertions, and/or deletions as compared to the reference genome, and these variations need to be accounted for in performing an alignment.

Hence, along with the predicted alignment a probability score that the predicted alignment is correct may also be given. This score indicates the best alignment for any given read amongst multiple locations where that read may align. For example, the alignment score is predicated upon how well a given read matches a potential map location and may include stretching, condensing, and changing bits and pieces of the read, e.g., nucleotide sequence(s), so as to get the best alignment. The score will reflect all the ways the read was changed so as to accommodate the reference. For instance, in order to generate an alignment between the read and the reference one or more gaps in the read may need to be inserted, wherein the insertion of each gap represents a deletion in the read over the reference. Likewise, deletions may need to be made in the read, wherein each deletion represents an insertion in the read over the reference.

Additionally, various bases in the compared sequences may need to be changed such as due to one or more substitutions. Each of these changes are made to make the read(s) more exactly align to the reference, but each change comes with a cost to the quality score, which score is a measure as to how well the entire read matches to some region of the reference. The confidence in such quality scores is then determined by looking at all the locations the read can be made to map to the genome and comparing the scores at each location, and choosing the one with the highest score. More particularly, where there are multiple positions with high quality scores, then confidence is low, but where the difference between the first and second best scores is large, then confidence is high. At the end, all the proposed reads and confidence scores are evaluated and the best fit is selected.

Once the reads are assigned a position relative to the reference genome, which may include identifying to which chromosome the read belongs and its offset from the beginning of that chromosome, they may be sorted, such as by position. This enables downstream analyses to take advantage of the various oversampling protocols described herein. All of the reads that overlap a given position in the genome may be positioned adjacent to each other after sorting and they can be piled up and readily examined to determine if the majority of them agree with the reference value or not. If they do not, as indicated above, a variant can be flagged.

Accordingly, as indicated above with respect to mapping, the FASTQ file obtained from the sequencer is comprised of a plurality, e.g., millions to a billion or more, of reads consisting of short strings of nucleotide sequence data representing a portion or the entire genome of an individual. Mapping, in general, involves plotting the reads to all the locations in the reference genome to where there is a match. For example, dependent on the size of the read there may be one or a plurality of locations where the read substantially matches a corresponding sequence in the reference genome. Hence, the mapping and/or other functions disclosed herein may be configured for determining where out of all the possible locations one or more reads may match to in the reference genome is actually the true location to where they map.

For instance, in various instances, an index of a reference genome may be generated or otherwise provided, so that the reads or portions of the reads may be looked up, e.g., within a Look-Up Table (LUT), in reference to the index, thereby retrieving indications of locations in the reference, so as to map the reads to the reference. Such an index of the reference can be constructed in various forms and queried in various manners. In some methods, the index may include a prefix and/or a suffix tree. Particularly, a prefix and/or suffix tree is a data structure that is built up from the reference genome, such that each link from a parent node to a child node is labeled or associated with a nucleotide or sequence of nucleotides, and each path from a root node through various links and nodes traces a path whose associated aggregate nucleotide sequence matches some continuous subsequence of the reference genome. The node reached by such a path is implicitly associated with the reference subsequence traced by its path from the root. Proceeding from the root node, subsequences in a prefix tree grow forward in the reference genome, whereas subsequences in a suffix tree grow backward in the reference genome.

Both a prefix tree and a suffix tree may be used in a hybrid prefix/suffix algorithm, so that subsequences may grow in either direction. Prefix and suffix trees may also contain additional links, such as jumping from a node associated with one reference subsequence to another node associated with a shorter reference subsequence. For instance, a tree-like data structure serving as an index of the reference genome may be queried by tracing a path through the tree, corresponding to a subsequence of a read being mapped, that is built up by adding nucleotides to the subsequence, using the added nucleotides to select next links to traverse in the tree, and going as deep as necessary until a unique sequence has been generated. This unique sequence may also be termed a seed, and may represent a branch and/or root of the sequence tree data structure.

Alternatively, the tree descent may be terminated before the accumulated subsequence is fully unique, so that a seed may map to multiple locations in the reference genome. The tree may be built out for every starting position for the reference genome, then the generated reads may be compared against the branches and/or roots of the tree and these sequences may be walked through the tree to find where in the reference genome the read fits. More particularly, the reads of the FASTQ file may be compared to the branches and roots of the reference tree and once matched therewith the location of the reads in the reference genome may be determined. For example, a sample read may be walked along the tree until a position is reached whereby it is determined that the accumulated subsequence is unique enough so as to identify that the read really does align to a particular position in the reference, such as walking through the tree until a leaf node is reached.

In particular methods, the index may be derived from a Burrows/Wheeler transform of the reference. Hence, alternatively, or in addition to employing a prefix or a suffix tree, a Burrows/Wheeler transform can be performed on the data. For instance, a Burrows/Wheeler transform may be used to store a tree-like data structure abstractly equivalent to a prefix and/or suffix tree, in a compact format, such as in the space allocated for storing the reference genome. In various instances, the data stored is not in a tree-like structure, but rather the reference sequence data is in a linear list that may have been scrambled into a different order so as to transform it in a very particular way such that the accompanying algorithm allows the reference to be searched with reference to the sample reads so as to effectively walk the "tree".

An advantage of the Burrows/Wheeler transform, such as over a prefix and/or suffix tree, is that it typically requires less memory to store, and an advantage over a hash function is that it supports a variable seed length, and hence it can be searched until a unique sequence is determined and a match found. For instance, as with the prefix/suffix tree, however many nucleotides it takes for a given sequence to be unique, or to map to a sufficiently small number of reference positions, determines the length of the seed. Whereas for a hash table, the seeds are typically all of the same predetermined length. A disadvantage, however, for the Burrows/Wheeler transform is that it typically requires a multiplicity of lookups, such as two or more look ups, such as for every step down the tree.

Additionally, in various instances, the index may include one or more hash tables, and the methods disclosed herein may include a hash function that may be performed on one or more portions of the reads in an effort to map the reads to the reference, e.g., to the index of the reference. For instance, alternatively, or in addition to utilizing one or both a prefix/suffix tree and/or a Burrows/Wheeler transform on the reference genome and subject sequence data, so as to find where the one maps against the other, another such method involves the production of a hash table index and/or the performance of a hash function. The hash table index may be a large reference structure that is built up from sequences of the reference genome that may then be compared to one or more portions of the read to determine where the one may match to the other. Likewise, the hash table index may be built up from portions of the read that may then be compared to one or more sequences of the reference genome and thereby used to determine where the one may match to the other.

Particularly, with respect to hash tables, a hash table may be produced in many different ways. In one instance, a hash table may be built by dividing the reference genome into segments of standard length, e.g., seeds of about 16 to about 32 nucleotides or more in length, such as about 18 to about 28 nucleotides, formatting them into a searchable table, and making an index of all the reference segments, "seeds," from which sequenced DNA/RNA, e.g., one or more reads, or a portion thereof, may be compared to determine matching. More particularly, a hash table index may be generated by breaking down the reference genome into segments of nucleotide sequences of known, uniform length, e.g., seeds, and storing them in random order into individual cubicles in a reference table, e.g., a hash table. This may be done for a portion or the entire reference genome so as to build an actual reference index table that may be used to compare portions of the reference genome with portions of one or more reads, such as from a FASTQ file, for the purpose of determining matching. Such methods may then be repeated in approximately the same manner for a portion, e.g., a majority or all, of the reads in the FASTQ file, so as to generate seeds of the appropriate, e.g., selected, length. Likewise, in various instances, the generated seeds of the reads may first be positioned within the hash table so as to form an index of read seeds, and seeds generated from the reference fed into the index and compared therewith.

Accordingly, in particular instances, the reference genome and/or the reads of the FASTQ file may be used to produce seeds of a predetermined length, which seeds may be converted into binary form and fed through a hash function and fit into a hash table index where the binary form of the read seeds may match up with the binary segments of the reference genome, so as to give the location as to where in the genome the sample seeds match with the position in the reference genome. For example, where the read is approximately 100 bases long, a typical seed may be about half or a about a third or about a quarter, e.g., about 16 to about 32 bases, e.g., about 27-30 bases long. Hence, in such an instance, for each read a multiplicity of seeds, e.g., approximately 3 or 4 seeds or more dependent on the length of the read and/or the length of the seeds, may be generated to cover the read. Each seed may then be converted into a binary form and/or then be fed into the hash table, or otherwise compared against the index, and a possible result as to the position of the seed/read with respect to the reference genome may be obtained.

In such instances, the entire read need not be compared to every possible position in the entire reference genome, or vice versa, rather only a portion of the reads, e.g., one or more of the generated sample seeds per read, need only be compared such as to an index containing equivalent seed portions of the reference genome. Hence, in various instances, a hash table may be configured such that by only one memory look up it can typically be determined where the sample seed and therefore read is positioned relative to the reference genome, e.g., via the index. However, in certain instances, it may be desirable to perform a hash function and look up on one or more overlapping sections of seeds from one read, e.g., in one or more lookups, such as a plurality of lookups, 2, 3, or 4. In particular instances, the seeds to be generated may be formed in such a manner that at least a portion of their sequence overlaps one another, such as in a pileup as discussed above. This may be useful for instance in getting around machine and/or human errors or differences between the subject and the reference genome and may promote exact matching.

In certain instances, the building of the hash table as well as the performance of one or more of the various comparisons is executed by a hash function. The hash function is in part a scrambler. It takes an input and gives what appears to be a random order to it. In this instance, the hash function scrambler breaks down the reference genome into segments of a preselected length and places them randomly in the hash table. The data may then be stored evenly across the whole storage space. Alternatively, the storage space may be segmented and/or storage therein may be weighted differently. More particularly, the hash function is a function that takes any input and gives a number, such as a binary pattern out, which number may typically be random except that for any one given input the same output is always returned. Hence, even if two inputs that are fed into the hash table are almost the same, because they are not an exact match, two completely, randomly different outputs will be returned.

Further, since the reference and read genetic material may be composed of four basic nucleotides, e.g., "A", "C", "G", and "T" (or "U" in the case of RNA), the individual nucleotides of the sequences, e.g., the reference segments and or reads, or portions thereof, to be fed into the hash table may be digitized and represented in binary format, such as where each of the four bases represents a two bit digital code, e.g., "A"=00, "C"=01, "G"=11, and "T"/"U"=10. Accordingly, in certain instances, it is this binary "seed" value that may then be randomly placed in the hash table at a known location having a value equal to its binary representation. The hash function, therefore, may work to break down the reference genome into binary representations of reference and read seeds and inserts each binary seed data into a random space, e.g., cubicle, in the hash table based on its numeric value.

Along with this digital binary code, e.g., access key, each cubicle may also include the actual entry points to where the segment originated from in the actual reference genome, e.g., the reference position. The reference position therefore may be a number indicating the position of the original reference seed in the genome. This may also be done for overlapping positions, which are put into the table, e.g., in random order but at a known location, such as by the hash function. In a manner such as this, an index, e.g., a hash table index, may be generated, wherein the index includes the digital binary code for a portion or all of a plurality of segments of one or more reference genomes, which may then be referenced by one or more digital binary codes representative of sequences of genetic material, e.g., one or more reads, or portions thereof, from one or more individuals.

Accordingly, a hash table and/or function as disclosed herein may be implemented as a module, such as a module in a pipeline of bioinformatics modules, in software and/or hardware (such as where the bit width is 2× the number of bases in the seed described above). In such instances, the hash table can be built so that the binary representation of the reference and/or read seeds can be any bit width desired. Specifically, as described herein throughout, any suitable seed length may be selected, but in certain instances, a seed length of about 18 to about 21 bases (e.g., k=21 bases, where k=a selected number of bases) or less may be selected, e.g., for shorter reads, and in other instances, a seed length up to about 27 to about 32 bases (k=27 bases) or more may be selected, such as for longer reads. In various instances, contiguous k-base seeds, "kmer" from one or more, e.g., all, overlapping reference genome start positions may be extracted from the reference, such as by a seed generator function, and considered for population into the hash table to be constructed, such as by the hash function.

As the seeds can be long or short, the binary representations can be greater or lesser, but typically the seed length should be chosen so as to be long enough to be unique, but not too long that it is too hard to find matches between the seeds of the genome reference and the seeds of the sample reads, such as because of errors or variants present in the reads. For instance, as indicated above, the human genome is made up of about 3.1 billion bases, and a typical read may be about 100 nucleotides in length. Hence, a useful seed length may be between about 16 or about 18 nucleotides or less in length to about 28 or about 30 or about 32 nucleotides or more in length. For example, in certain instances, the seed length may be a segment of 20 to 30 nucleotides in length. In particular instances, the seed length may be a segment of 28 nucleotides in length. Consequently, where the seed length is a segment of 20 nucleotides, each segment may be represented digitally by a 40 bit output, e.g., a 40 bit binary representation of the seed. For example, where 2 bits are selected to represent each nucleotide, e.g., such as where A=00, C=01, G=10, and T=11, a seed of 20 nucleotides×2 bits per nucleotide=a 40 bit (5 byte) vector, e.g., number. Where the seed length may be 28 nucleotides in length, the digital, e.g., binary, representation of the seed may be a 56 bit vector.

Hence, where the seed length is approximately 28 nucleotides in length, 56 bits can be employed to handle a 28 nucleotide seed length. More particularly, where the 56 bits represents the binary form of the seeds of the reference genome that have been randomly positioned in the hash table, a further 56 bits can be used to digitally represent the seeds of the read that are to be matched against the seeds of the reference. These 56 bits may be run through a polynomial that converts the 56 bits in to 56 bits out in a 1:1 correspondence. Without increasing or decreasing the number of bits of output, performing this operation randomizes the storage location of adjacent input values so that the various seed values will be uniformly distributed among all possible storage locations. This also serves to minimize collisions among values that hash to the same location.

In particular, in a typical hash table implementation described herein, only a portion of the 56 bits need be used as a lookup address to select a storage location and the remaining bits may be stored in that location for confirmation of a match. For instance, if a hashing function were not used, a great many patterns having the same address bits, but different stored bits may have to share the same hash location. More specifically, there may be similarity between the way the hash table is constructed, e.g., by software and/or hardware placing the reference genome seeds randomly in the hash table, and the way the hash table is accessed by the seeds of the reads being hashed such that they both access the table in the same way, e.g., in accordance with the hash function. Hence, seeds of the reference and seeds of the sample read that are the same, e.g., have the same binary code, will end up in the same location, e.g., address, in the table because they access the hash table in the same manner, e.g., for the same input pattern.

This is a fast method for performing a pattern match. Each lookup takes a nearly constant amount of time to perform. Such method may be contrasted with the Burrows-Wheeler method which may require many probes (the number may vary depending on how many bits are required to find a unique pattern) per query to find a match, or a binary search method that takes log 2(N) probes where N is the number of seed patterns in the table. Further, even though the hash function can break the reference genome down into segments of seeds of any given length, e.g., 28 base pairs, and can then convert the seeds into a digital, e.g., binary, representation of 56 bits, not all 56 bits need be accessed entirely at the same time or in the same way. For instance, the hash function can be implemented in such a manner that the address for each seed is designated by a number less than 56 bits, such as about 18 to about 44 or 46 bits, such as about 20 to about 40 bits, such as about 24 to about 36 bits, including about 28 to about 32 or about 30 bits may be used as an initial key or address so as to access the hash table. For example, in certain instances, about 26 to about 29 bits may be used as a primary access key for the hash table, leaving about 27 to about 30 bits left over, which may be employed as a means for double checking the first key, e.g., if both the first and second keys arrive at the same cell in the hash table, then it is relatively clear that said location is where they belong.

Specifically, in order to save space and reduce the memory requirements and/or processing time of the hash module, such as when the hash table and/or hash function are implemented in hardware, the about 26 to about 29 bits representing the primary access key derived from the original 56 bits representing the digitized seed of a particular sequenced read may be employed by the hashing function to comprise the primary address, leaving about 27 to about 30 bits that can be used in a double checking method. More particularly, in various instances, about 26 to about 29 bits from the 56 bits representing the binary form of a reference seed may be employed, e.g., as a primary access key, to comprise a primary address, which designated 26 to 29 bits may then be given a randomized location in the hash table, which in turn may then be populated with the location of where the reference seed originally came from along with the remaining 27 to 30 bits of the seed so that an exact match may be ascertained.

The query seeds representing the reads of the subject genome converted into binary form may also be hashed by the same function in such a manner that they as well are represented by 26 to 29 bits comprising a primary access key. If the 26 to 29 bits representing the reference seed are an exact match to the 26 to 29 bits representing the query seeds, they both will be directed to the same position in the hash table. If there is an exact match to the reference seed, then it would be expected to find an entry at that location containing the same remaining 27 to 30 bits. In such an instance, the 26 to 29 designated address bits of the reference sequence may then be looked up to identify the position in the reference to where the query read from which the query seed was derived, aligns. However, with respect to the left over 27 to 30 bits, these bits may represent a secondary access key that may also be imported into the hash table as well, such as for the purpose of ensuring the results of the first 26 to 29 bits of the primary access key.

Because the hash table may be configured to represent a perfect 1:1 scrambling of the 28 nucleotide/56 bit sequence, and only about 26 to about 29 of the bits are used to determine the address, these 26 to 29 bits of the primary access key have basically been checked, thereby determining the correct address in a first go around. This data, therefore, does not need to be confirmed. However, the remaining about 27 to about 30 bits of the secondary access key may also be checked. Accordingly, the remaining about 27 to 30 bits of the query seeds may be inserted into the hash table as a means for completing the match. Such an implementation may be shorter than storing the 56 bit whole key, and thus, saves space and reduces over all memory requirements and processing time of the module. The hash table, therefore, can be configured as an index where known sequences of one or more reference genomes that have been divided into sequences of predetermined lengths, e.g., seeds, such as of 28 nucleotides in length, are organized into a table randomly, and one or more sequenced reads, or "seed" portions thereof, derived from the sequencing of a subject's genomic DNA and/or RNA, may be passed through the hash table index, such as in accordance with a hash function, so as to look up the seed in the index, and one or more positions, e.g., locations in the reference genome, may be obtained from the table where the sample seed matches positions in the reference genome.

In particular instances, a brute force linear scan can be employed to compare the reference to the read, or portions thereof. However, using a brute force linear search to scan the reference genome for locations where a seed matches, over 3 billion locations may have to be checked. Which searching can be performed, in accordance with the methods disclosed herein, in software or hardware. Nevertheless, by using a hashing approach, as set forth herein, each seed lookup can occur in approximately a constant amount of time. Often, the location can be ascertained in a few, e.g., a single access. However, in cases where multiple seeds map to the same location in the table, e.g., they are not unique enough, a few additional accesses may be made to find the seed being currently looked up. Hence, even though there can be 30M or more possible locations for a given 100 nucleotide length read to match up to, with respect to a reference genome, the hash table and hash function can quickly determine where that read is going to show up in the reference genome. By using a hash table index, therefore, it is not necessary to search the whole reference genome, e.g., by brute force, to determine where the read maps and aligns.

However, as indicted above, chromosomes have a double helix structure that includes two opposed, complementary strands of nucleic acid sequences that are bound together so as to form the double helix. This results in two equal and opposite strands of nucleic acid sequences that are the complement of each other. More particularly, the bases of a nucleotide sequence of one strand will be mirrored by their complementary bases on the opposed strand resulting in two complementary strands, but where the bases are in reverse order. Consequently, the two strands of DNA sequences are reverse complemented. Specifically, the sequence order of one strand of the DNA when compared to the sequence order of other strand is reversed. Of course, both strands of the reference genome, e.g., the complement and its reverse complement, may be processed and hashed as described above, but this would make the hash table twice as big, and make the performance of the hash function take twice as long, e.g., it could require about twice the amount of processing to compare both complement and reverse complemented sequences of the two genomic sequences.

Accordingly, to save memory space, reduce processing power, and/or decrease the time of processing, in various instances, only one strand of the model genomic DNA need be stored in the hash table as a reference.

In various instances, since only one strand of the reference genome need be used to generate the hash table, half of the reads generated by the sequencing protocol may not match the particular strand, e.g., either the complement or its reverse complement, of the model genome reference, e.g., because half the time the read being processed is a reverse complement with respect to the hashed segments of the reference genome. Hence, only the reads generated from one strand of the DNA will match the indexed sequences of the reference genome, while the reads generated from the other strand will theoretically be their reverse complements and will not match anywhere in the reference genome. In view of the above, in order for mapping to proceed efficiently, in various instances, it not only must be determined where the read matches in the reference genome it must also be determined if the read is reverse complemented. Therefore, the hash table and/or function module should be constructed so as to be able to minimize these complications and/or the types of errors that may result therefrom. However, storing both strands of the reference genome in the hash index can require about twice as much storage space (e.g., instead of 32 gigabytes 64 gigabytes may be necessary), and may require twice the amount of processing resources and/or twice as much time for processing.

Accordingly, although the hash table index may be constructed to include both strands of the genomic reference sequence. In various instances, the hash table may be constructed so as to only include one strand of the model genome as a reference. This may be useful because storing the hash table in memory will require half of the storage and/or processing resources than would be required if both strands were to be stored and processed, and thus, the time required for a look up should also require less time. However, storing only one strand of the genome as a reference could cause complications because, as indicated above, where the sequenced subject DNA is double stranded, it is not typically known from which strand any given read was generated. In such an instance, therefore, the hash table should be constructed to account for the fact the read being mapped may be from either strand and thus can be the complement or reverse complement of the stored segments of the reference genome.

In various instances, such as where only one orientation of seeds from the reference are populated into the hash table, when performing the hash function on the seeds generated from the reads of the FASTQ file, the seed may first be looked up in its present orientation, and/or may then be reverse complemented and the reverse complement may be looked up. This may require two looks up in the hash index, e.g., twice as many, but one of the seed or its reverse complement should match its complementary segment in the reference genome, assuming no errors or variations, and it should reduce the overall processing resources, e.g., less memory is used, as well as reducing time, e.g., not as many sequences need to be compared. More particularly, such as where a seed in one particular orientation is comprised of 28 nucleotides, e.g., digitally represented in a 56 bit binary format, as described above, the seed can be reverse complemented and the reverse complement can also be represented digitally in a 56 bit binary format. The binary format for each representation of the seed sequence and its complement results in a number, e.g., an integer, having a value represented by that number. These two values, e.g., the two integers, may be compared and the number with the higher or lower value, e.g., higher or lower absolute value, e.g., of the 56 bit binary value, may be selected as the canonical choice of orientation and that is the one that can be stored in the hash table and/or subjected to the hash function. For instance, in certain instances, the number with the higher value may be selected for being processed by the hash function.

In such an instance, before hashing, the k-base seed (k=the number of nucleotides in the sequence) beginning at each reference offset may be extracted and considered as a 2 k-bit binary integer, that integer may then be compared with the integer for its reverse complement, so as to determine the arithmetically smaller between the two. The arithmetically smaller of these two may be considered the canonical representative, and only that version need be hashed, although the other may be hashed as well, if desired. Hence, once determined, the arithmetically smaller of these two may be selected to be hashed; however, in various instances, the larger of the 2 k-bit binary integer may be selected to be hashed. Particularly, during run-time queries, e.g., during read mapping, a procedure of hashing and looking up the smaller or larger of the query seed or its reverse complement may be implemented. The method, therefore, may allow seeds from reverse complemented reads to be quickly located without requiring double the amount of memory storage space and without requiring double the amount of accesses.

In various instances, the hash table can be structured such that it is comprised of 8 bytes, 16 bytes, 32 bytes, 64 bytes, 128 bytes, or the like. But in certain exemplary embodiments it may be useful for the hash table to be comprised of 64 bytes. This may be useful, for instance, where the hash function is to make use of accessing an external memory, such as a DRAM, e.g., in a standard DIMM or SODIMM form factor, such as where the minimum burst size is typically 64 bytes. In such an instance, the design of the processor for accessing a given memory will be such that the number of bytes needed to form a bucket in the hash table is also 64, and therefore a maximized efficiency may be realized. Hence, in instances where the optimal burst size of the memory access is at a given size, e.g., 64 bytes, the hash table can be structured so burst size of the memory is optimally exploited, such as where the bytes allocated for representing one or more bins or buckets in the hash table and processed by the mapping function, e.g., 64 bytes, are coincident with the burst size of the memory. Consequently, where the memory bandwidth is a constraint, the hash table can be structured so as to optimally exploit such constraints. Likewise, each hash record may be comprised of 64 bits, which 64 bits may include a 32-bit reference position, e.g., primary access key, 30 bits of a residual hash value, e.g., secondary access key, that may be used for comparison purposes, a reverse complement (RC) flag, if appropriate, indicating the reference seed was reverse-complemented before hashing, and/or a LAST flag facilitating early exits from hash table queries. For example, in various instances, eight records may be organized into a 64-byte hash bucket, which is the length of a minimum DDR3 burst, so that a full bucket can be fetched with each run-time memory, e.g., DRAM, access without suffering a performance penalty.

Specifically, it is useful to structure the hash table to avoid collisions. For instance, there may be multiple seeds that, because of various system artifacts will want to be inserted into the hash table at the same place regardless of whether there is a match there or not. Such instances are termed collisions. Often times, collisions can be avoided, in part, by the way the hash table is structured. Accordingly, in various instances the hash table may be structured so as to avoid collisions, and therefore may be configured to include one or more virtual hash buckets. Particularly, to prevent retrieving a wrong hash record without needing to store the entire hash keys in the records, a positional system may be used so as to form a series of buckets, such as for the storage of records, for example, for the storage of one or more portions of a hash key. In various embodiments, a plurality of hash buckets are provided where one or more of the buckets may be chained together, such as in series.

More specifically, a primary hash table can be configured to store hash records in one or more hash buckets, such as where each bucket may include about 8 bytes each with 8 records per hash bucket totaling 64 bytes per bucket. Accordingly, each hash bucket may be configured for storing one or more, e.g., a plurality, of hash records, such as in all or a portion of 64 bit file. In such an instance, the 64 bits may include a 32-bit reference position, 30 bits of a residual hash value that may be used for comparison purposes, a reverse complement (RC) flag, and/or a LAST flag. Accordingly, in various instances, one or more or all 8 records in a particular hash bucket can be read at once, or some sub-portion thereof. This may be useful in optimizing the processing speed of the system as, given the architecture described herein, e.g., hardware, it would cost the same time at the same speed to process all 8 records in the hash bucket as it would for simply processing 1 record. Accordingly, in certain instances, the mapping module may include a hash table that itself may include one or more subsections, e.g., virtual sections or buckets, wherein each bucket may have 1 or more slots, such as 8 slots, such that one or more different records can be inserted therein such as to allow for probing and to manage collisions.

However, in certain circumstances, one or more of such buckets may fill up with records, so a means may be provided for storing additional records in other buckets, and a means for recording information in the original bucket indicating that the hash table lookup mechanism needs to look further to find a match may also be provided. Hence, in certain instances it may be useful to employ one or more additional methods such as for managing collisions, such as a method including one or more of linear probing and/or hash chaining. For instance, if it is not known what exactly is being searched in the hash table or a portion thereof, such as in one bucket of the hash table, and the particular bucket is full, then a hash lookup function can be provided and be configured such that if one bucket is full and is searched and the desired record not found, then the function can be directed to step to the next bucket, e.g., the +1 bucket, and that bucket can then be checked. In such a manner, all buckets can be searched when looking for a particular record. Such searching, therefore, can be performed sequentially looking through one bucket to another until what is being looked for is found or it becomes clear that it is not going to be found, such as where an empty slot in at least one of the buckets is found. Particularly, where each bucket is filled sequentially, and each bucket is searched according to the sequence of filling, if an empty slot is found, such as when searching sequentially through buckets looking for a particular record, then the empty slot could be indicative of the record not existing, because if it did exist, it would at least have been positioned in the empty slot, if not in the preceding buckets.

A hash chaining system, therefore, may be employed so as to make searching easier and for minimizing the average number of accesses that have to be performed in retrieving the stored records, or portions thereof, within the series of buckets. Particularly, such hash buckets allow for a larger amount of records to be organized and stored, and hash chaining allows a wider region of buckets within which to store the records, and further by hash chaining, more excess hash records may generally be populated per chained bucket, which can be selected from a wider region than by simply probing the buckets sequentially one right after the other in sequence. Hence, for each hash record in one bucket containing overflow hash bits matching the same bits of the hash key in another bucket, a possible matching position in the reference genome may be reported. For the primary hash table therefore, up to 8 positions may be reported. Particularly, where 64 bytes are designated for storing the information in a hash bucket wherein 8 records are contained, upon receiving a fetched bucket, the mapping processing engine can operate on all 8 records simultaneously to determine which are matches and which are not. For instance, when performing a look up such as of a seed from a read obtained from the sequenced sample DNA/RNA against a seed generated from the reference genome, the digital, e.g., binary, representation of the sample seed can be compared against the digital, e.g., binary, reference seeds in all, e.g., 8, records so as to find a match.

In such an instance, several outcomes may result. A direct match may be found. A sample seed may go into the hash table and, in some instances, no match is found, e.g., because it is just not exactly the same as any corresponding seed in the reference, such as because there was a machine or sequencing error with respect to that seed or the read from which it is generated, or because the person has a genetic sequence that is different from the reference genome. Or a the seed may go into the hash table and a plurality of matches may be returned, such as where the sample seed matches to 2, 3, 5, 10, 15, 20, or more places in the table. In such an instance, multiple records may be returned all pointing to various different locations in the reference genome where that particular seed matches, the records for these matches may either be in the same bucket, or a multiplicity of buckets may have to be probed to return all of the significant, e.g., match, results.

For these purposes, in addition to stored record data, each chained bucket may contain a chain continuation format record, which contains a chain pointer pointing toward where the record is continued in the bucket chain, if required for such storage and retrieval. Particularly, this chain continuation record may appear in a slot of the bucket after all the "native" records corresponding to direct hash access have been stored, but before all remote records belonging to the chain in question are stored. Hence, during queries, before following any chain pointer, in a first bucket, any records appearing after the chain continuation record may be ignored, and after following any chain pointer to a second bucket, any records appearing before the chain continuation record may also be ignored. Therefore, a given number of excess hash records can typically be populated into a shorter sequence of chained buckets and more readily accessed than the necessary sequence of probing buckets, which likewise limits the number of accesses required to locate those excess records in a given search query. Nevertheless, probing, e.g., linear and/or sequential probing, remains valuable for smaller quantities of excess hash records, because probing does not require a bucket slot to be sacrificed for a chain pointer.

In certain instances, such as where space may become a limiting factor in the hash table, e.g., in the hash table buckets, an additional mechanism for resolving collisions and/or for saving space may be implemented. For instance, when space becomes limited, such as when more than 8 records need to be stored in a bucket, or when for other instances it is desirable, a hash chaining function may be performed. Hash chaining can involve, for example, replacing a record containing a specific position location in the genomic sequence with a record containing a chain pointer that instead of pointing to a location in the genome points to some other address, e.g., a second bucket, in the current hash table e.g. a primary or a secondary hash table. This has the advantage over the linear probing method of enabling the hash lookup mechanism to directly access the bucket containing the desired record rather than checking all buckets sequentially in order. Such a process may be useful given the system architecture. For instance, the primary seeds being hashed, such as in a primary lookup, are positioned at a given location in the table, e.g., their original position, whereas the seeds being chained are being put in a position that may be different from their original bucket.

Hence, as indicated above, a first portion of the digitally represented seed, e.g., about 26 to about 32, such as about 29 bits, can form a primary access key and be hashed and may be looked up in a first step. And, in a second step, the remaining about 27 to about 30 bits, e.g., a secondary access key, can be inserted into the hash table, such as in a hash chain, as a means for confirming the first pass. Accordingly, for any seed, its original address bits may be hashed in a first step, and the secondary address bits may be used in a second, confirmation step. In such an instance, the first portion of the seeds can be inserted into a primary record location, and the second portion may be fit into the table in a secondary record chain location. And, as indicated above, in various instances, these two different record locations may be positionally separated, such as by a chain format record.

Therefore, in any destination bucket of chaining a chain format record may positionally separate the entries/records that are for local primary first bucket accesses and probing and those records that are for the chain. Such hash chains can be continued for a multiplicity of lengths. An advantage of such chaining is that where one or more of the buckets include one or more, e.g., 2, 3, 4, 5, 6, or more empty record slots, these empty slots can be used to store the hash chain data. Accordingly, in certain instances, hash chaining may involve starting with an empty slot in one bucket and chaining that slot to another slot in another bucket, where the two buckets may be at remote locations in the hash table.

Additional care may be taken to avoid confusion between records placed in a remote bucket as part of a hash chain, and "native" records that hash directly into the same bucket. For instance, the remaining about 27 to about 30 bits of the secondary access key may be checked against corresponding about 27 to 30 bits stored in the records placed remotely in the chained bucket, but due to the distant placement of the chained bucket from the original hash bucket, confirming these about 27 to 30 bits may be useful to guarantee that a matching hash record corresponds to the original seed reaching this bucket by chaining, as opposed to some other seed reaching the same bucket by direct access (e.g., confirming the about 27 to 30 bits may be a full verification when the about 26 to 29 bits used for hash table addressing are implicitly checked by proximity to the initial hash bucket accessed.)

In view of the above, any suitable hash function may be employed for these purposes, however, in various instances, the hash function used to determine the table address for each seed may be a cyclic redundancy check (CRC) that may be based on a 2 k-bit primitive polynomial, as indicated above. Alternatively, a trivial hash function mapper may be employed such as by simply dropping some of the 2 k bits. However, in various instances, the CRC may be a stronger hash function that may better separate similar seeds while at the same time avoiding table congestion. This may especially be beneficial where there is no speed penalty when calculating CRCs such as with the dedicated hardware described herein. In such instances, the hash record populated for each seed may include the reference position where the seed occurred, and the flag indicating whether it was reverse complemented before hashing.

Additionally, the 2 k-bit CRC hash function may be employed to swiftly perform calculations in software and/or hardware, and in certain instances, may be a reversible (bijective) function. Due to such properties, for the query seed, in order to verify the hash record, all that needs to be verified is the hash value rather than the seed itself, as described above. Accordingly, an appropriate quantity of upper hash bits may be used for hash table addressing (which may be multiplied by a squeeze factor, e.g., R/64 for non-power-of-two table sizes), and at least the remaining lower hash bits may also be populated into the hash record, if desired, such as for verification purposes. Consequently, during hash table queries, only the lower hash bits, which may be present in each record, need to be checked to verify a seed match, because the upper bits are implicitly verified by accessing the address derived from them. Hence, the upper hash bits may be employed to derive a location, and the lower hash bits may be employed to verify that location is correct.

In certain instances, a few bits of overlap may be used, such as between "address" and "data" hash portions, so as to allow a limited-range linear probing in cases of hash address collisions without creating match ambiguity. However, where the hash table becomes locally congested, hash chains (e.g., linked lists), as described, may be used instead of linear probing, sacrificing one record in each bucket as a chain pointer to a possibly distant next bucket. Particularly, in certain instances, a seed may map to multiple positions. In such instances, when multiple matching reference positions are determined as a possibility for a given seed, these positions may be stored as multiple hash records. However, when this occurs, it may be helpful to enforce a limit such as between about 16 to about 32 positions per seed. In some instances, such a limit could be draconian, because mappable reference regions can have much higher match frequencies for 21-27 base seeds. Accordingly, the devices and methods as herein disclosed, may employ a system of dynamic seed extension so as to successfully populate approximately 85%, such as about 90%, for instance, approximately about 95% or about 99%, or more, of eligible seed positions.

Consequently, in various instances, an algorithm, like a Burrows-Wheeler based algorithm, may be employed so as to incrementally extend matches until the suffix interval becomes narrow enough to process a reasonable number of reference positions. Accordingly, in construction of the hash table, when a given seed occurs in a plurality, e.g., many reference positions, an EXTEND record may instead be populated, thereby encoding a selected asymmetric or symmetric extension length, and the many reference positions may be populated at various table addresses obtained by hashing the extended seeds. Hence, the EXTEND record may be populated into the hash table at the calculated address, encoding a selected extension length. And in various instances, the extension increment may be selected so as to be even, because seeds that are extended symmetrically may optimize the compatibility with reverse-complement handling. Therefore, when a particular seed matches up to a plurality, e.g., several, positions in the reference, each position may be stored in the table, such as at an address derived from the hash function of the seed.

Particularly, in certain instances, when a seed matches numerous positions in the reference, then a "seed extension" command may be saved in the table for the seed. Such procedures may be implemented, for instance, in those instances where a given seed has a high frequency of possible matches. In such an instance, positional disambiguation of such "high frequency" seeds may be achieved such as by extending each occurrence of the seed with its adjacent bases in the reference. The positions of these extended seeds may then be saved in the table. For instance, multiple reference positions matching a given seed may be stored as multiple hash records, either all in the same hash bucket, or spread by probing or chaining into additional buckets. Hence, if a given primary seed has a high frequency, the EXTEND record may instead be populated into the hash table at the calculated address, encoding a selected extension length.

The extension increment may be an even integer so that the seeds may be extended symmetrically, e.g., for best compatibility with handling reverse-complements. For example, a k=21 base primary seed occurring in 150 reference positions could be extended by 1, or 2 to 5, or more, adjoining bases left and/or right, yielding, in some cases, an extended seed, such as 31-base extended seed when the extension is 5 bases right and left. The seed may typically be extended any length so long as it is long enough that matches become unique or nearly so. In various instances, such seed extension can be iterated; e.g. if 50 of the 31-base extended seeds were still to be identical, that subset might be further extended to 43 bases, up to 64 bases total, etc. In particular instances, extension increments may be kept fairly short (e.g., 1-6 bases each way), permitting an optimal mix of net extension lengths from a single primary seed.

More particularly, in the instance where a 21-base seed matches 100 reference positions exactly, the hash table building tool will investigate the possible extension lengths, and determine what outcome would result if the seed is extended by X bases in each direction. For instance, if the seed is extended by X=5 bases on each side, the 31-base extended seed will no longer be identical at the 100 positions, but will break into smaller groups of identical 31-mers, perhaps 4 unique 31-mers and 12 groups of 8 identical 31-mers. In such an instance, an EXTEND record may be populated into the hash table, encoding the 10-base extension increment, and all 100 extended 31-base seeds may be hashed and populated into the hash table. At runtime, a first query to the hash table retrieves the EXTEND record, which induces the mapper engine to re-hash at 31-base length, and query the hash table again, retrieving either a single reference position or a group of 8 positions, assuming the extended seed still matches the reference somewhere. Run-time extension fails if the extended seed overruns either end of the read.

By default, extended seeds can be extended up to 64 bases long or more. However, long extensions may be achieved in increments, such as where a query for an already extended seed retrieves another EXTEND record indicating a further extension increment. Incremental extension is useful when a primary k-mer maps to a large number of reference positions, but subsets of the positions require different levels of k-mer extension to ensure adequate mapping uniqueness. For example, of 1000 identical 21-mers, perhaps 200 can resolve into small groups extended to 29 bases, but the other 800 remain in large clumps until the seeds extend to 49 bases. At run-time where the read matches any of the 1000 reference positions, the 21-base query will retrieve the EXTEND-8 record. Upon querying for the 29-base extended seed, if it matches one or more of the 200 positions, these will be retrieved. But if the read matches one of the 800 positions, an EXTEND-20 record will be found in the table, and matching reference positions will be found by querying the table again with the 49-base extended seed.

In general, the iterative extensions from a given high-frequency primary seed follow a seed extension tree, where multiple branches from a given node are all extension increments of a common length, but the increments for branches from any two nodes can be different. A dynamic programming algorithm may be used to find a cost-minimizing solution from the space of all possible extension trees for any given group of identical primary seeds, such as where the cost components are: extension length, number of hits reported together, and the number of extension increments. Under default settings, seed extension increments average about 7 bases (3.5 bases each way). When a sub-group of seed positions cannot be brought under the frequency limit by any extension under 64 bases, these positions are not individually populated in the hash table; a single HIFREQ record is populated in lieu of another EXTEND, which at run-time indicates seed mapping failure due to extreme high frequency, not due to variation from the reference.

Consequently, within the mapping processing engine pipeline, overlapping k-base seeds may first be extracted from each read, and may then be queued up for processing. In such an instance, each seed may be passed through the hash function, e.g., a CRC hash function, and queries of the hash table may be repeated with various seed lengths if one or more EXTEND records appear. The end result will be a plurality of seeds that match similar reference positions, which seeds may then be grouped into chains and aligned. As described herein, the alignment function may be constructed so as to allow for alignment drift, such as which may occur due to indels, as explained below. Additionally, a filter can be applied to the alignment function such that seed chains that are shorter than a given length, e.g., one fourth of the longest seed length chain, can be filtered out, such as by default.

Accordingly, in view of the above, at run-time, a mapping engine may first extract a sequence of seeds of the configured length k from each read, according to a specified seed lookup pattern. For instance, as a default pattern, the seed generator may extract seeds from 50% of possible positions, starting at the $1^{st}$ base, $3^{rd}$ base, $5^{th}$ base, etc. from the 5' end. In such an instance, a maximal extension "wing," which wing may potentially be added in each direction, may also be extracted just in case an extension is needed, such as where the maximum extension length is selected so as to not overrun either read end. Hence, as may be the case throughout the mapping and aligning hardware, each stage may continue without waiting for successive processing stages. In such instances, all seeds from every read may be rapidly queued up for further processing, and when the last seed is extracted from one read, extraction may immediately begin in the next read. For instance, as described herein, each extracted seed passes into and down the pipeline such as through the CRC hash function, followed by hash address calculation, and a hash bucket access request that is submitted to the DRAM subsystem. Additional requests for subsequent seeds may immediately follow without having to wait for the data from the previous hash bucket to return. For example, at any given time, around 100 or more hash bucket accesses may be pending in the chip.

Hence, as the hash bucket data returns from the DRAM to each processing engine, two hash records per cycle may be decoded and processed. The low hash bits may then be compared to ascertain full matches to the query seed, and reference positions and RC flags may be forwarded to the next stage. If not all the records that are sought after are found in a particular, e.g., first, hash bucket, the next, e.g., second, hash bucket may be fetched, such as in a linear probing model and/or a hash chain pointer may be followed to the next, e.g., n, bucket. These additional lookups may then be configured to loop back to the DRAM access stage, without stalling the pipeline. Likewise, matching EXTEND records may also be configured to loop an extended seed back to the CRC hash logic so as to not stall the pipeline flow.

As indicated, as the seeds are extracted and mapped, seed chaining may begin. In seed chaining matched reference positions are grouped into seed chains, where each seed chain has similar "diagonals" as in an abstract Smith-Waterman array employed herein. Particularly, a diagonal in a virtual Smith-Waterman array may be defined numerically as the difference between the reference position and read position (or the sum if it is reverse-complemented). Hence, by default, seeds with the same orientation and diagonals within about 28 bases of each other may be grouped into the same seed chain, but to facilitate very long reads, the seed chain diagonal be permitted to gradually drift.

For instance, in a particular instance, up to 512 seed chains can be tracked per selection of reads, and a local hash table within the seed chaining logic may be used to quickly locate existing seed chains that each new extracted seed may be eligible to join. In certain instances, conservative filtering may be applied to the completed seed chains, such as where an "inferior" seed chain may be filtered out if it substantially overlaps a read having a "superior" seed chain that is about three or four or more times longer than the inferior seed chain for that read. The length of the superior chain in this comparison is an effective length that may be calculated from its seed count, whereas the true length of the inferior chain is used, so that long but sparse chains do not easily filter out short chains. Such chains that have been so filtered out can be, but do not need to be, deleted at this stage, alternatively, they may simply be flagged.

Some special circumstances exist for paired end reads. For instance, for paired end reads, two lists of seed chains may be generated, and these two lists of seed chains may each be searched for reference positions in accordance with an expected separation and/or expected orientation. If no paired chains are found, however, a rescue scan may be triggered from one or each chain, so as to ensure better accuracy. In certain instances, even if some pairs are found, such as unpaired chains longer than a certain number of bases, e.g., 48 bases, a rescue trigger may be implemented. In such an instance, for each rescue from a given seed chain, the expected reference window for the mate read may be scanned. If such is the case, a 32 base k-mer from one or each end of the mate may be compared at every position, and may be considered "matching," e.g., if no more than 7 bases differ.

For example, for paired end reads, the N seed chains for one mate of the paired end reads may be compared in a pairwise manner with the M chains for the other mate. In a manner such as this a test may be performed so as to determine whether they are properly paired according to their expected insert orientation and size range, which may be calculated empirically from a sample of their corresponding reads. For N and M seed chains, their end points may be extrapolated to full read length so that an insert length calculation may be performed so as to determine if an actual mate pair exists. Consequently, whenever a pair is found, any 'filtered' flags may be canceled from either or both ends, and any or all unfiltered, unpaired seed chains that can be considered for possibly being a paired-end may undergo the rescue scan. By default, if no seed chains were found to be paired, all unfiltered chains may be eligible for the rescue scan(s), whereas if some pairs were found, only the unfiltered seed chains over a threshold length, e.g., 40 to 50 bases, such as 48 bases, will eligible for rescue.

If a rescue scan is to be performed for an unpaired seed chain in a one mate read so as to determine where the other mate may be found, then for each rescue scan generated, the window of reference data spanning the minimum to maximum insert lengths where the other mate may be found may be fetched from DRAM. In such an instance, one or more k-mers may be extracted from each end of the missing mate read, and the reference window may be further scanned, such as for low Hamming distance matches. By default, up to 7 differences in a 32-base k-mer signifies a match. Such matches that are found by these rescue scans may be translated into 'fabricated' seed chains, and may be used to trigger additional alignment operations downstream. Full-read gapless and/or gapped alignments may then be scored such as for each seed chain or rescue scan match.

The output returned from the performance of a mapping function may be a list of possibilities as to where one or more, e.g., each, read maps to one or more reference genomes. For instance, the output for each mapped read may be a list of possible locations the read may be mapped to a matching sequence in the reference genome. In various embodiments, an exact match to the reference for at least a piece, e.g., a seed of the read, if not all of the read may be sought. Accordingly, in various instances, it is not necessary for all portions of all the reads to match exactly to all the portions of the reference genome.

In various instances, one or more of these mapping methods or algorithms, as implemented in software or hardware, may be performed sequentially or at the same time so as to accurately determine where one or more, e.g., a substantial portion or every, read correctly matches with the reference genome. Each of these mapping methods, and their respective algorithms, may have advantages and/or disadvantages. For example, a disadvantage of a prefix and/or suffix tree is that it is a huge data structure that must be accessed a multiplicity of times as the tree is walked so as to map the reads to the reference genome. Additionally, a prefix and/or suffix Tree and/or a Burrows/Wheeler transformation may be performed on the sequence data in such a manner that the index of the reference genome is constructed and/or queried as a tree-like data structure, where starting from a single-base or short subsequence of a read, the subsequence is incrementally extended within the read, each incremental extension stimulating accesses to the index, tracing a path through the tree-like data structure, until the subsequence becomes unique enough, e.g., an optimal length has been attained, and/or a leaf node is reached in the tree-like data structure, the leaf or last-accessed tree node indicating one or more positions in the reference genome from which the read may have originated. These algorithms, therefore, typically do not have a fixed length for the read subsequences that may be mapped by querying the index.

A hash function, however, often employs a fixed length comparison unit that may be the entire length of the read, but is often times a length that is some sub-portion thereof, which sub-portion is termed a seed. Such seeds can be shorter or longer, but unlike with the prefix and/or suffix trees and/or the Burrows/Wheeler transformations, the seeds of the reads employed in a hash function are typically of a preselected, fixed length. An advantage of a hash table function, on the other hand, as described herein, is that once built, it typically only takes one look up to determine where, if anywhere, there may be a match between a seed and the reference. A prefix and/or suffix tree may typically take a plurality of look ups, e.g., 5, 10, 15, 20, 25, 50, 100, 1,000, or more, etc., in determining if and where there is a match. Further, due to the double helix structure of DNA, a reverse complement tree may also need to be built and searched, as the reverse complement to the reference genome may also need to be found.

With respect to the above, the data tree is described as being built from the reference genome which is then compared with the reads from the subject's sequenced DNA/RNA, however, it is to be understood that the data tree may initially be built from either the reference sequence or the sample reads, or both, and compared one to the other as described herein. More particularly, in any of the mapping algorithms described herein, such as for implementation in any of the method steps herein disclosed, one or all three mapping algorithms, or others known in the art, may be employed, in software or hardware, so as to map one or more sequences of a sample of sequenced DNA/RNA with one or more sequences of one or more reference genomes.

As described herein in, all of these operations may be performed via software or by being hardwired, such as into an integrated circuit, such as on a chip, for instance as part of a circuit board. For instance, the functioning of one or more of these algorithms may be embedded onto a chip, such as into a FPGA (field programmable gate array) or ASIC (application specific integrated circuit) chip, and may be optimized so as to perform more efficiently because of their implementation in such hardware. Additionally, one or more, e.g., two or all three, of these mapping functions may form a module, such as a mapping module, that may form part of a system, e.g., a pipeline, that is used in a process for determining an actual entire genomic sequence, or a portion thereof, of an individual.

An advantage of implementing the hash module in hardware is that the processes may be accelerated and therefore performed in a much faster manner. For instance, where software may include various instructions for performing one or more of these various functions, the implementation of such instructions often requires data and instructions to be stored and/or fetched and/or read and/or interpreted, such as prior to execution. As indicated above, however, and described in greater detail herein, a chip can be hardwired to perform these functions without having to fetch, interpret, and/or perform one or more of a sequence of instructions. Rather, the chip may be wired to perform such functions directly. Accordingly, in various aspects, the disclosure is directed to a custom hardwired machine that may be configured such that portions or all of the above described mapping, e.g., hashing, module may be implemented by one or more network circuits, such as integrated circuits hardwired on a chip, such as an FPGA or ASIC.

For example, in various instances, the hash table index may be constructed and the hash function may be performed on a chip, and in other instances, the hash table index may be generated off of the chip, such as via software run by a host CPU, but once generated it is loaded onto or otherwise made accessible to the hardware and employed by the chip, such as in running the hash module. Particularly, in various instances, the chip, such as an FPGA, may be configured so as to be tightly coupled to the host CPU, such as by a low latency interconnect, such as a QPI interconnect. More particularly, the chip and CPU may be configured so as to be tightly coupled together in such a manner so as to share one or more memory resources, e.g., a DRAM, in a cache coherent configuration, as described in more detail below. In such an instance, the host memory may build and/or include the reference index, e.g., the hash table, which may be stored in the host memory but be made readily accessible to the FPGA such as for its use in the performance of a hash or other mapping function. In particular embodiments, one or both of the CPU and the FPGA may include one or more caches or registers that may be coupled together so as to be in a coherent configuration such that stored data in one cache may be substantially mirrored by the other.

In certain instances, the chip may include any suitable number of gigabytes, such as 8 gigabytes, such as 16 gigabytes, such as 32 gigabytes, such as 64 gigabytes, such as about 128 gigabytes. In various instances, the chip may be configurable such that the various processes of the mapping module are performed employing only a portion or all the memory resources. For example, where a custom reference genome may be built, a large portion of the memory may be dedicated to storing the hash reference index and/or for storing reads and/or for reserving space for other functional modules to use, such as where 16 gigabytes are dedicated to storing the reads, 8 gigabytes may be dedicated to storing the hash index and another 8 gigabytes may be dedicated to other processing functions. In another example, where 32 gigabytes are dedicated to storing reads, 26 gigabytes may be dedicated for storing the primary hash table, 2.5 gigabytes may be dedicated for storing the secondary table, and 1.5 gigabytes may be dedicated for the reference genome.

Accordingly, in view of the above, at run-time, one or more previously constructed hash tables, e.g., containing an index of a reference genome, or a constructed or to be constructed hash table, may be loaded into onboard memory or may at least be made accessible by its host application, as described in greater detail herein below. In such an instance, reads, e.g., stored in FASTQ file format, may be sent by the host application to the onboard processing engines, e.g., a memory or cache or other register associated therewith, such as for use by a mapping and/or alignment and/or sorting engine, such as where the results thereof may be sent to and used for performing a variant call function. With respect thereto, as indicated above, in various instances, a pile up of overlapping seeds may be generated, e.g., via a seed generation function, and extracted from the sequenced reads, or read-pairs, and once generated the seeds may be hashed, such as against an index, and looked up in the hash table so as to determine candidate read mapping positions in the reference.

More particularly, in various instances, a mapping module may be provided, such as where the mapping module is configured to perform one or more mapping functions, such as in a hardwired configuration. Specifically, the hardwired mapping module may be configured to perform one or more functions typically performed by one or more algorithms run on a CPU, such as the functions that would typically be implemented in a software based algorithm that produces a prefix and/or suffix tree, a Burrows-Wheeler Transform, and/or runs a hash function, for instance, a hash function that makes use of, or otherwise relies on, a hash-table indexing, such as of a reference, e.g., a reference genome sequence. In such instances, the hash function may be structured so as to implement a strategy, such as an optimized mapping strategy that may be configured to minimize the number of memory accesses, e.g., large-memory random accesses, being performed so as to thereby maximize the utility of the on-board or otherwise associated memory bandwidth, which may fundamentally be constrained such as by space within the chip architecture.

Further, in certain instances, in order to make the system more efficient, the host CPU may be tightly coupled to the associated hardware, e.g., FPGA, such as by a low latency interface, e.g., Quick Path Interconnect ("QPI"), so as to allow the processing engines of the integrated circuit to have ready access to host memory. In particular instances, the interaction between the host CPU and the coupled chip and their respective associated memories, e.g., one or more DRAMs, may be configured so as to be cache coherent. Hence, in various embodiments, an integrated circuit may be provided wherein the integrated circuit has been pre-configured, e.g., prewired, in such a manner as to include one or more digital logic circuits that may be in a wired configuration, which may be interconnected, e.g., by one or a plurality of physical electrical interconnects, and in various embodiments, the hardwired digital logic circuits may be arranged into one or more processing engines so as to form one or more modules, such as a mapping module.

Accordingly, in various instances, a mapping module may be provided, such as in a first pre-configured wired, e.g., hardwired, configuration, where the mapping module is configured to perform various mapping functions. For instance, the mapping module may be configured so as to access, at least some of a sequence of nucleotides in a read of a plurality of reads, derived from a subject's sequenced genetic sample, and/or a genetic reference sequence, and/or an index of one or more genetic reference sequences, from a memory or a cache associated therewith, e.g., via a memory interface, such as a process interconnect, for instance, a Quick Path Interconnect, and the like. The mapping module may further be configured for mapping the read to one or more segments of the one or more genetic reference sequences, such as based on the index. For example, in various particular embodiments, the mapping algorithm and/or module presented herein, may be employed to build, or otherwise construct a hash table whereby the read, or a portion thereof, of the sequenced genetic material from the subject may be compared with one or more segments of a reference genome, so as to produce mapped reads. In such an instance, once mapping has been performed, an alignment may be performed.

For example, after it has been determined where all the possible matches are for the seeds against the reference genome, it must be determined which out of all the possible locations a given read may match to is in fact the correct position to which it aligns. Hence, after mapping there may be a multiplicity of positions that one or more reads appear to match in the reference genome. Consequently, there may be a plurality of seeds that appear to be indicating the exact same thing, e.g., they may match to the exact same position on the reference, if you take into account the position of the seed in the read. The actual alignment, therefore, must be determined for each given read. This determination may be made in several different ways.

In one instance, all the reads may be evaluated so as to determine their correct alignment with respect to the reference genome based on the positions indicated by every seed from the read that returned position information during the mapping, e.g., hash lookup, process. However, in various instances, prior to performing an alignment, a seed chain filtering function may be performed on one or more of the seeds. For instance, in certain instances, the seeds associated with a given read that appear to map to the same general place as against the reference genome may be aggregated into a single chain that references the same general region. All of the seeds associated with one read may be grouped into one or more seed chains such that each seed is a member of only one chain. It is such chain(s) that then cause the read to be aligned to each indicated position in the reference genome.

Specifically, in various instances, all the seeds that have the same supporting evidence indicating that they all belong to the same general location(s) in the reference may be gathered together to form one or more chains. The seeds that group together, therefore, or at least appear as they are going to be near one another in the reference genome, e.g., within a certain band, will be grouped into a chain of seeds, and those that are outside of this band will be made into a different chain of seeds. Once these various seeds have been aggregated into one or more various seed chains, it may be determined which of the chains actually represents the correct chain to be aligned. This may be done, at least in part, by use of a filtering algorithm that is a heuristic designed to eliminate weak seed chains which are highly unlikely to be the correct one.

Generally, longer seed chains, in terms of length spanned within the read, are more likely to be correct, and furthermore, seed chains with more contributing seeds are more likely to be correct. In one example, a heuristic may be applied wherein a relatively strong "superior" seed chain, e.g. long or having many seeds, filters out a relatively weak "inferior" seed chain, e.g. short or having few seeds. This process weeds out those seeds that have a low probability of having identified a region of the reference genome where a high quality alignment of the read can be found. It, therefore, may be useful because it reduces the number of alignments that need to be performed for each read thereby accelerating the processing speed and saving time. Accordingly, this process may be employed, in part, as a tuning feature, whereby when greater speed is desired, e.g., high speed mode, more detailed seed chain filtering is performed, and where greater overall accuracy is desired, e.g., enhanced accuracy mode, less seed chain filtering is performed, e.g., all the seed chains are evaluated.

Accordingly, in various embodiments, seed editing may be performed, such as prior to a seed chain filtering step. For instance, for each read, if all of the seeds of that read are subjected to a mapping function and none of them returned a hit, then there may be a high probability that there was one or more errors in the read, for instance, an error that the sequencer made. In such an instance, an editing function, such as a one-change editing process, e.g., an SNP editing process, can be performed on each seed, such as where a no match outcome was returned.

For example, at position X, a one change edit function may instruct that the designated nucleotide be substituted for one of the other 3 nucleotides and it is determined whether a hit, e.g., a match, is obtained by making that change, e.g., a SNP substitution. This one-change editing may be performed in the same manner on every position in the seed and/or on every seed of the read, e.g., substituting each alternative base for each position in the seed. Additionally, where one change is made in one seed, the effects that change would have on every other overlapping seed may be determined in view of that one change.

The outcome from performing one or more of these mapping, filtering, and/or editing functions is a list of reads which includes for each read a list of all the possible locations to where the read may matchup with the reference genome. Hence, a mapping function may be performed so as to quickly determine where the reads of the FASTQ file obtained from the sequencer map to the reference genome, e.g., to where in the whole genome the various reads map. However, if there is an error in any of the reads or a genetic variation, you may not get an exact match to the reference and/or there may be several places one or more reads appear to match. It, therefore, must be determined where the various reads actually align with respect to the genome as a whole.

Accordingly, after mapping and/or filtering and/or editing, the location positions for a large number of reads have been determined, where for some of the individual reads a multiplicity of location positions have been determined, and it now needs to be determined which out of all the possible locations is in fact the true or most likely location to which the various reads align. Such aligning may be performed by one or more algorithms, such as a dynamic programming algorithm that matches the mapped reads to the reference genome and runs an alignment function thereon. An exemplary aligning function compares one or more, e.g., all of the reads, to the reference, such as by placing them in a graphical relation to one another, e.g., such as in a table, e.g., a virtual array or matrix, where the sequence of one of the reference genome or the mapped reads is placed on one dimension or axis, e.g., the horizontal axis, and the other is placed on the opposed dimensions or axis, such as the vertical axis. A conceptual scoring wave front is then passed over the array so as to determine the alignment of the reads with the reference genome, such as by computing alignment scores for each cell in the matrix.

The scoring wave front represents one or more, e.g., all, the cells of the matrix, or a portion of those cells, which may be scored independently and/or simultaneously according to the rules of dynamic programming applicable in the alignment algorithm, such as Smith-Waterman, and/or Needleman-Wunsch, and/or related algorithms. For example, taking the origin of the matrix (corresponding to the beginning of the read and/or the beginning of a reference window of the conceptual scoring wave front) to be at the top-left corner, first only the top-left cell at coordinates (0,0) of the matrix may be scored, e.g., a 1-cell wave front; next, the two cells to the right and below at coordinates (0,1) and (1,0) may be scored, e.g., a 2-cell wave front; next the three cells at (0,2), (1,1), and (2,0) may be scored, e.g., a 3-cell wave front. These exemplary wave fronts may then extend diagonally in straight lines from bottom-left to top-right, and the motion of the wave front from step to step is diagonally from top-left to bottom-right through the matrix. Alignment scores may be computed sequentially or in other orders, such as by computing all the scores in the top row from left to right, followed by all the scores in the next row from left to right, etc. In this manner the diagonally sweeping diagonal wave front represents an optimal sequence of batches of scores computed simultaneously or in parallel in a series of wave front steps.

For instance, in one embodiment, a window of the reference genome containing the segment to which a read was mapped is placed on the horizontal axis, and the read is positioned on the vertical axis. In a manner such as this an array or matrix is generated, e.g., a virtual matrix, whereby the nucleotide at each position in the read may be compared with the nucleotide at each position in the reference window. As the wave front passes over the array, all potential ways of aligning the read to the reference window are considered, including if changes to one sequence would be required to make the read match the reference sequence, such as by changing one or more nucleotides of the read to other nucleotides, or inserting one or more new nucleotides into one sequence, or deleting one or more nucleotides from one sequence.

An alignment score, representing the extent of the changes that would be required to be made to achieve an exact alignment, is generated, wherein this score and/or other associated data may be stored in the given cells of the array. Each cell of the array corresponds to the possibility that the nucleotide at its position on the read axis aligns to the nucleotide at its position on the reference axis, and the score generated for each cell represents the partial alignment terminating with the cell's positions in the read and the reference window. The highest score generated in any cell represents the best overall alignment of the read to the reference window. In various instances, the alignment may be global, where the entire read must be aligned to some portion of the reference window, such as using a Needleman-Wunsch or similar algorithm; or in other instances, the alignment may be local, where only a portion of the read may be aligned to a portion of the reference window, such as by using a Smith-Waterman or similar algorithm.

The size of the reference window may be any suitable size. For instance, since a typical read may be from about 100 to about 1,000 nucleotides long, the length of the reference window accordingly, in some instances, may be from about 100 to 1,000 nucleotides long or longer. However, in some instances, the length of the reads may be greater, and/or the length of the reference window can be greater such as about 10,000, 25,000, 50,000, 75,000, 100,000, 200,000 nucleotides long or more. It may be advantageous for the reference window to be padded somewhat longer than the read, such as including 32 or 64 or 128 or 200 or even 500 extra nucleotides in the reference window beyond the extremes of the reference genome segment to which the read was mapped, such as to permit insertions and/or deletions near the ends of the read to be fully evaluated.

For instance, if only a portion of the read was mapped to a segment of the reference, extra padding may be applied to the reference window corresponding to the unmapped portions of the read, or longer by some factor, such as 10% or 15% or 20% or 25% or even 50% or more, so as to allow the unmapped portions of the read space to fully align to the reference window. In some instances, however, the length of the reference window may be selected to be shorter than the length of the reads, such as where a long portion of the read is not mapped to the reference, such as more or less than 1000 nucleotides at one end of the read, such as in order to focus the alignment on the mapped portion. The alignment wave front may be of unlimited length, or limited to any suitable fixed length, or of variable length. For instance, all cells along the entire diagonal line of each wave front step extending fully from one axis to the other axis may be scored. Alternatively, a limited length, such as 64 cells wide, may be scored on each wave front step, such as by tracing a diagonally 64-cell wide band of scored cells through the matrix, and leaving cells outside of this band unscored. In some instances, it may be unnecessary to calculate scores far from a band around the true alignment path, and substantial work may be saved by computing scores only in a limited bandwidth, using a fixed length scoring wave front, as herein described.

Accordingly, in various instances, an alignment function may be performed, such as on the data obtained from the mapping module. Hence, in various instances, an alignment function may form a module, such as an alignment module, that may form part of a system, e.g., a pipeline, that is used, such as in addition with a mapping module, in a process for determining the actual entire genomic sequence, or a portion thereof, of an individual. For instance, the output returned from the performance of the mapping function, such as from a mapping module, e.g., the list of possibilities as to where one or more or all of the reads maps to one or more positions in one or more reference genomes, may be employed by the alignment function so as to determine the actual sequence alignment of the subject's sequenced DNA.

Such an alignment function may at times be useful because, as described above, often times, for a variety of different reasons, the sequenced reads do not always match exactly to the reference genome. For instance, there may be an SNP (single nucleotide polymorphism) in one or more of the reads, e.g., a substitution of one nucleotide for another at a single position; there may be an "indel," insertion or deletion of one or more bases along one or more of the read sequences, which insertion or deletion is not present in the reference genome; and/or there may be a sequencing error (e.g., errors in sample prep and/or sequencer read and/or sequencer output, etc.) causing one or more of these apparent variations. Accordingly, when a read varies from the reference, such as by an SNP or indel, this may be because the reference differs from the true DNA sequence sampled, or because the read differs from the true DNA sequence sampled. The problem is to figure out how to correctly align the reads to the reference genome given the fact that in all likelihood the two sequences are going to vary from one another in a multiplicity of different ways.

In various instances, the input into an alignment function, such as from a mapping function, such as a prefix/suffix tree, or a Burrows/Wheeler transform, or a hash table and/or hash function, may be a list of possibilities as to where one or more reads may match to one or more positions of one or more reference sequences. For instance, for any given read, it may match any number of positions in the reference genome, such as at 1 location or 16, or 32, or 64, or 100, or 500, or 1,000 or more locations where a given read maps to in the genome. However, any individual read was derived, e.g., sequenced, from only one specific portion of the genome. Hence, in order to find the true location from where a given particular read was derived, an alignment function may be performed, e.g., a Smith-Waterman gapped or gapless alignment, a Needleman-Wunsch alignment, etc., so as to determine where in the genome one or more of the reads was actually derived, such as by comparing all of the possible locations where a match occurs and determining which of all the possibilities is the most likely location in the genome from which the read was sequenced, on the basis of which location's alignment score is greatest.

As indicated, typically, an algorithm is used to perform such an alignment function. For example, a Smith-Waterman and/or a Needleman-Wunsch alignment algorithm may be employed to align two or more sequences against one another. In this instance, they may be employed in a manner so as to determine the probabilities that for any given position where the read maps to the reference genome that the mapping is in fact the position from where the read originated. Typically these algorithms are configured so as to be performed by software, however, in various instances, such as herein presented, one or more of these algorithms can be configured so as to be executed in hardware, as described in greater detail herein below.

In particular, the alignment function operates, at least in part, to align one or more, e.g., all, of the reads to the reference genome despite the presence of one or more portions of mismatches, e.g., SNPs, insertions, deletions, structural artifacts, etc. so as to determine where the reads are likely to fit in the genome correctly. For instance, the one or more reads are compared against the reference genome, and the best possible fit for the read against the genome is determined, while accounting for substitutions and/or indels and/or structural variants. However, to better determine which of the modified versions of the read best fits against the reference genome, the proposed changes must be accounted for, and as such a scoring function may also be performed.

For example, a scoring function may be performed, e.g., as part of an overall alignment function, whereby as the alignment module performs its function and introduces one or more changes into a sequence being compared to another, e.g., so as to achieve a better or best fit between the two, for each change that is made so as to achieve the better alignment, a number is detracted from a starting score, e.g., either a perfect score, or a zero starting score, in a manner such that as the alignment is performed the score for the alignment is also determined, such as where matches are detected the score is increased, and for each change introduced a penalty is incurred, and thus, the best fit for the possible alignments can be determined, for example, by figuring out which of all the possible modified reads fits to the genome with the highest score. Accordingly, in various instances, the alignment function may be configured to determine the best combination of changes that need to be made to the read(s) to achieve the highest scoring alignment, which alignment may then be determined to be the correct or most likely alignment.

In view of the above, there are, therefore, at least two goals that may be achieved from performing an alignment function. One is a report of the best alignment, including position in the reference genome and a description of what changes are necessary to make the read match the reference segment at that position, and the other is the alignment quality score. For instance, in various instances, the output from a the alignment module may be a Compact Idiosyncratic Gapped Alignment Report, e.g., a CIGAR string, wherein the CIGAR string output is a report detailing all the changes that were made to the reads so as to achieve their best fit alignment, e.g., detailed alignment instructions indicating how the query actually aligns with the reference. Such a CIGAR string readout may be useful in further stages of processing so as to better determine that for the given subject's genomic nucleotide sequence, the predicted variations as compared against a reference genome are in fact true variations, and not just due to machine, software, or human error.

As set forth above, in various embodiments, alignment is typically performed in a sequential manner, wherein the algorithm and/or firmware receives read sequence data, such as from a mapping module, pertaining to a read and one or more possible locations where the read may potentially map to the one or more reference genomes, and further receives genomic sequence data, such as from one or more memories, such as associated DRAMs, pertaining to the one or more positions in the one or more reference genomes to which the read may map. In particular, in various embodiments, the mapping module processes the reads, such as from a FASTQ file, and maps each of them to one or more positions in the reference genome to where they may possibly align. The aligner then takes these predicted positions and uses them to align the reads to the reference genome, such as by building a virtual array by which the reads can be compared with the reference genome.

In performing this function the aligner evaluates each mapped position for each individual read and particularly evaluates those reads that map to multiple possible locations in the reference genome and scores the possibility that each position is the correct position. It then compares the best scores, e.g., the two best scores, and makes a decision as to where the particular read actually aligns. For instance, in comparing the first and second best alignment scores, the aligner looks at the difference between the scores, and if the difference between them is great, then the confidence score that the one with the bigger score is correct will be high. However, where the difference between them is small, e.g., zero, then the confidence score in being able to tell from which of the two positions the read actually is derived is low, and more processing may be useful in being able to clearly determine the true location in the reference genome from where the read is derived.

Hence, the aligner in part is looking for the biggest difference between the first and second best confidence scores in making its call that a given read maps to a given location in the reference genome. Ideally, the score of the best possible choice of alignment is significantly greater than the score for the second best alignment for that sequence. There are many different ways an alignment scoring methodology may be implemented, for instance, each cell of the array may be scored or a sub-portion of cells may be scored, such as in accordance with the methods disclosed herein. Typically, each alignment match, corresponding to a diagonal step in the alignment matrix, contributes a positive score, such as +1, if the corresponding read and reference nucleotides match; and a negative score, such as −4, if the two nucleotides mismatch. Further, each deletion from the reference, corresponding to a horizontal step in the alignment matrix, contributes a negative score, such as −7, and each insertion into the reference, corresponding to a vertical step in the alignment matrix, contributes a negative score, such as −7.

In various instances, scoring parameters for nucleotide matches, nucleotide mismatches, insertions, and deletions may have any various positive or negative or zero values. In various instances, these scoring parameters may be modified based on available information. For instance, in certain instances, alignment gaps (insertions or deletions) are penalized by an affine function of the gap length, for example −7 for the first deleted (resp. inserted) nucleotide, but only −1 for each additional deleted (resp. inserted) nucleotide in continuous sequence. In various implementations, affine gap penalties may be achieved by splitting gap (insertion or deletion) penalties into two components, such as a gap open penalty, e.g. −6, applied to the first step in a gap; and a gap extend penalty, e.g. −1, applied to every or further steps in the gap. Affine gap penalties may yield more accurate alignments, such as by letting alignments containing long insertions or deletions achieve appropriately high scores. Further, each lateral move may have the same or different costs, such as the same cost per step, and/or where gaps occur, such gaps can come at a higher or lower costs, such that the cost for lateral movements of the aligner may be less expensive than the costs for gaps.

Accordingly, in various embodiments, affine gap scoring may be implemented, however, this can be expensive in software and/or hardware, because it typically requires a plurality, e.g., 3 scores, for each cell to be scored, and hence, in various embodiments affine gap scoring is not implemented. In various instances, scoring parameters may also be sensitive to "base quality scores" corresponding to nucleotides in the read. Some sequenced DNA read data, in formats such as FASTQ, may include a base quality score associated with each nucleotide, indicating an estimated probability that the nucleotide is incorrect, e.g. due to a sequencing error. In some read data, base quality scores may indicate the likelihood that an insertion and/or deletion sequencing error is present in or adjacent to each position, or additional quality scores may provide this information separately. More accurate alignments, therefore, may be achieved by making scoring parameters, including any or all of nucleotide match scores, nucleotide mismatch scores, gap (insertion and/or deletion) penalties, gap open penalties, and/or gap extend penalties, vary according to a base quality score associated with the current read nucleotide or position. For example, score bonuses and/or penalties could be made smaller when a base quality score indicates a high probability a sequencing or other error being present. Base quality sensitive scoring may be implemented, for example, using a fixed or configurable lookup-table, accessed using a base quality score, which returns corresponding scoring parameters.

In a hardware implementation in an integrated circuit, such as an FPGA or ASIC, a scoring wave front may be implemented as a linear array of scoring cells, such as 16 cells, or 32 cells, or 64 cells, or 128 cells or the like. Each of the scoring cells may be built of digital logic elements in a wired configuration to compute alignment scores. Hence, for each step of the wave front, for instance, each clock cycle, or some other fixed or variable unit of time, each of the scoring cells, or a portion of the cells, computes the score or scores required for a new cell in the virtual alignment matrix. Notionally, the various scoring cells are considered to be in various positions in the alignment matrix, corresponding to a scoring wave front as discussed herein, e.g., along a straight line extending from bottom-left to top-right in the matrix. As is well understood in the field of digital logic design, the physical scoring cells and their comprised digital logic need not be physically arranged in like manner on the integrated circuit.

Accordingly, as the wave front takes steps to sweep through the virtual alignment matrix, the notional positions of the scoring cells correspondingly update each cell, for example, notionally "moving" a step to the right, or for example, a step downward in the alignment matrix. All scoring cells make the same relative notional movement, keeping the diagonal wave front arrangement intact. Each time the wave front moves to a new position, e.g., with a vertical downward step, or a horizontal rightward step in the matrix, the scoring cells arrive in new notional positions, and compute alignment scores for the virtual alignment matrix cells they have entered. In such an implementation, neighboring scoring cells in the linear array are coupled to communicate query (read) nucleotides, reference nucleotides, and previously calculated alignment scores. The nucleotides of the reference window may be fed sequentially into one end of the wave front, e.g., the top-right scoring cell in the linear array, and may shift from there sequentially down the length of the wave front, so that at any given time, a segment of reference nucleotides equal in length to the number of scoring cells is present within the cells, one successive nucleotide in each successive scoring cell.

For instance, each time the wave front steps horizontally, another reference nucleotide is fed into the top-right cell, and other reference nucleotides shift down-left through the wave front. This shifting of reference nucleotides may be the underlying reality of the notional movement of the wave front of scoring cells rightward through the alignment matrix. Hence, the nucleotides of the read may be fed sequentially into the opposite end of the wave front, e.g. the bottom-left scoring cell in the linear array, and shift from there sequentially up the length of the wave front, so that at any given time, a segment of query nucleotides equal in length to the number of scoring cells is present within the cells, one successive nucleotide in each successive scoring cell. Likewise, each time the wave front steps vertically, another query nucleotide is fed into the bottom-left cell, and other query nucleotides shift up-right through the wave front. This shifting of query nucleotides is the underlying reality of the notional movement of the wave front of scoring cells downward through the alignment matrix. Accordingly, by commanding a shift of reference nucleotides, the wave front may be moved a step horizontally, and by commanding a shift of query nucleotides, the wave front may be moved a step vertically. Hence, to produce generally diagonal wave front movement, such as to follow a typical alignment of query and reference sequences without insertions or deletions, wave front steps may be commanded in alternating vertical and horizontal directions.

Accordingly, neighboring scoring cells in the linear array may be coupled to communicate previously calculated alignment scores. In various alignment scoring algorithms, such as a Smith-Waterman or Needleman-Wunsch, or such variant, the alignment score(s) in each cell of the virtual alignment matrix may be calculated using previously calculated scores in other cells of the matrix, such as the three cells positioned immediately to the left of the current cell, above the current cell, and diagonally up-left of the current cell. When a scoring cell calculates new score(s) for another matrix position it has entered, it must retrieve such previously calculated scores corresponding to such other matrix positions. These previously calculated scores may be obtained from storage of previously calculated scores within the same cell, and/or from storage of previously calculated scores in the one or two neighboring scoring cells in the linear array. This is because the three contributing score positions in the virtual alignment matrix (immediately left, above, and diagonally up-left) would have been scored either by the current scoring cell, or by one of its neighboring scoring cells in the linear array.

For instance, the cell immediately to the left in the matrix would have been scored by the current scoring cell, if the most recent wave front step was horizontal (rightward), or would have been scored by the neighboring cell down-left in the linear array, if the most recent wave front step was vertical (downward). Similarly, the cell immediately above in the matrix would have been scored by the current scoring cell, if the most recent wave front step was vertical (downward), or would have been scored by the neighboring cell up-right in the linear array, if the most recent wave front step was horizontal (rightward). Particularly, the cell diagonally up-left in the matrix would have been scored by the current scoring cell, if the most recent two wave front steps were in different directions, e.g., down then right, or right then down, or would have been scored by the neighboring cell up-right in the linear array, if the most recent two wave front steps were both horizontal (rightward), or would have been scored by the neighboring cell down-left in the linear array, if the most recent two wave front steps were both vertical (downward).

Accordingly, by considering information on the last one or two wave front step directions, a scoring cell may select the appropriate previously calculated scores, accessing them within itself, and/or within neighboring scoring cells, utilizing the coupling between neighboring cells. In a variation, scoring cells at the two ends of the wave front may have their outward score inputs hard-wired to invalid, or zero, or minimum-value scores, so that they will not affect new score calculations in these extreme cells. A wave front being thus implemented in a linear array of scoring cells, with such coupling for shifting reference and query nucleotides through the array in opposing directions, in order to notionally move the wave front in vertical and horizontal, e.g., diagonal, steps, and coupling for accessing scores previously computed by neighboring cells in order to compute alignment score(s) in new virtual matrix cell positions entered by the wave front, it is accordingly possible to score a band of cells in the virtual matrix, the width of the wave front, such as by commanding successive steps of the wave front to sweep it through the matrix.

For a new read and reference window to be aligned, therefore, the wave front may begin positioned inside the scoring matrix, or, advantageously, may gradually enter the scoring matrix from outside, beginning e.g., to the left, or above, or diagonally left and above the top-left corner of the matrix. For instance, the wave front may begin with its top-left scoring cell positioned just left of the top-left cell of the virtual matrix, and the wave front may then sweep rightward into the matrix by a series of horizontal steps, scoring a horizontal band of cells in the top-left region of the matrix. When the wave front reaches a predicted alignment relationship between the reference and query, or when matching is detected from increasing alignment scores, the wave front may begin to sweep diagonally down-right, by alternating vertical and horizontal steps, scoring a diagonal band of cells through the middle of the matrix. When the bottom-left wave front scoring cell reaches the bottom of the alignment matrix, the wave front may begin sweeping rightward again by successive horizontal steps, until some or all wave front cells sweep out of the boundaries of the alignment matrix, scoring a horizontal band of cells in the bottom-right region of the matrix.

In a variation, increased efficiency may be obtained from the alignment wave front by sharing its scoring cells between two successive alignment operations. A next alignment matrix having been established in advance, as the top-right portion of the wave front exits the bottom-right region of the current alignment matrix, it may enter, immediately, or after crossing a minimum gap such as one cell or three cells, the top-right region of the next alignment matrix. In this manner, the horizontal wave front sweep out of one alignment matrix can be the same motion as the horizontal wave front sweep into the next alignment matrix. Doing this may include the reference and query bases of the next alignment to be fed into those scoring cells crossing into the next alignment matrix, and can reduce the average time consumed per alignment by the time to execute a number of wave front steps almost equal to the number of alignment cells in the wave front, e.g., such as 64 or 63 or 61 steps, which may take e.g. 64 or 63 or 61 clock cycles.

The number of scoring cells in an implementation of an alignment wave front may be selected to balance various factors, including alignment accuracy, maximum insertion and deletion length, area, cost, and power consumption of the digital logic, clock frequency of the aligner logic, and performance of the overall integrated circuit. A long wave front is desirable for good alignment accuracy, especially because a wave front of N cells can align across indels approximately N nucleotides long, or slightly shorter. But a longer wave front costs more logic, which consumes more power. Further, a longer wave front can increase wire routing complexity and delays on the integrated circuit, leading to lower maximum clock frequencies, reducing net aligner performance. Further still, if an integrated circuit has a limited size or power consumption, using a longer wave front may require less logic to be implemented on the integrated circuit elsewhere, such as replicating fewer entire wave fronts, or other aligner or mapper logic components, this decreasing net performance of the integrated circuit. In one particular embodiment, 64 scoring cells in the wave front may give an acceptable balance of these factors.

Accordingly, where the wave front is X, e.g., 64 scoring cells wide, the scored band in the alignment matrix will likewise be 64 cells wide (measured diagonally). The matrix cells outside of this band do not necessarily need to be processed nor their scores calculated, provided that the optimal (best-scoring) alignment path through the matrix stays within the scored band. In a relatively small matrix, therefore, used to align relatively short reads, e.g., 100 nucleotide or 250 nucleotide reads, this may be a safe assumption, such as if the wave front sweeps a perfect diagonal along the predicted aligned position of the read. However, in some instances, such as in a large alignment matrix used to align long reads, e.g., 1000 or 10,000 or 100,000 nucleotides, there may be a substantial risk of accumulated indels causing the true alignment to deviate from a perfect diagonal, sufficiently far in aggregate that it may escape the scored band.

In such instances, it may be useful to steer the wave front so that the highest set of scores will be near the center of the wave front. Consequently, as the wave front performs its sweep, if the highest scores start to move one way or the other, e.g., left to right, the wave front is shifted over to track this move. For instance, if the highest scores are observed in scoring cells substantially up-right from the center of the wave front, the wave front may be steered some distance straight rightward by successive horizontal steps, until the highest scores return near the center of the wave front. Accordingly, an automatic steering mechanism may be implemented in the wave front control logic, to determine a steering target position within the length of the wave front, based on current and past scores observed in the wave front scoring cells, and to steer the wave front toward this target if it is off-center. More particularly, the position of the maximum score in the most recently scored wave front position may be used as a steering target. This is an effective method in some instances. In some instances, however, the maximum score position may be a poor steering target. For instance, with some combinations of alignment scoring parameters, when a long indel commences, and scores accordingly begin to decline, a pattern of two higher-score peaks with a lower-score valley between them can form along the wave front, the two peaks drifting apart as the indel continues.

Because it cannot be easily determined whether the event in progress is an insertion or a deletion, it is important for the wave front to track diagonally until successful matching commences again, either some distance to the right for a deletion, or some distance downward for an insertion. But if two spreading score peaks form, one of them is likely to be slightly higher than the other, and could pull the automatic steering in that direction, causing the wave front to lose the alignment if the actual indel was in the other direction. A more robust method, therefore, may be to subtract a delta value from the maximum observed wave front score to determine a threshold score, identify the two extreme scoring cells at least equal to this threshold score, and use the midpoint between these extreme cells as the steering target. This will tend to guide diagonally between a two-peak score pattern. Other steering criteria can readily be applied, however, which serve to keep higher scores near the center of the wave front. If there is a delayed reaction between obtaining scores from wave front scoring cells and making a corresponding steering decision, hysteresis can advantageously be applied to compensate for steering decisions made in the intervening time, to avoid oscillating patterns of automatic wave front steering.

One or more of such alignment procedures may be performed by any suitable alignment algorithm, such as a Needleman-Wunsch alignment algorithm and/or a Smith-Waterman alignment algorithm that may have been modified to accommodate the functionality herein described. In general both of these algorithms and those like them basically perform, in some instances, in a similar manner. For instance, as set forth above, these alignment algorithms typically build the virtual array in a similar manner such that, in various instances, the horizontal top boundary may be configured to represent the genomic reference sequence, which may be laid out across the top row of the array according to its base pair composition. Likewise, the vertical boundary may be configured to represent the sequenced and mapped query sequences that have been positioned in order, downwards along the first column, such that their nucleotide sequence order is generally matched to the nucleotide sequence of the reference to which they mapped. The intervening cells may then be populated with scores as to the probability that the relevant base of the query at a given position, is positioned at that location relative to the reference. In performing this function, a swath may be moved diagonally across the matrix populating scores within the intervening cells and the probability for each base of the query being in the indicated position may be determined.

With respect to a Needleman-Wunsch alignment function, which generates optimal global (or semi-global) alignments, aligning the entire read sequence to some segment of the reference genome, the wave front steering may be configured such that it typically sweeps all the way from the top edge of the alignment matrix to the bottom edge. When the wave front sweep is complete, the maximum score on the bottom edge of the alignment matrix (corresponding to the end of the read) is selected, and the alignment is back-traced to a cell on the top edge of the matrix (corresponding to the beginning of the read). In various of the instances disclosed herein, the reads can be any length long, can be any size, and there need not be extensive read parameters as to how the alignment is performed, e.g., in various instances, the read can be as long as a chromosome. In such an instance, however, the memory size and chromosome length may be limiting factor.

With respect to a Smith-Waterman algorithm, which generates optimal local alignments, aligning the entire read sequence or part of the read sequence to some segment of the reference genome, this algorithm may be configured for finding the best scoring possible based on a full or partial alignment of the read. Hence, in various instances, the wave front-scored band may not extend to the top and/or bottom edges of the alignment matrix, such as if a very long read had only seeds in its middle mapping to the reference genome, but commonly the wave front may still score from top to bottom of the matrix. Local alignment is typically achieved by two adjustments. First, alignment scores are never allowed to fall below zero (or some other floor), and if a cell score otherwise calculated would be negative, a zero score is substituted, representing the start of a new alignment. Second, the maximum alignment score produced in any cell in the matrix, not necessarily along the bottom edge, is used as the terminus of the alignment. The alignment is backtraced from this maximum score up and left through the matrix to a zero score, which is used as the start position of the local alignment, even if it is not on the top row of the matrix.

In view of the above, there are several different possible pathways through the virtual array. In various embodiments, the wave front starts from the upper left corner of the virtual array, and moves downwards towards identifiers of the maximum score. For instance, the results of all possible aligns can be gathered, processed, correlated, and scored to determine the maximum score. When the end of a boundary or the end of the array has been reached and/or a computation leading to the highest score for all of the processed cells is determined (e.g., the overall highest score identified) then a backtrace may be performed so as to find the pathway that was taken to achieve that highest score. For example, a pathway that leads to a predicted maximum score may be identified, and once identified an audit may be performed so as to determine how that maximum score was derived, for instance, by moving backwards following the best score alignment arrows retracing the pathway that led to achieving the identified maximum score, such as calculated by the wave front scoring cells.

This backwards reconstruction or backtrace involves starting from a determined maximum score, and working backward through the previous cells navigating the path of cells having the scores that led to achieving the maximum score all the way up the table and back to an initial boundary, such as the beginning of the array, or a zero score in the case of local alignment. During a backtrace, having reached a particular cell in the alignment matrix, the next backtrace step is to the neighboring cell, immediately leftward, or above, or diagonally up-left, which contributed the best score that was selected to construct the score in the current cell. In this manner, the evolution of the maximum score may be determined, thereby figuring out how the maximum score was achieved. The backtrace may end at a corner, or an edge, or a boundary, or may end at a zero score, such as in the upper left hand corner of the array. Accordingly, it is such a back trace that identifies the proper alignment and thereby produces the CIGAR strand readout, e.g., 3M, 2D, 8M, 4I, 16M, etc., that represents how the sample genomic sequence derived from the individual, or a portion thereof, matches to, or otherwise aligns with, the genomic sequence of the reference DNA.

Once it has been determined where each read is mapped, and further determined where each read is aligned, e.g., each relevant read has been given a position and a quality score reflecting the probability that the position is the correct alignment, such that the nucleotide sequence for the subject's DNA is known, then the order of the various reads and/or genomic nucleic acid sequence of the subject may be verified, such as by performing a back trace function moving backwards up through the array so as to determine the identity of every nucleic acid in its proper order in the sample genomic sequence. Consequently, in some aspects, the present disclosure is directed to a back trace function, such as is part of an alignment module that performs both an alignment and a back trace function, such as a module that may be part of a pipeline of modules, such as a pipeline that is directed at taking raw sequence read data, such as form a genomic sample form an individual, and mapping and/or aligning that data, which data may then be sorted.

To facilitate the backtrace operation, it is useful to store a scoring vector for each scored cell in the alignment matrix, encoding the score-selection decision. For classical Smith-Waterman and/or Needleman-Wunsch scoring implementations with linear gap penalties, the scoring vector can encode four possibilities, which may optionally be stored as a 2-bit integer from 0 to 3, for example: 0=new alignment (null score selected); 1=vertical alignment (score from the cell above selected, modified by gap penalty); 2=horizontal alignment (score from the cell to the left selected, modified by gap penalty); 3=diagonal alignment (score from the cell up and left selected, modified by nucleotide match or mismatch score). Optionally, the computed score(s) for each scored matrix cell may also be stored (in addition to the maximum achieved alignment score which is standardly stored), but this is not generally necessary for backtrace, and can consume large amounts of memory. Performing backtrace then becomes a matter of following the scoring vectors; when the backtrace has reached a given cell in the matrix, the next backtrace step is determined by the stored scoring vector for that cell, e.g.: 0=terminate backtrace; 1=backtrace upward; 2=backtrace leftward; 3=backtrace diagonally up-left.

Such scoring vectors may be stored in a two-dimensional table arranged according to the dimensions of the alignment matrix, wherein only entries corresponding to cells scored by the wave front are populated. Alternatively, to conserve memory, more easily record scoring vectors as they are generated, and more easily accommodate alignment matrices of various sizes, scoring vectors may be stored in a table with each row sized to store scoring vectors from a single wave front of scoring cells, e.g. 128 bits to store 64 2-bit scoring vectors from a 64-cell wave front, and a number of rows equal to the maximum number of wave front steps in an alignment operation. Additionally, for this option, a record may be kept of the directions of the various wavefront steps, e.g., storing an extra, e.g., 129.sup.th, bit in each table row, encoding e.g., 0 for vertical wavefront step preceding this wavefront position, and 1 for horizontal wavefront step preceding this wavefront position. This extra bit can be used during backtrace to keep track of which virtual scoring matrix positions the scoring vectors in each table row correspond to, so that the proper scoring vector can be retrieved after each successive backtrace step. When a backtrace step is vertical or horizontal, the next scoring vector should be retrieved from the previous table row, but when a backtrace step is diagonal, the next scoring vector should be retrieved from two rows previous, because the wavefront had to take two steps to move from scoring any one cell to scoring the cell diagonally right-down from it.

In the case of affine gap scoring, scoring vector information may be extended, e.g. to 4 bits per scored cell. In addition to the e.g., 2-bit score-choice direction indicator, two 1-bit flags may be added, a vertical extend flag, and a horizontal extend flag. According to the methods of affine gap scoring extensions to Smith-Waterman or Needleman-Wunsch or similar alignment algorithms, for each cell, in addition to the primary alignment score representing the best-scoring alignment terminating in that cell, a 'vertical score' should be generated, corresponding to the maximum alignment score reaching that cell with a final vertical step, and a 'horizontal score' should be generated, corresponding to the maximum alignment score reaching that cell with a final horizontal step; and when computing any of the three scores, a vertical step into the cell may be computed either using the primary score from the cell above minus a gap-open penalty, or using the vertical score from the cell above minus a gap-extend penalty, whichever is greater; and a horizontal step into the cell may be computed either using the primary score from the cell to the left minus a gap-open penalty, or using the horizontal score from the cell to the left minus a gap-extend penalty, whichever is greater. In cases where the vertical score minus a gap extend penalty is selected, the vertical extend flag in the scoring vector should be set, e.g. '1', and otherwise it should be unset, e.g. '0'.

In cases when the horizontal score minus a gap extend penalty is selected, the horizontal extend flag in the scoring vector should be set, e.g. '1', and otherwise it should be unset, e.g. '0'. During backtrace for affine gap scoring, any time backtrace takes a vertical step upward from a given cell, if that cell's scoring vector's vertical extend flag is set, the following backtrace step must also be vertical, regardless of the scoring vector for the cell above. Likewise, any time backtrace takes a horizontal step leftward from a given cell, if that cell's scoring vector's horizontal extend flag is set, the following backtrace step must also be horizontal, regardless of the scoring vector for the cell to the left. Accordingly, such a table of scoring vectors, e.g. 129 bits per row for 64 cells using linear gap scoring, or 257 bits per row for 64 cells using affine gap scoring, with some number NR of rows, is adequate to support backtrace after concluding alignment scoring where the scoring wavefront took NR steps or fewer.

For example, when aligning 300-nucleotide reads, the number of wavefront steps required may always be less than 1024, so the table may be 257.times.1024 bits, or approximately 32 kilobytes, which in many cases may be a reasonable local memory inside the integrated circuit. But if very long reads are to be aligned, e.g. 100,000 nucleotides, the memory requirements for scoring vectors may be quite large, e.g. 8 megabytes, which may be very costly to include as local memory inside the integrated circuit. For such support, scoring vector information may be recorded to bulk memory outside the integrated circuit, e.g. DRAM, but then the bandwidth requirements, e.g. 257 bits per clock cycle per aligner module, may be excessive, which may bottleneck and dramatically reduce aligner performance. Accordingly, it is desirable to have a method for disposing of scoring vectors before completing alignment, so their storage requirements can be kept bounded, e.g. to perform incremental backtraces, generating incremental partial CIGAR strings for example, from early portions of an alignment's scoring vector history, so that such early portions of the scoring vectors may then be discarded. The challenge is that the backtrace is supposed to begin in the alignment's terminal, maximum scoring cell, which unknown until the alignment scoring completes, so any backtrace begun before alignment completes may begin from the wrong cell, not along the eventual final optimal alignment path.

Hence, a method is given for performing incremental backtrace from partial alignment information, e.g., comprising partial scoring vector information for alignment matrix cells scored so far. From a currently completed alignment boundary, e.g., a particular scored wave front position, backtrace is initiated from all cell positions on the boundary. Such backtrace from all boundary cells may be performed sequentially, or advantageously, especially in a hardware implementation, all the backtraces may be performed together. It is not necessary to extract alignment notations, e.g., CIGAR strings, from these multiple backtraces; only to determine what alignment matrix positions they pass through during the backtrace. In an implementation of simultaneous backtrace from a scoring boundary, a number of 1-bit registers may be utilized, corresponding to the number of alignment cells, initialized e.g., all to '1' s, representing whether any of the backtraces pass through a corresponding position. For each step of simultaneous backtrace, scoring vectors corresponding to all the current '1' s in these registers, e.g. from one row of the scoring vector table, can be examined, to determine a next backtrace step corresponding to each '1' in the registers, leading to a following position for each '1' in the registers, for the next simultaneous backtrace step.

Importantly, it is easily possible for multiple '1' s in the registers to merge into common positions, corresponding to multiple of the simultaneous backtraces merging together onto common backtrace paths. Once two or more of the simultaneous backtraces merge together, they remain merged indefinitely, because henceforth they will utilize scoring vector information from the same cell. It has been observed, empirically and for theoretical reasons, that with high probability, all of the simultaneous backtraces merge into a singular backtrace path, in a relatively small number of backtrace steps, which e.g. may be a small multiple, e.g. 8, times the number of scoring cells in the wavefront. For example, with a 64-cell wavefront, with high probability, all backtraces from a given wavefront boundary merge into a single backtrace path within 512 backtrace steps. Alternatively, it is also possible, and not uncommon, for all backtraces to terminate within the number, e.g. 512, of backtrace steps.

Accordingly, the multiple simultaneous backtraces may be performed from a scoring boundary, e.g. a scored wavefront position, far enough back that they all either terminate or merge into a single backtrace path, e.g. in 512 backtrace steps or fewer. If they all merge together into a singular backtrace path, then from the location in the scoring matrix where they merge, or any distance further back along the singular backtrace path, an incremental backtrace from partial alignment information is possible. Further backtrace from the merge point, or any distance further back, is commenced, by normal singular backtrace methods, including recording the corresponding alignment notation, e.g., a partial CIGAR string. This incremental backtrace, and e.g., partial CIGAR string, must be part of any possible final backtrace, and e.g., full CIGAR string, that would result after alignment completes, unless such final backtrace would terminate before reaching the scoring boundary where simultaneous backtrace began, because if it reaches the scoring boundary, it must follow one of the simultaneous backtrace paths, and merge into the singular backtrace path, now incrementally extracted.

Therefore, all scoring vectors for the matrix regions corresponding to the incrementally extracted backtrace, e.g., in all table rows for wave front positions preceding the start of the extracted singular backtrace, may be safely discarded. When the final backtrace is performed from a maximum scoring cell, if it terminates before reaching the scoring boundary (or alternatively, if it terminates before reaching the start of the extracted singular backtrace), the incremental alignment notation, e.g. partial CIGAR string, may be discarded. If the final backtrace continues to the start of the extracted singular backtrace, its alignment notation, e.g., CIGAR string, may then be grafted onto the incremental alignment notation, e.g., partial CIGAR string. Furthermore, in a very long alignment, the process of performing a simultaneous backtrace from a scoring boundary, e.g., scored wave front position, until all backtraces terminate or merge, followed by a singular backtrace with alignment notation extraction, may be repeated multiple times, from various successive scoring boundaries. The incremental alignment notation, e.g. partial CIGAR string, from each successive incremental backtrace may then be grafted onto the accumulated previous alignment notations, unless the new simultaneous backtrace or singular backtrace terminates early, in which case accumulated previous alignment notations may be discarded. The eventual final backtrace likewise grafts its alignment notation onto the most recent accumulated alignment notations, for a complete backtrace description, e.g. CIGAR string.

Accordingly, in this manner, the memory to store scoring vectors may be kept bounded, assuming simultaneous backtraces always merge together in a bounded number of steps, e.g. 512 steps. In rare cases where simultaneous backtraces fail to merge or terminate in the bounded number of steps, various exceptional actions may be taken, including failing the current alignment, or repeating it with a higher bound or with no bound, perhaps by a different or traditional method, such as storing all scoring vectors for the complete alignment, such as in external DRAM. In a variation, it may be reasonable to fail such an alignment, because it is extremely rare, and even rarer that such a failed alignment would have been a best-scoring alignment to be used in alignment reporting.

In an optional variation, scoring vector storage may be divided, physically or logically, into a number of distinct blocks, e.g. 512 rows each, and the final row in each block may be used as a scoring boundary to commence a simultaneous backtrace. Optionally, a simultaneous backtrace may be required to terminate or merge within the single block, e.g. 512 steps. Optionally, if simultaneous backtraces merge in fewer steps, the merged backtrace may nevertheless be continued through the whole block, before commencing an extraction of a singular backtrace in the previous block. Accordingly, after scoring vectors are fully written to block N, and begin writing to block N+1, a simultaneous backtrace may commence in block N, followed by a singular backtrace and alignment notation extraction in block N-1. If the speed of the simultaneous backtrace, the singular backtrace, and alignment scoring are all similar or identical, and can be performed simultaneously, e.g., in parallel hardware in an integrated circuit, then the singular backtrace in block N-1 may be simultaneous with scoring vectors filling block N+2, and when block N+3 is to be filled, block N-1 may be released and recycled.

Thus, in such an implementation, a minimum of 4 scoring vector blocks may be employed, and may be utilized cyclically. Hence, the total scoring vector storage for an aligner module may be 4 blocks of 257×512 bits each, for example, or approximately 64 kilobytes. In a variation, if the current maximum alignment score corresponds to an earlier block than the current wavefront position, this block and the previous block may be preserved rather than recycled, so that a final backtrace may commence from this position if it remains the maximum score; having an extra 2 blocks to keep preserved in this manner brings the minimum, e.g., to 6 blocks.

In another variation, to support overlapped alignments, the scoring wave front crossing gradually from one alignment matrix to the next as described above, additional blocks, e.g. 1 or 2 additional blocks, may be utilized, e.g., 8 blocks total, e.g., approximately 128 kilobytes. Accordingly, if such a limited number of blocks, e.g., 4 blocks or 8 blocks, is used cyclically, alignment and backtrace of arbitrarily long reads is possible, e.g., 100,000 nucleotides, or an entire chromosome, without the use of external memory for scoring vectors. It is to be understood, such as with reference to the above, that although a mapping function may in some instances have been described, such as with reference to a mapper, and/or an alignment function may have in some instances been described, such as with reference to an aligner, these different functions may be performed sequentially by the same architecture, which has commonly been referenced in the art as an aligner. Accordingly, in various instances, both the mapping function and the aligning function, as herein described may be performed by a common architecture that may be understood to be an aligner, especially in those instances wherein to perform an alignment function, a mapping function need first be performed.

In view of the above, in particular embodiments, a banded Smith-Waterman alignment may be performed, such as by a suitably configured integrated circuit, by generating a virtual matrix of all possible alignments between the mapped seeds and the reference, and running a banded wavefront of a given number of parallel scoring cells through the matrix so as to score the various potential alignments. The number of parallel scoring cells may be any suitable number, but in certain instances, may be about 56 parallel scoring cells. The wavefront can be configured such that it sweeps through the virtual alignment matrix, scoring cells it passes over. In such an instance, the wavefront may further be configured to automatically steer itself so as to track accumulated indels, such as in long reads. Score sums for candidate alignment pairs may be compared, such as where penalties for divergence of observed from expected insert length may be applied. Alignment records for best pair scores, with CIGAR strings and estimated MAPQs, may then be streamed back to the host memory by DMA over PCIe or other interconnect, e.g., QPI, and written to the file system, such as in SAM or BAM format, such as for further processing, such as to be used in the performance of a sorting and/or a variant call operation, as herein described below.

More particularly, as set forth herein, in various instances, an integrated circuit is provided where the integrated circuit is formed of a plurality of pre-configured hardwired digital logic circuits that have been arranged as processing engines. In various such instances, the processing engine may be configured to perform one or more pre-configured steps, such as in the operation of an alignment function. Accordingly, the processing engine may be configured for performing an alignment step, such as part of a sequence analysis pipeline. Particularly, in such an instance, the integrated circuit may include one or more processing engines that are in a preconfigured, hardwired arrangement so as to form an alignment module for performing an alignment function, such as to align a selected read to one or more positions in one or more segments of one or more genetic reference sequences.

A central concern in performing an alignment operation as described herein, however, is to be able to achieve better quality results at better speeds than can be achieved otherwise, such as by performing a typical alignment function in software known in the art. Accordingly, in various instances, the devices, systems, and their methods of use, as herein disclosed, may be directed to optimizing the speed, performance, and efficiency of performing an alignment function. For instance, in some embodiments, such enhancements may be achieved by using regressive settings, such as for enhancing preexisting configurations, and in some embodiments, these enhancements may be achieved by reconfiguring the devices and systems herein disclosed. For example, an alignment function, as herein disclosed, may be enhanced such as by configuring the alignment protocol so as to be performed in stages.

More particularly, in various instances, the devices, systems, and their methods of use of the present disclosure may be configured for performing one or more of a full-read gapless and/or gapped alignments that may then be scored so as to determine the appropriate alignment for the reads in the dataset. However, in various instances, a gapless alignment procedure may be performed on data to be processed, which gapless alignment procedure may then be followed by one or more of a gapped alignment, and/or by a selective Smith-Waterman alignment procedure. For instance, in a first step, a gapless alignment chain may be generated. As described herein, such gapless alignment functions may be performed quickly, such as without the need for accounting for gaps, which after a first step of performing a gapless alignment, may then be followed by then performing a gapped alignment.

For example, an alignment function may be performed in order to determine how any given nucleotide sequence, e.g., read, aligns to a reference sequence without the need for inserting gaps in one or more of the reads and/or reference. An important part of performing such an alignment function is determining where and how there are mismatches in the sequence in question versus the sequence of the reference genome. However, because of the great homology within the human genome, in theory, any given nucleotide sequence is going to largely match a representative reference sequence. Where there are mismatches, these will likely be due to a single nucleotide polymorphism, which is relatively easy to detect, or they will be due to an insertion or deletion in the sequences in question, which are much more difficult to detect.

Consequently, in performing an alignment function, the majority of the time, the sequence in question is going to match the reference sequence, and where there is a mismatch due to an SNP, this will easily be determined. Hence, a relatively large amount of processing power is not required to perform such analysis. Difficulties arise, however, where there are insertions or deletions in the sequence in question with respect to the reference sequence, because such insertions and deletions amount to gaps in the alignment. Such gaps require a more extensive and complicated processing platform so as to determine the correct alignment. Nevertheless, because there will only be a small percentage of indels, only a relatively smaller percentage of gapped alignment protocols need be performed as compared to the millions of gapless alignments performed. Hence, only a small percentage of all of the gapless alignment functions result in a need for further processing due to the presence of an indel in the sequence, and therefore will need a gapped alignment.

When an indel is indicated in a gapless alignment procedure, only those sequences get passed on to an alignment engine for further processing, such as an alignment engine configured for performing an advanced alignment function, such as a Smith Waterman alignment (SWA). Thus, because either a gapless or a gapped alignment is to be performed, the devices and systems disclosed herein are a much more efficient use of resources. More particularly, in certain embodiments, both a gapless and a gapped alignment may be performed on a given selection of sequences, e.g., one right after the other, then the results are compared for each sequence, and the best result is chosen. Such an arrangement may be implemented, for instance, where an enhancement in accuracy is desired, and an increased amount of time and resources for performing the required processing is acceptable.

However, in various instances, the processes and devices set forth herein may be configured in such a manner as to only perform a gapless alignment on a given sequence when that sequence has been identified as likely to have an indel present in the sequence, and where an indel is discovered, only then is a more intensive processing protocol, such as a Smith Waterman alignment, performed. In such an instance, where a gapless alignment is being performed and the results indicate that an indel may be present, those gapless alignment results may be discarded and a gapped alignment may be initiated and performed. Hence, typically, comparing and choosing the best results between a gapped and a gapless alignment may not be required, and processing time and resources are saved. For example, a perfect alignment protocol may be employed, such as without the need for employing a more resource intensive alignment function, and where there is evidence that an indel may be present in the alignment, only then a gapped alignment may be performed.

Particularly, in various instances, a first alignment step may be performed without engaging a processing intensive Smith Waterman function. Hence, a plurality of gapless alignments may be performed in a less resource intensive, less time consuming manner, and because less resources are needed less space need be dedicated for such processing on the chip. Thus, more processing may be performed, using less processing elements, requiring less time, therefore, more alignments can be done, and better accuracy can be achieved. More particularly, less chip resource-implementations for performing Smith Waterman alignments need be dedicated using less chip area, as it does not require as much chip area for the processing elements required to perform gapless alignments as it does for performing a gapped alignment. As the chip resource requirements go down, the more processing can be performed in a shorter period of time, and with the more processing that can be performed, the better the accuracy can be achieved.

Accordingly, in such instances, a gapless alignment protocol, e.g., to be performed by suitably configured gapless alignment resources, may be employed. For example, as disclosed herein, in various embodiments, an alignment processing engine is provided such as where the processing engine is configured for receiving digital signals, e.g., representing one or more reads of genomic data, such as digital data denoting one or more nucleotide sequences, from an electronic data source, and mapping and/or aligning that data to a reference sequence, such as by first performing a gapless alignment function on that data, which gapless alignment function may then be followed, if necessary, by a gapped alignment function, such as by performing a Smith Waterman alignment protocol.

Consequently, in various instances, a gapless alignment function is performed on a contiguous portion of the read, e.g., employing a gapless aligner, and if the gapless alignment goes from end to end, e.g., the read is complete, a gapped alignment is not performed. However, if the results of the gapless alignment are indicative of their being an indel present, e.g., the read is clipped or otherwise incomplete, then a gapped alignment may be performed. Thus, the ungapped alignment results may be used to determine if a gapped alignment is needed, for instance, where the ungapped alignment is extended into a gap region but does not extend the entire length of the read, such as where the read may be clipped, e.g., soft clipped to some degree, and where clipped then a gapped alignment may be performed.

Hence, in various embodiments, based on the completeness and alignment scores, it is only if the gapless alignment ends up being clipped, e.g., does not go end to end, that a gapped alignment is performed. More particularly, in various embodiments, the best identifiable gapless and/or gapped alignment score may be estimated and used as a cutoff line for deciding if the score is good enough to warrant further analysis, such as by performing a gapped alignment. Thus, the completeness of alignment, and its score, may be employed such that a high score is indicative of the alignment being complete, and therefore, ungapped, and a lower score is indicative of the alignment not being complete, and a gapped alignment needing to be performed. Hence, where a high score is attained a gapped alignment is not performed, but only when the score is low enough is the gapped alignment performed.

Of course, in various instances a brute force alignment approach may be employed such that the number of gapped and/or gapless aligners are deployed in the chip architecture, so as to allow for a greater number of alignments to be performed, and thus a larger amount of data may be looked at. For instance, a larger number of Smith-Waterman aligners may be fabricated into the silicon space on the chip allowing for greater parallel alignment processing. Nevertheless, even though a lot more data may be processed a lot more time for performing such processing may be required making the run time longer. However, in such an instance, this may be implemented in an FPGA or it may be implemented in a Structured ASIC or ASIC.

More particularly, in various embodiments, each mapping and/or aligning engine may include one or more, e.g., two Smith-Waterman, aligner modules. In certain instances, these modules may be configured so as to support global (end-to-end) gapless alignment and/or local (clipped) gapped alignment, perform affine gap scoring, and can be configured for generating unclipped score bonuses at each end. Base-quality sensitive match and mismatch scoring may also be supported. Where two alignment modules are included, e.g., as part of the integrated circuit, for example, each Smith-Waterman aligner may be constructed as an anti-diagonal wavefront of scoring cells, which wavefront 'moves' through a virtual alignment rectangle, scoring cells that it sweeps through.

The wavefront may be of any suitable size but may typically range from about 30 to about 80 scoring cells, such as from about 40 to about 70, for instance about 50 to about 60, including 56 scoring cells long. In such an instance, for every clock cycle, the 56 wavefront cells move diagonally down through the matrix and calculate all 3 scores necessary for the performance of the Smith-Waterman with affine gap scoring methodology, e.g., for each 56 new cells in the matrix. So being for each clock cycle, the wavefront, or alignment window, can step either one cell horizontally, or one cell vertically, where this virtual movement is accomplished by shifting either the reference and/or query data window seen by the wavefront. Hence, by alternating the horizontal and vertical steps, the wavefront can accomplish a downward diagonal movement thereby scoring a diagonal band through the alignment matrix rectangle. Note that the width of this scored band is 56 cells measured diagonally, but 112 cells measured horizontally or vertically, and thus indels of more than 50 bases are capable of being detected.

However, as described above, for longer reads, the Smith-Waterman wavefront may also be configured to support automatic steering, so as to track the best alignment through accumulated indels, such as to ensure that the alignment wavefront and cells being scored do not escape the scoring band. In the background, logic engines may be configured to examine current wavefront scores, find the maximums, flag the subsets of cells over a threshold distance below the maximum, and target the midpoint between the two extreme flags. In such an instance, auto-steering may be configured to run diagonally when the target is at the wavefront center, but may be configured to run straight horizontally or vertically as needed to re-center the target if it drifts, such as due to the presence of indels.

For instance, in execution, during diagonal matching, the wavefront exhibits a high score ridge along the true alignment, which keeps the alignment window centered. However, when an indel is entered, persistent matching temporarily stops, and scores may decay across the wavefront. During this period, the target remains near the center, and the wavefront tracks diagonally. Yet, after the indel is traversed, matching commences again at some corresponding horizontal or vertical offset, and the scores start increasing off-center in the wavefront. When this becomes unmistakable, the target position jumps to the new high scores, and auto-steering veers the wavefront in that direction, until the high score ridge is again centered.

Score choice information (e.g., 4 bits per wavefront cell, or 224 bits per cycle) paints into local memories during alignment, and an alignment backtrace may be performed and accomplished by re-reading it in the background while the next alignment is being scored. Thus, in a manner such as this, the wavefront may be kept busy almost full time. For alignments longer than a few thousand bases, an incremental backtrace method may be used to keep the local memory footprint bounded, so no DRAM bandwidth is consumed during alignment except to fetch the reference sequence itself.

Accordingly, as a preliminary stage, each single-diagonal seed chain may be extended through the matrix by gapless alignment to the reference. Hence, for single-ended reads, the best local alignment score is reported in a SAM/BAM output. Whereas seed chains with seeds on multiple diagonals, or rescue scans with inconsistent match positions, may be forwarded to a gapped alignment module. Consequently, in various instances, a Gapped Smith-Waterman alignment (GSWA) may be performed. However, to conserve resources, the GSWA may typically be performed only for gapless alignments that meet one or both of the following criteria: (a) the alignments were clipped, and (b) assuming indels as the explanation, could potentially contend for best alignments. In certain instances, inconsistent alignments of mapped seeds and/or rescue matches may also be considered evidence of indels, and in such instances may automatically trigger a gapped Smith-Waterman alignment. Accordingly, soft clipping may be supported as with gapped alignment, but in such instances no indels may be permitted. The scores and clipping of gapless alignments may then be examined so as to determine if and where gapped alignment should follow.

For example, in addition to the primary alignment, up to three supplementary (chimeric) alignments can be reported per read. In such an instance, clipped local alignment results may be considered in competition with each other if they overlap in the read by at least half the shorter alignment length; otherwise they may be eligible to be reported separately. Optionally, secondary (suboptimal) alignments can also be reported, up to a limit, e.g., of four alignments total per read. Hence, for paired ends, alignment pair scores may be calculated, such as by subtracting a pairing penalty from the sum of the two alignment scores. This pairing penalty may represent the log likelihood of an insert length so far from the empirical mean, up to a maximum for unpaired alignments. The best pair score is then selected for output.

Consequently, if a gapless alignment is found to extend to both ends without clipping, then its results are taken to be accurate and such alignment need not be submitted to the more expensive gapped alignment stage. Furthermore, if one gapless alignment is near the maximum score, it can often be determined that low-scoring clipped gapless alignments are not in contention for achieving the best gapped alignment score, even if their clipping is explained by short indels with good potential matching afterward. In such an instance, these alignments likewise need not be submitted to the gapped alignment stage, although their scores may be retained so as to improve the MAPQ estimates for better determining other winning alignments.

MAPQ is estimated primarily in proportion to the difference between the best alignment or pair score and the second-best competing score (e.g., competing with alignments substantially overlapping in the read). The second-best pair score may be determined separately for each read in a pair, considering only alignment pairs (properly paired or otherwise) not duplicating the best-pair alignment of the current read, and thus MAPQ estimates may sometimes differ in paired alignments. In determining MAPQ, MAPQ may be further penalized in proportion to the log of the count of alignment or pair scores very near the second-best score. The coefficient translating alignment score deltas to Phred scale MAPQ shrinks in proportion to the square of the log of the read length, so that a given number of SNP differences yields higher mapping confidence with short reads, and lower confidence with long reads.

Accordingly, read alignment via a gapless or gapped Smith-Waterman type of algorithm may be triggered at each candidate position. Alignment scores for read-pairs may be adjusted according to a calculated and expected insert size(s). The best alignment and the associated MAPQ score for each read may then be sent from the board back to the host software. Alignments then may be sorted, as described herein above, and/or marked as duplicates and saved to a disk, such as in a SAM or BAM format. The platform pipeline may further be configured such that it reads compressed or uncompressed FASTQ files, and writes SAM or compressed/uncompressed BAM files, such as by using hardware acceleration for compression/decompression. The pipeline can also be constructed so as to also convert base calling format (BCL) files to reads and base qualities.

The output from the alignment module is a SAM (Text) or BAM (e.g., binary version of a SAM) file along with a mapping quality score (MAPA), which quality score reflects the confidence that the predicted and aligned location of the read to the reference is actually where the read is derived. Accordingly, once it has been determined where each read is mapped, and further determined where each read is aligned, e.g., each relevant read has been given a position and a quality score reflecting the probability that the position is the correct alignment, such that the nucleotide sequence for the subject's DNA is known as well as how the subject's DNA differs from that of the reference (e.g., the CIGAR string has been determined), then the various reads representing the genomic nucleic acid sequence of the subject may be sorted by chromosome location, so that the exact location of the read on the chromosomes may be determined. Consequently, in some aspects, the present disclosure is directed to a sorting function, such as may be performed by a sorting module, which sorting module may be part of a pipeline of modules, such as a pipeline that is directed at taking raw sequence read data, such as form a genomic sample form an individual, and mapping and/or aligning that data, which data may then be sorted.

More particularly, once the reads have been assigned a position, such as relative to the reference genome, which may include identifying to which chromosome the read belongs and/or its offset from the beginning of that chromosome, the reads may be sorted by position. Sorting may be useful, such as in downstream analyses, whereby all of the reads that overlap a given position in the genome may be formed into a pile up so as to be adjacent to one another, such as after being processed through the sorting module, whereby it can be readily determined if the majority of the reads agree with the reference value or not. Hence, where the majority of reads do not agree with the reference value a variant call can be flagged. Sorting, therefore, may involve one or more of sorting the reads that align to the relatively same position, such as the same chromosome position, so as to produce a pileup, such that all the reads that cover the same location are physically grouped together; and may further involve analyzing the reads of the pileup to determine where the reads may indicate an actual variant in the genome, as compared to the reference genome, which variant may be distinguishable, such as by the consensus of the pileup, from an error, such as a machine read error or error an error in the sequencing methods which may be exhibited by a small minority of the reads.

Once the data has been obtained there are one or more other modules that may be run so as to clean up the data. For instance, one module that may be included, for example, in a sequence analysis pipeline, such as for determining the genomic sequence of an individual, may be a local realignment module. For example, it is often difficult to determine insertions and deletions that occur at the end of the read. This is because the Smith-Waterman or equivalent alignment process lacks enough context beyond the indel to allow the scoring to detect its presence. Consequently, the actual indel may be reported as one or more SNPs. In such an instance, the accuracy of the predicted location for any given read may be enhanced by performing a local realignment on the mapped and/or aligned and/or sorted read data.

In such instances, pileups may be used to help clarify the proper alignment, such as where a position in question is at the end of any given read, that same position is likely to be at the middle of some other read in the pileup. Accordingly, in performing a local realignment the various reads in a pileup may be analyzed so as to determine if some of the reads in the pile up indicate that there was an insertion or a deletion at a given position where an other read does not include the indel, or rather includes a substitution, at that position, then the indel may be inserted, such as into the reference, where it is not present, and the reads in the local pileup that overlap that region may be realigned to see if collectively a better score is achieved then when the insertion and/or deletion was not there. If there is an improvement, the whole set of reads in the pileup may be reviewed and if the score of the overall set has improved then it is clear to make the call that there really was an indel at that position. In a manner such as this, the fact that there is not enough context to more accurately align a read at the end of a chromosome, for any individual read, may be compensated for. Hence, when performing a local realignment, one or more pileups where one or more indels may be positioned are examined, and it is determined if by adding an indel at any given position the overall alignment score may be enhanced.

Another module that may be included, for example, in a sequence analysis pipeline, such as for determining the genomic sequence of an individual, may be a duplicate marking module. For instance, a duplicate marking function may be performed so as to compensate for chemistry errors that may occur during the sequencing phase. For example, as described above, during some sequencing procedures nucleic acid sequences are attached to beads and built up from there using labeled nucleotide bases. Ideally there will be only one read per bead. However, sometimes multiple reads become attached to a single bead and this results in an excessive number of copies of the attached read. This phenomenon is known as read duplication.

After an alignment is performed and the results obtained, and/or a sorting function, local realignment, and/or a de-duplication is performed, a variant call function may be employed on the resultant data. For instance, a typical variant call function or parts thereof may be configured so as to be implemented in a software and/or hardwired configuration, such as on an integrated circuit. Particularly, variant calling is a process that involves positioning all the reads that align to a given location on the reference into groupings such that all overlapping regions from all the various aligned reads form a "pile up." Then the pileup of reads covering a given region of the reference genome are analyzed to determine what the most likely actual content of the sampled individual's DNA/RNA is within that region. This is then repeated, step wise, for every region of the genome. The determined content generates a list of differences termed "variations" or "variants" from the reference genome, each with an associated confidence level along with other metadata.

The most common variants are single nucleotide polymorphisms (SNPs), in which a single base differs from the reference. SNPs occur at about 1 in 1000 positions in a human genome. Next most common are insertions (into the reference) and deletions (from the reference), or "indels" collectively. These are more common at shorter lengths, but can be of any length. Additional complications arise, however, because the collection of sequenced segments ("reads") is random, some regions will have deeper coverage than others. There are also more complex variants that include multi-base substitutions, and combinations of indels and substitutions that can be thought of as length-altering substitutions. Standard software based variant callers have difficulty identifying all of these, and with various limits on variant lengths. More specialized variant callers in both software and/or hardware are needed to identify longer variations, and many varieties of exotic "structural variants" involving large alterations of the chromosomes.

Most of the human genome is diploid, meaning there are two non-identical copies of each chromosome 1–22 in each cell nucleus, one from each parent. The sex chromosomes X and Y are haploid (single copy), with some caveats, and the mitochondrial "chromosome" ChrM is haploid. For diploid regions, each variant can be homozygous, meaning it occurs in both copies, or heterozygous, meaning it occurs in only one copy. Each read, such as sequenced segment of nucleotides, e.g., arranged in the pile up, comes from a random "strand" in diploid regions. Rarely, two heterozygous variants can occur at the same locus.

Complications in these regards arise by the very nature of the way these sequences are produced for analysis in the first place. In order to determine the nucleotide order for any given genomic region, the sequence coding for this region must first be cloned and amplified, such as by using Polyclonal Reaction (PCR) amplification. However, PCR amplification (cloning) of the DNA sample can lead to multiple exact duplicate DNA segments getting sequenced, which can then make distinguishing true variant calls from false variants created by PCR artifacts increasingly difficult. For instance, indels and SNPs can be introduced into various regions of the sequence by PCR and/or other sample prep steps.

Additionally, the Next Gen Sequencer itself can make mistakes, such as by adding phantom SNPs and/or homopolymer length inaccuracies appearing as indels into the sequences, with an error model varying from one NGS technology to another. Because of the predominance of these machine based errors, the likelihood of a sequencer error at a given base may be estimated and demarcated by associating a base quality score, e.g., on a logarithmic "Phred" scale, with every read sequence being scored.

Further, mapping and/or aligning errors may also occur, such as where reads are aligned to the wrong place in the reference genome. Consequently, the likelihood that a mapping and/or aligning error has occurred for a given mapped and/or aligned read can also be estimated and be associated with a map quality score "MAPQ," which may also be on a logarithmic "Phred" scale. Particularly, for alignment errors, typical alignment errors may involve reads that have been mapped to the correct position, but may nevertheless be reported with untrue detailed alignments (CIGAR strings). Commonly, an actual indel may be reported instead as one or more SNPs, or vice versa. Also, as described herein, alignments may be clipped, such that it is not explained how bases near one end align, or if they align at all in a given location, and hence there is simply a natural ambiguity about the positions of indels in repetitive sequences.

Given all these complexities, variant calling is a difficult procedure to implement in software, and worlds of magnitude more difficult to deploy in hardware. In order to account for and/or detect these types of errors, typical variant callers may perform one or more of the following tasks. For instance, they may come up with a set of hypothesis genotypes (content of the one or two chromosomes at a locus), use Bayesian calculations to estimate the posterior probability that each genotype is the truth given the observed evidence, and report the most likely genotype along with its confidence level. As such variant callers may be simple or complex. Simpler variant callers look only at the column of bases in the aligned read pileup at the precise position of a call being made. More advanced variant callers are "haplotype based callers", which may be configured to take into account context, such as in a window, around the call being made.

A "haplotype" is particular DNA content (nucleotide sequence, list of variants, etc.) in a single common "strand", e.g. one of two diploid strands in a region, and a haplotype based caller considers the Bayesian implications of which differences are linked by appearing in the same read. Accordingly, a variant call protocol, as proposed herein, may implement one or more improved functions such as those performed in a Genome Analysis Tool Kit (GATK) haplotype caller and/or using a Hidden Markov Model (HMM) tool and/or a de Bruijn Graph function, such as where one or more these functions typically employed by a GATK haplotype caller, and/or a MINI tool, and/or a de Bruijn Graph function may be implemented in software and/or in hardware.

More particularly, as implemented herein, various different variant call operations may be configured so as to be performed in software or hardware, and may include one or more of the following steps. For instance, variant call function may include an active region identification, such as for identifying places where multiple reads disagree with the reference, and for generating a window around the identified active region, so that only these regions may be selected for further processing. Additionally, localized haplotype assembly may take place, such as where, for each given active region, all the overlapping reads may be assembled into a "de Bruijn graph" (DBG) matrix. From this DBG, various paths through the matrix may be extracted, where each path constitutes a candidate haplotype, e.g., hypotheses, for what the true DNA sequence may be on at least one strand. Further, haplotype alignment may take place, such as where each extracted haplotype candidate may be aligned, e.g., Smith-Waterman aligned, back to the reference genome, so as to determine what variation(s) from the reference it implies. Furthermore, a read likelihood calculation may be performed, such as where each read may be tested against each haplotype, or hypothesis, to estimate a probability of observing the read assuming the haplotype was the true original DNA sampled.

With respect to these processes, the read likelihood calculation will typically be the most resource intensive and time consuming operation to be performed, often requiring a pair HMM evaluation. Additionally, the constructing of de Bruijn graphs for each pileup of reads, with associated operations of identifying locally and globally unique K-mers, as described below may also be resource intensive and/or time consuming. Accordingly, in various embodiments, one or more of the various calculations involved in performing one or more of these steps may be configured so as to be implemented in optimized software fashion or hardware, such as for being performed in an accelerated manner by an integrated circuit, as herein described.

As indicated above, in various embodiments, a Haplotype Caller of the disclosure, implemented in software and/or in hardware or a combination thereof may be configured to include one or more of the following operations: Active Region Identification, Localized Haplotype Assembly, Haplotype Alignment, Read Likelihood Calculation, and/or Genotyping. For instance, the devices, systems, and/or methods of the disclosure may be configured to perform one or more of a mapping, aligning, and/or a sorting operation on data obtained from a subject's sequenced DNA to generate mapped, aligned, and/or sorted results data. This results data may then be cleaned up, such as by performing a de duplication operation on it and/or that data may be communicated to one or more dedicated haplotype caller processing engines for performing a variant call operation, including one or more of the aforementioned steps, on that results data so as to generate a variant call file with respect thereto. Hence, all the reads that have been sequenced and/or been mapped and/or aligned to particular positions in the reference genome may be subjected to further processing so as to determine how the determined sequence differs from a reference sequence at any given point in the reference genome.

Accordingly, in various embodiments, a device, system, and/or method of its use, as herein disclosed, may include a variant or haplotype caller system that is implemented in a software and/or hardwired configuration to perform an active region identification operation on the obtained results data. Active region identification involves identifying and determining places where multiple reads, e.g., in a pile up of reads, disagree with a reference, and further involves generating one or more windows around the disagreements ("active regions") such that the region within the window may be selected for further processing. For example, during a mapping and/or aligning step, identified reads are mapped and/or aligned to the regions in the reference genome where they are expected to have originated in the subject's genetic sequence. However, as the sequencing is performed in such a manner so as to create an oversampling of sequenced reads for any given region of the genome, at any given position in the reference sequence may be seen a pile up of any and/all of the sequenced reads that line up and align with that region. All of these reads that align and/or overlap in a given region or pile up position may be input into the variant caller system. Hence, for any given read being analyzed, the read may be compared to the reference at its suspected region of overlap, and that read may be compared to the reference to determine if it shows any difference in its sequence from the known sequence of the reference. If the read lines up to the reference, without any insertions or deletions and all the bases are the same, then the alignment is determined to be good.

However, for any given mapped and/or aligned read, the read may have bases that are different from the reference, e.g., the read may include one or more SNPs, creating a position where a base is mismatched; and/or the read may have one or more of an insertion and/or deletion, e.g., creating a gap in the alignment. Hence, in any of these instances, there will be one or more mismatches that need to be accounted for by further processing. Nevertheless, to save time and increase efficiency, such further processing should be limited to those instances where a perceived mismatch is non-trivial, e.g., a non-noise difference. In determining the significance of a mismatch, places where multiple reads in a pile up disagree from the reference may be identified as an active region, a window around the active region may then be used to select a locus of disagreement that may then be subjected to further processing. The disagreement, however, should be non-trivial. This may be determined in many ways, for instance, the non-reference probability may be calculated for each locus in question, such as by analyzing base match vs mismatch quality scores, such as above a given threshold deemed to be a sufficiently significant amount of indication from those reads that disagree with the reference in a significant way.

For instance, if 30 of the mapped and/or aligned reads all line up and/or overlap so as to form a pile up at a given position in the reference, e.g., an active region, and only 1 or 2 out of the 30 reads disagrees with the reference, then the minimal threshold for further processing may be deemed to not have been met, and the non-agreeing read(s) can be disregarded in view of the 28 or 29 reads that do agree. However, if 3 or 4, or 5, or 10, or more of the reads in the pile up disagree, then the disagreement may be statistically significant enough to warrant further processing, and an active region around the identified region(s) of difference might be determined. In such an instance, an active region window ascertaining the bases surrounding that difference may be taken to give enhanced context to the region surrounding the difference, and additional processing steps, such as performing a Gaussian distribution and sum of non-reference probabilities distributed across neighboring positions, may be taken to further investigate and process that region to figure out if and active region should be declared and if so what variances from the reference actually are present within that region if any. Therefore, the determining of an active region identifies those regions where extra processing may be needed to clearly determine if a true variance or a read error has occurred.

The boundary of the active region window may be defined based on the number and type of observed differences and the number of bases required to be included within the region so as to give a statistically significant context to the analysis. In such an instance, the size of the active region window may be increased to encompass from one or ten to hundreds and thousands of bases, which may be added to one or both sides of the locus of divergence, so as to form an extended, contextualized active region that may be subjected to further processing. Sub-regions within a window, such as at the locus with the lowest active probability, may also be identified and analyzed. All reads, therefore, which overlap the extended region, may be included in the final active region output.

Accordingly, because in many instances it is not desirable to subject every region in a pile up of sequences to further processing, an active region can be identified whereby it is only those regions where extra processing may be needed to clearly determine if a true variance or a read error has occurred that may be determined as needing of further processing. And, as indicated above, it may be the size of the supposed variance that determines the size of the window of the active region. For instance, in various instances, the bounds of the active window may vary from 1 or 2 or about 10 or 20 or even about 25 or about 50 to about 200 or about 300, or about 500 or about 1000 bases long or more, where it is only within the bounds of the active window that further processing is taking place. Of course, the size of the active window can be any suitable length so long as it provides the context to determine the statistical importance of a difference.

Hence, if there is only one or two isolated differences, then the active window may only need to cover a one or more to a few dozen bases in the active region so as to have enough context to make a statistical call that an actual variant is present. However, if there is a cluster or a bunch of differences, or if there are indels present for which more context is desired, then the window may be configured so as to be larger. In either instance, it may be desirable to analyze any and all the differences that might occur in clusters, so as to analyze them all in one active region, because to do so can provide supporting information about each individual difference and will save processing time by decreasing the number of active windows engaged. In various instances, the active region boundaries may be determined by active probabilities that pass a given threshold, such as about 0.00001 or about 0.00001 or about 0.0001 or less to about 0.002 or about 0.02 or about 0.2 or more. And, as indicated above, if the active region is longer than a given threshold, e.g., about 300-500 bases or 1000 bases or more, then the region can be broken up into sub-regions, such as by sub-regions defined by the locus with the lowest active probability score.

In various instances, after an active region is identified, a localized haplotype assembly procedure may be performed. For instance, in each active region, all the piled up and/or overlapping reads may be assembled into a "de Bruijn graph" (DBG). Such a DBG, therefore, may be a directed graph based on all the reads that overlapped the selected active region, which active region may be about 200 or about 300 to about 400 or about 500 bases long, within which active region the presence and/or identity of variants are going to be determined. In various instances, as indicated above, the active region can be extended, e.g., by including another about 100 or about 200 or more bases in each direction of the locus in question so as to generate an extended active region, such as where additional context surrounding a difference may be desired. Accordingly, it is from the active region window, extended or not, that all of the reads that have portions that overlap the active region are piled up, the overlapping portions are identified, and the read sequences are threaded into the haplotype caller system and are thereby assembled together in the form of a De Bruin graph, much like the pieces of a puzzle.

It is to be understood that any given particular read may be shorter then the actual length of the active window, e.g., the read length may be about 100 bases long, or they could be longer, e.g., 1,000 or 5000 or more bases long, and the active window may be 1, 10, 100, 300, 500, or even 1,000 or more bases longer. Accordingly, where the reads are shorter, they will not cover the entire active region. Consequently, some reads will overlap and/or be at the beginning of the active region, some will be entirely within the middle of the active window, and some will overlap or be at the end of the active region window.

Hence, for any given active window there will be reads in the pile up such that en masse, the pile up will include a sequence pathway that through overlapping regions of various reads in the pile up covers the entire sequence within the active window. So at any one locus in the active region, there will be a plurality of reads overlapping it, albeit any given read may not extend the entire active region. The result of this is that various regions of various reads within a pileup are employed by the DBG in determining whether a variant actually is present or not for any given locus in the sequence within the active region. As it is only within the active window that this determination is being made, it is only those portions of any given read within the borders of the active window that are considered, and those portions that are outside of the active window may be discarded.

As indicated, it is only those sections of the reads that overlap the reference within the active region that are fed into the DBG system. The DBG system then assembles the reads like a puzzle into a graph, and then for each position in the sequence, it is determined based on the collection of overlapping reads for that position, whether there is a match or a mismatch, and if there is a mismatch, what the probability of that mismatch is. For instance, where there are discrete places where segments of the reads in the pile up overlap each other, they may be aligned to one another based on their areas of matching, and from stringing the matching reads together, as determined by their points of matching, it can be established for each position within that segment, whether and to what extent the reads at any given position match each other. Hence, if two reads being compiled line up and match each other identically for a while, a graph having a single string will result, however when the reads come to a point of difference, a branch in the graph will form, and two divergent strings will result, until matching between the two reads resumes.

As reads may be about a hundred to several hundreds to thousands of bases long, it may be desirable to increase accuracy and/or efficiency in compiling a DBG and/or thereby determining matching and/or mismatching between the reads of the pile up and the reference sequence, by breaking the reads down into overlapping segments where each overlapping segment is analyzed in determining matching. In such an instance, a "Kmer" may be used for processing the overlapping reads within an identified active region. In this instance, a k-mer may be a variable length of segment "k" bases long, where k may be as small as 2, 3, 5, 10, 15, 20, 25, even up to 50, 55, 60, 65, 70, 75, or 100 or more bases long, but is often selected to be shorter than the actual length of the individual reads being considered. In such an instance, those k-mers, of the determined base length, that overlap one another, will be extracted from all of the reads within the active region pile up, and will be used to construct and score the DBG.

For example, both the reference sequence and the reads of the pile up may be broken down into k-mers, e.g., 10 or 20 or more bases long, and can be thread into a graph generation processor, starting from the first unique k-mer. These k-mers can be reassembled into a graph matrix based on their matching of one another. Particularly, the reference sequence may be broken down into k-mers that may be reassembled to form the backbone of the graph matrix, e.g., a main pathway traversing through the graph, e.g., from left to right. As given k-mers from the various reads within the active region are generated that match the graphed backbone line of reference k-mers, these k-mers will be aligned to the main backbone of the graph thereby supporting its main pathway.

More particularly, in various instances, there may be a large number of reads in the pile up, e.g., 2,000 or more, within an active region. K-mers may be extracted from each of these reads, in a one base offsetting manner, so that every possible 10 base sequence that can be derived from the sequence of a single read within the window may be generated and threaded into the system. This k-mer generation may then be repeated for all of the reads in the pile up, whereby the k-mers are generated and threaded into the system in such a manner that whenever any given k-mer from two or more different reads and/or the reference (and/or from two different places in the same read or reference) match one another, e.g., they have the same 10 base sequence, they will be positioned in the same place in the graph and be represented by one node and/or one vertex within the graph. Hence, all instances of the same 10 base k-mer sequence will be positioned together within the graph at the same node or vertex, and whenever two or more of the extracted k-mers overlap one another an edge will be formed thereby. Note that where an edge already exists within the graph, e.g., because the same two k-mers overlapped in another previous read, a new edge is not formed, rather a count represented by that edge is increased.

Likewise, if two consecutive k-mers from the same read are generated in a one base offsetting manner such that they overlap each other 9 bases out of the 10, e.g., 2 10 base k-mers are generated from the same read and thread into the graph, where one is just shifted by one base from the other, the 9 overlapping bases will be the same in each of the two k-mer strings, and where this overlap ends two nodes and two vertices with an edge between them will be formed. In such instances, the vertices in such a graph will represent distinct 10 base sequences, and where the vertices occur between two nodes, the two k-mers will be overlapped by all but 1 base.

Hence, if all the k-mers from one read that matches the reference exactly are thread into the graph matrix, and/or along with the k-mers from the reference itself, so as to build the graph, a linear graph will result, because there will be no variation in the read and/or reference as compared to itself. The resultant graph will be represented by a selection of vertices that are connected in a line, because the first two k-mers overlap each other by all but one base, and the next two k-mers overlap each other by all but one base, etc. without variation until all possible k-mers generated from the read and/or reference by offsetting itself by one base have been generated and fed into the system. A straight line graph therefore will result when all the vertices match the reference. In such an instance, the initial path score through the matrix will be the sum of all edge likelihoods in the path. For example, the edge likelihood may be a function of likelihoods of all outgoing edges from a given vertex. If no assembled results are generated, e.g., due to cycle, the k-mer size may be incremented, such as by 5, 10, 15, 20 or more, and assembly can be retired. In various instances, a maximum, e.g., 128, of the highest scoring paths per graph may be retained.

However, the paths through the graph are often not a straight line. For instance, where the k-mers of a read varies from the k-mers of the reference and/or the k-mers from one or more overlapping reads, a "bubble" will be formed in the graph at the point of difference resulting in two divergent strings that will continue along two different path lines until matching between the two sequences resumes. Each vertex may be given a weighted score identifying how many times the respective k-mers overlap in all of the reads in the pile up. Particularly, each pathway extending through the generated graph from one side to the other may be given a count. And where the same k-mers are generated from a multiplicity of reads, e.g., where each k-mer has the same sequence pattern, they may be accounted for in the graph by increasing the count for that pathway where the k-mer overlaps an already existing k-mer pathway. Hence, where the same k-mer is generated from a multiplicity of overlapping reads having the same sequence, the pattern of the pathway between the graph will be repeated over and over again and the count for traversing this pathway through the graph will be increased incrementally in correspondence therewith. In such an instance, the pattern is only recorded for the first instance of the k-mer, and the count is incrementally increased for each k-mer that repeats that pattern. In this mode the various reads in the pile up can be harvested to determine what variations occur and where.

In a manner such as this, a graph matrix may be formed by taking all possible 10 base k-mers that can be generated from each given read by sequentially walking the length of the read in ten base segments, where the beginning of each new ten base segment is off set by one base from the last generated 10 base segment. This procedure may then be repeated by doing the same for every read in the pile up within the active window. The generated k-mers may then be aligned with one another such that areas of identical matching between the generated k-mers are matched to the areas where they overlap, so as to build up a data structure that may then be scanned and the percentage of matching and mismatching may be determined. Particularly, the reference and any previously processed k-mers aligned therewith may be scanned with respect to the next generated k-mer to determine if the instant generated k-mer matches and/or overlaps any portion of a previously generated k-mer, and where it is found to match the instant generated k-mer can then be inserted into the graph at the appropriate position.

Once built, the graph can be scanned and it may be determined based on this matching whether any given SNPs and/or indels in the reads with respect to the reference are likely to be an actual variation in the subject's genetic code or the result of a processing or other error. For instance, if all or a significant portion of the k-mers, of all or a significant portion of all of the reads, in a given region include the same SNP and/or indel mismatch, but differ from the reference in the same manner, then it may be determined that there is an actually SNP and/or indel variation in the subject's genome as compared to the reference genome. However, if only a limited number of k-mers from a limited number of reads evidence the artifact, it is likely to be caused by machine and/or processing and/or other error and not indicative of a true variation at the position in question.

As indicated, where there is a suspected variance, a bubble will be formed within the graph. Specifically, where all of the k-mers within all of a given region of reads all match the reference, they will line up in such a manner as to from a linear graph. However, where there is a difference between the bases at a given locus, at that locus of difference that graph will branch. This branching may be at any position within the k-mer, and consequently at that point of difference the 10 base k-mer, including that difference, will diverge from the rest of the k-mers in the graph. In such an instance, a new node, forming a different pathway through the graph will be formed.

Hence, where everything may have been agreeing, e.g., the sequence in the given new k-mer being graphed is matching the sequence to which it aligns in the graph, up to the point of difference the pathway for that k-mer will match the pathway for the graph generally and will be linear, but post the point of difference, a new pathway through the graph will emerge to accommodate the difference represented in the sequence of the newly graphed k-mer. This divergence being represented by a new node within the graph. In such an instance, any new k-mers to be added to the graph that match the newly divergent pathway will increase the count at that node. Hence, for every read that supports the arc, the count will be increased incrementally.

In various of such instances, the k-mer and/or the read it represents will once again start matching, e.g., after the point of divergence, such that there is now a point of convergence where the k-mer begins matching the main pathway through the graph represented by the k-mers of the reference sequence. For instance, naturally after a while the read(s) that support the branched node should rejoin the graph over time. Thus, over time, the k-mers for that read will rejoin the main pathway again. More particularly, for an SNP at a given locus within a read, the k-mer starting at that SNP will diverge from the main graph and will stay separate for about 10 nodes, because there are 10 bases per k-mer that overlap that locus of mismatching between the read and the reference. Hence, for an SNP, at the $11^{th}$ position, the k-mers covering that locus within the read will rejoin the main pathway as exact matching is resumed. Consequently, it will take ten shifts for the k-mers of a read having an SNP at a given locus to rejoin the main graph represented by the reference sequence.

As indicated above, there is one line or backbone that is the reference path, and where there is a divergence a bubble is formed at a node where there is a difference between a read and the backbone graph. Thus there are some reads that diverge from the backbone and form a bubble, which divergence may be indicative of the presence of a variant. As the graph is processed, bubbles within bubbles within bubbles may be formed along the reference backbone, so that they are stacked up and a plurality of pathways through the graph may be created. In such an instance, there may be the main path represented by the reference backbone, one path of a first divergence, and a further path of a second divergence within the first divergence, all within a given window, each pathway through the graph may represent an actual variation or may be an artifact such as caused by sequencing error, and/or PCR error, and/or a processing error, and the like.

This determination, however, may further be complicated by the fact that, as indicated above, the human genome is diploid, and because of which, at any given position, the subject may be homozygous or heterozygous for a variant. For instance, if there is a large pile up, e.g., of 2000 reads, and some of them have differences that actually appear in the subject's genetic sequence, e.g., the subject has a real variant, the variant may be present on one chromosome, but not present on the non-identical copy of its analogous chromosome, e.g., the subject may be heterozygous for the variation. In such an instance, the genetic code encoded by one chromosome will indicate the variant, but the other will not, e.g., it will match the reference sequence. In such an instance, half of the reads from the subject will follow the reference backbone for the given region, and the other will branch off at the position of the variation and follow a second arc represented by the presence of the variation.

Accordingly, once such a graph has been produced, it must be determined which pathways through the graph represent actual variations present within the sample genome and which are mere artifacts. Albeit, it is expected that reads containing handling or machine errors will not be supported by the majority of reads in the sample pileup, however, this is not always the case. For instance, errors in PCR processing may typically be the result of a cloning mistake that occurs when preparing the DNA sample, such mistakes tend to result in an insertion and/or a deletion being added to the cloned sequence. Such indel errors may be a more consistent among reads, and can wind up with generating multiple reads that have the same error from this mistake in PCR cloning. Consequently, a higher count line for such a point of divergence may result because of such errors.

Hence, once a graph matrix has been formed, with many paths through the graph, the next stage is to traverse and thereby extract all of the paths through the graph, e.g., left to right. One path will be the reference backbone, but there will be other paths that follow various bubbles along the way. All paths must be traversed and there count tabulated. For instance, if the graph includes a pathway with a two level bubble in one spot and a three level bubble in another spot, there will be $(2\times3)^6$ paths through that graph. So each of the paths will individually need to be extracted, which extracted paths are termed the candidate haplotypes. Such candidate haplotypes represent theories for what could really be representative of the subject's actual DNA that was sequenced, and the following processing steps, including one or more of haplotype alignment, read likelihood calculation, and/or genotyping may be employed to test these theories so as to find out the probabilities that anyone and/or each of these theories is correct. The implementation of a DeBruijn graph reconstruction therefore represents a way to reliably extract a good set of hypotheses to test.

For instance, in performing a variant call function, as disclosed herein, an active region identification operation may be implemented, such as for identifying places where multiple reads in a pile up within a given region disagree with the reference, and for generating a window around the identified active region, so that only these regions may be selected for further processing. Additionally, localized haplotype assembly may take place, such as where, for each given active region, all the overlapping reads in the pile up may be assembled into a "de Bruijn graph" (DBG) matrix. From this DBG, various paths through the matrix may be extracted, where each path constitutes a candidate haplotype, e.g., hypotheses, for what the true DNA sequence may be on at least one strand.

Further, haplotype alignment may take place, such as where each extracted haplotype candidate may be aligned, e.g., Smith-Waterman aligned, back to the reference genome, so as to determine what variation(s) from the reference it implies. Furthermore, a read likelihood calculation may be performed, such as where each read may be tested against each haplotype, to estimate a probability of observing the read assuming the haplotype was the true original DNA sampled. Finally, a genotyping operation may be implement, and a variant call file produced. As indicated above, any or all of these operations may be configured so as to be implemented in an optimized manner in software and/or in hardware, and in various instances, because of the resource intensive and time consuming nature of building a DBG matrix and extracting candidate haplotypes therefrom, and/or because of the resource intensive and time consuming nature of performing a haplotype alignment and/or a read likelihood calculation, which may include the engagement of an Hidden Markov Model (HMM) evaluation, these operations (e.g., localized haplotype assembly, and/or haplotype alignment, and/or read likelihood calculation) or a portion thereof may be configured so as to have one or more functions of their operation implemented in a hardwired form, such as for being performed in an accelerated manner by an integrated circuit as described herein.

Accordingly, in various instances, the devices, systems, and methods for performing the same may be configured so as to perform a haplotype alignment and/or a read likelihood calculation. For instance, as indicated, each extracted haplotype may be aligned, such as Smith-Waterman aligned, back to the reference genome, so as to determine what variation(s) from the reference it implies. In various instances, scoring may take place, such as in accordance with the following exemplary scoring parameters: a match=20.0; a mismatch=−15.0; a gap open −26.0; and a gap extend=−1.1. Accordingly, in this manner, a CIGAR strand may be generated and associated with the haplotype to produce an assembled haplotype, which assembled haplotype may eventually be used to identify variants.

In certain instances, the haplotype may be trimmed. For instance, the active window may be extended, such as by 25 bases on each side of the initial active window, so as to produce an extended active region. A variant span may be defined, such as where the range begins at the start of the first variant and finishes at the end of the last variant in the active region. An ideal span may be generated, such as where the variant span includes padding, such as 20 bases on each side of an SNP and up to 150 bases for indels. Further, an additional, e.g., final, span may be generated having a maximum span intersect, which may be a combination of the variant span and the ideal span. In such an instance, only those reads covering the final span may be considered in the real likelihood calculation, and/or overlapping reads may be clipped. Accordingly, in a manner such as this, the likelihood of a given read being associated with a given haplotype may be calculated for all read/haplotype combinations. In such instances, the likelihood may be calculated using a Hidden Markov Model (HMM).

For instance, the various assembled haplotypes may be aligned in accordance with a dynamic programing model similar to a SW alignment. In such an instance, a virtual matrix may be generated such as where the haplotype may be positioned on one axis of a virtual array, and the read may be positioned on the other axis. The matrix may then be filled out with the scores generated by traversing the extracted paths through the graph and calculating the probabilities that any given path is the true path. Hence, in such an instance, a difference in this alignment protocol from a typical SW alignment protocol is that with respect to finding the most likely path through the array, a maximum likelihood calculation is used, such as a calculation performed by an HMM model that is configured to provide the total probability for alignment of the reads to the haplotype. Hence, an actual CIGAR strand alignment, in this instance, need not be produced. Rather all possible alignments are considered and their possibilities are summed. The pair HMM evaluation is resource and time intensive, and thus, implementing its operations within a hardwired configuration within an integrated circuit is very advantageous.

For example, each read may be tested against each candidate haplotype, so as to estimate a probability of observing the read assuming the haplotype is the true representative of the original DNA sampled. In various instances, this calculation may be performed by evaluating a "pair hidden Markov model" (HMM), which may be configured to model the various possible ways the haplotype candidate might have been modified, such as by PCR or sequencing errors, and the like, and a variation introduced into the read observed. In such instances, the HMM evaluation may employ a dynamic programming method to calculate the total probability of any series of Markov state transitions arriving at the observed read in view of the possibility that any divergence in the read may be the result of an error model. Accordingly, such HMM calculations may be configured to analyze all the possible SNPs and Indels that could have been introduced into one or more of the reads, such as by amplification and/or sequencing artifacts.

Particularly, PCR introduced errors can be modeled and accounted for based on the probabilities that such errors would occur. For instance, insertion and deletion base qualities can be calculated at each position, such as based on the type of errors that typically occur due to this process and the artifacts, e.g., tandem repeats, it routinely produces in the sequences it generates, which information may be inserted into the array, and in view of such respective base qualities may be adjusted. In such instances, the HMM process may generate the probability of all the multiplicity of all conceivable errors that could in combination produce the same read result hypothesis, because there are very many ways, e.g., modifications that can take place and still get to the same answer.

More particularly, paired HMM considers in the virtual matrix all the possible alignments of the read to the reference haplotype along with a probability associated with each of them, where all probabilities are added up. The sum of all of the probabilities of all the variants along a given path is added up to get one overarching probability for each read. This process is then performed for every pair, for every haplotype, read pair. For example, if there is a six pile up cluster overlapping a given region, e.g., a region of six haplotype candidates, and if the pile up includes about one hundred reads, 600 HMM operations will then need to be performed. More particularly, if there are 6 haplotypes then there are going to be 6 branches through the path and the probability that each one is the correct pathway that matches the subject's actual genetic code for that region must be calculated. Consequently, each pathway for all of the reads must be considered, and the probability for each read that you would arrive at this given haplotype is to be calculated.

The pair Hidden Markov Model is an approximate model for how a true haplotype in the sampled DNA may transform into a possible different detected read. It has been observed that these types of transformations are a combination of SNPs and indels that have been introduced into the genetic sample set by the PCR process, by one or more of the other sample preparation steps, and/or by an error caused by the sequencing process, and the like. As can be seen with respect to FIG. 1, to account for these types of errors, an underlying 3-state base model may be employed, such as where: {M=alignment match, I=insertion, D=deletion}, further where any transition is possible except I<−>D.

As can be seen with respect to the above figure, the 3-state base model transitions are not in a time sequence, but rather are in a sequence of progression through the candidate haplotype and read sequences, beginning at position 0 in each sequence, where the first base is position 1. A transition to M implies position +1 in both sequences; a transition to I implies position +1 in the read sequence only; and a transition to D implies position +1 in the haplotype sequence only. The same 3-state model may be configured to underlie the Smith-Waterman and/or Needleman-Wunsch alignments, as herein described, as well. Accordingly, such a 3-state model, as set forth herein, may be employed in a SW and/or NW process thereby allowing for affine gap (indel) scoring, in which gap opening (entering the I or D state) is assumed to be less likely than gap extension (remaining in the I or D state). Hence, in this instance, the pair HMM can be seen as alignment, and a CIGAR string may be produced to encode a sequence of the various state transitions.

For example, a given haplotype sequence "ACGTCA-CATTTC" (SEQ ID NO:1) and read sequence "ACGT-CACTTC" (SEQ ID NO:2), could be aligned with CIGAR string "4M2D6M" (state sequence MMMMDDMMM-MMM), like this:

```
ACGTCACATTTC (SEQ ID NO: 1))
||||  |x |||
ACGT--CACTTC (SEQ ID NO: 2)
```

As can be seen with respect to the compared sequences above, there is an SNP where the SNP (haplotype 'T' to read 'C') is considered an alignment "match." However, in such an instance, it is understood that a "match" in this instance means that the two bases line up, even though they are not a corresponding match. Nevertheless, there is no separate state for a nucleotide mismatch.

Typically, the haplotype is often longer than the read, and because of this, the read may not represent the entire haplotype transformed by any SNPs and indels, but rather may only represent a portion of the haplotype transformed by such SNPs and indels. In such an instance, the various state transitions may actually begin at a haplotype position greater than zero, and terminate at a position before the haplotype ends. By contrast, the system may be configured such that the state transitions run from zero to the end of the read sequence.

In various instances, the 3-state base model may be complicated by allowing the transition probabilities to vary by position. For instance, the probabilities of all M transitions may be multiplied by the prior probabilities of observing the next read base given its base quality score, and the corresponding next haplotype base. In such an instance, the base quality scores may translate to a probability of a sequencing SNP error. When the two bases match, the prior probability is taken as one minus this error probability, and when they mismatch, it is taken as the error probability divided by 3, since there are 3 possible SNP results.

In such instances, the 3 states are no longer a true Markov model, both because transition probabilities from a given state do not sum to 1, and because the dependence on sequence position, which implies a dependence on previous state transitions, and thus violates the Markov property of dependence only on the current state. Such a Markov property can be salvaged if one instead considers the Markov model to have 3(N+1)(M+1) states, where N and M are the haplotype and read lengths, and there are distinct M, I, and D states for each haplotype/read coordinate. Further, the sum of probabilities to 1 can be salvaged if an additional "FAIL" state is assumed, with transition probability from each other state of (1−MPriorProb)(MTransProb). Furthermore, the relative balance of M transitions vs. I and D transitions also varies by position in the read. This is according to an assumed PCR error model, in which PCR indel errors are more likely in tandem repeat regions. Thus, there is a preprocessing of the read sequence, examining repetitive material surrounding each base, and deriving a local probability for M->I and M->D transitions; M->M transitions get the remainder (one minus the sum of these two), times the M prior.

The above discussion is regarding an abstract "Markovish" model. In various instances, the maximum-likelihood transition sequence may also be determined, which is termed herein as an alignment, and may be performed using a Needleman-Wunsch or other dynamic programming algorithm. But, in various instances, in performing a variant calling function, as disclosed herein, the maximum likelihood alignment, or any particular alignment, need not be a primary concern. Rather, the total probability may be computed, for instance, by computing the total probability of observing the read given the haplotype, which is the sum of the probabilities of all possible transition paths through the graph, from read position zero at any haplotype position, to the read end position, at any haplotype position, each component path probability being simply the product of the various constituent transition probabilities.

Finding the sum of pathway probabilities may also be performed by employing a virtual array and using a dynamic programming algorithm, as described above, such that in each cell of a (0 . . . N)×(0 . . . M) matrix, there are three probability values calculated, corresponding to M, D, and I transition states. (Or equivalently, there are 3 matrices.) The top row (read position zero) of the matrix may be initialized to probability 1.0 in the D states, and 0.0 in the I and M states; and the rest of the left column (haplotype position zero) may be initialized to all zeros. (In software, the initial D probabilities may be set near the double-precision max value, e.g. $2^{1020}$, so as to avoid underflow, but this factor may be normalized out later.)

In such an instance, setting the D probability 1 in the top row has the effect of allowing the alignment to begin anywhere in the haplotype. It may also position an initial M transition into the second row, rather than permitting I transitions into the second row. Typically, I transitions may be permitted in the bottom row. In various instances, the initial 1.0 values may be put in M slots of the top row. Each other cell, however, may have its 3 probabilities computed from its 3 adjacent neighboring cells: above, left, and above-left. These 9 input probabilities may then contribute to the 3 result probabilities according to the state transition probabilities, and the sequence movement rules: transition to D horizontally, to I vertically, and to M diagonally.

This 3-to-1 computation dependency restricts the order that cells may be computed. They can be computed left to right in each row, progressing through rows from top to bottom, or top to bottom in each column, progressing rightward. Additionally, they may be computed in anti-diagonal wavefronts, where the next step is to compute all cells (n,m) where n+m equals the incremented step number. This wavefront order has the advantage that all cells in the anti-diagonal may be computed independently of each other. The bottom row of the matrix then, at the final read position, may be configured to represent the completed alignments. In such an instance, the Haplotype Caller will work by summing the I and M probabilities of all bottom row cells. In various embodiments, the system may be set up so that no D transitions are permitted within the bottom row, or a D transition probability of 0.0 may be used there, so as to avoid double counting.

As described herein, in various instances, each HMM evaluation may operate on a sequence pair, such as on a haplotype and a read pair. For instance, within a given active region, each of a set of haplotypes may be HMM-evaluated vs. each of a set of reads. In such an instance, the hardware input bandwidth may be reduced and/or minimized by transferring the set of reads and the set of haplotypes once, and letting HW generate the N×M pair operations. In certain instances, Smith-Waterman may be configured to queue up individual HMM operations, each with its own copy of read and haplotype data. This has the advantage of simplicity, low memory requirements, and flexibility if there is a need to perform other than precisely the N×M possible pairs.

Haplotype Input:
   Length
   Bases
      In addition to [ACGT], at least support N, which matches any base
      Not sure about other multi-base IUB codes [RYKMSWBDHV]
      Could use a 4-bit mask most generally Read Input:
   Length
   For each position:
      Base [ACGT]
      Phred quality (0–63), Q0 indicating base=N
      insGOP (gap open penalty)
      delGOP
      insGCP (gap continuation penalty)
      delGCP
   The GOP and GCP values are 6-bit Phred integers in software, so the above could pack in 32 bits Result Output:
   Log scale probability of observing the read given the haplotype
      Probably nothing wrong with emitting the internal fixed-point format Although a Smith-Waterman (SW) alignment may be configured to run the pair HMM calculation in linear space, with double-precision probabilities (scaled upward from 1.0->$2^{1020}$, but still linear), the HW may operate in log probability space. This is useful to keep precision across the huge range of probability values with fixed-point values. However, in other instances, floating point operations may be used. In such instances, each cell calculation may include 8 multiplies (addition in log space) and only 4 adds. Log base 2 may be most convenient, and that's what I will assume below. In various instances, phred scale (10 log 10) may also be used. For software, in various instances, natural logs may be used. Whatever the base, negative logs may be employed; since probabilities don't exceed 1.0, their logs won't exceed 0.0.

Right of the binary point, substantial precision is useful especially because M->M transitions multiply by probabilities very close to 1.0. The insert gap open penalty (insGOP) and delete gap open penalty (delGOP) parameters cap at Phred 40 (prob 0.000126), so M->M transition −log 2 probability is at least (−log 2(1−2*0.0001))=0×0.0012F. Various NGS base quality scores currently cap at Phred 41 (error prob 0.0000794), so the M transition −log 2 prior may be at least 0×0.00078. This suggests that 16 to 20 or more fractional bits may be used.

Left of the binary point, substantial precision may be useful to achieve extremely small probabilities as products of up to ~1000 partial probabilities. The final probability sum may be bounded below by the particular probability of N insertions, or N mismatched bases, where N is the read length. The gap continuation probability (GCP) used may be Phred 10 (prob 0.1), and reads may be trimmed to well under 1000 bases for the active region, so the total −log 2 probability should be at most −log 2(0.1^1000)=3322. 14 integer bits may be used for these purposes, but this could be increased if smaller GCP is used.

In certain instances, various NextGen Sequencer base qualities cap at Phred 41 (error prob 0.0000794), the −log 2 probability for mismatching every base should be at most −log 2(0.0000794)*1000=13620. 16 integer bits therefore may be adequate for this, but sequencer base qualities could increase. Haplotype Caller may be configured to perform the pair HMM calculation with double precision floating point arithmetic, where probability 1.0 is scaled up to 2^1020 to maximize the dynamic range. Underflow of normals then may occur at probability 2^−2042, or of subnormals at 2^−2094. This suggests that 11-12 integer bits are adequate to match software if there is overflow detection. The logic for cell calculations may be configured to be as tight as possible, because many pipelines may be instantiated for target performance, such as for "12.16" fixed point format for log2 space.

In log space, of course, multiplication becomes simple division, but addition becomes challenging. For instance, one may want to compute C=A+B, but with each term represented in −log2 space:

$a=-\log2(A)$ $b=-\log2(B)$ $c=-\log2(C)$

In such an instance, the main calculation that may be used is:

$c=-\log2(A+B)=-\log2(2^{-a}+2^{-b})=-\log2(2^{-b}*(2^{(b-a)}+1))$ $c=b-\log2(1+2^{-(a-b)})$ $c=b-f(\Delta)$, where $\Delta=a-b$, and $f(x)=\log2(1+2^{-x})$ When a≥b (swapping the inputs if necessary), Δ is nonnegative, and f(Δ) goes rapidly to zero as Δ increases. In fact, f(Δ)=0 to 16 bits of precision if Δ≥16, so we can approximate:

$c=b (a-b≥16)$ $c=b-f(\Delta) (0≤a-b<16)$

Then all that is needed is to do is approximate f(Δ) over the range [0,16). For this, it looks adequate to use a lookup table on ~6 most significant bits of Δ (bits 3:−2), with linear interpolation between these 64 samples. That is, the 64-entry lookup table can return:

X=f(Δ[3:−2])
Y=f(Δ[3:−2])−f(Δ[3:−2]+0.25)
And the piecewise linear approximation is:

$f(\Delta) \approx X - Y*\Delta[-3:-16]$

An aggressive pipeline for this calculation is:
1. Compare inputs a and b
2. Possibly swap inputs, then subtract
3. Access f(Δ) lookup table; register Y and Δ[−3:−16] for multiply
4. Multiplier pipeline register; subtract b−X
5. Multiplier output register
6. Correct (b−X) by subtracting product The longest pole in computing the M, I, and D probabilities for a new cell is M.

Match cell=prior[i][j]*(mm[i−1][j−1]*transition[i][MtoM]+im[i−1][j−1]*transition[i][IToM]+dm[i−1][j−1]*transition[i][DToM])

There are three parallel multiplications (e.g., additions in log space), then two serial additions (~5-6 stage approximation pipelines), then an additional multiplication. In such an instance, the full pipeline may be about L=12-16 cycles long. The I & D calculations may be about half the length. The pipeline may be fed a multiplicity of input probabilities, such as 2 or 3 or 5 or 7 or more input probabilities each cycle, such as from one or more already computed neighboring cells (M and/or D from the left, M and/or I from above, and/or M and/or I and/or D from above-left). It may also include one or more haplotype bases, and/or one or more read bases such as with associated parameters, e.g., pre-processed parameters, each cycle. It outputs the M & I & D result set for one cell each cycle, after fall-through latency.

Figure 2:
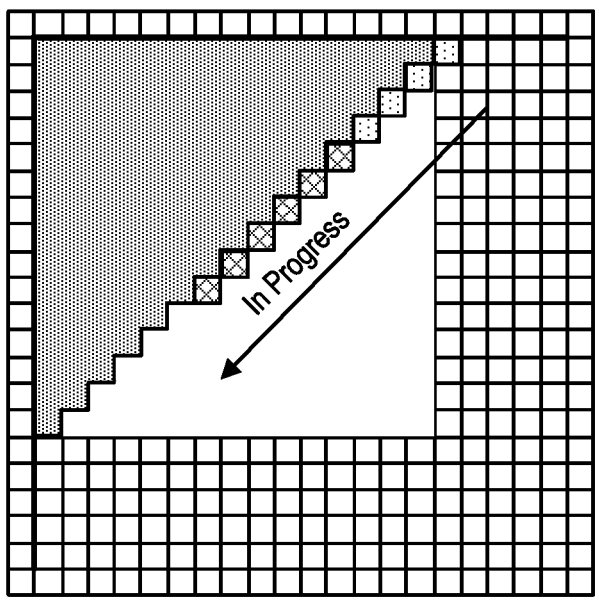
FIG. 2 depicts an exemplary HMM matrix showing an anti-diagonal processing wavefront or swath.

To keep the pipeline full, L independent cell calculations should be in progress at any one time. As can be seen with respect to FIG. 2, these could of course be from separate HMM matrices 30, but it is efficient for them to be along an anti-diagonal wavefront 35.

Figure 3:
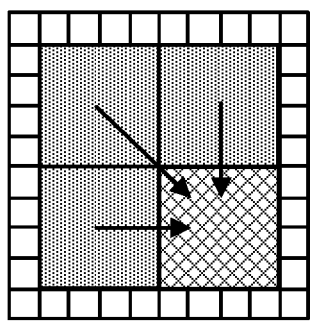
FIG. 3 depicts an exemplary cell to be processed in the HMM matrix of FIG. 2 and showing the data dependencies employed in calculating the transition state of the demarcated cell.

As can be seen with respect to FIG. 3, a difficulty is that the inputs to the pipeline for a new cell to compute come from one or more of its neighboring cells, such as its two or three neighboring cells of the matrix 30, such as depicted in FIG. 3.

Figure 4:
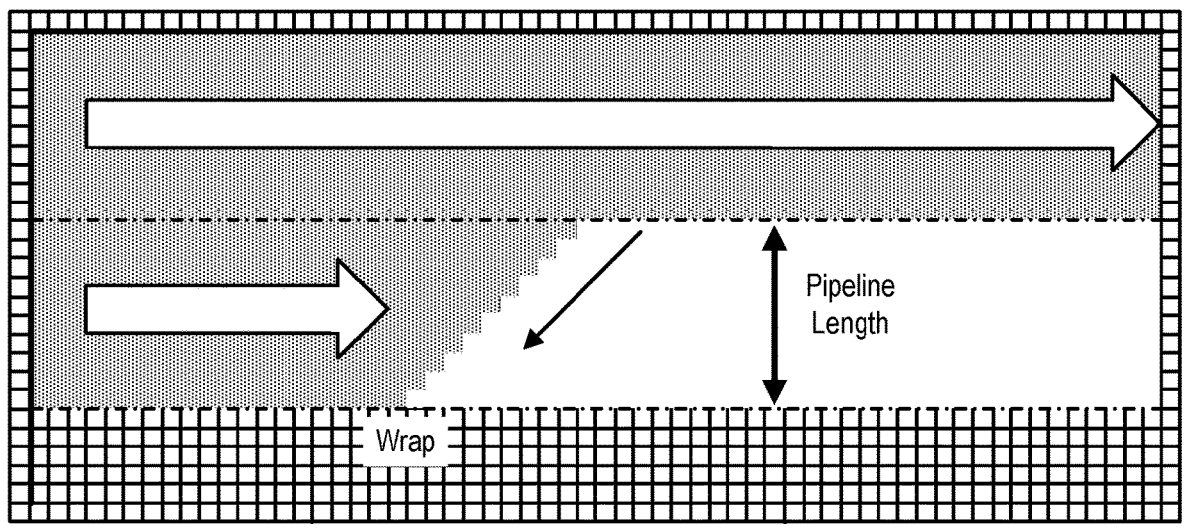
FIG. 4 depicts another exemplary matrix, this time with a horizontal processing swath.

In various instances, these neighboring cells in the matrix 30 can be computed as a variable, however such computations take a long time, which can become an issue with the time taken for storing and retrieving such intermediate results data. As can be seen with respect to FIG. 4, a single cell in a matrix 30 pipeline can be configured such as by employing a horizontal swath of processing engines of one row high for each pipeline stage. In such an instance, the pipeline can follow an anti-diagonal within the swath, wrapping from the bottom to top of the swath, and wrapping the swath itself when the right edge of the matrix is reached, as depicted FIG. 4.

Figure 5:
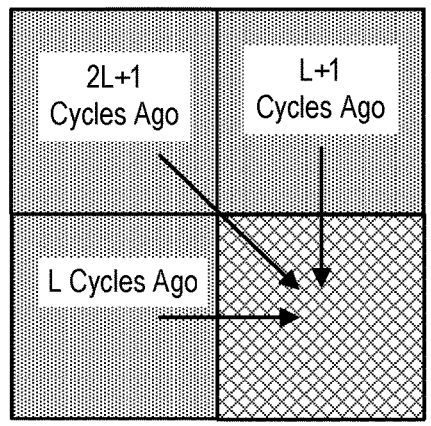
FIG. 5 depicts a block of exemplary cells of FIG. 3 showing the cycle dependencies with respect to the processing of the demarcated cell.

The advantage of this configuration is that the 3 neighboring cells employed for a new calculation of an instant neighboring cell have recently been computed prior to computing the neighboring cell in the matrix 30, such as a fixed number of cycles ago, as depicted in the FIG. 5.

Figure 6:
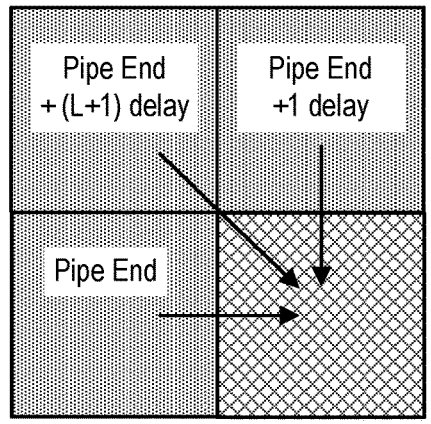
FIG. 6 depicts an exemplary output end for a cell at the end of a pipeline in the matrix of FIG. 2.

In various instances, current outputs at the pipeline's end are from a cell begun L cycles ago, so any time delays may be shortened by L, as depicted in FIG. 6.

In various instances, there may be a delay, such as a one or more cycle delay, which delay may be just a register slice, such as where the L+1 delay may be a shift register or a shallow circular buffer. Results at the bottom of the swath may be stored in a local memory, and may be re-injected into the pipeline each time the position wraps vertically in the next swath. Dead cycles may or may not be required while the pipeline is wrapping horizontally from one swath to the next. For instance, if the input feed is controlled carefully, and left-column nulls are injected in the right clock cycles, a pipeline anti-diagonal in progress should be able to straddle between the right end of one swath and the left end of the next.

Further, in various instances, multiple cell computing pipelines can be configured to cooperate so as to achieve a high overall throughput. For example, there are ~65T cells that may be configured to compute for a whole genome, such as in a target of 15 minutes on the high-end. In such an instance, the pipelines can compute one cell per cycle at 300 MHz, and in such an instance 240 pipelines could be employed, which are a lot of pipelines. Theoretically, each of them could be working on a separate HMM matrix 30, however, the amount of overhead logic to manage each matrix 30 will require additional resources, especially in the hardwired configuration, such as up to being multiplied by 240. In various instances, either of memory or logic could be a limiting factor. In such an instance, efficiency in the system may be enhanced such as by employing several pipelines that may be configured to cooperate with one another, so as to finish a single matrix 30 faster—if needed substantial management logic can be amortized.

To overcome any such limitations, the swath 35 cell order, as described above may be organized to make it easier for multiple pipelines to work on a single matrix. For instance, N pipelines could be configured to work on N swaths at a time, wherein each stays behind the compute wavefront 35 in the swath above. In such an instance, adjacent-swath $35_n$ pipelines may be configured so as to be synchronized, so that the lower one receives bottom-row results from the upper one at just the right moment, cutting down on memory requirements. To avoid N*L dead cycles at the start of each new matrix $35_n$, pipelines finishing their final swaths 35 in one matrix 30a can be configured to roll straight into upper swaths of the next matrix 30b.

The following stats are from Chromosome 21. The subset of Chr21 active in variant calling is about ⅛₅ of the active content of the whole genome, although some chance of things may not scale proportionally. Total HMM Tables (hG19:chr21): 43,890,690 (~44M)
⇒3.7G in whole genome
Total HMM Cells (hG19:chr21): 773,194,958,165 (~773B)
⇒65T in whole genome
Avg. Cells per Table (hG19:chr21): ~17,616

Figure 7:
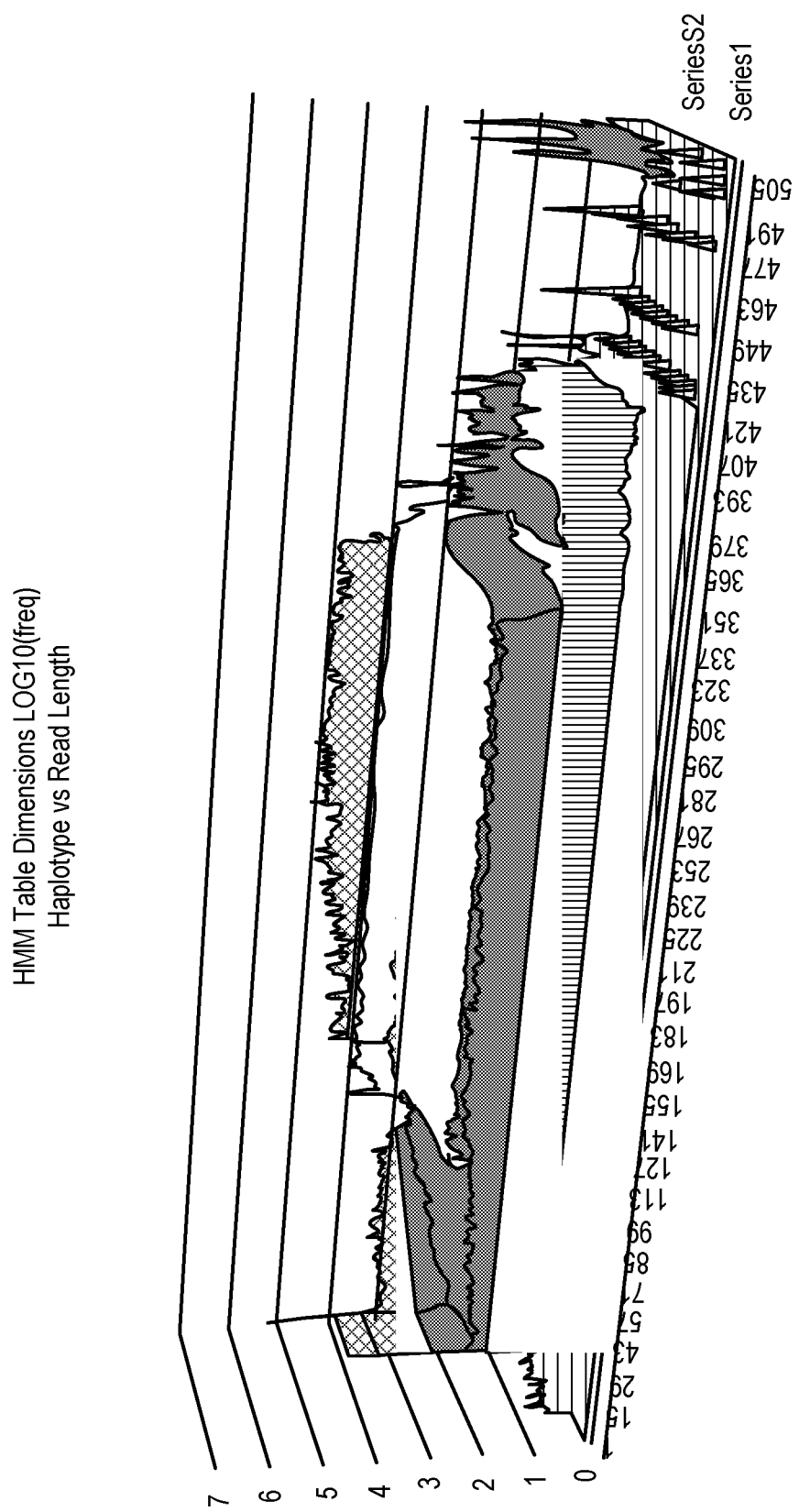
FIG. 7 depicts a histogram of an HMM table.

Further, as illustrated in FIG. 7 is a histogram of HMM table dimensions, for 101-base reads. The left-to-right axis is haplotype length, the front-to-back axis is read length, and the vertical axis is log count.

From the high wall at the back, you can see the most common case by far is for the whole 101-base read to be used. This case represents about 35%, and the balance is distributed near evenly among lengths 10-100. The processed read length was not less than 10, in this instance. The high wall on the left is at haplotype length 41, about 5.4% of cases. Very few haplotypes were shorter, and the shortest was 9 bases. The longest haplotypes were 515 bases. The central plateau, from 136 bases to 349 bases, represents 87% of cases. The diagonal wall at the back-left is where haplotype length equals read length. Typically, the read sequence for HMM is clipped to the window length spanned by the haplotype, so it is rare for the read to be longer than the haplotype, and equal lengths are common. This distribution of matrix dimensions may contribute to a well-performing architecture, particularly if there are inefficiencies from dead cycles between matrices or swaths, uneven swath coverage, and the like.

As indicated above, in performing a variant call function, as disclosed herein, a De Bruijn Graph may be formulated, and when all of the reads in a pile up are identical, the DBG will be linear. However, where there are differences, the graph will form "bubbles" that are indicative of regions of differences resulting in multiple paths diverging from matching the reference alignment and then later re-joining in matching alignment. From this DBG, various paths may be extracted, which form candidate haplotypes, e.g., hypotheses for what the true DNA sequence may be on at least one strand, which hypotheses may be tested by performing an HMM, or modified HMM, operation on the data. Further still, a genotyping function may be employed such as where the possible diploid combinations of the candidate haplotypes may be formed, and for each of them, a conditional probability of observing the entire read pileup may be calculated. These results may then be fed into a Bayesian formula to calculate an absolute probability that each genotype is the truth, given the entire read pileup observed.

Hence, in accordance with the devices, systems, and methods of their use described herein, in various instances, a genotyping operation may be performed, which genotyping operation may be configured so as to be implemented in an optimized manner in software and/or in hardware. For instance, the possible diploid combinations of the candidate haplotypes may be formed, and for each combination, a conditional probability of observing the entire read pileup may be calculated, such as by using the constituent probabilities of observing each read given each haplotype from the pair HMM evaluation. The results of these calculations feed into a Bayesian formula so as to calculate an absolute probability that each genotype is the truth, given the entire read pileup observed.

Accordingly, in various aspects, the present disclosure is directed to a system for performing a haplotype or variant call operation on generated and/or supplied data so as to produce a variant call file with respect thereto. Specifically, as described herein above, in particular instances, a variant call file may be a digital or other such file that encodes the difference between one sequence and another, such as a the difference between a sample sequence and a reference sequence. Specifically, in various instances, the variant call file may be a text file that sets forth or otherwise details the genetic and/or structural variations in a person's genetic makeup as compared to one or more reference genomes.

For instance, a haplotype is a set of genetic, e.g., DNA and/or RNA, variations, such as polymorphisms that reside in a person's chromosomes and as such may be passed on to offspring and thereby inherited together. Particularly, a haplotype can refer to a combination of alleles, e.g., one of a plurality of alternative forms of a gene such as may arise by mutation, which allelic variations are typically found at the same place on a chromosome. Hence, in determining the identity of a person's genome it is important to know which form of various different possible alleles a specific person's genetic sequence codes for. In particular instances, a haplotype may refer to one or more, e.g., a set, of nucleotide polymorphisms (e.g., SNPs) that may be found at the same position on the same chromosome.

Typically, in various embodiments, in order to determine the genotype, e.g., allelic haplotypes, for a subject, as described herein and above, a software based algorithm is engaged, such as an algorithm employing a haplotype call program, e.g., GATK, for simultaneously determining SNPs and/or insertions and/or deletions, i.e., indels, in an individual's genetic sequence. In particular, the algorithm may involve one or more haplotype assembly protocols such as for local de-novo assembly of a haplotype in one or more active regions of the genetic sequence being processed. Such processing typically involves the deployment of a processing function called a Hidden Markov Model (HMM) that is a stochastic and/or statistical model used to exemplify randomly changing systems such as where it is assumed that future states within the system depend only on the present state and not on the sequence of events that precedes it.

In such instances, the system being modeled bears the characteristics or is otherwise assumed to be a Markov process with unobserved (hidden) states. In particular instances, the model may involve a simple dynamic Bayesian network. Particularly, with respect to determining genetic variation, in its simplest form, there is one of four possibilities for the identity of any given base in a sequence being processed, such as when comparing a segment of a reference sequence, e.g., a hypothetical haplotype, and that of a subject's DNA or RNA, e.g., a read derived from a sequencer. However, in order to determine such variation, in a first instance, a subject's DNA/RNA must be sequenced, e.g., via a Next Gen Sequencer ("NGS"), to produce a readout or "reads" that identify the subject's genetic code. Next, once the subject's genome has been sequenced to produce one or more reads, the various reads, representative of the subject's DNA and/or RNA need to be mapped and/or aligned, as herein described above in great detail. The next step in the process then is to determine how the genes of the subject that have just been determined, e.g., having been mapped and/or aligned, vary from that of a prototypical reference sequence. In performing such analysis, therefore, it is assumed that the read potentially representing a given gene of a subject is a representation of the prototypical haplotype albeit with various SNPs and/or indels that are to presently be determined.

Accordingly, there exist commonly used software implementations for performing one or a series of such bioinformatics based analytical techniques so as to determine the various different genetic variations a subject may have in his or her genome. However, a common characteristic of such software based bioinformatics methods and systems employed for these purposes is that they are labor intensive, take a long time to execute on general purpose processors, and are prone to errors. A bioinformatics system, therefore, that could perform the algorithms or functions implemented by such software, e.g., various variant call functions, in a less labor and/or processing intensive manner with a greater percentage accuracy would be useful. However, the cost of analyzing, storing, and sharing this raw digital data has far outpaced the cost of producing it. This data analysis bottleneck is a key obstacle standing between these ever-growing raw data and the real medical insight we seek from it. The devices, systems, and methods of using the same, as presented herein, resolves these and other such needs in the art. Additionally, employing general purpose CPUs to perform specialized, repetitive mathematical computations are bulky, costly, and inefficient. So too, the power consumption, computation time, and physical footprint of an array of servers programmed to perform the HMM computations associated with the genome variant call operations, as disclosed herein, will all be undesirable compared to the traits of a system that performs such computations within a purpose-built, highly parallel microchip that is the subject of this disclosure.

Specifically, in particular aspects, devices, systems, and/or methods for practicing the same, such as for performing a haplotype and/or variant call function, such as deploying an HMM function, for instance, in an accelerated haplotype caller is provided. In various instances, in order to overcome these and other such various problems known in the art, the HMM accelerator herein presented may be configured to be operated in a manner so as to be implemented in software, implemented in hardware, or a combination of being implemented and/or otherwise controlled in part by software and/or in part by hardware. For instance, in a particular aspect, the disclosure is directed to a method by which data pertaining to the DNA and/or RNA sequence identity of a subject and/or how the subject's genetic information may differ from that of a reference genome may be determined.

In such an instance, the method may be performed by the implementation of a haplotype or variant call function, such as employing an HMM protocol. Particularly, the HMM function may be performed in hardware, such as on an accelerated device, in accordance with a method described herein. In such an instance, the hardware based HMM accelerator may be configured to receive and process the sequenced, mapped, and/or aligned data, to process the same, e.g., to produce a variant call file, as well as to transmit the processed data back throughout the system. Accordingly, the method may include deploying a system where data may be sent from a processor, such as a software-controlled CPU, to a haplotype caller implementing an accelerated HMM, which haplotype caller may be deployed on a microprocessor chip, such as an FPGA, ASIC, or structured ASIC. The method may further include the steps for processing the data to produce HMM result data, which results may then be fed back to the CPU.

Figure 8:
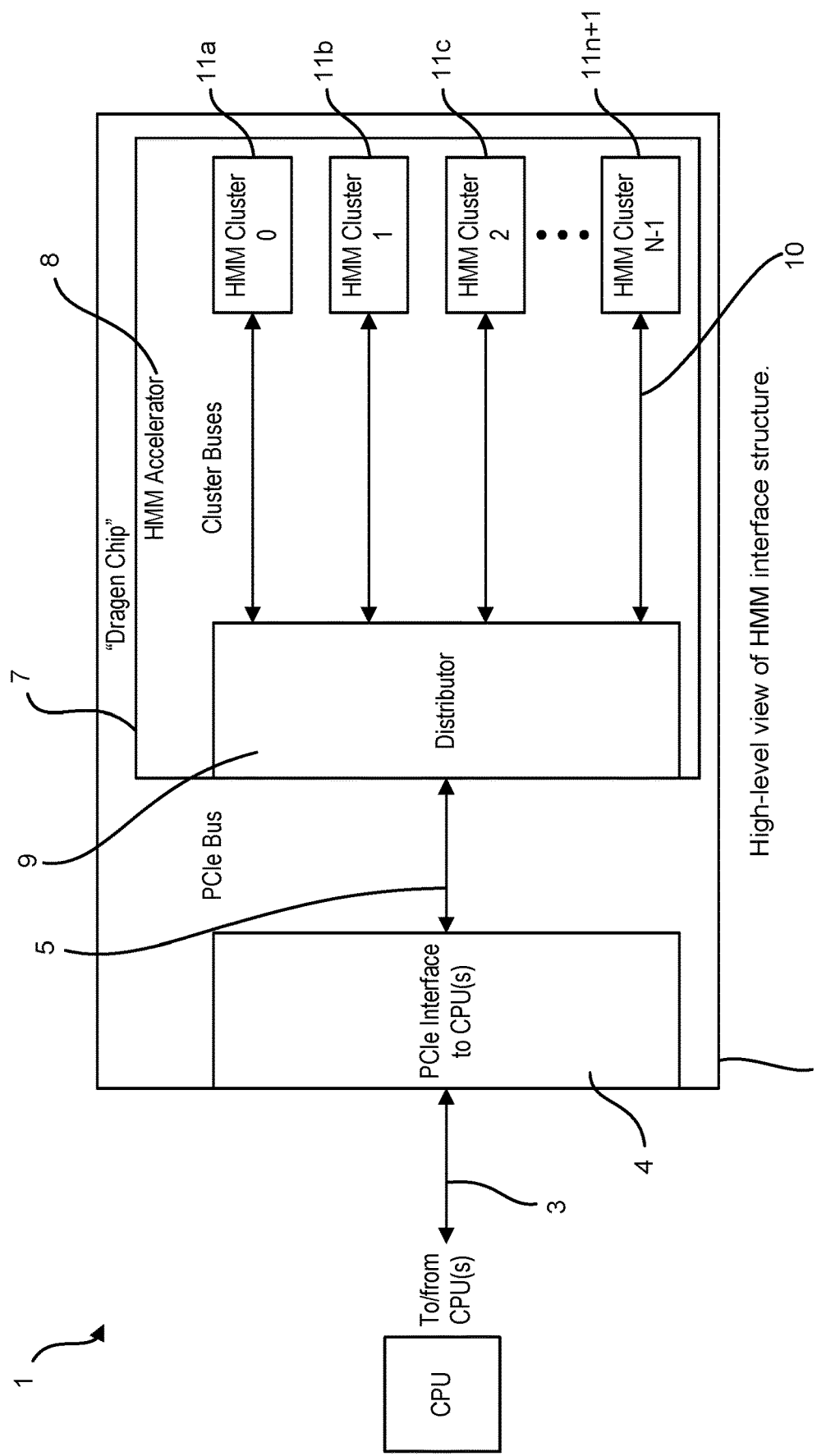
FIG. 8 depicts a high-level view of an integrated circuit of the disclosure including a HMM interface structure.

Particularly, in one embodiment, as can be seen with respect to FIG. 8, a variant call system 1 is provided. Specifically, FIG. 8 provides a high level view of an MINI interface structure. In particular embodiments, the variant call system 1 is configured to accelerate at least a portion of a variant call operation, such as an HMM operation. Hence, in various instances, a variant call system may be referenced herein as an HMM system 1. The system 1 includes a server having one or more central processing units (CPU) 1000 configured for performing one or more routines related to the sequencing and/or processing of genetic information.

Additionally, the system 1 includes a peripheral device 2, such as an expansion card, that includes a microchip 7, such as an FPGA, ASIC, or sASIC. It is to be noted that the term ASIC may refer equally to a sASIC, where appropriate. The peripheral device 2 includes an interconnect 3 and a bus interface 4, such as a parallel or serial bus, which connects the CPU 1000 with the chip 7. For instance, the device 2 may comprise a peripheral component interconnect, such as a PCI, PCI-X, PCIe, or QPI, and may include a bus interface 4, that is adapted to operably and/or communicably connect the CPU 1000 to the peripheral device 2, such as for low latency, high data transfer rates. Accordingly, in particular instances, the interface may be a peripheral component interconnect express (PCIe) 4 that is associated with the microchip 7, which microchip includes an HMM accelerator 8. For example, in particular instances, the HMM accelerator 8 is configured for performing an accelerated HMM function, such as where the HMM function, in certain embodiments, may at least partially be implemented in the hardware of the FPGA, AISC, or sASIC.

Specifically, FIG. 8 presents a high-level figure of an HMM accelerator 8 having an exemplary organization of one or more engines 13, such as a plurality of processing engines 13*a*-13$_{m+1}$, for performing one or more processes of a variant call function, such as including an MINI task. Accordingly, the HMM accelerator 8 may be composed of a data distributor 9, e.g., CentCom, and one or a multiplicity of processing clusters 11-11$_{n+1}$ that may be organized as or otherwise include one or more instances 13, such as where each instance may be configured as a processing engine, such as a small engine $13a$-$13_{m+1}$. For instance, the distributor 9 may be configured for receiving data, such as from the CPU 1000, and distributing or otherwise transferring that data to one or more of the multiplicity of HMM processing clusters 11.

Particularly, in certain embodiments, the distributor 9 may be positioned logically between the on-board PCIe interface 4 and the HMM accelerator module 8, such as where the interface 4 communicates with the distributor 9 such as over an interconnect or other suitably configured bus 5, e.g., PCIe bus. The distributor module 9 may be adapted for communicating with one or more HMM accelerator clusters 11 such as over one or more cluster buses 10. For instance, the HMM accelerator module 8 may be configured as or otherwise include an array of clusters $11a$-$11_{n+1}$, such as where each HMM cluster 11 may be configured as or otherwise includes a cluster hub 11 and/or may include one or more instances 13, which instance may be configured as a processing engine 13 that is adapted for performing one or more operations on data received thereby. Accordingly, in various embodiments, each cluster 11 may be formed as or otherwise include a cluster hub $11a$-$11_{n+1}$, where each of the hubs may be operably associated with multiple HMM accelerator engine instances $13a$-$13_{m+1}$, such as where each cluster hub 11 may be configured for directing data to a plurality of the processing engines $13a$-$13_{m+1}$ within the cluster 11.

In various instances, the HMM accelerator 8 is configured for comparing each base of a subject's sequenced genetic code, such as in read format, with the various known haplotypes of a reference sequence and determining the probability that any given base at a position being considered either matches or doesn't match the relevant haplotype, i.e., the read includes an SNP, an insertion, or a deletion, thereby resulting in a variation of the base at the position being considered. Particularly, in various embodiments, the HMM accelerator 8 is configured to assign transition probabilities for the sequence of the bases of the read going between each of these states, Match ("M"), Insert ("I"), or Delete ("D") as described in greater detail herein below.

More particularly, dependent on the configuration, the HMM acceleration function may be implemented in either software, such as by the CPU 1000 and/or microchip 7, and/or may be implemented in hardware and may be present within the microchip 7, such as positioned on the peripheral expansion card or board 2. In various embodiments, this functionality may be implemented partially as software, e.g., run by the CPU 1000, and partially as hardware, implemented on the chip 7. Accordingly, in various embodiments, the chip 7 may be present on the motherboard of the CPU 1000, or it may be part of the peripheral device 2, or both. Consequently, the HMM accelerator module 8 may include or otherwise be associated with various interfaces, e.g., 3, 5, 10, and/or 12 so as to allow the efficient transfer of data to and from the processing engines 13.

Accordingly, as can be seen with respect to FIG. 8, in various embodiments, a microchip 7 configured for performing a variant, e.g., haplotype, call function is provided. The microchip 7 may be associated with a CPU 1000 such as directly coupled therewith, e.g., included on the motherboard of a computer, or indirectly coupled thereto, such as being included as part of a peripheral device 2 that is operably coupled to the CPU 1000, such as via one or more interconnects, e.g., 3, 4, 5, 10, and/or 12. In this instance, the microchip 7 is present on the peripheral device 2.

Hence, the peripheral device 2 may include a parallel or serial expansion bus 4 such as for connecting the peripheral device 2 to the central processing unit (CPU) 1000 of a computer and/or server, such as via an interface 3, e.g., DMA. In particular instances, the peripheral device 2 and/or serial expansion bus 4 may be a Peripheral Component Interconnect express (PCIe) that is configured to communicate with or otherwise include the microchip 7, such as via connection 5. As described herein, the microchip 7 may at least partially be configured as or may otherwise include an HMM accelerator 8. The HMM accelerator 8 may be configured as part of the microchip 7, e.g., as hardwired and/or as code to be run in association therewith, and is configured for performing a variant call function, such as for performing one or more operations of a Hidden Markov Model, on data supplied to the microchip 7 by the CPU 1000, such as over the PCIe interface 4. Likewise, once one or more variant call functions have been performed, e.g., one or more HMM operations run, the results thereof may be transferred from the HMM accelerator 8 of the chip 7 over the bus 4 to the CPU 1000, such as via connection 3.

For instance, in particular instances, a CPU 1000 for processing and/or transferring information and/or executing instructions is provided along with a microchip 7 that is at least partially configured as an HMM accelerator 8. The CPU 1000 communicates with the microchip 7 over an interface 5 that is adapted to facilitate the communication between the CPU 1000 and the HMM accelerator 8 of the microchip 7 and therefore may communicably connect the CPU 1000 to the HMM accelerator 8 that is part of the microchip 7. To facilitate these functions, the microchip 7 includes a distributor module 9, which may be a CentCom, that is configured for transferring data to a multiplicity of HMM engines 13, e.g., via one or more clusters 11, where each engine 13 is configured for receiving and processing the data, such as by running an HMM protocol thereon, computing final values, outputting the results thereof, and repeating the same. In various instances, the performance of an HMM protocol may include determining one or more transition probabilities, as described herein below. Particularly, each HMM engine 13 may be configured for performing a job such as including one or more of the generating and/or evaluating of an HMM virtual matrix to produce and output a final sum value with respect thereto, which final sum expresses the probable likelihood that the called base matches or is different from a corresponding base in a hypothetical haplotype sequence, as described herein below.

Figure 9:
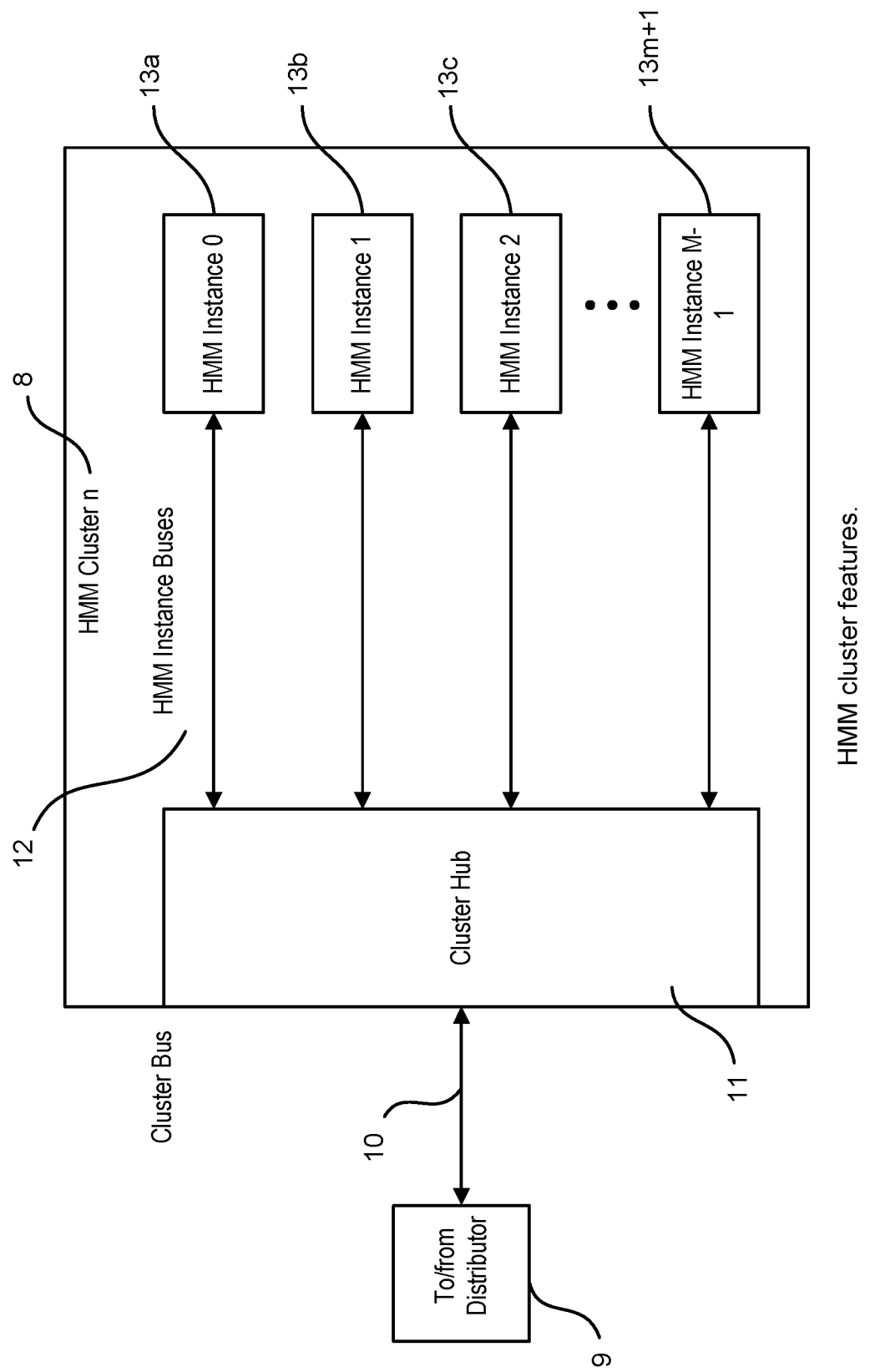
FIG. 9 depicts the integrated circuit of FIG. 8, showing an HMM cluster features in greater detail.

FIG. 9 presents a detailed depiction of the MINI cluster 11 of FIG. 8. In various embodiments, each MINI cluster 11 includes one or more HMM instances 13. One or a number of clusters may be provided, such as desired in accordance with the amount of resources provided, such as on the chip. Particularly, a HMM cluster may be provided, where the cluster is configured as a cluster hub 11. The cluster hub 11 takes the data pertaining to one or more jobs 20 from the distributor 9, and is further communicably connected to one or more, e.g., a plurality of, HMM instances 13, such as via one or more HMM instance busses 12, to which the cluster hub 11 transmits the job data 20.

The bandwidth for the transfer of data throughout the system may be relatively low bandwidth process, and once a job 20 is received, the system 1 may be configured for completing the job, such as without having to go off chip 7 for memory. In various embodiments, one job $20a$ is sent to one processing engine $13a$ at any given time, but several jobs $20_{a-n}$ may be distributed by the cluster hub 11 to several different processing engines $13a$-$13_{m+1}$, such as where each of the processing engines 13 will be working on a single job 20, e.g., a single comparison between one or more reads and one or more haplotype sequences, in parallel and at high speeds. As described below, the performance of such a job 20 may typically involve the generation of a virtual matrix whereby the subject's "read" sequences may be compared to one or more, e.g., two, hypothetical haplotype sequences, so as to determine the differences there between. In such instances, a single job 20 may involve the processing of one or more matrices having a multiplicity of cells therein that need to be processed for each comparison being made, such as on a base by base basis. As the human genome is about 3 billion base pairs, there may be on the order of 1 to 2 billion different jobs to be performed when analyzing a 30× oversampling of a human genome (which is equitable to about 20 trillion cells in the matrices of all associated HMM jobs).

Accordingly, as described herein, each HMM instance 13 may be adapted so as to perform an HMM protocol, e.g., the generating and processing of an HMM matrix, on sequence data, such as data received thereby from the CPU 1000. For example, as explained above, in sequencing a subject's genetic material, such as DNA, the DNA is broken down into segments, such as up to about 100 bases in length. The identity of these 100 base segments are then determined, such as by an automated sequencer, and "read" into a FASTQ text based file format that stores both each base identity of the read along with a Phred quality score (e.g., typically a number between 0 and 63 in log scale, where a score of 0 indicates the least amount of confidence that the called base is correct, with scores between 20 to 45 generally being acceptable as relatively accurate).

Particularly, as indicated above, a Phred quality score is a quality indicator that measures the quality of the identification of the nucleobase identities generated by the sequencing processor, e.g., by the automated DNA/RNA sequencer. Hence, each read base includes its own quality, e.g., Phred, score based on what the sequencer evaluated the quality of that specific identification to be. The Phred represents the confidence with which the sequencer estimates that it got the called base identity correct. This Phred score is then used by the implemented HMM module 8, as described in detail below, to further determine the accuracy of each called base in the read as compared to the haplotype to which it has been mapped and/or aligned, such as by determining its Match, Insertion, and/or Deletion transition probabilities, e.g., in and out of the Match state. It is to be noted that in various embodiments, the system 1 may modify or otherwise adjust the initial Phred score prior to the performance of an HMM protocol thereon, such as by taking into account neighboring bases/scores and/or fragments of neighboring DNA and allowing such factors to influence the Phred score of the base, e.g., cell, under examination.

Figure 10:
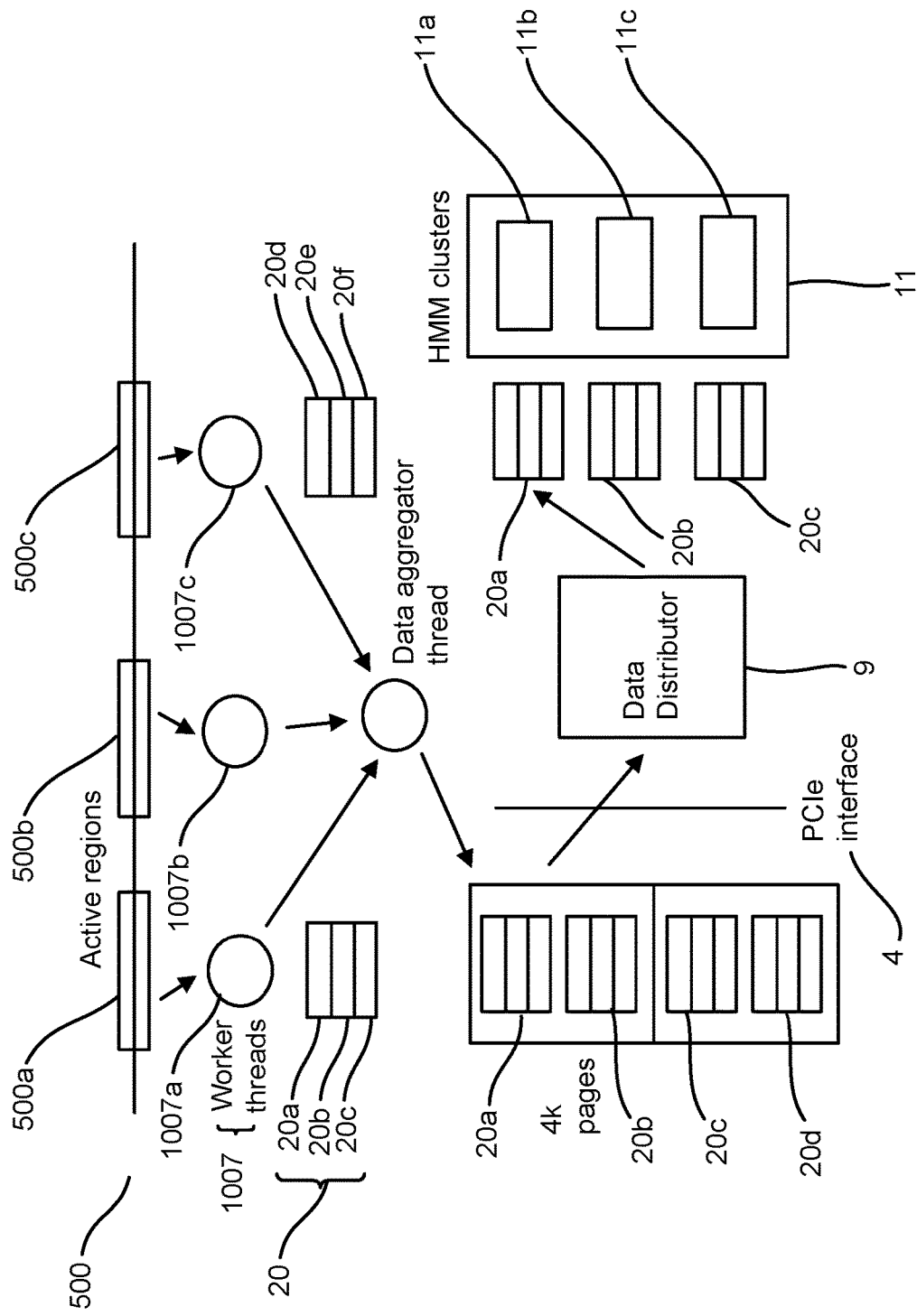
FIG. 10 depicts an overview of HMM related data flow throughout the system including both software and hardware interactions.

In such instances, as can be seen with respect to FIG. 10, the system 1, e.g., computer software, may determine and identify various active regions 500$_n$ within the sequenced genome that may be explored and/or otherwise subjected to further processing as herein described, which may be broken down into jobs 20$_n$ that may be parallelized amongst the various cores and available threads 1007 throughout the system 1. For instance, such active regions 500 may be identified as being sources of variation between the sequenced and reference genomes. Particularly, the CPU 1000 may have multiple threads 1007 running, identifying active regions 500$a$, 500$b$, and 500$c$, compiling and aggregating various different jobs 20$_n$ to be worked on, e.g., via a suitably configured aggregator 1008, based on the active region(s) 500$a$-$c$ currently being examined. Any suitable number of threads 1007 may be employed so as to allow the system 1 to run at maximum efficiency, e.g., the more threads present the less active time spent waiting.

Once identified, compiled, and/or aggregated, the threads 1007/1008 will then transfer the active jobs 20 to the data distributor 9, e.g., CentCom, of the HMM module 8, such as via PCIe interface 4, e.g., in a fire and forget manner, and will then move on to a different process while waiting for the HMM 8 to send the output data back so as to be matched back up to the corresponding active region 500 to which it maps and/or aligns. The data distributor 9 will then distribute the jobs 20 to the various different HMM clusters 11, such as on a job-by-job manner. If everything is running efficiently, this may be on a first in first out format, but such does not need to be the case. For instance, in various embodiments, raw jobs data and processed job results data may be sent through and across the system as they become available.

Particularly, as can be seen with respect to FIG. 3, the various job data 20 may be aggregated into 4K byte pages of data, which may be sent via the PCIe 4 to and through the CentCom 9 and on to the processing engines 13, e.g., via the clusters 11. The amount of data being sent may be more or less than 4K bytes, but will typically include about 100 HMM jobs per 4K (e.g., 1024) page of data. Particularly, these data may then get digested by the data distributor 9 and are fed to each cluster 11, such as where one 4K page is sent to one cluster 11. However, such need not be the case as any given job 20 may be sent to any given cluster 11, based on the clusters that become available and when. Accordingly, as can be seen with respect to FIGS. 12 and 13, each job 20 may have a job ID that accompany each job, which job ID flows through the overall process substantially unmodified so the system, e.g., software and/or hardware, can use those identifications so that it can be maintained to which active region 500 each particular job 20 and/or result refers.

Accordingly, the cluster 11 approach as presented here efficiently distributes incoming data to the processing engines 13 at high-speed. Specifically, as data arrives at the PCIe interface 4 from the CPU 1000, e.g., over DMA connection 3, the received data may then be sent over the PCIe bus 5 to the CentCom distributor 9 of the variant caller microchip 7. The distributor 9 then sends the data to one or more HMM processing clusters 11, such as over one or more cluster dedicated buses 10, which cluster 11 may then transmit the data to one or more processing instances 13, e.g., via one or more instance buses 12, such as for processing. In this instance, the PCIe interface 4 is adapted to provide data through the peripheral expansion bus 5, distributor 9, and/or cluster 10 and/or instance 12 busses at a rapid rate, such as at a rate that can keep one or more, e.g., all, of the HMM accelerator instances 13$_{a-(m+1)}$ within one or more, e.g., all, of the HMM clusters 11$_{a-(n+1)}$ busy, such as over a prolonged period of time, e.g., full time, during the period over which the system 1 is being run, the jobs 20 are being processed, and whilst also keeping up with the output of the processed MINI data that is to be sent back to one or more CPUs 1000, over the PCIe interface 4.

For instance, any inefficiency in the interfaces 3, 5, 10, and/or 12 that leads to idle time for one or more of the HMM accelerator instances 13 may directly add to the overall processing time of the system 1. Particularly, when analyzing a human genome, there may be on the order of two or more billion different jobs 20 that need to be distributed to the various MINI clusters 11 and processed over the course of a time period, such as under 1 hour, under 45 minutes, under 30 minutes, under 20 minutes including 15 minutes, 10 minutes, 5 minutes, or less.

For example, each typical job 20 may have on the order of a few hundred bytes of write data associated with it. In such an instance, the total amount of write data may be on the order of several hundred Gigabytes to one or more thousand of Gigabytes, such as over 1 Terabyte of data, such as over the course of processing a whole genome. However, in an instance such as this, the data to be fed back to the CPU 1000 may be as little as 16-bytes per job 20. Hence, there is a need for efficient data distribution and collection, which need may not arise as much from the amount of data (~1.1 Gbyte/s average write rate, ~64 Mbyte/s average read rate), as from the requirement that the data be sliced up and parsed out to (or collected from) one or more of the various parallel jobs 20 being performed by the one or more clusters 11 and/or one or more instances 13.

More particularly, if it is assumed that 200 MHz is the speed of the clock associated with the Cluster Buses 10 and a data width of 32 bits is moving through the bus of each HMM cluster 11 during each clock cycle, as described in detail below, then something on the order of six HMM clusters 11*a-f* will provide a data write data bandwidth capability that exceeds the ~1.1 GB/sec average requirement, such as by a factor of four, or greater. Accordingly, in one exemplary embodiment, an initial configuration for the Cluster Buses 10 may involve a 200 MHz clock and data transfer rate as well as six HMM clusters 11*a-f*. However, as routing and/or throughput requirements evolve, the number of clusters 11 or the speed for the Cluster Buses 10 may be adjusted, so the cluster count and Cluster Bus 10 speed be may be parametrize-able so as to meet evolving needs.

Accordingly, FIG. 10 sets forth an overview of the data flow throughout the software and/or hardware of the system 1, as described generally above. As can be seen with respect to FIG. 10, the system 1 may be configured in part to transfer data, such as between the PCIe interface 4 and the distributor 9, e.g., CentCom, such as over the PCIe bus 5. Additionally, the system 1 may further be configured in part to transfer the received data, such as between the distributor 9 and the one or more HMM clusters 11, such as over the one or more cluster buses 10. Hence, in various embodiments, the HMM accelerator 8 may include one or more clusters 11, such as one or more clusters 11 configured for performing one or more processes of an HMM function. In such an instance, there is an interface, such as a cluster bus 10, that connects the CentCom 9 to the HMM cluster 11.

Figure 11:
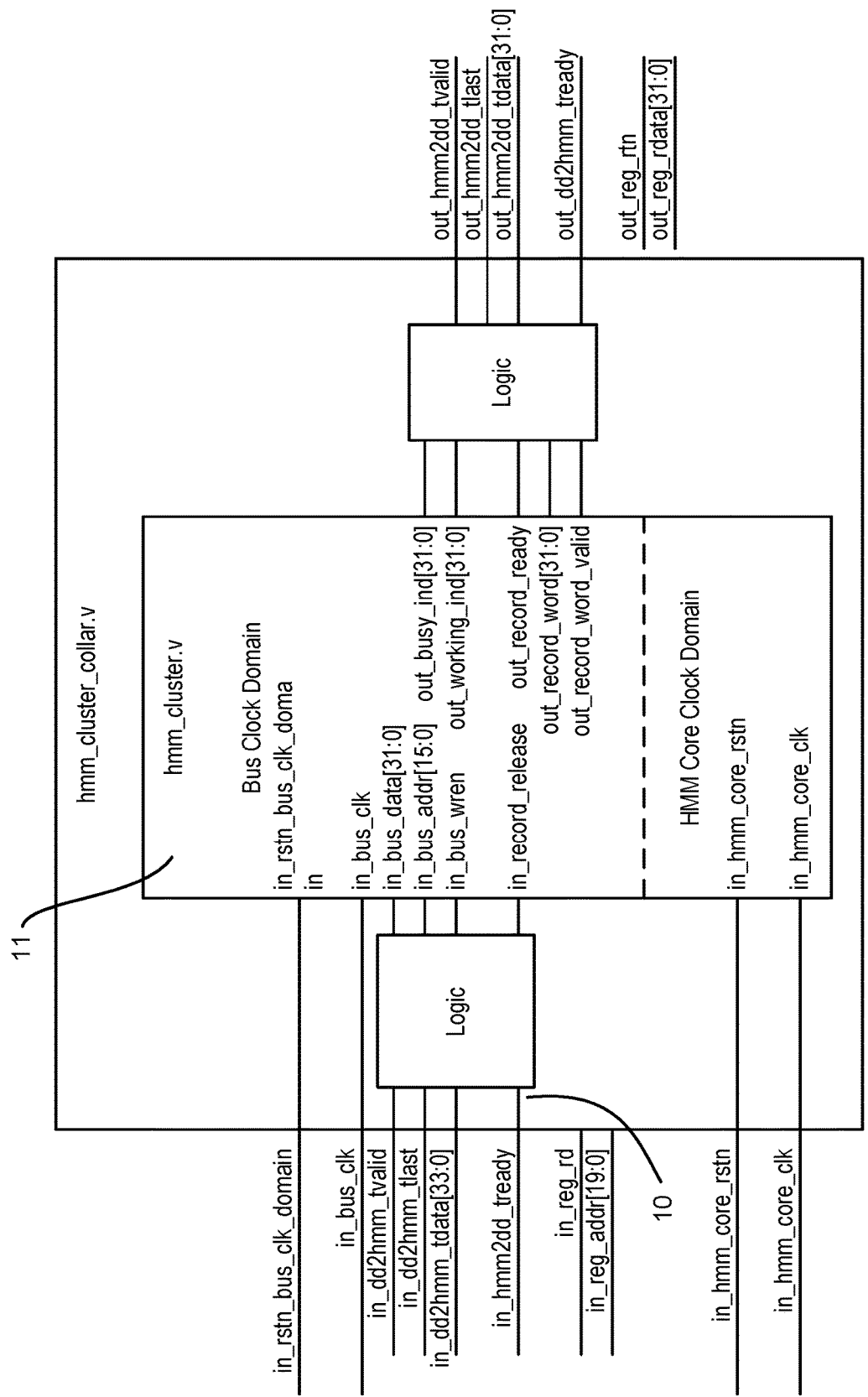
FIG. 11 depicts exemplary MINI cluster collar connections.

For instance, FIG. 11 is a high level diagram depicting the interface in to and out of the HMM module 8, such as into and out of a cluster module. As can be seen with respect to FIG. 11, each HMM cluster 11 may be configured to communicate with, e.g., receive data from and/or send final result data, e.g., sum data, to the CentCom data distributor 9 through a dedicated cluster bus 10. Particularly, any suitable interface or bus 5 may be provided so long as it allows the PCIe interface 4 to communicate with the data distributor 9. More particularly, the bus 5 may be an interconnect that includes the interpretation logic useful in talking to the data distributor 9, which interpretation logic may be configured to accommodate any protocol employed to provide this functionality. Specifically, in various instances, the interconnect may be configured as a PCIe bus 5. Additionally, the cluster 11 may be configured such that single or multiple clock domains may be employed therein, and hence, one or more clocks may be present within the cluster 11. In particular instances, multiple clock domains will be provided. For example, a slower clock may be provided, such as for communications, e.g., to and from the cluster 11. Additionally, a faster, e.g., a high speed, clock may be provided which may be employed by the HMM instances 13 for use in performing the various state calculations described herein.

Particularly, in various embodiments, as can be seen with respect to FIG. 11, the system 1 may be set up such that, in a first instance, as the data distributor 9 leverages the existing CentCom IP, a collar, such as a gasket, may be provided, where the gasket is configured for translating signals to and from the CentCom interface 5 from and to the HMM cluster interface or bus 10. For instance, an HMM cluster bus 10 may communicably and/or operably connect the CPU 1000 to the various clusters 11 of the HMM accelerator module 8.

Hence, as can be seen with respect to FIG. 11, structured write and/or read data for each haplotype and/or for each read may be sent throughout the system 1. Particularly, as can be seen with respect to FIG. 12, an exemplary write data structure 22 is provided, such as where the data structure may include one or more, e.g., a plurality, of 32 bit words, such as on a top layer that function as control words and/or contain the haplotype length and/or other control data, e.g., in the reserved area. The next layer of data may also be a 32 bit word such as includes the haplotype ID, which ID may be used by the system software to take the output results and correlate them back to where it came from in the associated active region being processed. With respect to analyzing the haplotype sequence, 8-four bit bases may be provided for each 32 bit word, and two haplotype sequences may be analyzed at a given time, e.g., thereby filling layers 3 and 4 of the data structure. It is to be noted that the word layers need not be 32 bits, but in various instances, the use of a 32-bit word may be particularly efficient.

Accordingly, with respect to the transfer of write data, one or more, e.g., each, HMM engine instance 13 within or otherwise associated with the HMM cluster hub 11 may be configured to include or otherwise be operably connected with one, two, or more separate one or two-port memories, such as 1 read port and/or 1 write port memory. These memories may be a HMEM 16 and/or an RMEM 18, such as where each memory includes both a read and a write port. FIG. 5 exemplifies the possible contents of a single HMEM data structure 22, while FIG. 6, as explained below, exemplifies the possible contents of a single RMEM data structure 24. In such instances, the data distributor 9 may be configured to access the write port, and the HMM engine instance 13 may be configured to access the read port of the HMEM and RMEM memories.

Specifically, in various instances, one or more of the interfaces, such as the cluster bus interface 10 may be associated with a clock, such as a cluster bus interface clock, which may be run at a relatively slower cycle speed. Additionally, various other components of the system 1, e.g., the HMM instance 13, may be associated with one or more other clocks of the system, such as a core domain clock, which clock may be run at a relatively faster cycle speed. In such instances, therefore, the write port on both the HMEM 16 and the RMEM 18 may be connected to the cluster bus interface clock, while the read port on both the HMEM 16 and the RMEM 18 may be connected to the HMM engine core clock domain. Consequently, these memories may form a synchronous or an asynchronous boundary between the slower cluster bus interface clock domain and the faster HMM engine core clock domain.

Figure 12:
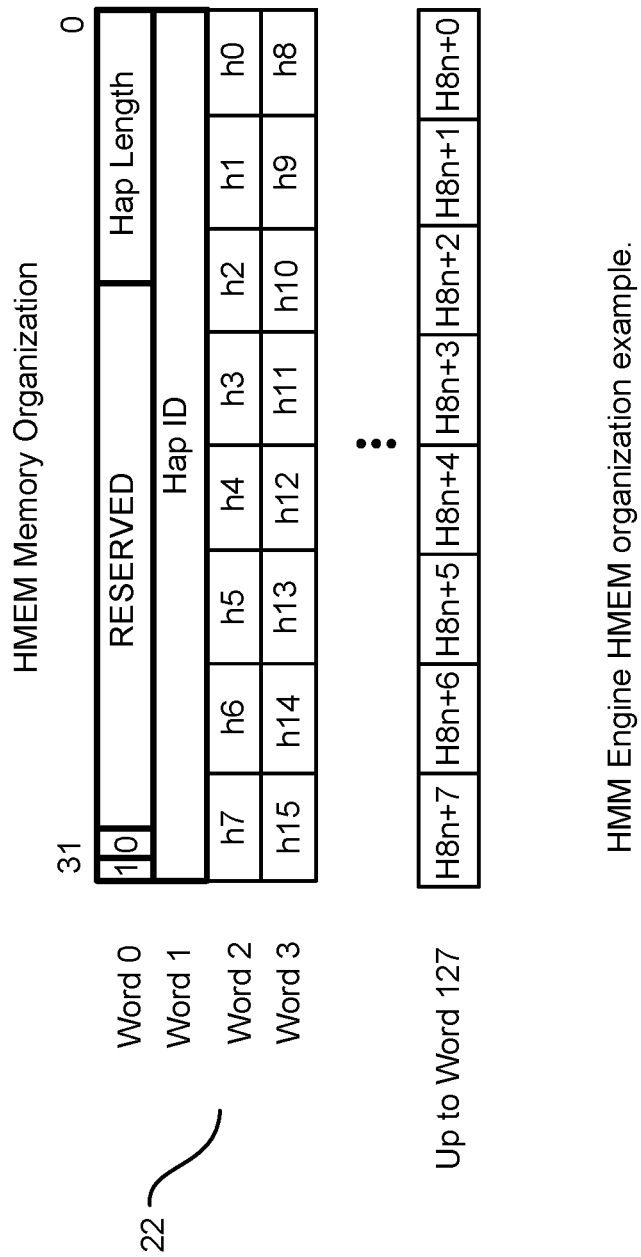
FIG. 12 depicts an exemplary MINI engine HMEM organization.

Additionally, as shown with respect to FIG. 12, the HMEM 16 may be used to hold the reference haplotype base identifier and other related control information. Each reference haplotype base identifier may be represented within the data structure 22 as four bits, such as by using a mapping scheme such as: 0 implies haplotype base is "A;" 1 implies haplotype base is "C;" 2 implies haplotype base is "G;" 3 implies haplotype base is "T;" and 15 implies haplotype base is "N." It is to be noted that other various sequences and combinations of coding for the same may be employed without departing form the nature of this embodiment. Accordingly, in particular instances, A, C, G, and T, may be defined as 0, 1, 2, and 3, and where there is an "N" base, e.g., where the reference cannot make a good call as to the identity of a particular base, it may be defined as 15. All other four-bit values may be RESERVED. It is to be noted that each HMM engine instance 13 may have one, two, or more logical HMEM instances. Also note that bits [31:30] of the first word of each haplotype record may be written as "10" binary.

As indicated, these haplotype base identifiers may be packed as eight 4-bit values per 32-bit write word, with base identifiers corresponding to earlier values in the reference sequence being located closer to bit 0 of the 32 bit word (see FIG. 12, for more information on the packing scheme). Accordingly, enough space is provisioned in the HMEM to hold one, two, or more complete reference sequences per HMM job 20, and these complete sequences may be thought of as being held in separate logical HMEM instances. This allows better use of both interface 4 and HMM engine 13 resources, as a read sequence that is to be compared to one or more, e.g., multiple, different reference haplotype sequences need only be written to an HMM engine instance 13 once.

In addition to the reference haplotype base identifiers, the HMEM may also contain a haplotype length field, and a 32-bit haplotype ID. For example, the haplotype length field communicates the length of the reference haplotype sequence. The haplotype ID may be a value generated by the variant call software of the CPU 1000, e.g., a thread 1007 thereof, and may be included with the final output sum that is fed back to the CPU 1000. Such "Hap ID" may therefore be used by the variant call software of the system 1 to associate a final HMM sum output with a specific reference haplotype. For instance, in various instances, different jobs 20 may take different amounts of time to complete, so there is no guarantee that the order in which the thread 1007 issues the jobs 20 to the hardware accelerator 8 will be the order in which it will receive the results back from those jobs.

Figure 13:
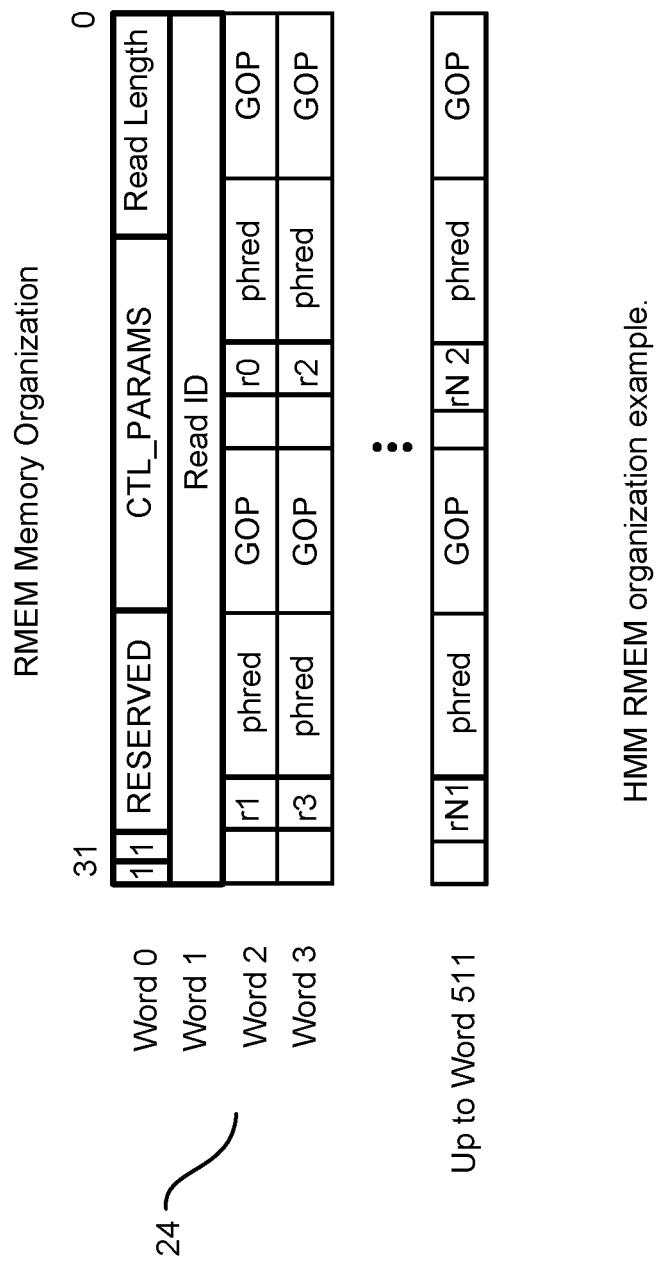
FIG. 13 depicts an exemplary MINI engine RMEM organization.

As can be seen with respect to FIG. 13, an exemplary read data structure 24 is provided, such as where the data structure may include one or more 32 bit words, such as on the top layer that function as control words and/or contain the read length, job-specific control information and/or other control data, e.g., in the reserved area. These data may include instructions regarding specific parameters directing the software to perform certain calculations so that the hardware need not calculate them. Such data could be calculated by the hardware but it may in certain instances be more efficient to perform such tasks in software as they need only be calculated once per job.

The next layer of data may also be a 32 bit word such as includes the read ID, which when taken with the haplotype ID defines what the job 20 is and where it is from in the associated active region 500 being processed. With respect to analyzing the read sequence, for each read base the Phred quality score may be provided and a gap open penalty (GOP), as explained below, may be provided, both of which may be in 6-bits. It is to be noted that the read memory 18 may be deeper than the haplotype memory for a given sequence length, and this is in part because instead of simply including 8 bases per 32-bit word, only 2 bases per 32-bit road may be used, since the Phred score and GOP is also included. Again, it is to be noted that the word layers need not be 32 bits, but in various instances, the use of a 32-bit word may be particularly efficient. In various embodiments, the HMEM 16 and RMEM 18 may be configured so as to have enough space to hold the data associated with a haplotype or read sequence(s) up to a length of 1000 or more, such as 1020 or more, such as 1050 or 1080 or more bases. Of course, shorter or longer sequences could be tolerated with the corresponding increase in memory-dedicated resources.

Accordingly, the data structure associated with each read base is set forth in FIG. 13. In this instance, a 2-bit base identifier, with a {0,1,2,3} specifies {A,C,G,T}, respectively. Further, a 6-bit base quality may be present in Phred space (where a quality=0 or other determined base quality is used to imply a base identifier of "N") as well as a 6-bit insertion/deletion gap open penalty. Accordingly, the data associated with the two read bases may be packed into each 32-bit word that is delivered to the HMM cluster 11, with read base information corresponding to earlier values in the read sequence being located in the lower half of the 32-bit word (see FIG. 6 for more information on the packing scheme).

In addition to the read base identifiers, per-read-base quality information, and per-read-base gap open penalty, the RMEM 18 may also contain the read length field, the job-specific control information field, and a 32-bit read ID. The read length field can be configured to communicate the length of the read sequence. The read ID may be a value generated by the CPU 1000, or a thread 1007 thereof, which may be included with the final output sum to be fed back to the CPU 1000. This "Read ID" may be used by the system 1 to associate a final HMM sum output with a specific reference read sequence (as before, it is noted that different jobs may take different amounts of time, so there is no guarantee that the order in which the CPU 1000 issues the jobs is the order in which it will receive the results from those jobs).

Accordingly, when each HMM engine instance 13 completes a job, a 128-bit record is made available to the data distributor 9 for reading. In order to efficiently utilize the interface 4, e.g., PCIe interface, and associated bandwidth, the data distributor 9 may collect records from multiple completed jobs $20_n$ before sending the data upstream to the CPU 1000. The record associated with each completed job 20 may contain the following information: Job Status Word, Hap ID, Read ID, and the Final HMM Sum Value. Accordingly, when the computing has been completed, there are 4–32 bit words that are then returned to the variant call software of the CPU 1000, the status word characterizes the job 20, the haplotype and read IDs map the job 20 back to its corresponding active region 500, and the final sum value, is described in greater detail below.

For instance, the Read ID and Hap ID are typically those 32 bit values that the CPU 1000, or thread 1007 thereof, provides in the write stream to use in identifying job 20 results. Since, the jobs may not complete in the order that they were issued, the Read and Hap IDs are the mechanism the system 1 uses to properly associate jobs with results. The final HMM sum value may be a 32-bit value that is the output of the HMM matrix computation and summing process, described below. This value may be in a variant of floating point format, such as with a number of mantissa and exponent bits that are programmable.

Following a job 20 being input into the HMM engine, an HMM engine 13 may typically start either: a) immediately, if it is IDLE, or b) after it has completed its currently assigned task. It is to be noted that each HMM accelerator engine 13 can handle ping and pong inputs (e.g., can be working on one data set while the other is being loaded), thus minimizing downtime between jobs. Additionally, the HMM cluster collar 11 may be configured to automatically take the input job 20 sent by the data distributor 9 and assign it to one of the HMM engine instances 13 in the cluster 11 that can receive a new job. There need not be a control on the software side that can select a specific HMM engine instance 13 for a specific job 20. However, in various instances, the software can be configured to control such instances.

Accordingly, in view of the above, the system 1 may be streamlined when transferring the results data back to the CPU, and because of this efficiency there is not much data that needs to go back to the CPU to achieve the usefulness of the results. This allows the system to achieve about a 30 minute or less, such as about a 25 or about a 20 minute or less, for instance, about a 18 or about a 15 minute or less, including about a 10 or about a 7 minute or less, even about a 5 or about a 3 minute or less variant call operation, dependent on the system configuration.

Figure 14:
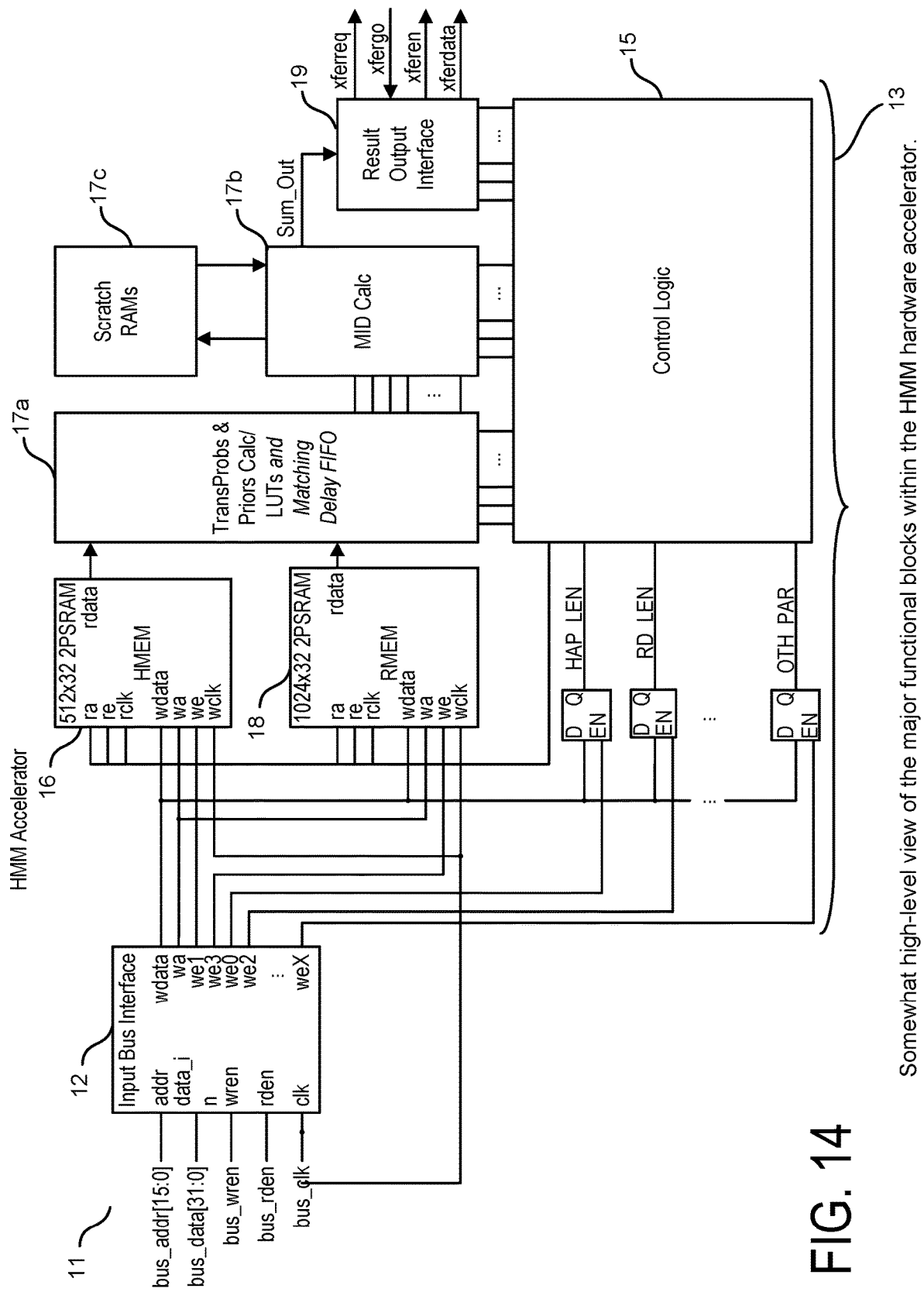
FIG. 14 depicts a high-level view of the major functional blocks within an exemplary MINI hardware accelerator.

FIG. 14 presents a high-level view of various functional blocks within an exemplary HMM engine 13 within a hardware accelerator 8, on the FPGA or ASIC 7. Specifically, within the hardware MINI accelerator 8 there are multiple clusters 11, and within each cluster 11 there are multiple engines 13. FIG. 14 presents a single instance of an MINI engine 13. As can be seen with respect to FIG. 14, the engine 13 may include an instance bus interface 12, a plurality of memories, e.g., an HMEM 16 and an RMEM 18, various other components 17, MINI control logic 15, as well as a result output interface 19. Particularly, on the engine side, the HMM instance bus 12 is operably connected to the memories, HMEM 16 and RMEM 18, and may include interface logic that communicates with the cluster hub 11, which hub is in communications with the distributor 9, which in turn is communicating with the PCIe interface 4 that communicates with the variant call software being run by the CPU and/or server 1000. The HMM instance bus 12, therefore, receives the data from the CPU 1000 and loads it into one or more of the memories, e.g., the HMEM and RMEM.

In such an instance, enough memory space should be allocated such that at least one or two or more haplotypes, e.g., two haplotypes, may be loaded, e.g., in the HMEM 16, per given read sequence that is loaded, e.g., into the RMEM 18, which when multiple haplotypes are loaded results in an easing of the burden on the PCIe bus 5 bandwidth. In particular instances, two haplotypes and two read sequences may be loaded into their respective memories, which would allow the four sequences to be processed together in all relevant combinations. In other instances four, or eight, or sixteen sequences, e.g., pairs of sequences, may be loaded, and in like manner be processed in combination, such as to further ease the bandwidth when desired.

Additionally, enough memory may be reserved such that a ping-pong structure may be implemented therein such that once the memories are loaded with a new job 20a, such as on the ping side of the memory, a new job signal is indicated, and the control logic 15 may begin processing the new job 20a, such as by generating the matrix and performing the requisite calculations, as described herein and below. Accordingly, this leaves the pong side of the memory available so as to be loaded up with another job 20b, which may be loaded therein while the first job 20a is being processed, such that as the first job 20a is finished, the second job 20b may immediately begin to be processed by the control logic 15.

In such an instance, the matrix for job 20b may be preprocessed so that there is virtually no down time, e.g., one or two clock cycles, from the ending of processing of the first job 20a, and the beginning of processing of the second job 20b. Hence, when utilizing both the ping and pong side of the memory structures, the HMEM 16 may typically store 4 haplotype sequences, e.g., two a piece, and the RMEM 18 may typically store 2 read sequences. This ping-pong configuration is useful because it simply requires a little extra memory space, but allows for a doubling of the throughput of the engine 13.

During and/or after processing the memories 16, 18 feed into the transition probabilities calculator and lookup table (LUT) block 17a, which is configured for calculating various information related to "Priors" data, as explained below, which in turn feeds the Prior results data into the M, I, and D state calculator block 17b, for use when calculating transition probabilities. One or more scratch RAMs 17c may also be included, such as for holding the M, I, and D states at the boundary of the swath, e.g., the values of the bottom row of the processing swath, which as indicated, in various instances, may be any suitable amount of cells, e.g., about 10 cells, in length so as to be commensurate with the length of the swath 35.

Additionally included is a separate results output interface block 19 so when the sums are finished they, e.g., the 4 32-bit words, can immediately be transmitted back to the variant call software of the CPU 1000. It is to be noted that this configuration may be adapted so that the system 1, specifically the M, I, and D calculator 17b is not held up waiting for the output interface 19 to clear, e.g., so long as it does not take as long to clear the results as it does to perform the job 20. Hence, in this configuration, there may be three pipeline steps functioning in concert to make an overall systems pipeline, such as loading the memory, performing the MID calculations, and outputting the results. Further, it is noted that any given HMM engine 13 is one of many with their own output interface 19, however they may share a common interface 10 back to the data distributor 9. Hence, the cluster hub 11 will include management capabilities to manage the transfer ("xfer") of information through the HMM accelerator 8 so as to avoid collisions.

Accordingly, the following details the processes being performed within each module of the HMM engines 13 as it receives the haplotype and read sequence data, processes it, and outputs results data pertaining to the same, as generally outlined above. Specifically, the high-bandwidth computations in the HMM engine 13, within the HMM cluster 11, are directed to computing and/or updating the match (M), insert (I), and delete (D) state values, which are employed in determining whether the particular read being examined matches the haplotype reference as well as the extent of the same, as described above. Particularly, the read along with the Phred score anf GOP value for each base in the read is transmitted to the cluster 11 from the distributor 9 and is thereby assigned to a particular processing engine 13 for processing. These data are then used by the M, I, and D calculator 17 of the processing engine 13 to determine whether the called base in the read is more or less likely to be correct and/or to be a match to its respective base in the haplotype, or to be the product of a variation, e.g., an insert or deletion; and/or if there is a variation, whether such variation is the likely result of a true variability in the haplotype or rather an artifact of an error in the sequence generating and/or mapping and/or aligning systems.

As indicated above, a part of such analysis includes the MID calculator 17 determining the transition probabilities from one base to another in the read going from one M, I, or D state to another in comparison to the reference, such as from a matching state to another matching state, or a matching state to either an insertion state or to a deletion state. In making such determinations each of the associated transition probabilities is determined and considered when evaluating whether any observed variation between the read and the reference is a true variation and not just some machine or processing error. For these purposes, the Phred score for each base being considered is useful in determining the transition probabilities in and out of the match state, such as going from a match state to an insert or deletion, e.g., a gapped, state in the comparison. Likewise, the transition probabilities of continuing a gapped state or going from a gapped state, e.g., an insert or deletion state, back to a match state are also determined. In particular instances, the probabilities in or out of the delete or insert state, e.g., exiting a gap continuation state, may be a fixed value, and may be referenced herein as the gap continuation probability or penalty. Nevertheless, in various instances, such gap continuation penalties may be floating and therefore subject to change dependent on the accuracy demands of the system configuration.

Figure 15:
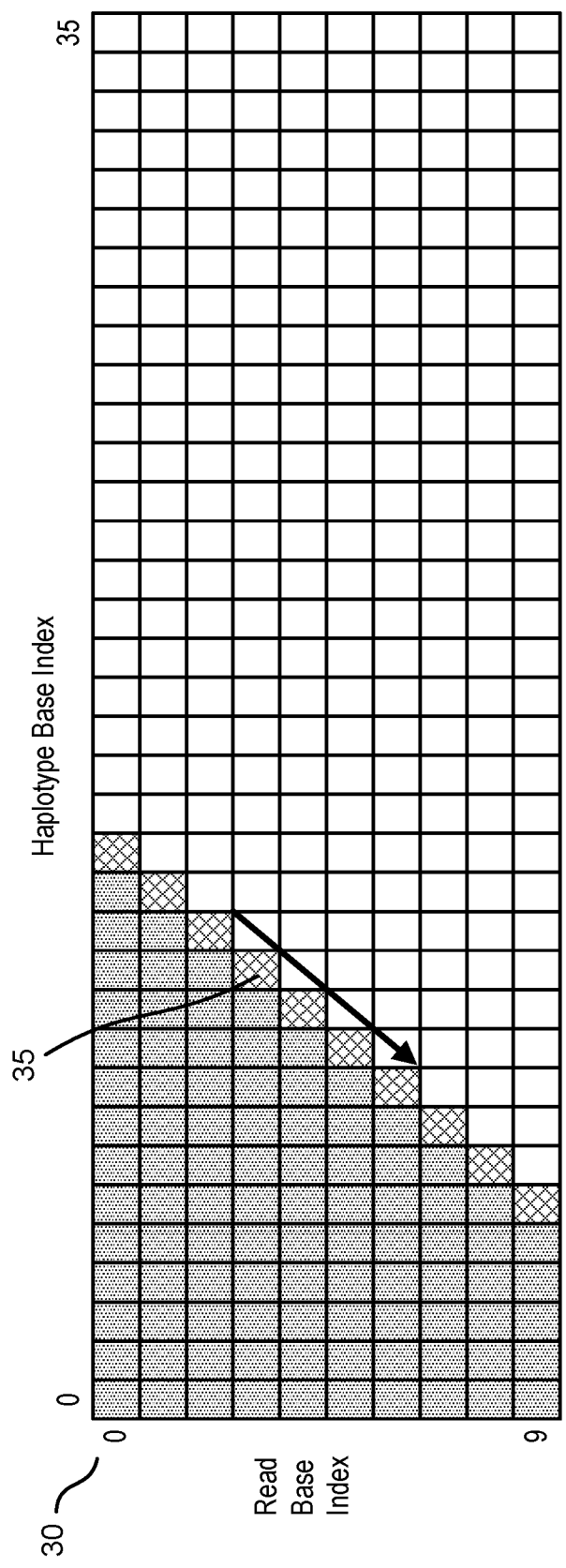
FIG. 15 depicts an exemplary HMM matrix structure and hardware processing flow.
Figure 16:
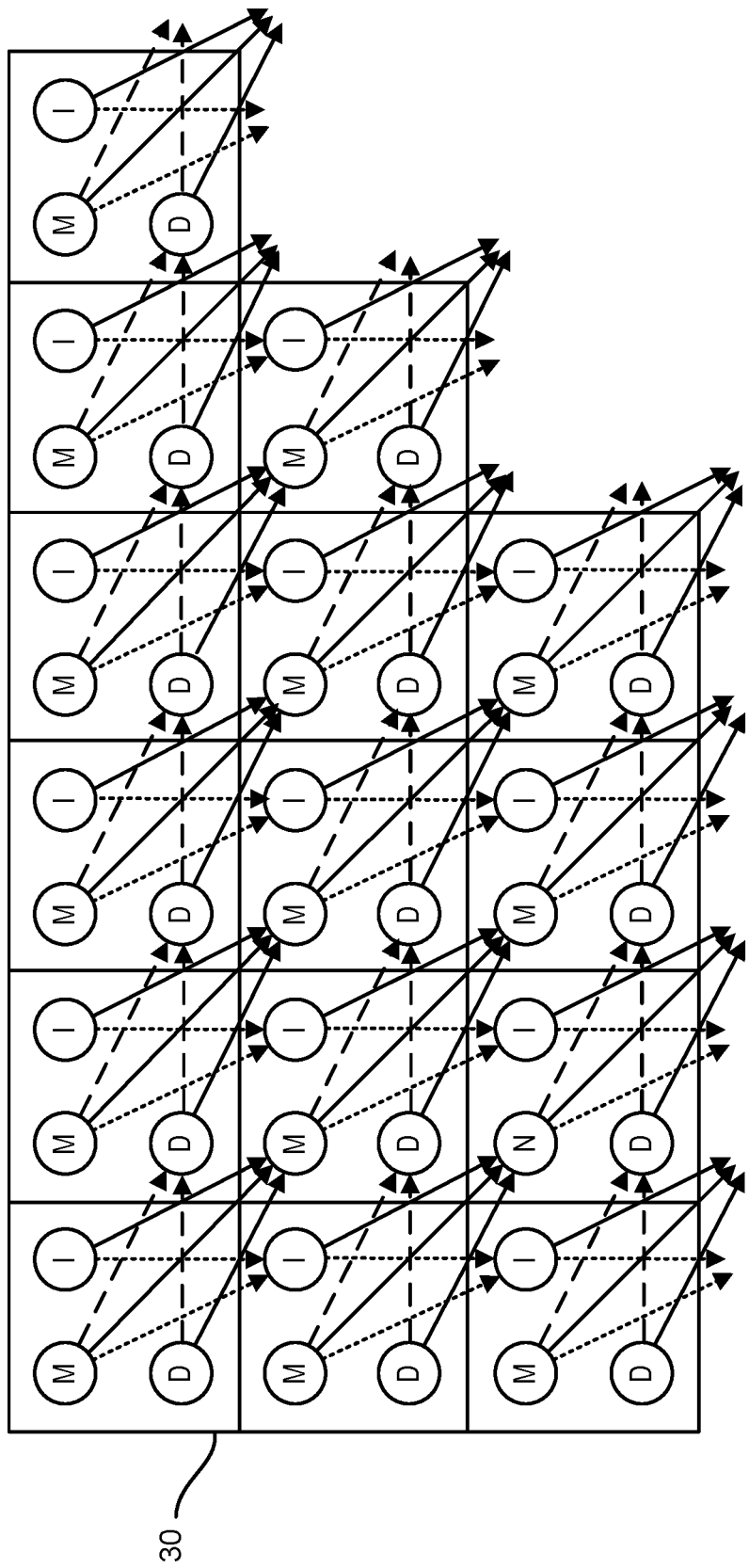
FIG. 16 depicts an enlarged view of a portion of FIG. 2 showing the data flow and dependencies between nearby cells in the HMM M, I, and D state computations within the matrix.

Accordingly, as depicted with respect to FIGS. 15 and 16 each of the M, I, and D state values are computed for each possible read and haplotype base pairing. In such an instance, a virtual matrix 30 of cells containing the read sequence being evaluated on one axis of the matrix and the associated haplotype sequence on the other axis may be formed, such as where each cell in the matrix represents a base position in the read and haplotype reference. Hence, if the read and haplotype sequences are each 100 bases in length, the matrix 30 will include 100 by 100 cells, a given portion of which may need to be processed in order to determine the likelihood and/or extent to which this particular read matches up with this particular reference. Hence, once virtually formed, the matrix 30 may then be used to determine the various state transitions that take place when moving from one base in the read sequence to another and comparing the same to that of the haplotype sequence, such as depicted in FIGS. 15 and 16. Specifically, the processing engine 13 is configured such that a multiplicity of cells may be processed in parallel and/or sequential fashion when traversing the matrix with the control logic 15. For instance, as depicted in FIG. 15, a virtual processing swath 35 is propagated and moves across and down the matrix 30, such as from left to right, processing the individual cells of the matrix 30 down the right to left diagonal.

More specifically, as can be seen with respect to FIG. 15, each individual virtual cell within the matrix 30 includes an M, I, and D state value that needs to be calculated so as to asses the nature of the identity of the called base, and as depicted in FIG. 15 the data dependencies for each cell in this process may clearly be seen. Hence, for determining a given M state of a present cell being processed, the Match, Insert, and Delete states of the cell diagonally above the present cell need to be pushed into the present cell and used in the calculation of the M state of the cell presently being calculated (e.g., thus, the diagonal downwards, forwards progression through the matrix is indicative of matching).

However, for determining the I state, only the Match and Insert states for the cell directly above the present cell need be pushed into the present cell being processed (thus, the vertical downwards "gapped" progression when continuing in an insertion state). Likewise, for determining the D state, only the Match and Delete states for the cell directly left of the present cell need be pushed into the present cell (thus, the horizontal cross-wards "gapped" progression when continuing in a deletion state). As can be seen with respect to FIG. 15, after computation of cell 1 (the shaded cell in the top most row) begins, the processing of cell 2 (the shaded cell in the second row) can also begin, without waiting for any results from cell 1, because there is no data dependencies between this cell in row 2 and the cell of row 1 where processing begins. This forms a reverse diagonal 35 where processing proceeds downwards and to the left, as shown by the red arrow. This reverse diagonal 35 processing approach increases the processing efficiency and throughput of the overall system. Likewise, the data generated in cell 1, can immediately be pushed forward to the cell down and forward to the right of the top most cell 1, thereby advancing the swath 35 forward.

For instance, FIG. 15 depicts an exemplary HMM matrix structure 35 showing the hardware processing flow. The matrix 35 includes the haplotype base index, e.g., containing 36 bases, positioned to run along the top edge of the horizontal axis, and further includes the base read index, e.g., 10 bases, positioned to fall along the side edge of the vertical axis in such a manner to from a structure of cells where a selection of the cells may be populated with an M, I, and D probability state, and the transition probabilities of transitioning from the present state to a neighboring state. In such an instance, as described in greater detail above, a move from a match state to a match state results in a forwards diagonal progression through the matrix 30, while moving from a match state to an insertion state results in a vertical downwards progressing gap, and a move from a match state to a deletion state results in a horizontal progressing gap. Hence, as depicted in FIG. 16, for a given cell, when determining the match, insert, and delete states for each cell, the match, insert, and delete probabilities of its three adjoining cells are employed.

The downwards arrow in FIG. 15 represents the parallel and sequential nature of the processing engine(s) that are configured so as to produce a processing swath or wave 35 that moves progressively along the virtual matrix in accordance with the data dependencies, see FIGS. 15 and 16, for determining the M, I, and D states for each particular cell in the structure 30. Accordingly, in certain instances, it may be desirable to calculate the identities of each cell in a downwards and diagonal manner, as explained above, rather than simply calculating each cell along a vertical or horizontal axis exclusively, although this can be done if desired. This is due to the increased wait time, e.g., latency, that would be required when processing the virtual cells of the matrix 35 individually and sequentially along the vertical or horizontal axis alone, such as via the hardware configuration.

For instance, in such an instance, when moving linearly and sequentially through the virtual matrix 30, such as in a row by row or column by column manner, in order to process each new cell the state computations of each preceding cell would have to be completed, thereby increasing latency time overall. However, when propagating the M, I, D probabilities of each new cell in a downwards and diagonal fashion, the system 1 does not have to wait for the processing of its preceding cell, e.g., of row one, to complete before beginning the processing of an adjoining cell in row two of the matrix. This allows for parallel and sequential processing of cells in a diagonal arrangement to occur, and further allows the various computational delays of the pipeline associated with the M, I, and D state calculations to be hidden. Accordingly, as the swath 35 moves across the matrix 30 from left to right, the computational processing moves diagonally downwards, e.g., towards the left (as shown by the arrow in FIG. 15). This configuration may be particularly useful for hardware implementations, such as where the memory and/or clock-by-clock latency are a primary concern.

However, when implementing an HMM function, as herein described, in software, the memory and/or clock-by-clock latency concerns are secondary. Hence, when running an HMM function, as herein described, in software, a nested "for" loop process may be implemented. For instance, when implemented in software, the code may be configured so as to calculate all the possible state values in the virtual HMM matrix such as exemplified herein: "for haplotype_index=0 to (haplotype_length−1); for read_index=0 to (read_length−1); Update M, I, and D state values for (haplotype_index, read_index) base pairing; end. end." In its essence, this code instructs the system to go from beginning to end, such as going from the beginning of the row to the end, and/or from the beginning of the column to the end, looping down the rows and/or across the columns, or vice versa, all the way from the beginning to the end. Accordingly, where latency timing is not an issue, the system can simply begin at the first available bases in each of the haplotype and read sequence indices, compare them with one another to determine a match or mismatch probability, and then move to a comparison of the next subsequent base in the sequences to update the probabilities accordingly. In such an instance, a downwards diagonal processing swath need not be promulgated.

However, this row-by-row, column-by-column computation of the HMM states, as determined by the referenced exemplary code above, may not be as useful when providing an accelerator that is at least partially implemented in hardware. Particularly, where clock cycles are important and latencies thereof must be managed to achieve maximal efficiency, the swath based processing configuration of FIGS. 15 and 16 may be particularly useful. For example, there may be a one or more, such as a ten or twenty or more, such as a twenty five or fifty or more cycle latency to calculate any given state, and so the system can be configured so as to push more data into the cells of the matrix during such latency periods instead of just waiting around and doing nothing during such latency periods, thereby increasing throughput without affecting accuracy.

Hence, as can be seen with respect to FIGS. 15 and 16, new data may be pushed into the system every single clock cycle, even though the pipeline itself may take ten or twenty or more clock cycles to complete its processing of any particular state of a given cell or group of cells. Particularly, if the pipeline delay through the M, I, and D state calculation, e.g., the clock cycle latencies thereof, is known, the processing of the matrix 30 may be configured, e.g., the processing swath 35 length adapted, such that by the time that the first, e.g., top, cell of the swath 35*a* is done being calculated, the system loops around and the beginning of the processing of the next swath 35*b* may be initiated, as described in greater detail with respect to FIG. 24.

Accordingly, the length of the swath 35 may be configured so as to correlate with the latency of the clock cycles needed to determine the state values for given selection of cells. An increased latency period therefore would result in an increased number of cells being processed within any given length of swath 35, and vice-versa with respect to decreased latency times. This then reduces the need and/or storing times for results data, such as in FIFO memories. Again, such a configuration is particularly useful in hardware implementations where memory resources and lookup times are important considerations. A further advantage of such hardware implementations is that the processing of such matrices 30$_n$ may be performed in a highly parallelized manner, e.g., such as tens to hundreds to thousands of matrices being processed all at the same time performing various different read to haplotype comparisons, which cannot easily be achieved by employing core computing facilities running various known software implementations.

In these configurations, the actual value output from each call of an HMM engine 13, e.g., after having calculated the entire matrix 30, may be a bottom row (e.g., Row 35 of FIG. 21) containing M, I, and D states, where the M and I states may be summed (the D states may be ignored at this point having already fulfilled their function in processing the calculations above), so as to produce a final sum value that may be a single probability that estimates, for each read and haplotype index, the probability of observing the read, e.g., assuming the haplotype was the true original DNA sampled.

Particularly, the outcome of the processing of the matrix 30, e.g., of FIG. 15, may be a single value representing the probability that the read is an actual representation of that haplotype. This probability is a value between 0 and 1 and is formed by summing all of the M and I states from the bottom row of cells in the HMM matrix 30. Essentially, what is being assessed is the possibility that something could have gone wrong in the sequencer, or associated DNA preparation methods prior to sequencing, so as to incorrectly produce a mismatch, insertion, or deletion into the read that is not actually present within the subject's genetic sequence. In such an instance, the read is not a true reflection of the subject's actual DNA.

Hence, accounting for such production errors, it can be determined what any given read actually represents with respect to the haplotype, and thereby allows the system to better determine how the subject's genetic sequence, e.g., en masse, may differ from that of a reference sequence. For instance, many haplotypes may be run against many read sequences, generating scores for all of them, and determining based on which matches have the best scores, what the actual genomic sequence identity of the individual is and/or how it truly varies from a reference genome.

More particularly, FIG. 16 depicts an enlarged view of a portion of the HMM state matrix 30 from FIG. 15. As shown in FIG. 16, given the internal composition of each cell in the matrix 30, as well as the structure of the matrix as a whole, the M, I, and D state probability for any given "new" cell being calculated is dependent on the M, I, and D states of several of its surrounding neighbors that have already been calculated. Particularly, as shown in greater detail with respect to FIGS. 1 and 16, in an exemplary configuration, there may be an approximately a 0.9998 probability of going from a match state to another match state, and there may be only a 0.0001 probability (gap open penalty) of going from a match state to either an insertion or a deletion, e.g., gapped, state. Further, when in either a gapped insertion or gapped deletion state there may be only a 0.1 probability (gap extension or continuation penalty) of staying in that gapped state, while there is a 0.9 probability of returning to a match state. It is to be noted that according to this model, all of the probabilities in to or out of a given state should sum to one. Particularly, the processing of the matrix 30 revolves around calculating the transition probabilities, accounting for the various gap open or gap continuation penalties and a final sum is calculated.

Hence, these calculated state transition probabilities are derived mainly from the directly adjoining cells in the matrix 30, such as from the cells that are immediately to the left of, the top of, and diagonally up and left of that given cell presently being calculated, as seen in FIG. 16. Additionally, the state transition probabilities may in part be derived from the "Phred" quality score that accompanies each read base. These transition probabilities, therefore, are useful in computing the M, I, and D state values for that particular cell, and likewise for any associated new cell being calculated. It is to be noted that as described herein, the gap open and gap continuation penalties may be fixed values, however, in various instances, the gap open and gap continuation penalties may be variable and therefore programmable within the system, albeit by employing additional hardware resources dedicated to determining such variable transition probability calculations. Such instances may be useful where greater accuracy is desired. Nevertheless, when such values are assumed to be constant, smaller resource usage and/or chip size may be achieved, leading to greater processing speed, as explained below.

Figure 17:
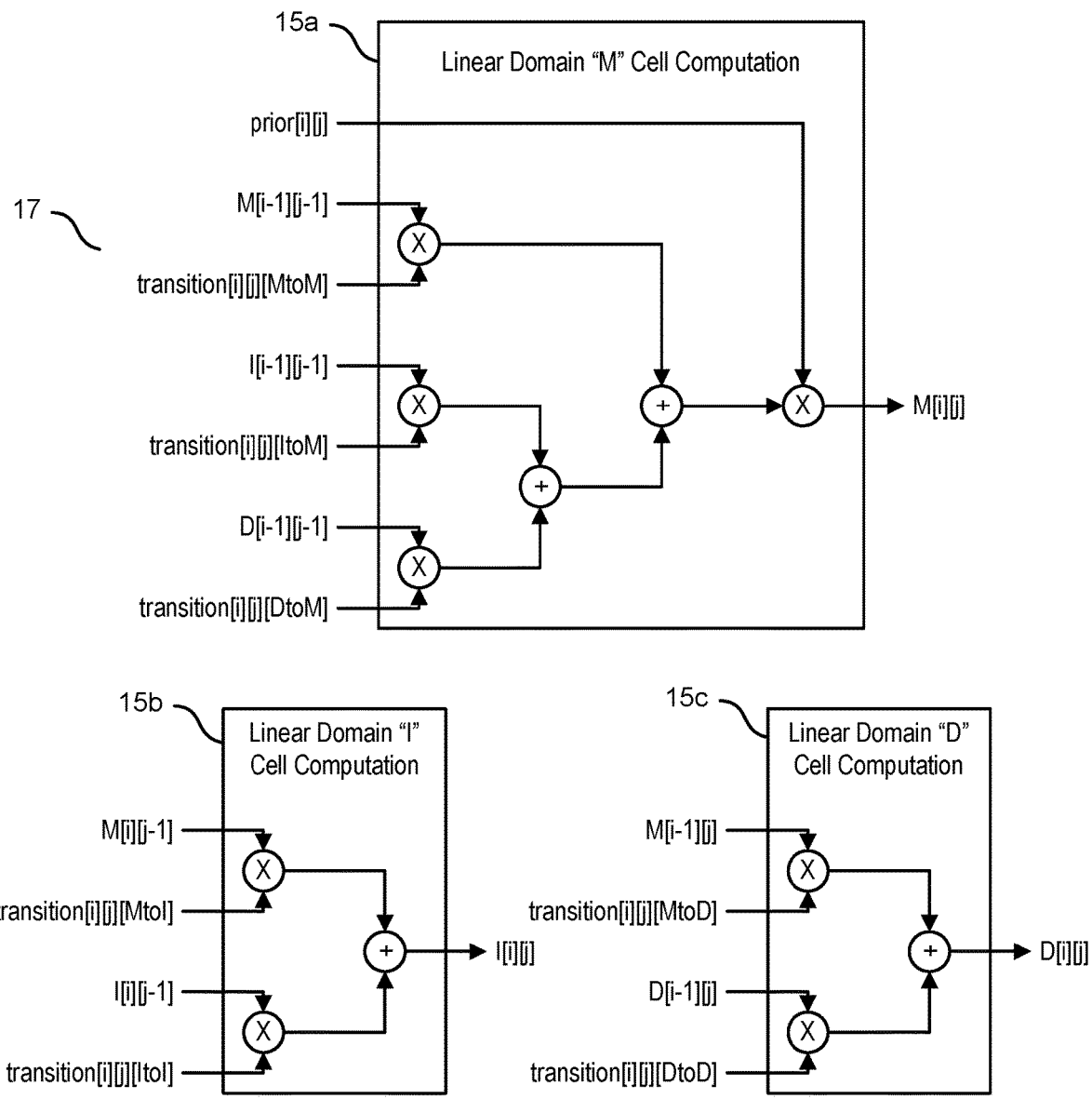
FIG. 17 depicts exemplary computations useful for M, I, D state updates.

Accordingly, there is a multiplicity of calculations and/or other mathematical computations, such as multiplications and/or additions, which are involved in deriving each new M, I, and D state value (see FIG. 17). In such an instance, such as for calculating maximum throughput, the primitive mathematical computations involved in each M, I, and D transition state calculation may be pipelined. Such pipelining may be configured in a way that the corresponding clock frequencies are high, but where the pipeline depth may be non-trivial. Further, such a pipeline may be configured to have a finite depth, and in such instances it may take more than one clock cycle to complete the operations.

For instance, these computations may be run at high speeds inside the processor 7, such as at about 300 MHz. This may be achieved such as by pipelining the FPGA or ASIC heavily with registers so little mathematical computation occurs between each flip-flop. This pipeline structure results in multiple cycles of latency in going from the input of the match state to the output, but given the reverse diagonal computing structure, set forth in FIG. 15 above, these latencies may be hidden over the entire HMM matrix 30, such as where each cell represents one clock cycle.

Accordingly, the number of M, I, and D state calculations may be limited. In such an instance, the processing engine 13 may be configured in such a manner that a grouping, e.g., swath 35, of cells in a number of rows of the matrix 30 may be processed as a group (such as in a down-and-left-diagonal fashion as illustrated by the arrow in FIG. 8) before proceeding to the processing of a second swath below, e.g., where the second swath contains the same number of cells in rows to be processed as the first. In a manner such as this, a hardware implementation of an accelerator 8, as described herein, may be adapted so as to make the overall system more efficient, as described above.

Figure 21:
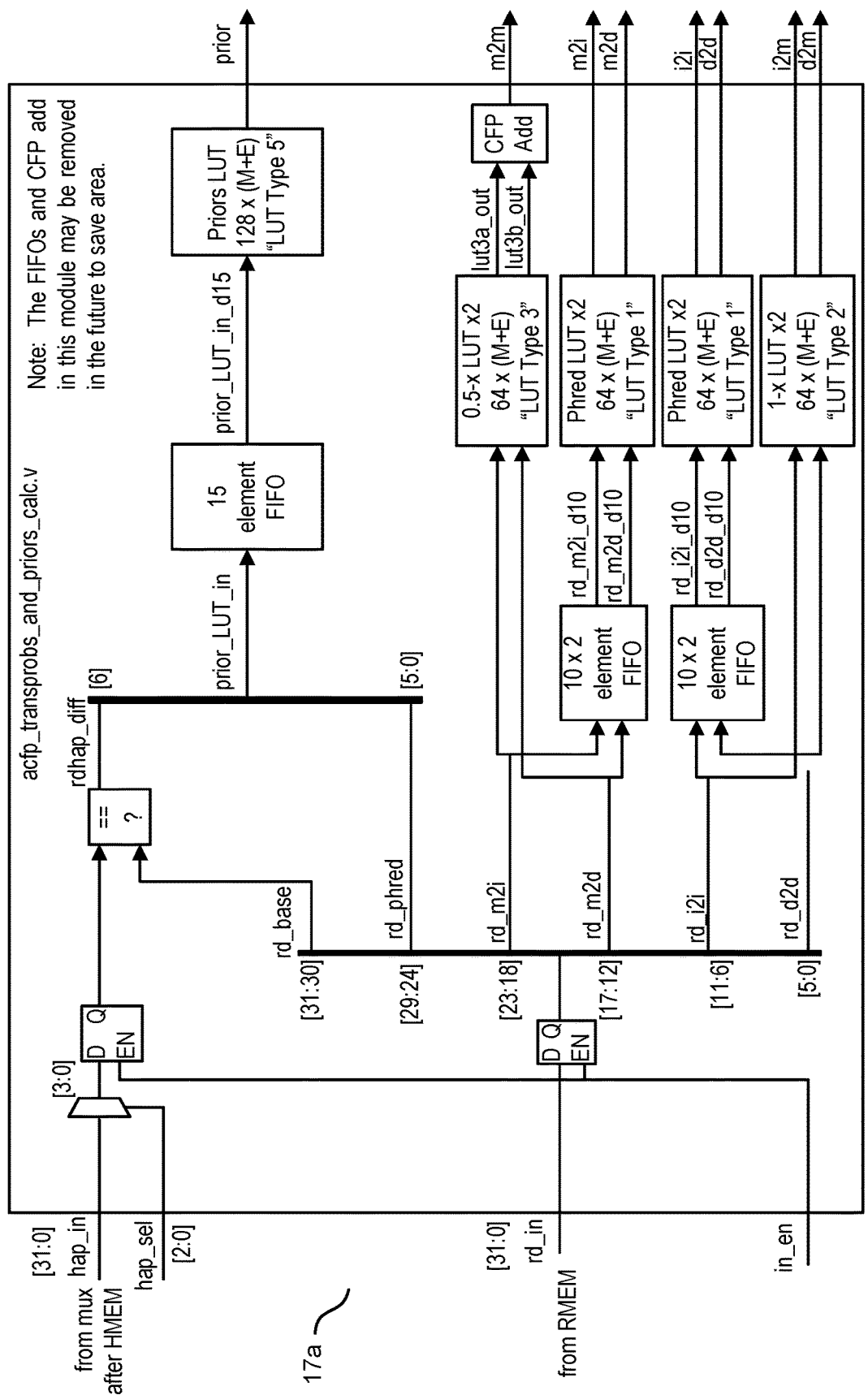
FIG. 21 depicts an HMM Transprobs and Priors generation circuit to support the general state transition diagram of FIG. 20.

A further efficiency may be achieved in instances such as this by limiting state storage requirements to a single row of M, I, and D state values, such as at the bottom edge of the grouping 35 (see row 35 of FIG. 21). Hence, when starting the processing from one swath 35a to the next 35b, e.g., grouping of rows, (below the current swath or grouping), the M, I, and D state values that were stored in the state memory for the previous swath 35a may be used as the edge and/or initial conditions for the cells in the top row of the next swath, e.g., grouping, of cells 35b to be processed. For instance, in an exemplary embodiment, the swath 35a is configured to be 10 cells in length, consequently, the next grouping of cells to be processed 35b will include the next 10 rows of virtual cells in the matrix, such as where the values set for the final row of the first swath 35a being processed set the edge for the values of the next swath 35b of cells to be processed. It is to be noted that the swath length can be any suitable length, such as 2 or 4 or 5 or 10 or 15 or 20 or 25 or 50 cells in length or more.

Particularly, FIG. 17 sets forth an exemplary computational structure for performing the various state processing calculations herein described. More particularly, FIG. 17 sets forth three dedicated logic blocks 17 of the processing engine 13 for computing the state computations involved in generating each M, I, and D state value for each particular cell, or grouping of cells, being processed in the HMM matrix 30. As can be seen with respect to FIG. 10, the match state computation 15a is more involved than either of the insert 15b or deletion 15c computations, this is because in calculating the match state 15a of the present cell being processed, all of the previous match, insert, and delete states of the adjoining cells along with various "Priors" data are included in the present match computation (see FIGS. 16 and 17), whereas only the match and either the insert and delete states are included in their respective calculations. Hence, as can be seen with respect to FIG. 17, in calculating a match state, three state multipliers, as well as two adders, and a final multiplier, which accounts for the Prior, e.g. Phred, data are included. However, for calculating the I or D state, only two multipliers and one adder are included. It is noted that in hardware, multipliers are more resource intensive than adders.

Accordingly, to various extents, the M, I, and D state values for processing each new cell in the HMM matrix 30 uses the knowledge or pre-computation of the following values, such as the "previous" M, I, and D state values from left, above, and/or diagonally left and above of the currently-being-computed cell in the HMM matrix. Additionally, such values representing the prior information, or "Priors", may at least in part be based on the "Phred" quality score, and whether the read base and the reference base at a given cell in the matrix 30 match or are different. Such information is particularly useful when determining a match state. Specifically, as can be seen with respect to FIG. 10, in such instances, there are basically seven "transition probabilities" (M-to-M, I-to-M, D-to-M, I-to-I, M-to-I, D-to-D, and M-to-D) that indicate and/or estimate the probability of seeing a gap open, e.g., of seeing a transition from a match state to an insert or delete state; seeing a gap close; e.g., going from an insert or delete state back to a match state; and seeing the next state continuing in the same state as the previous state, e.g., Match-to-Match, Insert-to-Insert, Delete-to-Delete.

The state values (e.g., in any cell to be processed in the HMM matrix 30), Priors, and transition probabilities are all values in the range of [0,1]. Additionally, there are also known starting conditions for cells that are on the left or top edge of the HMM matrix 30. As can be seen from the logic 15a of FIG. 10, there are four multiplication and two addition computations that may be employed in the particular M state calculation being determined for any given cell being processed. Likewise, as can be seen from the logic of 15b and 15c there are two multiplications and one addition involved for each I state and each D state calculation, respectively. Collectively, along with the priors multiplier this sums to a total of eight multiplications and four addition operations for the M, I, and D state calculations associated with each single cell in the HMM matrix 8 to be processed.

Figure 28:
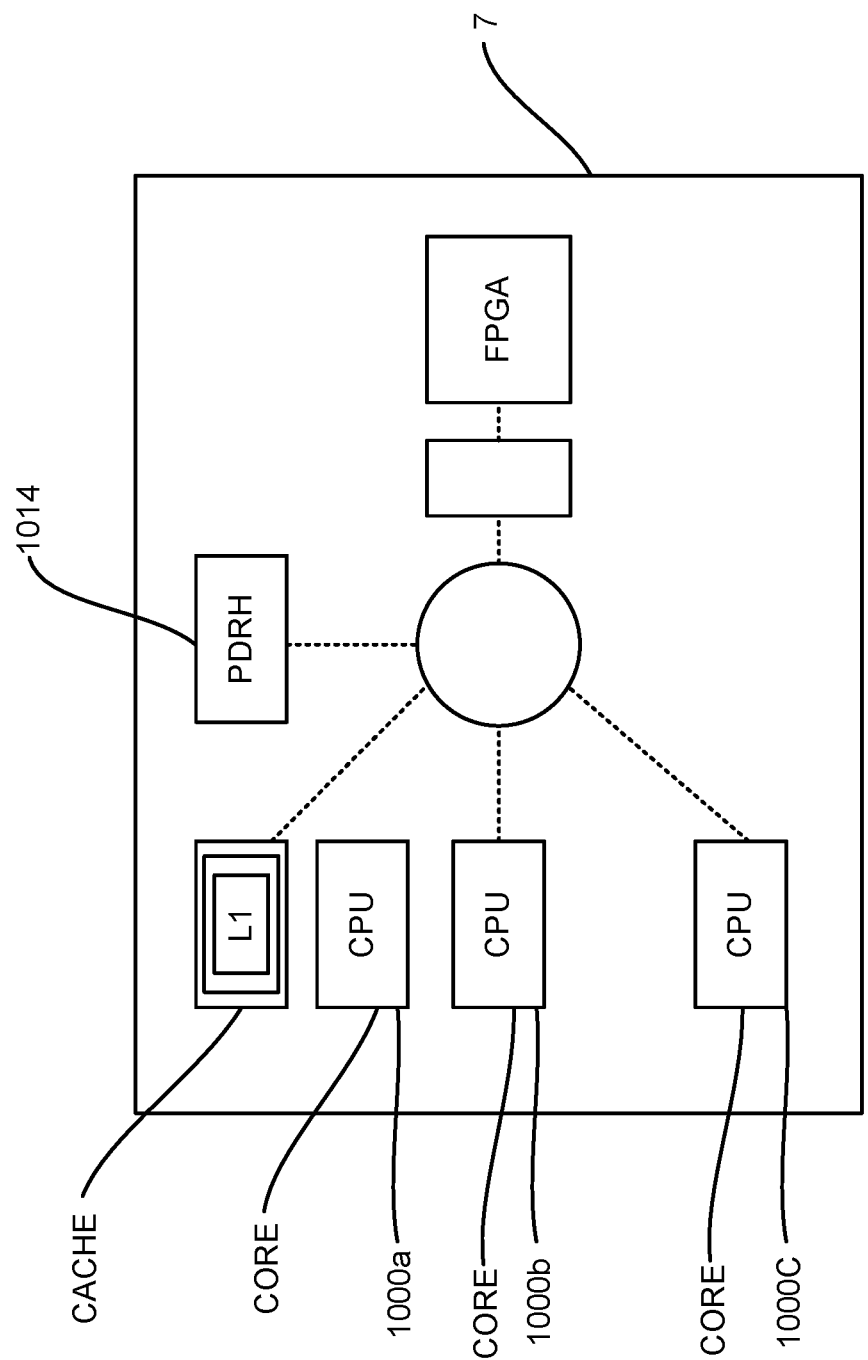
FIG. 28 illustrates a core of CPUs sharing one or more memories and/or caches, wherein the CPUs are configured for communicating with one or more FPGAs that may also include a shared or common memory or caches.

As can be seen with respect to FIG. 28, the final sum output, e.g., row 34, of the computation of the matrix 30, e.g., for a single job 20 of comparing one read to one or two haplotypes, is the summation of the final M and I states across the entire bottom row 34 of the matrix 30, which is the final sum value that is output from the HMM accelerator 8 and delivered to the CPU 1000. This final summed value represents how well the read matches the haplotype(s). The value is a probability, e.g., of less than one, for a single job 20*a* that may then be compared to the output resulting from another job 20*b* such as form the same active region 500. It is noted that there are on the order of 20 trillion HMM cells to evaluate in a "typical" human genome at 30× coverage, where these 20 trillion HMM cells are spread across about 1 to 2 billion HMM matrices 30 of all associated HMM jobs 20.

The results of such calculations may then be compared one against the other so as to determine, in a more precise manner, how the genetic sequence of a subject differs, e.g., on a base by base comparison, from that of one or more reference genomes. For the final sum calculation, the adders already employed for calculating the M, I, and/or D states of the individual cells may be re-deployed so as to compute the final sum value, such as by including a mux into a selection of the re-deployed adders thereby including one last additional row, e.g., with respect to calculation time, to the matrix so as to calculate this final sum, which if the read length is 100 bases amounts to about a 1% overhead. In alternative embodiments, dedicated hardware resources can be used for performing such calculations. In various instances, the logic for the adders for the M and D state calculations may be deployed for calculating the final sum, which D state adder may be efficiently deployed since it is not otherwise being used in the final processing leading to the summing values.

In certain instances, these calculations and relevant processes may be configured so as to correspond to the output of a given sequencing platform, such as including an ensemble of sequencers, which as a collective may be capable of outputting (on average) a new human genome at 30× coverage every 28 minutes (though they come out of the sequencer ensemble in groups of about 150 genomes every three days). In such an instance, when the present mapping, aligning, and variant calling operations are configured to fit within such a sequencing platform of processing technologies, a portion of the 28 minutes (e.g., about 10 minutes) it takes for the sequencing cluster to sequence a genome, may be used by a suitably configured mapper and/or aligner, as herein described, so as to take the FASTQ file results from the sequencer and perform the steps of mapping and/or aligning the genome, e.g., post-sequencer processing. That leaves about 18 minutes of the sequencing time period for performing the variant calling step, of which the HMM operation is the main computational component, such as prior to the nucleotide sequencer sequencing the next genome, such as over the next 28 minutes. Accordingly, in such instances, 18 minutes may be budgeted to computing the 20 trillion HMM cells that need to be processed in accordance with the processing of a genome, such as where each of the HMM cells to be processed includes about twelve mathematical operations (e.g., eight multiplications and/or four addition operations). Such a throughput allows for the following computational dynamics (20 trillion MINI cells)×(12 math ops per cell)/(18 minutes×60 seconds/minute), which is about 222 billion operations per second of sustained throughput.

Assuming there will be around 10% overhead in loading data into the MINI accelerator, reading results from the accelerator, and in general control of the overhead, one can derive that about 65~70 MINI cells need to be computed each clock cycle. Hence, in various instances, the system may be configured to take 18 minutes for computing the 20 trillion HMM cells so as to achieve a throughput of about 222 billion operations per second. In such an instance, the HMM accelerator can be run at a frequency of 300 MHz so as to achieve this throughput. If more computations are needed to be performed, the computing resources and/or clock frequencies, e.g., higher frequencies, may be configured to accommodate the increased computations In these embodiments, the HMM matrix 30, set forth in FIG. 15, and its resultant computations may not be particularly latency-sensitive. For instance, even with just one HMM cell computed per clock cycle at 300 MHz, the average HMM job (computing all the M, I, and D states and final sum value) will complete in about 60 microseconds. Further, if the memory is limited with respect to a given chip configuration, the fixed cost of the input memories (for read and haplotype data) and the M, I, D state memories may be amortized over multiple HMM cell computation engines 13 per HMM job (per HMM matrix computation 20).

Figure 18:
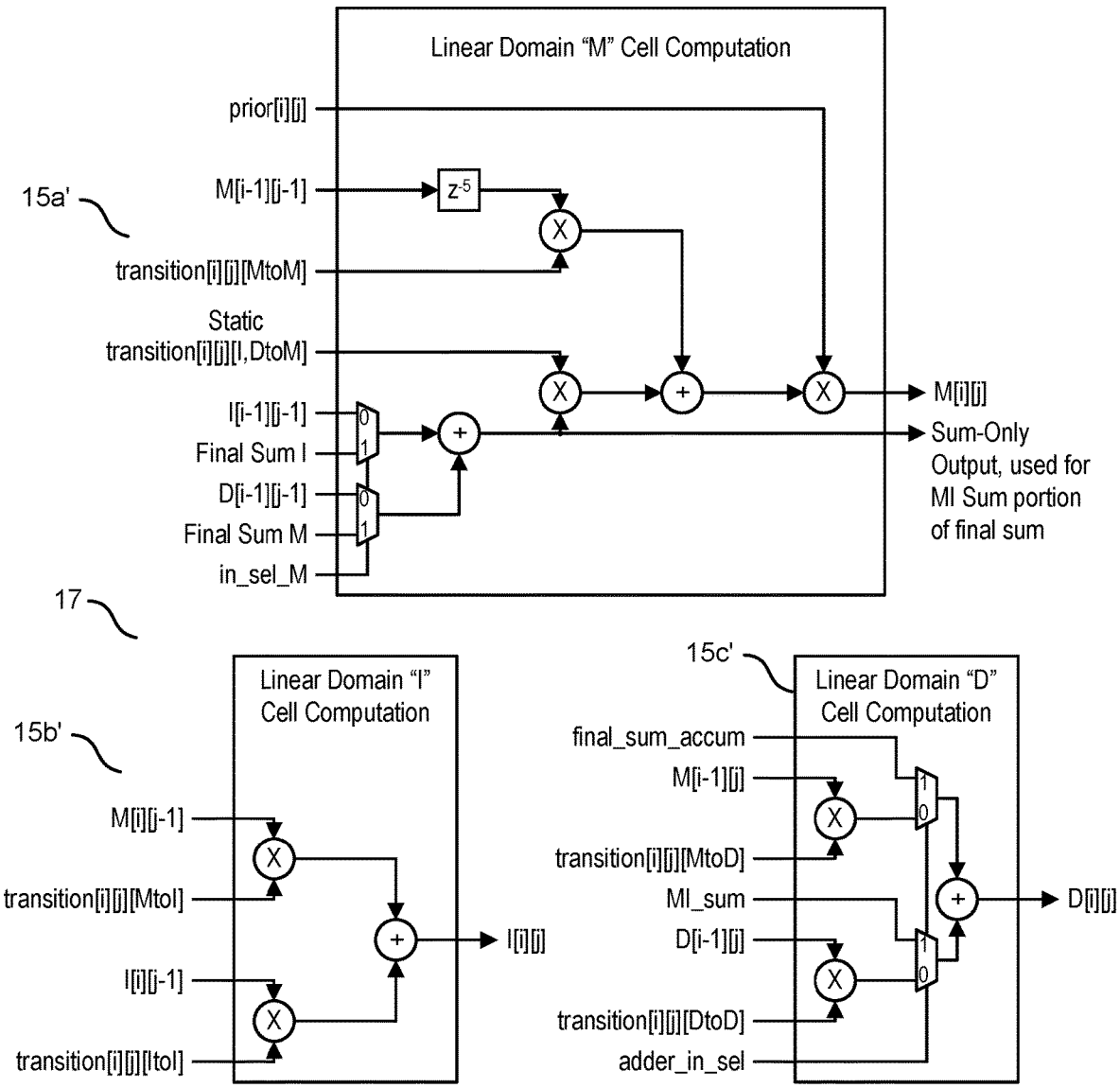
FIG. 18 depicts M, I, and D state update circuits, including the effects of simplifying assumptions of FIG. 9 related to transition probabilities and the effect of sharing some M, I, D adder resources with the final sum operations.

FIG. 18 sets forth the logic blocks 17 of the processing engine of FIG. 17 including exemplary M, I, and D state update circuits that present a simplification of the circuit provided in FIG. 17. The system may be configured so as to not be memory-limited, so a single HMM engine instance 13 (e.g., that computes all of the single cells in the HMM matrix 30 at a rate of one cell per clock cycle, on average, plus overheads) may be replicated multiple times (at least 65~70 times to make the throughput efficient, as described above). Nevertheless, to minimize the size of the hardware, e.g., the size of the chip 2 and/or its associated resource usage, and/or in a further effort to include as many HMM engine instances 13 on the chip 2 as desirable and/or possible, simplifications may be made with regard to the logic blocks 15*a'*-c' of the processing instance 13 for computing one or more of the transition probabilities to be calculated.

In particular, it may be assumed that the gap open penalty (GOP) and gap continuation penalty (GCP), as described above, such as for inserts and deletes are the same and are known prior to chip configuration. This simplification implies that the I-to-M and D-to-M transition probabilities are identical, e.g., see FIG. 26. In such an instance, one or more of the multipliers, e.g., set forth in FIG. 17, may be eliminated, such as by pre-adding I and D states before multiplying by a common Indel-to-M transition probability. For instance, in various instances, if the I and D state calculations are assumed to be the same, then the state calculations per cell can be simplified as presented in FIG. 26. Particularly, if the I and D state values are the same, then the I state and the D state may be added and then that sum may be multiplied by a single value, thereby saving a multiply. This may be done because, as seen with respect to FIG. 26, the gap continuation and/or close penalties for the I and D states are the same. However, as indicated above, the system can be configured to calculate different values for both the I and D transition state probabilities, and in such an instance, this simplification would not be employed.

Figure 24:
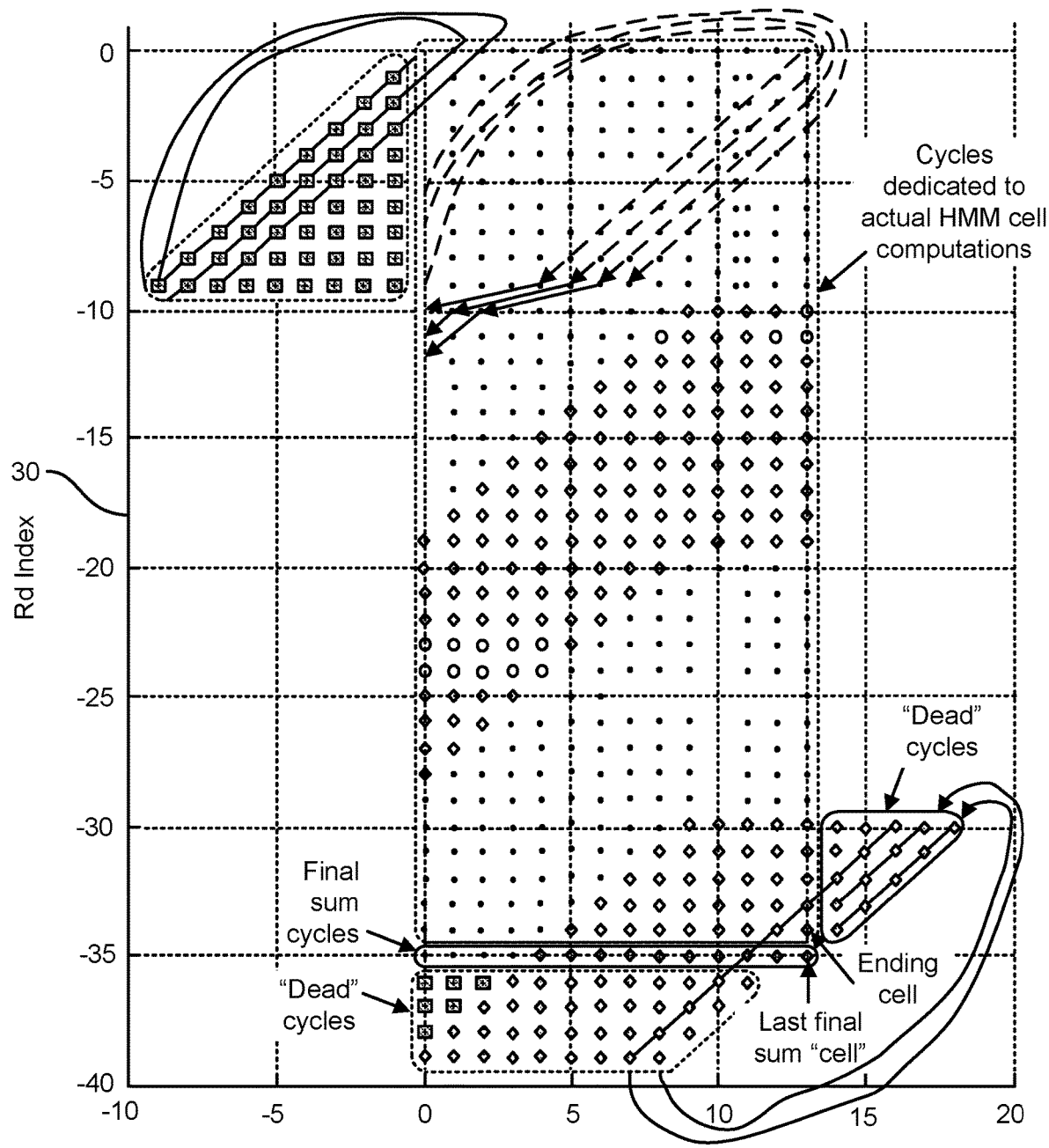
FIG. 24 depicts an exemplary theoretical HMM matrix and illustrates how such an HMM matrix may be traversed.

Additionally, in a further simplification, rather than dedicate chip resources configured specifically to perform the final sum operation at the bottom of the HMM matrix, e.g., see row 34 of FIG. 24, the present HMM accelerator 8 may be configured so as to effectively append one or more additional rows to the MINI matrix 30, with respect to computational time, e.g., overhead, it takes to perform the calculation, and may also be configured to "borrow" one or more adders from the M-state 15a and D-state 15c computation logic such as by MUXing in the final sum values to the existing adders as needed, so as to perform the actual final summing calculation. In such an instance, the final logic, including the M logic 15a, I logic 15b, and D logic 15c blocks, which blocks together form part of the HMM MID instance 17, may include 7 multipliers and 4 adders along with the various MUXing involved.

Accordingly, FIG. 18 sets forth the M, I, and D state update circuits 15a', 15b', and 15c' including the effects of simplifying assumptions related to transition probabilities, as well as the effect of sharing various M, I, and/or D resources, e.g., adder resources, for the final sum operations. A delay block may also be added to the M-state path in the M-state computation block, as shown in FIG. 18. This delay may be added to compensate for delays in the actual hardware implementations of the multiply and addition operations, and/or to simplify the control logic, e.g., 15.

As shown in FIGS. 17 and 18, these respective multipliers and/or adders may be floating point multipliers and adders. However, in various instances, as can be seen with respect to FIG. 19, a log domain configuration may be implemented where in such configuration all of the multiplies turn into adds. FIG. 19 presents what log domain calculation would look like if all the multipliers turned into adders, e.g., 15a", 15b", and 15c", such as occurs when employing a log domain computational configuration. Particularly, all of the multiplier logic turns into an adder, but the adder itself turns into or otherwise includes a function where the function such as: $f(a,b)=\max(a,b)-\log_2(1+2^{(-[a-b])})$, such as where the log portion of the equation may be maintained within a LUT whose depth and physical size is determined by the precision required.

Given the typical read and haplotype sequence lengths as well as the values typically seen for read quality (Phred) scores and for the related transition probabilities, the dynamic range requirements on the internal HMM state values may be quite severe. For instance, when implementing the HMM module in software, various of the HMM jobs 20 may result in underruns, such as when implemented on single-precision (32-bit) floating-point state values. This implies a dynamic range that is greater than 80 powers of 10, thereby requiring the variant call software to bump up to double-precision (64-bit) floating point state values. However, full 64-bit double-precision floating-point representation may, in various instances, have some negative implications, such as if compact, high-speed hardware is to be implemented, both storage and compute pipeline resource requirements will need to be increased, thereby occupying greater chip space, and/or slowing timing. In such instances, a fixed-point-only linear-domain number representation may be implemented. Nevertheless, the dynamic range demands on the state values, in this embodiment, make the bit widths involved in certain circumstances less than desirable. Accordingly, in such instances, fixed-point-only log-domain number representation may be implemented, as described herein.

In such a scheme, as can be seen with respect to FIG. 19, instead of representing the actual state value in memory and computations, the −log-base-2 of the number may be represented. This may have several advantages, including employing multiply operations in linear space that translate into add operations in log space; and/or this log domain representation of numbers inherently supports wider dynamic range with only small increases in the number of integer bits. These log-domain M, I, D state update calculations are set forth in FIG. 19.

As can be seen when comparing the logic 17 configuration of FIG. 19 with that of FIG. 17, the multiply operations go away in the log-domain. Rather, they are replaced by add operations, and the add operations are morphed into a function that can be expressed as a max operation followed by a correction factor addition, e.g., via a LUT, where the correction factor is a function of the difference between the two values being summed in the log-domain. Such a correction factor can be either computed or generated from the look-up-table. Whether a correction factor computation or look-up-table implementation is more efficient to be used depends on the required precision (bit width) on the difference between the sum values. In particular instances, therefore, the number of log-domain bits for state representation can be in the neighborhood of 8 to 12 integer bits plus 6 to 24 fractional bits, depending on the level of quality desired for any given implementation. This implies somewhere between 14 and 36 bits total for log-domain state value representation. Further, it has been determined that there are log-domain fixed-point representations that can provide acceptable quality and acceptable hardware size and speed.

In various instances, there are three main utilizations of RAM (or RAM-like) storage within each HMM engine instance 13, which includes the haplotype sequence data storage 16, read sequence data storage 18, and M, I, D state storage at the bottom edge of the region (or swath), e.g., via a scratch pad memory. Particularly, the haplotype sequence data, such as received by the system 1 from the CPU 1000, or a suitably configured sequencer coupled therewith, may contain a 4-bit indicator by which each particular base in the haplotype may be represented, as described above with respect to FIG. 5. For instance, in various embodiments, a suitable haplotype length for use in the present system may be up to 1008 bases, more or less, dependent on the system configuration. In addition to the haplotype sequence, there are a 32-bit control word and 32-bit haplotype ID that may be stored in the same memory 16. Accordingly, together, this represents a 128 word×32 bits/word HMEM memory 16, and the organization for each block of haplotype memory is given in FIG. 12.

For throughput reasons, and to better utilize the PCIe Bus connection 5 to the microchip 7, in various instances, the hardware may be configured to allow one, or two, or more haplotypes to be associated with a given read in a given HMM job 20. Additionally, as indicated, a ping-pong buffer may be set up to give various software implemented functions the ability to write new HMM job data 20b, while a current job 20a is still being worked on by a given engine instance 13. Taken together, this means that there may be four blocks of 128×32 memory associated with haplotype storage, e.g., HMEM 16, and these may be joined together in a single 512×32 two-port memory (one port for write, one port for read, e.g., with separate clocks for write and read ports), as shown in FIG. 12.

Likewise, in certain instances, the read sequence data may contain a 2-bit indicator for representing what each base in the read is supposed to be, a 6-bit read quality score (Phred value) per read base, and a 6-bit gap open penalty (GOP) value (also in Phred-like domain). Together these represent 14-bits per read base. Hence, as can be seen with respect to FIG. 13, the HMM accelerator 8 may be configured such that information associated with two read bases (e.g., 28-bits total, per above) may be packed into a single 32-bit word. Additionally, a 32-bit control word and a 32-bit read ID may be stored in the same memory 18 as the read sequence data. This all may be packed into a 512 word×32-bits/word RMEM memory 18, thereby indicating that in certain embodiments, the read sequence length may be about 1020 in length more or less.

In these instances, one read sequence is typically processed for each HMM job 20, which as indicated may include a comparison against two haplotype sequences. And like above for the haplotype memory, a ping-pong structure may also be used in the read sequence memory 18 to allow various software implemented functions the ability to write new HMM job information 20b while a current job 20a is still being processed by the HMM engine instance 13. Hence, a read sequence storage requirement may be for a single 1024×32 two-port memory (such as one port for write, one port for read, and/or separate clocks for write and read ports).

Particularly, as described above, in various instances, the architecture employed by the system 1 is configured such that in determining whether a given base in a sequenced sample genome matches that of a corresponding base in one or more reference genomes, a virtual matrix 30 is formed, wherein the reference genome is theoretically set across a horizontal axis, while the sequenced reads, representing the sample genome, is theoretically set in descending fashion down the vertical axis. Consequently, in performing an HMM calculation, the MINI processing engine 13, as herein described, is configured to traverse this virtual HMM matrix 30. Such processing can be depicted as in FIG. 15, as a swath 35 moving diagonally down and across the virtual array performing the various MINI calculations for each cell of the virtual array, as seen in FIG. 16.

More particularly, this theoretical traversal involves processing a first grouping of rows of cells 35a from the matrix 30 in its entirety, such as for all haplotype and read bases within the grouping, before proceeding down to the next grouping of rows 35b (e.g., the next group of read bases). In such an instance, the M, I, and D state values for the first grouping are stored at the bottom edge of that initial grouping of rows so that these M, I, and D state values can then be used to feed the top row of the next grouping (swath) down in the matrix 30. In various instances, the system 1 may be configured to allow up to 1008 length haplotypes and/or reads in the HMM accelerator 8, and since the numerical representation employs W-bits for each state, this implies a 1008 word×W-bit memory for M, I, and D state storage.

Accordingly, as indicated, such memory could be either a single-port or double-port memory. Additionally, a cluster-level, scratch pad memory, e.g., for storing the results of the swath boundary, may also be provided. For instance, in accordance with the disclosure above, the memories discussed already are configured for a per-engine-instance 13 basis. In particular HMM implementations, multiple engine instances $13a\text{-}_{(n+1)}$ may be grouped into a cluster 11 that is serviced by a single connection, e.g., PCIe bus 5, to the PCIe interface 4 and DMA 3 via CentCom 9. Multiple clusters $11a\text{-}_{(n+1)}$ can be instantiated so as to more efficiently utilize PCIe bandwidth using the existing CentCom 9 functionality.

Hence, in a typical configuration, somewhere between 16 and 64 engines $13_m$ are instantiated within a cluster $11_n$, and one to four clusters might be instantiated in a typical FPGA/ASIC implementation of the HMM 8 (e.g., depending on whether it is a dedicated HMM FPGA image or whether the HMM has to share FPGA real estate with the sequencer/mapper/aligner and/or other modules, as herein disclosed). In particular instances, there may be a small amount of memory used at the cluster-level 11 in the HMM hardware. This memory may be used as an elastic First In First Out ("FIFO") to capture output data from the HMM engine instances 13 in the cluster and pass it on to CentCom 9 for further transmittal back to the software of the CPU 1000 via the DMA 3 and PCIe 4. In theory, this FIFO could be very small (on the order of two 32-bit words), as data are typically passed on to CentCom 9 almost immediately after arriving in the FIFO. However, to absorb potential disrupts in the output data path, the size of this FIFO may be made parametrizable. In particular instances, the FIFO may be used with a depth of 512 words. Thus, the cluster-level storage requirements may be a single 512×32 two-port memory (separate read and write ports, same clock domain).

Figure 20:
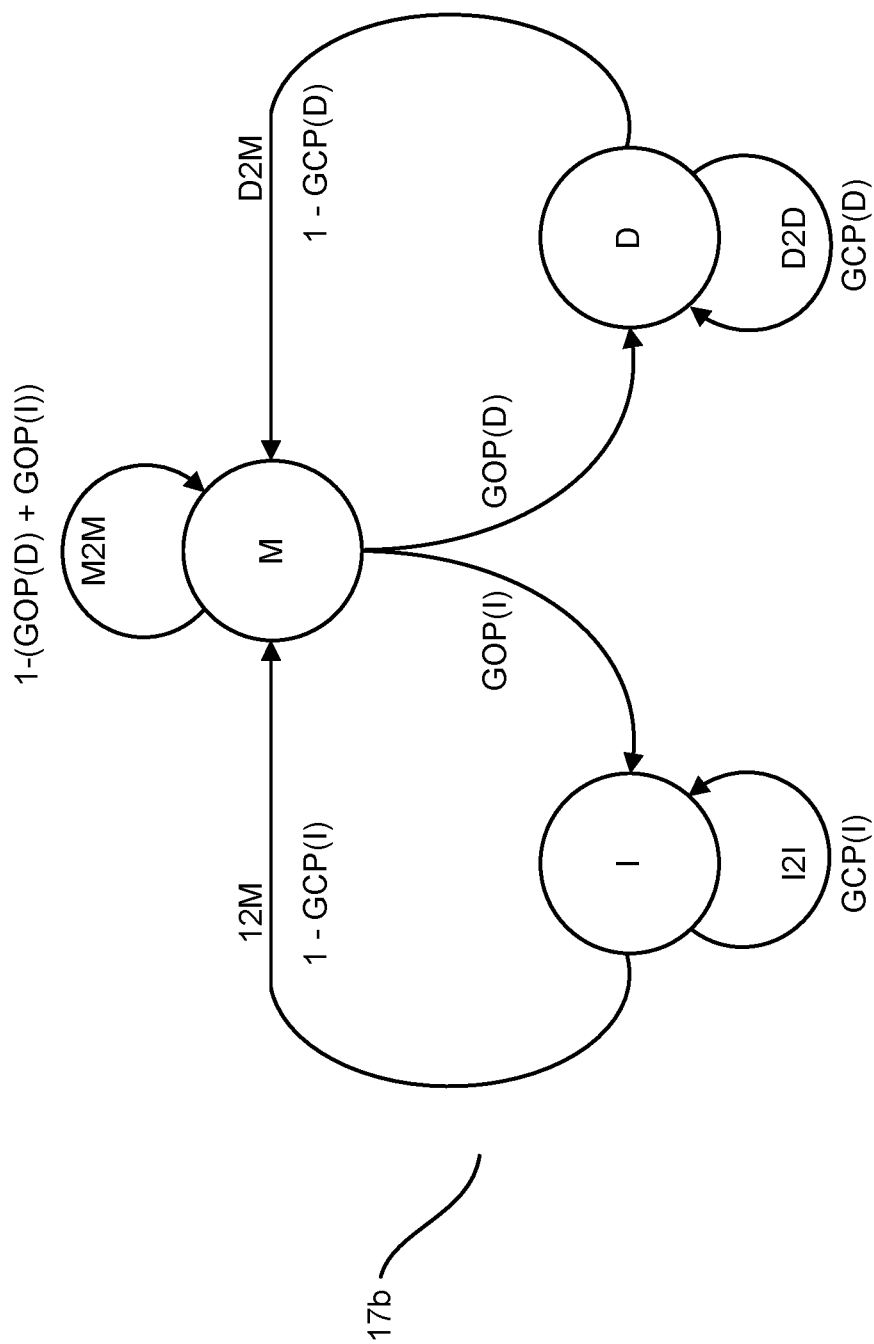
FIG. 20 depicts an HMM state transition diagram showing the relation between GOP, GCP and transition probabilities.

FIG. 20 sets forth the various HMM state transitions 17b depicting the relationship between Gap Open Penalties (GOP), Gap Close Penalties (GCP), and transition probabilities involved in determining whether and how well a given read sequence matches a particular haplotype sequence. In performing such an analysis, the HMM engine 13 includes at least three logic blocks 17b, such as a logic block for determining a match state 15a, a logic block for determining an insert state 15b, and a logic block for determining a delete state 15c. These M, I, and D state calculation logic 17 when appropriately configured function efficiently to avoid high-bandwidth bottlenecks, such as of the HMM computational flow. However, once the M, I, D core computation architecture is determined, other system enhancements may also be configured and implemented so as to avoid the development of other bottlenecks within the system.

Particularly, the system 1 may be configured so as to maximize the process of efficiently feeding information from the computing core 1000 to the variant caller module 2 and back again, so as not to produce other bottlenecks that would limit overall throughput. One such block that feeds the HMM core M, I, D state computation logic 17 is the transition probabilities and priors calculation block. For instance, as can be seen with respect to FIG. 17, each clock cycle employs the presentation of seven transition probabilities and one Prior at the input to the M, I, D state computation block 15a. However, after the simplifications that result in the architecture of FIG. 18, only four unique transition probabilities and one Prior are employed for each clock cycle at the input of the M, I, D state computation block. Accordingly, in various instances, these calculations may be simplified and the resulting values generated. Thus, increasing throughput, efficiency, and reducing the possibility of a bottleneck forming at this stage in the process.

Additionally, as described above, the Priors are values generated via the read quality, e.g., Phred score, of the particular base being investigated and whether, or not, that base matches the hypothesis haplotype base for the current cell being evaluated in the virtual HMM matrix 30. The relationship can be described via the equations bellow: First, the read Phred in question may be expressed as a probability=$10^{\wedge}(-(\text{read Phred}/10))$. Then the Prior can be computed based on whether the read base matches the hypothesis haplotype base: If the read base and hypothesis haplotype base match: Prior=1−read Phred expressed as a probability. Otherwise: Prior=(read Phred expressed as probability)/3. The divide-by-three operation in this last equation reflects the fact that there are only four possible bases (A, C, G, T). Hence, if the read and haplotype base did not match, then it must be one of the three remaining possible bases that does match, and each of the three possibilities is modeled as being equally likely.

The per-read-base Phred scores are delivered to the HMM hardware accelerator 8 as 6-bit values. The equations to derive the Priors, then, have 64 possible outcomes for the "match" case and an additional 64 possible outcomes for the "don't match" case. This may be efficiently implemented in the hardware as a 128 word look-up-table, where the address into the look-up-table is a 7-bit quantity formed by concatenating the Phred value with a single bit that indicates whether, or not, the read base matches the hypothesis haplotype base.

Further, with respect to determining the match to insert and/or match to delete probabilities, in various implementations of the architecture for the MINI hardware accelerator 8, separate gap open penalties (GOP) can be specified for the Match-to-Insert state transition, and the Match-to-Delete state transition, as indicated above. This equates to the M2I and M2D values in the state transition diagram of FIG. 20 being different. As the GOP values are delivered to the MINI hardware accelerator 8 as 6-bit Phred-like values, the gap open transition probabilities can be computed in accordance with the following equations: M2I transition probability=10^(−(read GOP(I)/10)) and M2D transition probability=10^(−(read GOP(D)/10)). Similar to the Priors derivation in hardware, a simple 64 word look-up-table can be used to derive the M2I and M2D values. If GOP(I) and GOP(D) are inputted to the HMM hardware 8 as potentially different values, then two such look-up-tables (or one resource-shared look-up-table, potentially clocked at twice the frequency of the rest of the circuit) may be utilized.

Furthermore, with respect to determining match to match transition probabilities, in various instances, the match-to-match transition probability may be calculated as: M2M transition probability=1−(M2I transition probability+M2D transition probability). If the M2I and M2D transition probabilities can be configured to be less than or equal to a value of ½, then in various embodiments the equation above can be implemented in hardware in a manner so as to increase overall efficiency and throughput, such as by reworking the equation to be: M2M transition probability=(0.5−M2I transition probability)+(0.5−M2D transition probability). This rewriting of the equation allows M2M to be derived using two 64 element look-up-tables followed by an adder, where the look-up-tables store the results.

Further still, with respect to determining the Insert to Insert and/or Delete to Delete transition probabilities, the I2I and D2D transition probabilities are functions of the gap continuation probability (GCP) values inputted to the HMM hardware accelerator 8. In various instances, these GCP values may be 6-bit Phred-like values given on a per-read-base basis. The I2I and D2D values may then be derived as shown: I2I transition probability=10^(−(read GCP(I)/10)), and D2D transition probability=10^(−(read GCP(D)/10)). Similar to some of the other transition probabilities discussed above, the I2I and D2D values may be efficiently implemented in hardware, and may include two look-up-tables (or one resource-shared look-up-table), such as having the same form and contents as the Match-to-Indel look-up-tables discussed previously. That is, each look-up-table may have 64 words.

Additionally, with respect to determining the Inset and/or Delete to Match probabilities, the I2M and D2M transition probabilities are functions of the gap continuation probability (GCP) values and may be computed as: I2M transition probability=1−I2I transition probability, and D2M transition probability=1−D2D transition probability, where the I2I and D2D transition probabilities may be derived as discussed above. A simple subtract operation to implement the equations above may be more expensive in hardware resources than simply implementing another 64 word look-up-table and using two copies of it to implement the I2M and D2M derivations. In such instances, each look-up-table may have 64 words. Of course, in all relevant embodiments, simple or complex subtract operations may be formed with the suitably configured hardware.

FIG. 21 provides the circuitry 17a for a simplified calculation for HMM transition probabilities and Priors, as described above, which supports the general state transition diagram of FIG. 20. As can be seen with respect to FIG. 18, in various instances, a simple HMM hardware accelerator architecture 17a is presented, which accelerator may be configured to include separate GOP values for Insert and Delete transitions, and/or there may be separate GCP values for Insert and Delete transitions. In such an instance, the cost of generating the seven unique transition probabilities and one Prior each clock cycle may be configured as set forth below: eight 64 word look-up-tables, one 128 word look-up-table, and one adder.

Further, in various instances, the hardware 2, as presented herein, may be configured so as to fit as many HMM engine instances 13 as possible onto the given chip target (such as on an FPGA, sASIC, or ASIC). In such an instance, the cost to implement the transition probabilities and priors generation logic 17a can be substantially reduced relative to the costs as provided by the below configurations. Firstly, rather than supporting a more general version of the state transitions, such as set forth in FIG. 21, e.g., where there may be separate values for GOP(I) and GOP(D), rather, in various instances, it may be assumed that the GOP values for insert and delete transitions are the same for a given base. This results in several simplifications to the hardware, as indicated above.

In such instances, only one 64 word look-up-table may be employed so as to generate a single M2Indel value, replacing both the M2I and M2D transition probability values, whereas two tables are typically employed in the more general case. Likewise, only one 64 word look-up-table may be used to generate the M2M transition probability value, whereas two tables and an add may typically be employed in the general case, as M2M may now be calculated as 1−2×M2Indel.

Secondly, the assumption may be made that the sequencer-dependent GCP value for both insert and delete are the same AND that this value does not change over the course of an HMM job 20. This means that: a single Indel2Indel transition probability may be calculated instead of separate I2I and D2D values, using one 64 word look-up-table instead of two tables; and single Indel2Match transition probability may be calculated instead of separate I2M and D2M values, using one 64 word look-up-table instead of two tables.

Additionally, a further simplifying assumption can be made D) and Insert2Match and Delete2Match (I2M and that assumes the Inset2Insert and Delete2Delete (I2I and D2D2M) values are not only identical between insert and delete transitions, but may be static for the particular HMM job 20. Thus, the four look-up-tables associated in the more general architecture with I2I, D2D, I2M, and D2M transition prob0abilities can be eliminated altogether. In various of these instances, the static Indel2Indel and Indel2Match probabilities could be made to be entered via software or via an RTL parameter (and so would be bitstream programmable in an FPGA). In certain instances, these values may be made bitstream-programmable, and in certain instances, a training mode may be implemented employing a training sequence so as to further refine transition probability accuracy for a given sequencer run or genome analysis.

Figure 22:
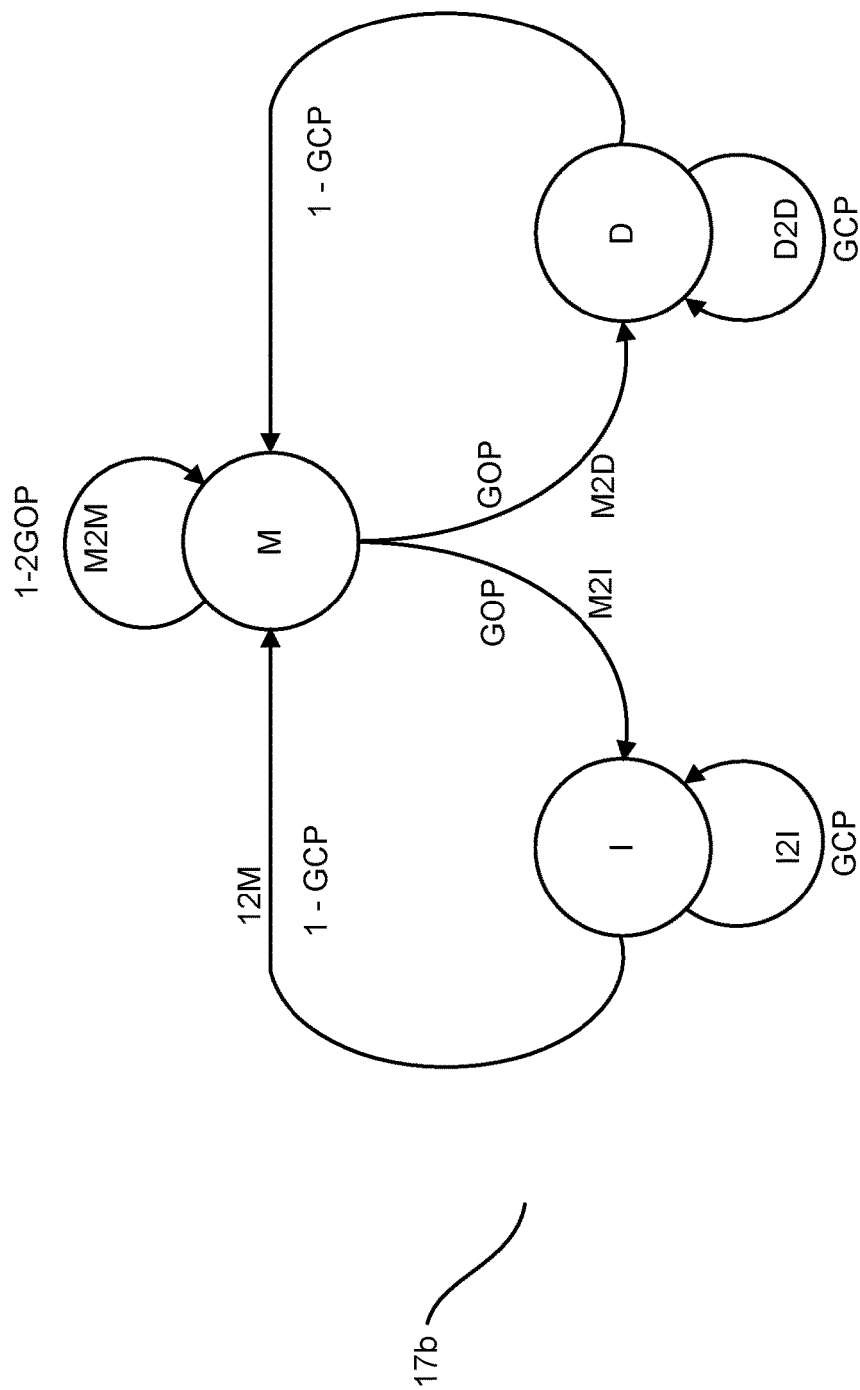
FIG. 22 depicts a simplified HMM state transition diagram showing the relation between GOP, GCP and transition probabilities.

FIG. 22 sets forth what the new state transition 17b diagram may look like when implementing these various simplifying assumptions. Specifically, FIG. 22 sets forth the simplified HMM state transition diagram depicting the relationship between GOP, GCP, and transition probabilities with the simplifications set forth above.

Figure 23:
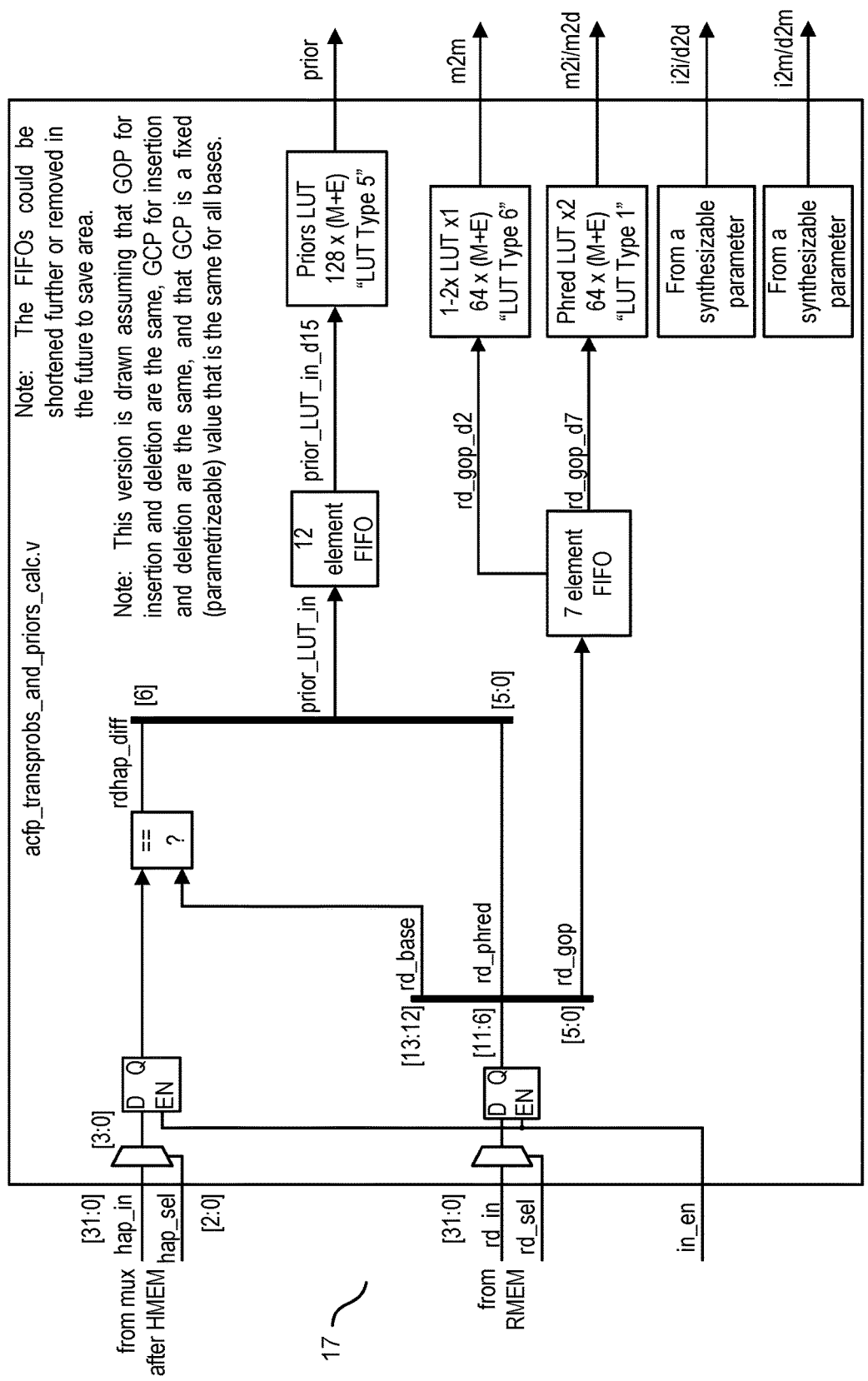
FIG. 23 depicts a HMM Transprobs and Priors generation circuit to support the simplified state transition.

Likewise, FIG. 23 sets forth the circuitry 17a,b for the HMM transition probabilities and priors generation, which supports the simplified state transition diagram of FIG. 22. As seen with respect to FIG. 23, a circuit realization of that state transition diagram is provided. Thus, in various instances, for the HMM hardware accelerator 8, the cost of generating the transition probabilities and one Prior each clock cycle reduces to: Two 64 word look-up-tables, and One 128 word look-up-table.

As set forth above, the engine control logic 15 is configured for generating the virtual matrix and/or traversing the matrix so as to reach the edge of the swath, e.g., via high-level engine state machines, where result data may be finally summed, e.g., via final sum control logic 19, and stored, e.g., via put/get logic. FIG. 28 presents a representation of an exemplary virtual matrix 30 with the hypothesis haplotype sequence index positioned along the horizontal axis and the read sequence index positioned along the vertical axis. Specifically, FIG. 24 illustrates an exemplary method by which such a virtual HMM matrix 30 may be traversed.

Accordingly, as can be seen with respect to FIG. 24, in various embodiments, a method for producing and/or traversing an HMM cell matrix 30 is provided. Specifically, FIG. 24 sets forth an example of how the MINI accelerator control logic 15 goes about traversing the virtual cells in the HMM matrix. For instance, assuming for exemplary purposes, a 5 clock cycle latency for each multiply and each add operation, the worst-case latency through the M, I, D state update calculations would be the 20 clock cycles it would take to propagate through the M update calculation, e.g., see FIG. 16. There are half as many operations in the I and D state update calculations, implying a 10 clock cycle latency for those operations.

These latency implications of the M, I, and D compute operations can be understood with respect to FIG. 16, which sets forth various examples of the cell-to-cell data dependencies. In such instances, the M and D state information of a given cell feed the D state computations of the cell in the HMM matrix that is immediately to the right (e.g., having the same read base as the given cell, but having the next haplotype base). Likewise, the M and I state information for the given cell feed the I state computations of the cell in the HMM matrix that is immediately below (e.g., having the same haplotype base as the give cell, but having the next read base). So, in particular instances, the M, I, and D states of a given cell feed the D and I state computations of cells in the next diagonal of the HMM cell matrix.

Similarly, the M, I, and D states of a given cell feed the M state computation of the cell that is to the right one and down one (e.g., having both the next haplotype base AND the next read base). This cell is actually two diagonals away from the cell that feeds it (whereas, the I and D state calculations rely on states from a cell that is one diagonal away). This quality of the I and D state calculations relying on cells one diagonal away, while the M state calculations rely on cells two diagonals away, has a beneficial result for hardware design.

Particularly, given these configurations, I and D state calculations may be adapted to take half as long (e.g., 10 cycles) as the M state calculations (e.g., 20 cycles). Hence, if M state calculations are started 10 cycles before I and D state calculations for the same cell, then the M, I, and D state computations for a cell in the MINI matrix 30 will all complete at the same time. Additionally, if the matrix 30 is traversed in a diagonal fashion, such as having a swath 35 of about 10 cells each within it (e.g., that spans ten read bases), then: The M and D states produced by a given cell at (hap, rd) coordinates (i, j) can be used by cell (i+1, j) D state calculations as soon as they are all the way through the compute pipeline of the cell at (i, j).

The M and I states produced by a given cell at (hap, rd) coordinates (i, j) can be used by cell (i, j+1) I state calculations one clock cycle after they are all the way through the compute pipeline of the cell at (i, j). Likewise, the M, I and D states produced by a given cell at (hap, rd) coordinates (i, j) can be used by cell (i+1, j+1) M state calculations one clock cycle after they are all the way through the compute pipeline of the cell at (i, j). Taken together, the above points establish that very little dedicated storage is needed for the M, I, and D states along the diagonal of the swath path that spans the swath length, e.g., of ten reads. In such an instance, just the registers required to delay cell (i, j) M, I, and D state values one clock cycle for use in cell (i+1, j+1) M calculations and cell (i, j+1) I calculations by one clock cycle). Moreover, there is somewhat of a virtuous cycle here as the M state computations for a given cell are begun 10 clock cycles before the I and D state calculations for that same cell, natively outputting the new M, I, and D states for any given cell simultaneously.

In view of the above, and as can be seen with respect to FIG. 24, the HMM accelerator control logic 15 may be configured to process the data within each of the cells of the virtual matrix 30 in a manner so as to traverse the matrix. Particularly, in various embodiments, operations start at cell (0, 0), with M state calculations beginning 10 clock cycles before I and D state calculations begin. The next cell to traverse should be cell (1, 0). However, there is a ten cycle latency after the start of I and D calculations before the results from cell (0, 0) will be available. The hardware, therefore, inserts nine "dead" cycles into the compute pipeline. These are shown as the cells with haplotype index less than zero in FIG. 24.

After completing the dead cycle that has an effective cell position in the matrix of (−9, −9), the M, I, and D state values for cell (0, 0) are available. These (e.g., the M and D state outputs of cell (0, 0)) may now be used straight away to start the D state computations of cell (0, 1). One clock cycle later, the M, I, and D state values from cell (0, 0) may be used to begin the I state computations of cell (0, 1) and the M state computations of cell (1, 1).

The next cell to be traversed may be cell (2, 0). However, there is a ten cycle latency after the start of I and D calculations before the results from cell (1, 0) will be available. The hardware, therefore, inserts eight dead cycles into the compute pipeline. These are shown as the cells with haplotype index less than zero, as in FIG. 24 along the same diagonal as cells (1, 0) and (0, 1). After completing the dead cycle that has an effective cell position in the matrix of (−8, −9), the M, I, and D state values for cell (1, 0) are available.

These (e.g., the M and D state outputs of cell (1, 0)) are now used straight away to start the D state computations of cell (2, 0).

One clock cycle later, the M, I, and D state values from cell (1, 0) may be used to begin the I state computations of cell (1, 1) and the M state computations of cell (2, 1). The M and D state values from cell (0, 1) may then be used at that same time to start the D state calculations of cell (1, 1). One clock cycle later, the M, I, and D state values from cell (0, 1) are used to begin the I state computations of cell (0, 2) and the M state computations of cell (1, 2).

Now, the next cell to traverse may be cell (3, 0). However, there is a ten-cycle latency after the start of I and D calculations before the results from cell (2, 0) will be available. The hardware, therefore, inserts seven dead cycles into the compute pipeline. These are again shown as the cells with haplotype index less than zero in FIG. 24 along the same diagonal as cells (2, 0), (1, 1), and (0, 2). After completing the dead cycle that has an effective cell position in the matrix of (−7, −9), the M, I, and D state values for cell (2, 0) are available. These (e.g., the M and D state outputs of cell (2, 0)) are now used straight away to start the D state computations of cell (3, 0). And, so, computation for another ten cells in the diagonal begins.

Such processing may continue until the end of the last full diagonal in the swath 35a, which, in this example (that has a read length of 35 and haplotype length of 14), will occur after the diagonal that begins with the cell at (hap, rd) coordinates of (13, 0) is completed. After the cell (4, 9) in FIG. 28 is traversed, the next cell to traverse should be cell (13, 1). However, there is a ten-cycle latency after the start of the I and D calculations before the results from cell (12, 1) will be available.

The hardware may be configured, therefore, to start operations associated with the first cell in the next swath 35b, such as at coordinates (0, 10). Following the processing of cell (0, 10), then cell (13, 1) can be traversed. The whole diagonal of cells beginning with cell (13, 1) is then traversed until cell (5, 9) is reached. Likewise, after the cell (5, 9) is traversed, the next cell to traverse should be cell (13, 2). However, as before there may be a ten cycle latency after the start of I and D calculations before the results from cell (12, 2) will be available. Hence, the hardware may be configured to start operations associated with the first cell in the second diagonal of the next swath 35b, such as at coordinates (1, 10), followed by cell (0, 11).

Following the processing of cell (0, 11), the cell (13, 2) can be traversed, in accordance with the methods disclosed above. The whole diagonal 35 of cells beginning with cell (13,2) is then traversed until cell (6, 9) is reached. Additionally, after the cell (6, 9) is traversed, the next cell to be traversed should be cell (13, 3). However, here again there may be a ten-cycle latency period after the start of the I and D calculations before the results from cell (12, 3) will be available. The hardware, therefore, may be configured to start operations associated with the first cell in the third diagonal of the next swath 35c, such as at coordinates (2, 10), followed by cells (1, 11) and (0, 12), and likewise.

This continues as indicated, in accordance with the above until the last cell in the first swath 35a (the cell at (hap, rd) coordinates (13, 9)) is traversed, at which point the logic can be fully dedicated to traversing diagonals in the second swath 35b, starting with the cell at (9, 10). The pattern outlined above repeats for as many swaths of 10 reads as necessary, until the bottom swath 35c (those cells in this example that are associated with read bases having index 30, or greater) is reached.

In the bottom swath 35, more dead cells may be inserted, as shown in FIG. 24 as cells with read indices greater than 35 and with haplotype indices greater than 13. Additionally, in the final swath 35c, an additional row of cells may effectively be added. These cells are indicated at line 35 in FIG. 28, and relate to a dedicated clock cycle in each diagonal of the final swath where the final sum operations are occurring. In these cycles, the M and I states of the cell immediately above are added together, and that result is itself summed with a running final sum (that is initialized to zero at the left edge of the HMM matrix 30).

Taking the discussion above as context, and in view of FIG. 24, it is possible to see that, for this example of read length of 35 and haplotype length of 14, there are 102 dead cycles, 14 cycles associated with final sum operations, and 20 cycles of pipeline latency, for a total of 102+14+20=146 cycles of overhead. It can also be seen that, for any HMM job 20 with a read length greater than 10, the dead cycles in the upper left corner of FIG. 28 are independent of read length. It can also be seen that the dead cycles at the bottom and bottom right portion of FIG. 24 are dependent on read length, with fewest dead cycles for reads having mod(read length, 10)=9 and most dead cycles for mod(read length, 10)=0. It can further be seen that the overhead cycles become smaller as a total percentage of HMM matrix 30 evaluation cycles as the haplotype lengths increase (bigger matrix, partially fixed number of overhead cycles) or as the read lengths increase (note: this refers to the percentage of overhead associated with the final sum row in the matrix being reduced as read length-row-count-increases). Using such histogram data from representative whole human genome runs, it has been determined that traversing the HMM matrix in the manner described above results in less than 10% overhead for the whole genome processing.

Further methods may be employed to reduce the amount of overhead cycles including: Having dedicated logic for the final sum operations rather than sharing adders with the M and D state calculation logic. This eliminates one row of the HMM matrix 30. Using dead cycles to begin HMM matrix operations for the next HMM job in the queue.

Each grouping of ten rows of the HMM matrix 30 constitutes a "swath" 35 in the HMM accelerator function. It is noted that the length of the swath may be increased or decreased so as to meet the efficiency and/or throughput demands of the system. Hence, the swatch length may be about five rows or less to about fifty rows or more, such as about ten rows to about forty-five rows, for instance, about fifteen or about twenty rows to about forty rows or about thirty five rows, including about twenty five rows to about thirty rows of cells in length.

With the exceptions noted in the section, above, related to harvesting cycles that would otherwise be dead cycles at the right edge of the matrix of FIG. 24, the HMM matrix may be processed one swath at a time. As can be seen with respect to FIG. 24, the states of the cells in the bottom row of each swath 35a feed the state computation logic in the top row of the next swath 35b. Consequently, there may be a need to store (put) and retrieve (get) the state information for those cells in the bottom row, or edge, of each swath.

The logic to do this may include one or more of the following: when the M, I, and D state computations for a cell in the HMM matrix 30 complete for a cell with mod(read index, 10)=9, save the result to the M, I, D state storage memory. When M and I state computations (e.g., where D state computations do not require information from cells above them in the matrix) for a cell in the MINI matrix 30 begin for a cell with mod(read index, 10)=0, retrieve the previously saved M, I, and D state information from the appropriate place in the M, I, D state storage memory. Note in these instances that M, I, and D state values that feed row 0 (the top row) M and I state calculations in the HMM matrix 30 are simply a predetermined constant value and do not need to be recalled from memory, as is true for the M and D state values that feed column 0 (the left column) D state calculations.

As noted above, the HMM accelerator may or may not include a dedicated summing resource in the MINI hardware accelerator such that exist simply for the purpose of the final sum operations. However, in particular instances, as described herein, an additional row may be added to the bottom of the MINI matrix 30, and the clock cycles associated with this extra row may be used for final summing operations. For instance, the sum itself may be achieved by borrowing (e.g., as per FIG. 21) an adder from the M state computation logic to do the M+I operation, and further by borrowing an adder from the D state computation logic to add the newly formed M+I sum to the running final sum accumulation value. In such an instance, the control logic to activate the final sum operation may kick in whenever the read index that guides the HMM traversing operation is equal to the length of the inputted read sequence for the job. These operations can be seen at line 34 toward the bottom of the sample HMM matrix 30 of FIG. 24.

Accordingly, in view of the above, for embodiments involving FPGA-accelerated mapping, alignment, sorting, and/or variant calling applications, one or more of these functions may be implemented in one or both of software and hardware (HW) processing components, such as software running on a traditional CPU, and/or HW such as may be embodied in an FPGA, ASIC, sASIC, and the like. In such instances, the CPU and FPGA need to be able to communicate so as to pass results from one step on one device, e.g., the CPU or FPGA, to be processed in a next step on the other device. For instance, where a mapping function is run, the building of large data structures, such as an index of the reference, may be implemented by the CPU, where the running of a hash function with respect thereto may be implemented by the FPGA. In such an instance, the CPU may build the data structure, store it in an associated memory, such as a DRAM, which memory may then be accessed by the processing engines running on the FPGA.

For instance, in some embodiments, communications between the CPU and the FPGA may be implemented by any suitable interconnect such as a peripheral bus, such as a PCIe bus, USB, or a networking interface such as Ethernet. However, a PCIe bus may be a comparatively loose integration between the CPU and FPGA, whereby transmission latencies between the two may be relatively high. Accordingly, although one device e.g., (the CPU or FPGA) may access the memory attached to the other device (e.g., by a DMA transfer), the memory region(s) accessed are non-cacheable, because there is no facility to maintain cache coherency between the two devices. As a consequence, transmissions between the CPU and FPGA are constrained to occur between large, high-level processing steps, and a large amount of input and output must be queued up between the devices so they don't slow each other down waiting for high latency operations. This slows down the various processing operations disclosed herein. Furthermore, when the FPGA accesses non-cacheable CPU memory, the full load of such access is imposed on the CPU's external memory interfaces, which are bandwidth-limited compared to its internal cache interfaces.

Accordingly, because of such loose CPU/FPGA integrations, it is generally necessary to have "centralized" software control over the FPGA interface. In such instances, the various software threads may be processing various data units, but when these threads generate work for the FPGA engine to perform, the work must be aggregated in "central" buffers, such as either by a single aggregator software thread, or by multiple threads locking aggregation access via semaphores, with transmission of aggregated work via DMA packets managed by a central software module, such as a kernel-space driver. Hence, as results are produced by the HW engines, the reverse process occurs, with a software driver receiving DMA packets from the HW, and a de-aggregator thread distributing results to the various waiting software worker threads. However, this centralized software control of communication with HW FPGA logic is cumbersome and expensive in resource usage, reduces the efficiency of software threading and HW/software communication, limits the practical HW/software communication bandwidth, and dramatically increases its latency.

Figure 25A:
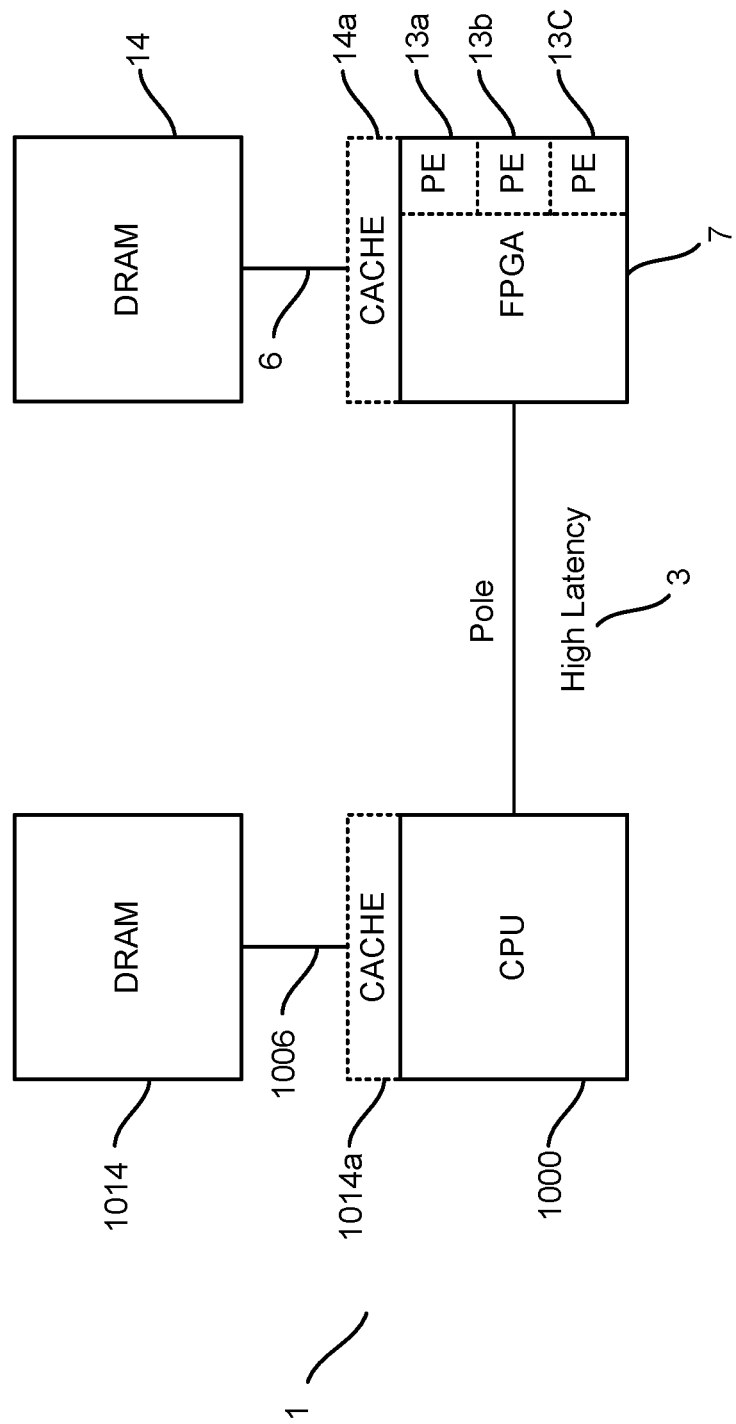
FIG. 25A depicts an exemplary architecture illustrating a loose coupling between a CPU and an FPGA of the disclosure.

Additionally, as can be seen with respect to FIG. 25A, a loose integration between the CPU 1000 and FPGA 7 may require each device to have its own dedicated external memory, such as DRAMs 1014, 14. As depicted in FIG. 25A, the CPU(s) 1000 has its own DRAM 1014 on the system motherboard, such as DDR3 or DDR4 DIMMs, while the FPGA 7 has its own dedicated DRAMs 14, such as four 8 GB SODIMMs, that may be directly connected to the FPGA 7 via one or more DDR3 busses 6, such as a high latency PCIe bus. Likewise, the CPU 1000 may be communicably coupled to its own DRAM 1014, such as by a suitably configured bus 1006. As indicated above, the FPGA 7 may be configured to include one or more processing engines 13, which processing engines may be configured for performing one or more functions in a bioinformatics pipeline as herein described, such as where the FPGA 7 includes a mapping engine 13a, an alignment engine 13b, and a variant call engine 13c. Other engines as described herein may also be included. In various embodiments, one or both of the CPU may be configured so as to include a cache 1014a, 14a respectively, that is capable of storing data, such as result data that is transferred thereto by one or more of the various components of the system, such as one or more memories and/or processing engines.

Many of the operations disclosed herein, to be performed by the FPGA 7 for genomic processing, require large memory accesses for the performance of the underlying operations. Specifically, due to the large data units involved, e.g. 3+ billion nucleotide reference genomes, 100+ billion nucleotides of sequencer read data, etc., the FPGA 7 may need to access the host memory 1014 a large number of times such as for accessing an index, such as a 30 GB hash table or other reference genome index, such as for the purpose of mapping the seeds from a sequenced DNA/RNA query to a 3 Gbp reference genome, and/or for fetching candidate segments, e.g., from the reference genome, to align against.

Accordingly, in various implementations of the system herein disclosed, many rapid random memory accesses may need to occur by one or more of the hardwired processing engines 13, such as in the performance of a mapping, aligning, and/or variant calling operation. However, it may be prohibitively impractical for the FPGA 7 to make so many small random accesses over the peripheral bus 3 or other networking link to the memory 1014 attached to the host CPU 1000. For instance, in such instances, latencies of return data can be very high, bus efficiency can be very low, e.g., for such small random accesses, and the burden on the CPU external memory interface 1006 may be prohibitively great.

Additionally, as a result of each device needing its own dedicated external memory, the typical form factor of the full CPU 1000+FPGA 7 platform is forced to be larger than may be desirable, e.g., for some applications. In such instances, in addition to a standard system motherboard for one or more CPUs 1000 and supporting chips 7 and memories, 1014 and/or 14, room is needed on the board for a large FPGA package (which may even need to be larger so as to have enough pins for several external memory busses) and several memory modules, 1014, 14. Standard motherboards, however, do not include these components, nor would they easily have room for them, so a practical embodiment may be configured to utilize an expansion card 2, containing the FPGA 7, its memory 14, and other supporting components, such as power supply, e.g. connected to the PCIe expansion slot on the CPU motherboard. To have room for the expansion card 2, the system may be fabricated to be in a large enough chassis, such as a 1U or 2U or larger rack-mount server.

Figure 25B:
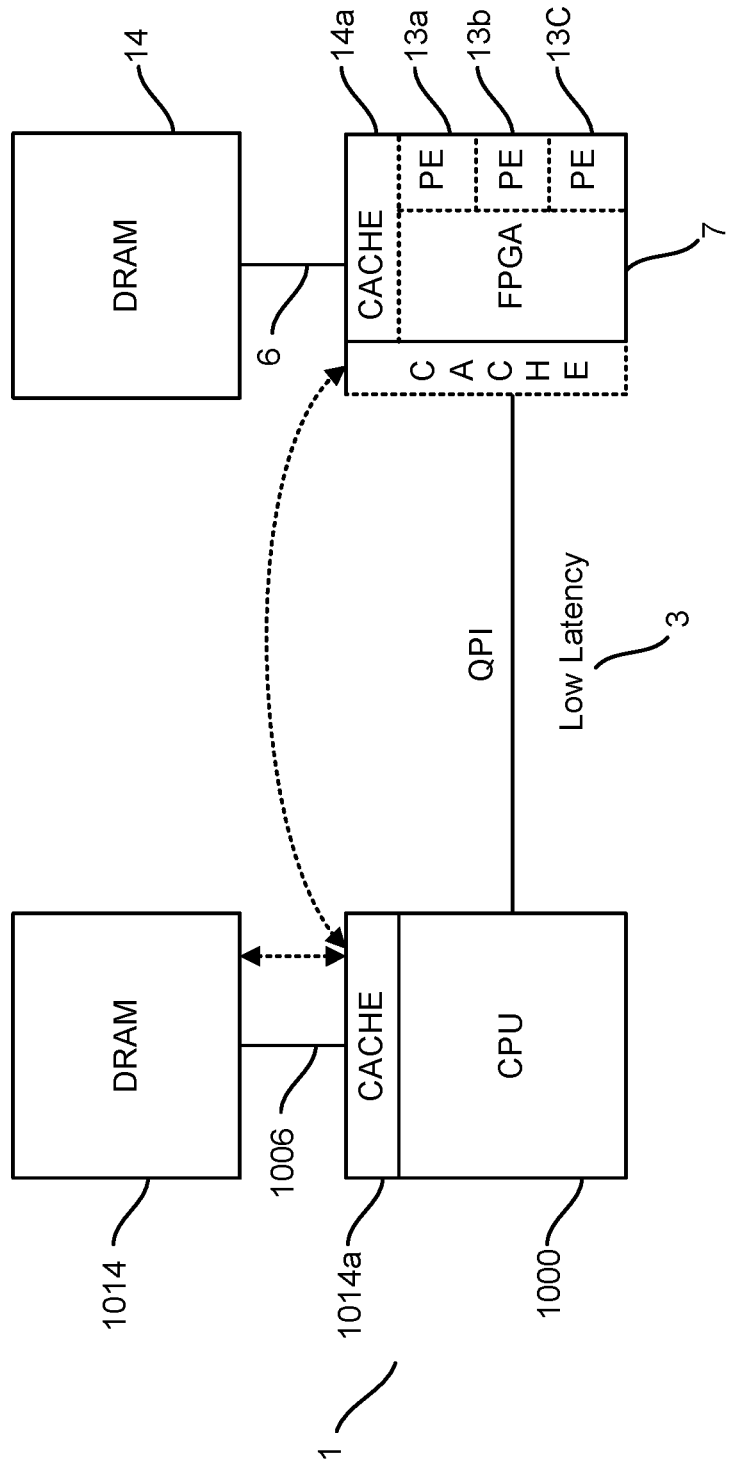
FIG. 25B depicts an exemplary architecture illustrating a tight coupling between a CPU and an FPGA of the disclosure.

In view of the above, in various instances, as can be seen with respect to FIG. 25B, to overcome these factors, it may be desirable to configure the CPU 1000 to be in a tight coupling arrangement with the FPGA 7. Particularly, in various instances, the FPGA 7 may be tightly coupled to the CPU 1000, such as by a low latency interconnect 3, such as a quick path interconnect (QPI). Specifically, to establish a tighter CPU+FPGA integration, the two devices may be connected by any suitable low latency interface, such as a "processor interconnect" or similar, such as INTELS® Quick Path Interconnect (QPI) or HyperTransport (HT).

Accordingly, as seen with respect to FIG. 25B, a system 1 is provided wherein the system includes both a CPU 1000 and a processor, such as an FPGA 7, wherein both devices are associated with one or more memory modules. For instance, as depicted, the CPU 1000 may be coupled, such as via a suitably configured bus 1006, to a DRAM 1014, and likewise, the FPGA 7 is communicably coupled to an associated memory 14 via a DDR3 bus 6. However, in this instance, instead of being coupled to one another such as by a typical high latency interconnect, e.g., PCIe interface, the CPU 1000 is coupled to the FPGA 7 by a low latency, hyper transport interconnect 3, such as a QPI. In such an instance, due to the inherent low latency nature of such interconnects, the associated memories 1014, 14 of the CPU 1000 and the FPGA 7 are readily accessible to one another. Additionally, in various instances, due to this tight coupling configuration, one or more caches 1114a/14a associated the devices may be configured so as to be coherent with respect to one another.

Some key properties of such a tightly coupled CPU/FPGA interconnect include a high bandwidth, e.g., 12.8 GB/s; low latency, e.g., 100–300 ns; an adapted protocol designed for allowing efficient remote memory accesses, and efficient small memory transfers, e.g., on the order of 64 bytes or less; and a supported protocol and CPU integration for cache access and cache coherency. In such instances, a natural interconnect for use for such tight integration with a given CPU 1000 may be its native CPU-to-CPU interconnect 1003, which may be employed herein to enable multiple cores and multiple CPUs to operate in parallel in a shared memory 1014 space, thereby allowing the accessing of each other's cache stacks and external memory in a cache-coherent manner.

Accordingly, as can be seen with respect to FIGS. 26A and 26B, a board 2 may be provided, such as where the board may be configured to receive one or more CPUs 1000, such as via a plurality of interconnects 1003, such as native CPU-CPU interconnects 1003a and 1003b. However, in this instance, as depicted in FIG. 26A, a CPU 1000 is configured so as to be coupled to the interconnect 1003a, but rather than another CPU being coupled therewith via interconnect 1003b, an FPGA 7 of the disclosure is configured so as to be coupled therewith. Additionally, the system 1 is configured such that the CPU 1000 may be coupled to the associated FPGA 7, such as by a low latency, tight coupling interconnect 3. In such instances, each memory 1014, 14 associated with the respective devices 1000, 7 may be made so as to accessible to each other, such as in a high-bandwidth, cache coherent manner.

Likewise, as can be seen with respect to FIG. 26B, the system can also be configured so as to receive packages 1002a and/or 1002b, such as where each of the packages include one or more CPUs 1000a, 1000b that are tightly coupled, e.g., via low latency interconnects 3a and 3b, to one or more FPGAs 7a, 7b, such as where given the system architecture, each package 2a and 2b may be coupled one with the other such as via a tight coupling interconnect 3. Further, as can be seen with respect to FIG. 27, in various instances, a package 1002a may be provided, wherein the package 1002a includes a CPU 1000 that has been fabricated in such a manner so as to be closely coupled with an integrated circuit such as an FPGA 7. In such an instance, because of the close coupling of the CPU 1000 and the FPGA 7, the system may be constructed such that they are able to directly share a cache 1014a in a manner that is consistent, coherent, and readily accessible by either device, such as with respect to the data stored therein.

Hence, in such instances, the FPGA 7, and or package 2a/2b, can, in effect, masquerade as another CPU, and thereby operate in a cache-coherent shared-memory environment with one or more CPUs, just as multiple CPUs would on a multi-socket motherboard 1002, or multiple CPU cores would within a multi-core CPU device. With such an FPGA/CPU interconnect, the FPGA 7 can efficiently share CPU memory 1014, rather than having its own dedicated external memory 14, which may or may not be included or accessed. Thus, in such a configuration, rapid, short, random accesses are supported efficiently by the interconnect 3, such as with low latency. This makes it practical and efficient for the various processing engines 13 in the FPGA 7 to access large data structures in CPU memory 1000.

Figure 29:
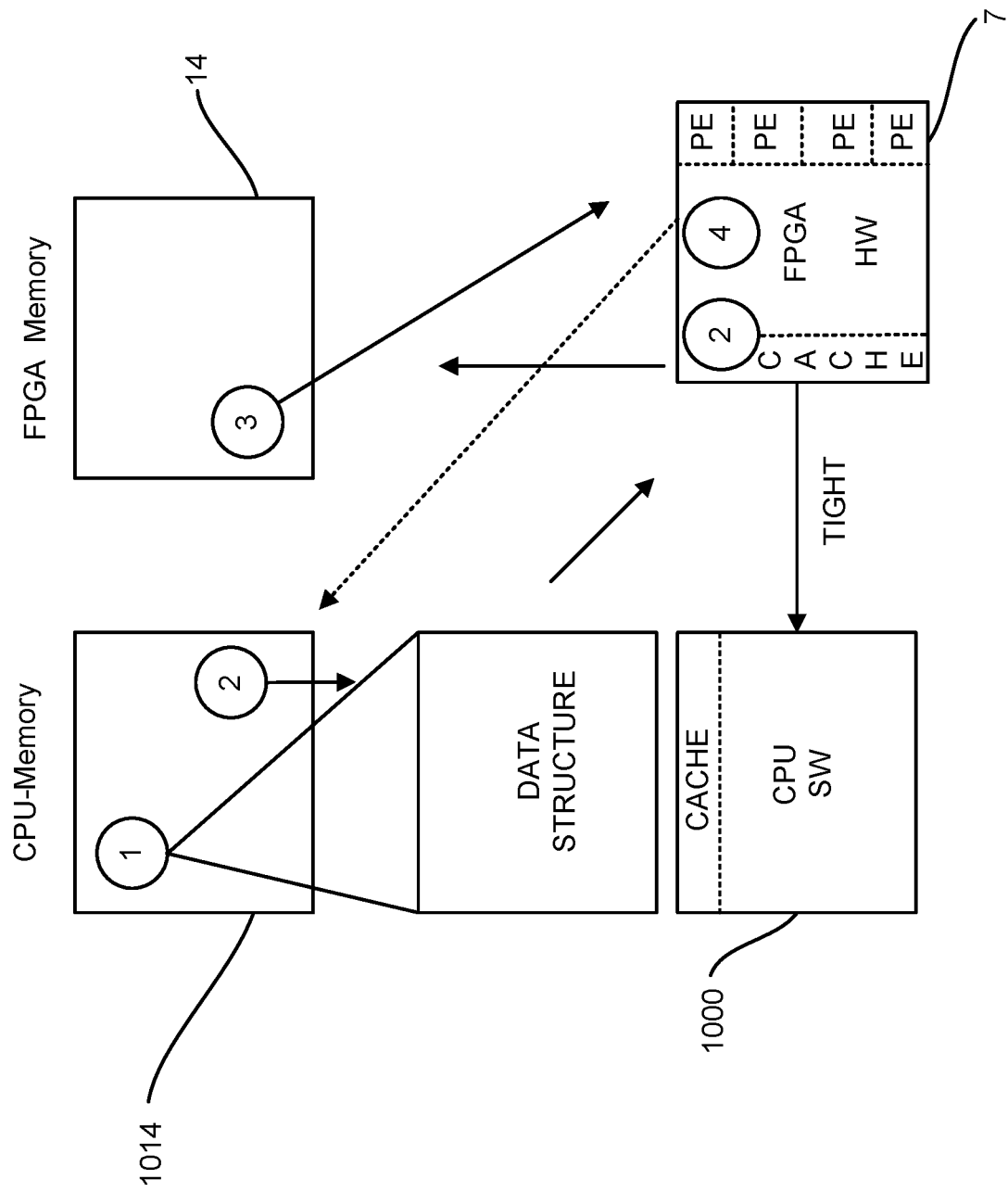
FIG. 29 illustrates an exemplary method of data transfer throughout the system.

For instance, as can be seen with respect to FIG. 29, a system for performing a method is provided, such as where the method includes one or more steps for performing a function of the disclosure, such as a mapping function, as described herein, in a shared manner. Particularly, in one step a data structure may be generated or otherwise provided, such as by a CPU 1000, which data structure may then be stored in an associated memory, such as a DRAM 1014. The data structure may be any data structure, such as with respect to those described herein, but in this instance may be a reference genome or an index of the reference genome, such as for the performance of a mapping and/or aligning or variant calling function. In a second step, such as with respect to a mapping function, an FPGA 7 associated with the CPU 1000, such as by a tight coupling interface 3, may access the CPU associated memory 1014, so as to perform one or more actions with respect to the reference genome and/or an index thereof. Particularly, the FPGA 7 may access the data structure so as to produce one or more seeds thereof, which seeds may be employed for the purposes of performing a hash function with respect thereto, such as to produce one or more reads that have been mapped to one or more positions with respect to the reference genome.

In a further step, the mapped result data may be stored, e.g., in either the host memory 1014 or in an associated DRAM 14. In such an instance, the FPGA 7, more particularly, a processing engine 13 thereof, e.g., an alignment engine, may then access the stored mapped data structure so as to perform an aligning function thereon, so as to produce one or more reads that have been aligned to the reference genome. In an additional step, the host CPU may then access the mapped and/or aligned data so as to perform one or more functions thereon, such as for the production of a De Brujin Graph, which DBG may then be stored in its associated memory. Likewise, in one or more additional steps, the FPGA 7 may once again access the host CPU memory 1014 so s to access the DBG and perform an HMM analysis thereon so as to produce one or more variant call files. In particular instances, the CPU 1000 and/or FPGA 7 may have one or more memory cache's which due to the tight coupling of the interface between the two devices will allow the separate caches to be coherent, such as with respect to the transitionary data, e.g., results data, stored thereon, such as results from the performance of one or more functions herein. In a manner such as this, data may be shared substantially seamlessly between the tightly coupled devices, thereby allowing a pipeline of functions to be weaved together such as in a bioinformatics pipeline. Thus, it is no longer necessary for the FPGA 7 to have its own dedicated external memory 14 attached, and hence, due to such a tight coupling configuration, the reference genome and/or reference genomic index, as herein described, may be intensively shared such as for read mapping and alignment, and other genomic data processing operations.

Additionally, the low latency and cache coherency, as well as other components discussed herein, allow smaller, lower-level operations to be performed in one device (e.g., in a CPU or FPGA) before handing a data unit or processing thread 20 back to the other device, such as for further processing. For example, rather than a CPU thread 20a queuing up large amounts of work for the FPGA hardware logic 13 to perform, and the same or another thread 20b processing a large queue of results at a substantially later time; a single CPU thread 20 might make a blocking "function call" to an FPGA hardware engine 13, resuming software execution as soon as the hardware function completes. Hence, rather than packaging up data structures in packets to stream by DMA 14 into the FPGA 7, and unpacking results when they return, a software thread 20 could simply provide a memory pointer to the FPGA engine 13, which could access and modify the shared memory 14 in place, in a cache-coherent manner.

Particularly, given the relationship between the structures provided herein, the granularity of the software/hardware cooperation can be much finer, with much smaller, lower level operations being allocated so as to be performed by various hardware engines 13, such as function calls from various allocated software threads 20. For example, in a loose CPU/FPGA interconnect platform, for efficient acceleration of DNA/RNA read mapping, alignment, and/or variant calling, a full mapping/aligning/variant calling pipeline may be constructed as one or more FPGA engines, with unmapped and unaligned reads streamed from software to hardware, and the fully mapped and aligned reads streamed from the hardware back to the software, where the process may be repeated, such as for variant calling. With respect to the configurations herein described, this can be very fast, however, in various instances, it may suffer from limitations of flexibility, complexity, and/or programmability, such because the whole map/align and/or variant call pipeline is implemented in hardware circuitry, which although reconfigurable in an FPGA, is generally much less flexible and programmable than software, and may therefore be limited to less algorithmic complexity.

Figure 30:
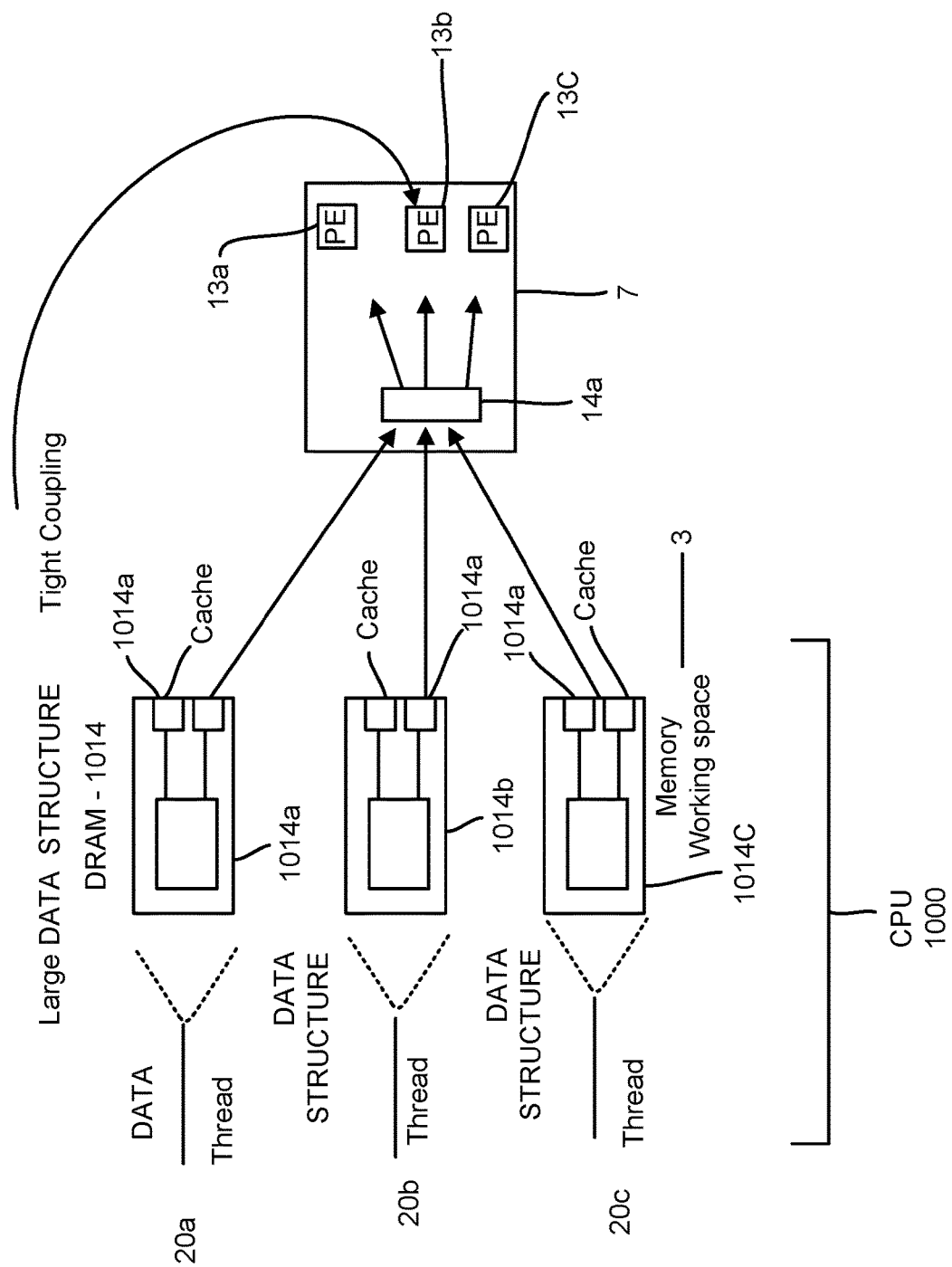
FIG. 30 depicts the embodiment of FIG. 28 in greater detail.

By contrast, using a tight CPU/FPGA interconnect, such as a QPI or other interconnect in the configurations disclosed herein, several resource expensive discrete operations, such as seed generation and/or mapping, rescue scanning, gapless alignment, gapped, e.g., Smith-Waterman, alignment, etc., can be implemented as distinct separately accessible hardware engines 13, e.g., see FIG. 30 and the overall mapping/alignment and/or variant call algorithms can be implemented in software, with low-level acceleration calls to the FPGA for the specific expensive processing steps. This framework allows full software programmability, outside the specific acceleration calls, and enables greater algorithmic complexity and flexibility, than standard hardware implemented operations.

Furthermore, in such a framework of software execution accelerated by discrete low-level FPGA hardware acceleration calls, hardware acceleration functions may more easily be shared for multiple purposes. For instance, when hardware engines 13 form large, monolithic pipelines, the individual pipeline subcomponents may generally be specialized to their environment, and interconnected only within one pipeline, which unless tightly coupled may not generally be accessible for any purpose. But many genomic data processing operations, such as Smith-Waterman alignment, gapless alignment, De Bruijn or assembly graph construction and other such operations, can be used in various higher level parent algorithms. For example, as described herein, Smith-Waterman alignment may be used in DNA/RNA read mapping such as with respect to a reference genome, but may also be configured so as to be used by haplotype-based variant callers, to align candidate haplotypes to a reference genome, or to each other, or to sequenced reads, such as in a HMM analysis. Hence, exposing various discrete low-level hardware acceleration functions via general software function calls may enable the same acceleration logic, e.g., 13, to be leveraged throughout a genomic data processing application.

It is also practical, with tight CPU/FPGA interconnection, to have distributed rather than centralized CPU 1000 software control over communication with the various FPGA hardware engines 13 described herein. In widespread practices of multi-threaded, multi-core, and multi-CPU software design, many software threads and processes communicate and cooperate seamlessly, without any central software modules, drivers, or threads to manage intercommunication. In such a format, this is practical because of the cache-coherent shared memory, which is visible to all threads in all cores in all of the CPUs; while physically, coherent memory sharing between the cores and CPUs occurs by intercommunication over the processor interconnect, e.g., QPI or HT.

In a similar manner, as can be seen with respect to FIGS. 28 and 30 with the tight CPU/FPGA interconnect disclosed herein, many threads 20a, b, c, and processes running on one or multiple cores and/or CPUs 1000a, 100b, and 1000c can communicate and cooperate in a distributed manner with the various different FPGA hardware acceleration engines, such as by the use of cache-coherent memory sharing between the various CPU(s) and FPGA(s). For instance, as can be seen with respect to FIG. 28, a multiplicity of CPU cores 1000a,

1000b, and 1000c can be coupled together in such a manner so as to share one or more memories, e.g., DRAMs, and/or one or more caches having one or more layers or levels associated therewith. Likewise, with respect to FIG. 30, in another embodiment, a single CPU may be configured to include multiple cores 1000a, 1000b, and 1000c that can be coupled together in such a manner so as to share one or more memories, e.g., DRAMs, and/or one or more caches having one or more layers or levels associated therewith. Hence, in either embodiment, data to be passed from one or more software threads 20 from one or more CPU cores 1000 to a hardware engine 13 or vice versa may simply be updated in the shared memory 1014, or a cache thereof, visible to both devices. Even requests to process data in shared memory 1014, or notification of results updated in shared memory, can be signaled between the software and hardware, such as over a DDR4 bus 1014, in queues implemented within the shared memory itself. Standard software mechanisms for control transfer and data protection, such as semaphores, mutexes, and atomic integers, can also be implemented similarly for software/hardware coordination.

Consequently, in some embodiments, with no need for the FPGA 7 to have its own dedicated memory 14 or other external resources, due to cache coherent memory-sharing over a tight CPU/FPGA interconnect, it becomes much more practical to package the FPGA 7 more compactly and natively within traditional CPU 1000 motherboards, without the use of expansion cards. See, for example FIGS. 26A and 26B and FIG. 27. Several packaging alternatives are available. Specifically, an FPGA 7 may be installed onto a multi-CPU motherboard in a CPU socket, as shown in FIGS. 26A and 26B, such as by use of an appropriate interposer, such as a small PC board 2, or alternative wire-bond packaging of an FPGA die within a CPU chip package 2a, to route CPU socket pins to FPGA pins, including power and ground, the processer interconnect 3 (QPI, HT, etc.), and system connections. Additionally, an FPGA die and CPU die may be included in the same multi-chip package (MCP) with necessary connections, including power, ground, and CPU/FPGA interconnect, made within the package 2a. Inter-die connections may be made by die-to-die wire-bonding, or by connection to a common substrate or interposer, or by bonded pads or through-silicon vias between stacked dice.

Figure 27:
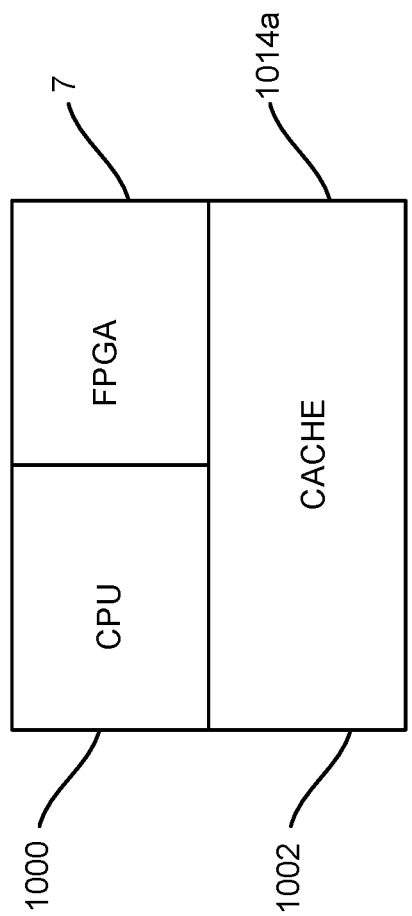
FIG. 27 depicts an embodiment of a package of a combined CPU and FPGA, where the two devices share a common memory and/or cache.

Further, FPGA and CPU cores may be fabricated on a single die, see FIG. 27, using system-on-a-chip (SOC) methodology. In any of these cases, custom logic, e.g., 17, may be instantiated inside the FPGA 7 to communicate over the CPU/FPGA interconnect 3 by its proper protocol, and to service and convert memory access requests from internal FPGA engines 13 to the CPU/FPGA interconnect 3 protocols. Alternatively, some or all of this logic may be hardened into custom silicon, to avoid using up FPGA logic real estate for this purpose, such as where the hardened logic may reside on the CPU die, and/or the FPGA die, or a separate die. Also, in any of these cases, power supply and heat dissipation requirements may be obeyed appropriately; such as within a single package (MCP or SOC), the FPGA size and CPU core count may be chosen to stay within a safe power envelope, or dynamic methods (clock frequency management, clock gating, core disabling, power islands, etc.) may be used to regulate power consumption according to changing the FPGA and/or the CPU computation demands.

All of these packaging options share several advantages. The tightly-integrated CPU/FPGA platform becomes compatible with standard motherboards and/or system chassis, of a variety of sizes. If the FPGA is installed via an interposer (not shown) in a CPU socket, see FIGS. 26A and 26B, then at least a dual-socket motherboard 1002 may be employed, and e.g. a quad-socket motherboard may be required to allow 3 CPUs+1 FPGA, 2 CPUs+2 FPGAs, or 1 CPU+3 FPGAs, etc. If each FPGA resides in the same chip package as a CPU (either MCP or SOC), see FIG. 26B, then even a single-socket motherboard is adequate, potentially in a very small chassis (although a dual socket motherboard is depicted); this also scales upward very well, e.g. 4 FPGAs and 4 multi-core CPUs on a 4-socket server motherboard, which nevertheless could operate in a compact chassis, such as a 1U rack-mount server.

In various instances, therefore, there may be no need for an expansion card to be installed so as to integrate the CPU and FPGA acceleration, because the FPGA 7 may be integrated in to the CPU 1000 socket. This implementation avoids the extra space and power requirements of an expansion card, as well as the additional failure point, expansion cards sometimes being relatively low-reliability components. Furthermore, standard CPU cooling solutions (head sinks, heat pipes, and/or fans), which are efficient yet low-cost since they are manufactured in high volumes, can be applied to FPGAs or CPU/FPGA packages in CPU sockets, whereas cooling for expansion cards can be expensive and inefficient.

Likewise, an FPGA/interposer or CPU/FPGA package is provided the full power supply of a CPU socket, e.g. 150 W, whereas a standard expansion card may be power limited, e.g. 25 W or 75 W from the PCIe bus. In various instances, for genomic data processing applications, all these packaging options may facilitate easy installation of a tightly-integrated CPU+FPGA compute platform, such as within a DNA sequencer. For instance, typical modern "next-generation" DNA sequencers contain the sequencing apparatus (sample and reagent storage, fluidics tubing and control, sensor arrays, primary image and/or signal processing) within a chassis that also contains a standard or custom server motherboard, wired to the sequencing apparatus for sequencing control and data acquisition. A tightly-integrated CPU+FPGA platform, as herein described, may be achieved in such a sequencer such as by simply installing one or more FPGA/interposer or FPGA/CPU packages in CPU sockets of its existing motherboard, or alternatively by installing a new motherboard with both CPU(s) and FPGA(s).

Further, all of these packaging options may be configured to facilitate easy deployment of the tightly-integrated CPU+FPGA platform such as into a cloud or datacenter server rack, which require compact/dense servers, and very high reliability/availability. Hence, in accordance with the teachings herein, there are many processing stages for data from DNA (or RNA) sequencing to mapping and aligning to variant calling, which can vary depending on the primary and/or secondary and/or tertiary processing technologies and the application. Such processing steps may include one or more: signal processing on electrical measurements from a sequencer, an image processing on optical measurements from the sequencer, base calling using processed signal or image data to determine the most likely nucleotide sequence and confidence scores, filtering sequenced reads with low quality or polyclonal clusters, detecting and trimming adapters, key sequences, barcodes, and low quality read ends, as well as De novo sequence assembly, generating and/or utilizing De Bruijn graphs and/or sequence graphs, e.g., De Bruijn and sequence graph construction, editing, trimming, cleanup, repair, coloring, annotation, comparison, transformation, splitting, splicing, analysis, subgraph selection, traversal, iteration, recursion, searching, filtering, import, export, including mapping reads to a reference genome, aligning reads to candidate mapping locations in the reference genome, local assembly of reads mapped to a reference region, sorting reads by aligned position, marking duplicate reads, including PCR or optical duplicates, re-alignment of multiple overlapping reads for indel consistency, base quality score recalibration, variant calling (single sample or joint), structural variant analysis, copy number variant analysis, somatic variant calling (e.g., tumor sample only, matched tumor/normal, or tumor/unmatched normal, etc.), RNA splice junction detection, RNA alternative splicing analysis, RNA transcript assembly, RNA transcript expression analysis, RNA differential expression analysis, RNA variant calling, DNA/RNA difference analysis, DNA methylation analysis and calling, variant quality score recalibration, variant filtering, variant annotation from known variant databases, sample contamination detection and estimation, phenotype prediction, disease testing, treatment response prediction, custom treatment design, ancestry and mutation history analysis, population DNA analysis, genetic marker identification, encoding genomic data into standard formats (e.g. FASTA, FASTQ, SAM, BAM, VCF, BCF), decoding genomic data from standard formats, querying, selecting or filtering genomic data subsets, general compression and decompression for genomic files (gzip, BAM compression), specialized compression and decompression for genomic data (CRAM), genomic data encryption and decryption, statistics calculation, comparison, and presentation from genomic data, genomic result data comparison, accuracy analysis and reporting, genomic file storage, archival, retrieval, backup, recovery, and transmission, as well as genomic database construction, querying, access management, data extraction, and the like.

Figure 31:
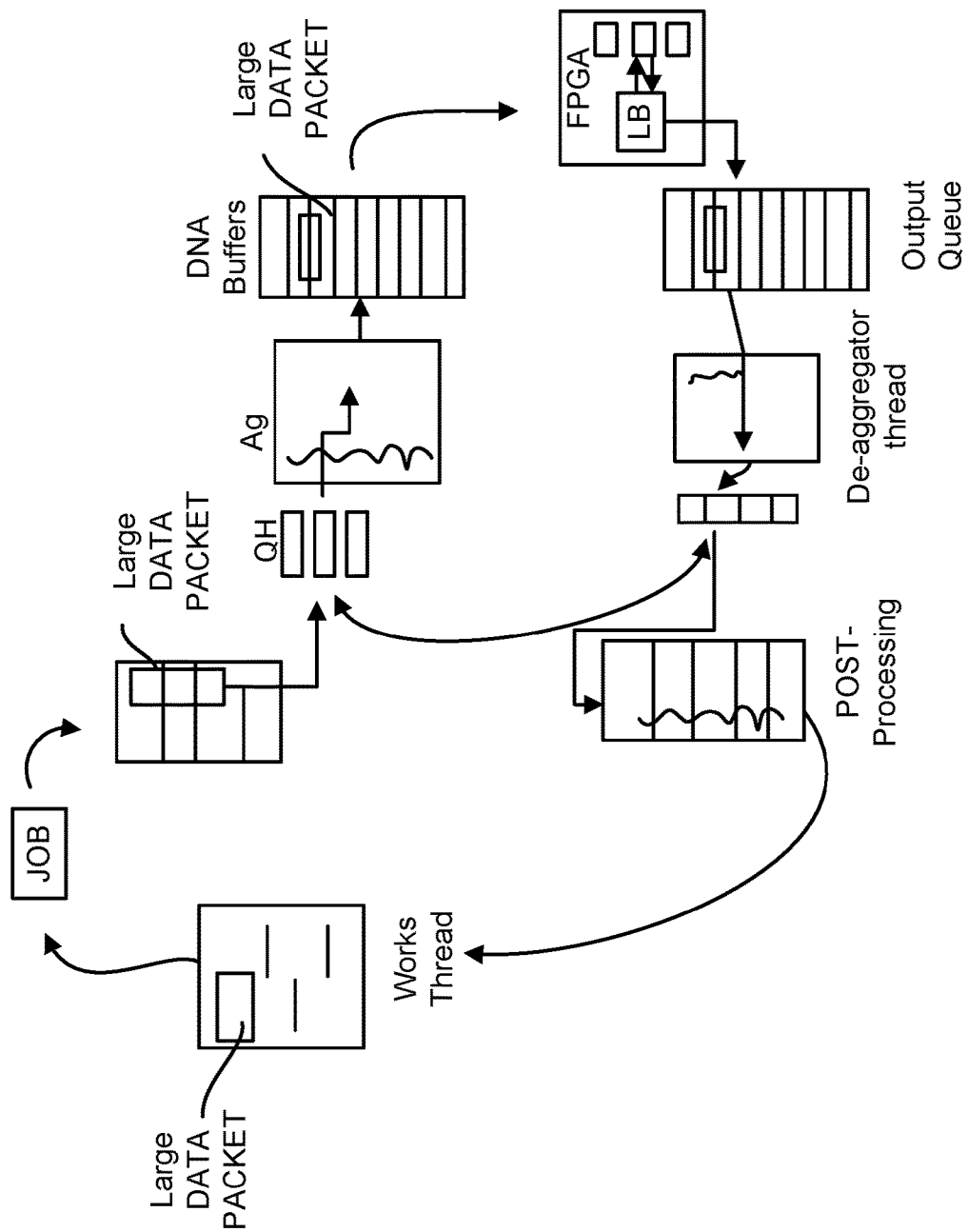
FIG. 31 depicts an exemplary method for the processing of one or more jobs of a system of the disclosure.

All of these operations can be quite slow and expensive when implemented on traditional compute platforms. The sluggishness of such exclusively software implemented operations may be due in part to the complexity of the algorithms, but is typically due to the very large input and output datasets that results in high latency with respect to moving the data. However, as can be seen with respect to FIG. 31, one or more, e.g., all of these operations, may be accelerated by cooperation of CPUs 1000 and FPGAs 7, such as in a distributed processing model, as described herein. For instance, in some cases (encryption, general compression, read mapping, and/or alignment), a whole operational function may be substantially or entirely implemented in custom FPGA logic (such as by hardware design methodology, e.g. RTL), such as where the CPU software mostly serves the function of compiling large data packets for preprocessing via worker threads 20, such as aggregating the data into various jobs to be processed by one or more hardware implemented processing engines, and feeding the various data inputs, such as in a first in first out format, to one or more of the FPGA engine(s) 13, and/or receives results therefrom.

For instance, in various embodiments, a worker thread generates various packets of job data that may be compiled and/or streamed into larger job packets that may be queued up and/or further aggregated in preparation for transfer, e.g., via a DDR3 to the FPGA 7, such as over a high bandwidth, low latency point to point interconnect protocol, e.g., QPI 3. In particular instances, the data may be buffered in accordance with the particular data sets being transferred to the FPGA. Once the packaged data is received by the FPGA 7, such as in a cache coherent manner, it may be processed and sent to one or more specialized clusters 11 whereby it may further be directed to one or more sets of processing engines for processing thereby in accordance with one or more of the pipeline operations herein described. Once processed, results data may then be sent back to the cluster and queued up for being sent back over the tight coupling point to point interconnect to the CPU for post processing. In certain embodiments, the data may be sent to a de-aggregator thread prior to post processing. Once post processing has occurred, the data may be sent back to the initial worker thread 20 that may be waiting on the data. Such distributed processing is particularly beneficial for the functions herein disclosed immediately above. Particularly, these functions are distinguishable by the facts that their algorithmic complexity (although having a very high net computational burden) are pretty limited, and they each may be configured so as to have a fairly uniform compute cost across their various sub-operations. However, in various cases, rather than processing the data in large packets, smaller sub-routines or discrete function protocols or elements may be performed, such as pertaining to one or more functions of a pipeline, rather than performing the entire processing functions for that pipeline on that data. Hence, a useful strategy may be to identify one or more critical compute-intensive sub-functions in any given operation, and then implement that sub-function in custom FPGA logic (hardware acceleration), such as for the intensive sub-function(s), while implementing the balance of the operation, and ideally much or most of the algorithmic complexity, in software to run on CPUs, as described herein, such as with respect to FIG. 31.

Generally, it is typical of many genomic data processing operations that a small percentage of the algorithmic complexity accounts for a large percentage of the overall computing load. For instance, as a typical example, 20% of the algorithmic complexity for the performance of a given function may account for 90% of the compute load, while the remaining 80% of the algorithmic complexity may only account for 10% of the compute load. Hence, in various instances, the system components herein described may be configured so as to implement the high, e.g., 20% or more, complexity portion so as to be run very efficiently in custom FPGA logic, which may be a tractable and maintainable in a hardware design, and thus, may be configured for executing this in FPGA; which in turn may reduce the CPU compute load by 90%, thereby enabling 10× overall acceleration. Other typical examples may be even more extreme, such as where 10% of the algorithmic complexity may account for 98% of the compute load, in which case applying FPGA acceleration, as herein described, to the 10% complexity portion be even easier, but may also enable up to 50× net acceleration.

However, such a "piecemeal" or distributed processing acceleration approaches may be more practical when implemented in a tightly integrated CPU+FPGA platform, rather than on a loosely integrated CPU+FPGA platform. Particularly, in a loosely integrated platform, the portion, e.g., the functions, to be implemented in FPGA logic may be selected so as to minimize the size of the input data to the FPGA engine(s), and to minimize the output data from the FPGA engine(s), such as for each data unit processed, and additionally may be configured so as to keep the software/hardware boundary tolerant of high latencies. In such instances, the boundary between the hardware and software portions may be forced, e.g., on the loosely-integrated platform, to be drawn through certain low-bandwidth/high-latency cut-points, which divisions may not otherwise be desirable when optimizing the partitioning of the algorithmic complexity and computational loads. This may often result either in enlarging the boundaries of the hardware portion, encompassing an undesirably large portion of the algorithmic complexity in the hardwired format, or in shrinking the boundaries of the hardware portion, undesirably excluding portions with dense compute load.

By contrast, on a tightly integrated CPU+FPGA platform, due to the cache-coherent shared memory and the high-bandwidth/low-latency CPU/FPGA interconnect, the low-complexity/high-compute-load portions of a genomic data processing operation can be selected very precisely for implementation in custom FPGA logic (e.g., via the hardware engine(s) described herein), with optimized software/hardware boundaries. In such an instance, even if a data unit is large at the desired software/hardware boundary, it can still be efficiently handed off to an FPGA hardware engine for processing, just by passing a pointer to the particular data unit. Particularly, in such an instance, as per FIG. 25B, the hardware engine 13 of the FPGA 7, may not need to access every element of the data unit stored within the DRAM 1014; rather, it can access the necessary elements, e.g., within the cache 1014a, with efficient small accesses over the low-latency interconnect 3' serviced by the CPU cache, thereby consuming less aggregate bandwidth than if the entire data unit had to be accessed and/or transferred to the FPGA 7, such as by DMA of the DRAM 1014, over a loose interconnect 3, as per FIG. 25A.

In such instances, the hardware engine 13 can annotate processing results into the data unit in-place in CPU memory 1014, without streaming an entire copy of the data unit by DMA to CPU memory. Even if the desired software/hardware boundary is not appropriate for a software thread 20 to make a high-latency, non-blocking queued handoff to the hardware engine 13, it can potentially make a blocking function call to the hardware engine 13, sleeping for a short latency until the hardware engine completes, the latency being dramatically reduced by the cache-coherent shared memory, the low-latency/high-bandwidth interconnect, and the distributed software/hardware coordination model, as in FIG. 25B.

In particular instances, because the specific algorithms and requirements of signal/image processing and base calling vary from one sequencer technology to another, and because the quantity of raw data from the sequencer's sensor is typically gargantuan (this being reduced to enormous after signal/image processing, and to merely huge after base calling), such signal/image processing and base calling may be efficiently performed within the sequencer itself, or on a nearby compute server connected by a high bandwidth transmission channel to the sequencer. However, DNA sequencers have been achieving increasingly high throughputs, at a rate of increase exceeding Moore's Law, such that existing CPU and/or GPU based signal/image processing and base calling have become increasingly inadequate to the task. Nevertheless, since a tightly integrated CPU+FPGA platform can be so compact and easily instantiated within such a sequencer, e.g., as CPU and/or FPGA chip positioned on the sequencer's motherboard, or easily installed in a server adjacent to the sequencer, such a sequencer may be an ideal platform to offer the massive compute acceleration offered by the custom FPGA hardware engines described herein.

For instance, signal/image processing and base calling algorithms generally require large amounts of floating point and/or fixed point math, notably additions and multiplications. Large modern FPGAs contain thousands of high-speed multiplication and addition resources, and custom engines implemented on them can perform parallel arithmetic operations at rates far exceeding the capabilities of CPUs. Likewise, GPUs, have more comparable parallel arithmetic resources, but they have awkward architectural limitations and programming restrictions that often prevent them from being fully utilized; whereas FPGA arithmetic resources can be wired up by design to operate in exactly the required manner with near 100% efficiency. Nevertheless, GPU cards may be added to expansion slots on a motherboard with tightly integrated CPU+FPGA, thereby allowing all three processor types to cooperate, although the GPU may still cooperate with all of its own limitations and the limitations of loose integration.

Accordingly, if a tightly integrated CPU+FPGA with shared memory platform is employed within a sequencer or attached server for signal/image processing and base calling functions, there may be an advantage achieved such as in an incremental development process. For instance, initially, a limited portion of the compute load, such as a dynamic programming function for base calling, may be implemented in one or more FPGA engines, where as other work may be done in the CPU and/or GPU expansion cards. However, the tight CPU/FPGA integration and shared memory model may be further configured, later, so as to make it easy to incrementally select additional compute-intensive functions for FPGA acceleration, which may then be implemented as FPGA hardware engines, and their functions may be offloaded for execution into the FPGA(s), thereby accelerating signal/image processing and base calling further. Such incremental advances can be implemented as needed to keep up with the increasing throughput of various sequencing technologies.

Likewise, read mapping and alignment, e.g., of one or more reads to a reference genome, may be benefited from such FPGA acceleration. Specifically, mapping and alignment, or portions thereof, may be implemented partially or entirely as custom FPGA logic, such as with the "to be aligned" reads streaming from the CPU memory into the FPGA map/align engines, and mapped and/or aligned read records streaming back out. This type of FPGA acceleration works on a loosely-integrated CPU+FPGA platform, and in the configurations described herein may be extremely fast. Nevertheless, there are some additional advantages that may be gained by moving to a tightly-integrated CPU+FPGA platform.

Hence, with respect to mapping and aligning, in some embodiments, a shared advantage of a tightly-integrated CPU+FPGA platform, as described herein, is that the map/align hardware acceleration can be efficiently split into several discrete compute-intensive operations, such as seed generation and/or mapping, seed chain formation, paired end rescue scans, gapless alignment, and gapped alignment (Smith-Waterman or Needleman-Wunsch), such as where the CPU software performs lighter (but not necessarily less complex) tasks, and may make acceleration calls to discrete hardware engines as needed. Such a model may be less efficient in a typical loosely-integrated CPU+FPGA platform, e.g., due to large amounts of data to transfer back and forth between steps and high latencies, but may be more efficient in a tightly-integrated CPU+FPGA platform with cache-coherent shared memory, high-bandwidth/low-latency interconnect, and distributed software/hardware coordination model. Additionally, both Hidden Markov model (HMM) and dynamic programming (DP) algorithms, including Viterbi and forward algorithms, may be implemented in association with a base calling operation, such as to compute the most likely original sequence explaining the observed sensor measurements, in a configuration so as to be well suited to the parallel cellular layout of FPGAs described herein.

Accordingly, an efficient utilization of hardware and software resources in a distributed processing configuration can result from reducing hardware acceleration to discrete compute-intensive functions. In such instances, several of the functions disclosed herein may be performed in a monolithic pure-hardware engine so as to not be very compute intensive, but may be nevertheless algorithmically complex, and therefore may consume large quantities of physical FPGA resources (lookup-tables, flip-flops, block-RAMs, etc.). In such instances, moving a portion or all of these functions to software could take up available CPU cycles, in return for relinquishing substantial amounts of FPGA area. In certain of these instances, the freed FPGA area can be used for establishing greater parallelism for the compute intensive map/align/variant call sub-functions, thus increasing acceleration, or for other genomic acceleration functions.

Hence, in various embodiments, the algorithmic complexity of the one or more functions disclosed herein may be somewhat lessened by being configured in a pure hardware implementation. However, some operations, such as comparing pairs of candidate alignments for paired-end reads, and performing subtle mapping quality (MAPA) estimations, represent very low compute loads, and thus could benefit from more complex and accurate processing in CPU software. Hence, in general, reducing the hardware processing to specific compute-intensive operations would allow more complex and accurate algorithms to be employed in the CPU portions.

Furthermore, the whole map/align operation could be configured so as to employ more algorithmic complexity at high levels, such as by calling compute-intensive hardware functions in a dynamic order or iteratively, whereas a monolithic pure-hardware design may be implemented in a manner so as to function more efficiently as a linear pipeline. For example, if during processing one Smith-Waterman alignment displayed evidence of the true alignment path escaping the scoring band, e.g., swath as described above, another Smith-Waterman alignment could be called to correct this. Hence, these configurations could essentially reduce the FPGA hardware acceleration to discrete functions, such as a form of procedural abstraction, which would allow higher level complexity to be built easily on top of it.

Additionally, in various instances, flexibility within the map/align algorithms and features thereof may be improved by reducing hardware acceleration to discrete compute-intensive functions, and configuring the system so as to perform other, e.g., less intensive parts, in the software of the CPU. For instance, although hardware algorithms can be modified and reconfigured in FPGAs, generally such changes to the hardware designs may require several times as much design effort as similar changes to software code. In such instances, the compute-intensive portions of mapping and alignment, such as seed mapping, seed chain formation, paired end rescue scans, gapless alignment, and gapped alignment, which are relatively well-defined, are thus stable functions and do not require frequent algorithmic changes. These functions, therefore, may be suitably optimized in hardware, whereas other functions, which could be executed by CPU software, are more appropriate for incremental improvement of algorithms, which is significantly easier in software. However, once fully developed could be implemented in hardware.

Likewise, in various instances, variant calling (with respect to DNA or RNA, single sample or joint, germline or somatic, etc.) may also benefit from FPGA acceleration, such as with respect to its various compute intensive functions. For instance, haplotype-based callers, which call bases on evidence derived from a context provided within a window around a potential variant, as described above, is often the most compute-intensive operation. These operations include comparing a candidate haplotype (e.g., a single-strand nucleotide sequence representing a theory of the true sequence of at least one of the sampled strands at the genome locus in question) to each sequencer read, such as to estimate a conditional probability of observing the read given the truth of the haplotype. Such an operation may be performed via a Pair Hidden Markov Model (pair-HMM) calculation that sums the probabilities of possible combinations of errors in sequencing or sample preparation (PCR, etc.) by a dynamic programming algorithm. Hence, with respect thereto, the system can be configured such that a pair-HMM calculation may be accelerated by one or more, e.g., parallel, FPGA hardware engines, whereas the CPU software may be configured so as to execute the remainder of the parent haplotype-based variant calling algorithm, either in a loosely-integrated or tightly-integrated CPU+FPGA platform. For instance, in a loose integration, software threads may construct and prepare a De Bruijn and/or assembly graph from the reads overlapping a chosen active region (a window or contiguous subset of the reference genome), extract candidate haplotypes from the graph, and queue up haplotype-read pairs for DMA transfer to FPGA hardware engines, such as for pair-HMM comparison. The same or other software threads can then receive the pair-HMM results queued and DMA-transferred back from the FPGA into the CPU memory, and perform genotyping and Bayesian probability calculations to make final variant calls.

For instance, as can be seen with respect to FIG. 30, the CPU 1000 may include one or more, e.g., a plurality, of threads 20*a*, 20*b*, and 20*c*, which may each have access to an associated DRAM 1014, which DRAM has work space 1014*a*, 1014*b*, and 1014*c*, within which each thread 20*a*, 20*b*, and 20*c*, may have access, respectively, so as to perform one or more operations on one or more data structures, such as large data structures. These memory portions and their data structures may be accessed, such as via respective cache portions 1014*a*', such as by one or more processing engines 13*a*, 13*b*, 13*c* of the FPGA 7, which processing engines may access the referenced data structures such as in the performance of one or more of the operations herein described, such as for mapping, aligning, and/or variant calling. Because of the high bandwidth, tight coupling interconnect 3, data pertaining to the data structures and/or related to the processing results may be shared substantially seamlessly between the CPU and the FPG A, such as in a cache coherent manner, so as to optimize processing efficiency.

Accordingly, in one aspect, as herein disclosed, a system may be provided wherein the system is configured for sharing memory resources amongst its component parts, such as in relation to performing some computational tasks or sub-functions via software, such as run by a CPU, and performing other computational tasks or sub functions via firmware, such as via the hardware of an associated chip. This may be achieved in a number of different ways, such as by a direct loose or tight coupling between the CPU and the chip, e.g., FPGA. Such configurations may be particularly useful when distributing operations related to the processing of large data structures, as herein described, that have large functions or subfunctions to be used and accessed by both the CPU and the chip. Particularly, in various embodiments, when processing data through a genomics pipeline, as herein described, such as to accelerate overall processing function, timing, and efficiency, a number of different operations may be run on the data, which operations may involve both software and hardware processing components.

Consequently, data may need to be shared and/or otherwise communicated, between the software component running on the CPU and the hardware component embodied in the chip, e.g., an FPGA. Accordingly, one or more of the various steps in the processing pipeline, or a portion thereof, may be performed by one device, e.g., the CPU, and one or more of the various steps may be performed by the other device, e.g., the FPGA. In such an instance, the CPU and the FPGA need to be communicably coupled, such as by a point to point interconnect, in such a manner to allow the efficient transmission of such data, which coupling may involve the shared use of memory resources. To achieve such distribution of tasks and the sharing of information for the performance of such tasks, the CPU may be loosely or tightly coupled to the FPGA, or other chip set.

Hence, in particular embodiments, a genomics analysis platform is provided. For instance, the platform may include a motherboard, a memory, and plurality of integrated circuits, such as forming one or more of a CPU, a mapping module, an alignment module, and/or a variant call module. Specifically, in particular embodiments, the platform may include a first integrated circuit, such as an integrated circuit forming a central processing unit (CPU) that is responsive to one or more software algorithms that are configured to instruct the CPU to perform one or more sets of genomics analysis functions, as described herein, such as where the CPU includes a first set of physical electronic interconnects to connect with the motherboard. In various instances, the memory may also be attached to the motherboard and may further be electronically connected with the CPU, such as via at least a portion of the first set of physical electronic interconnects. In such instances, the memory may be configured for storing a plurality of reads of genomic data, and/or at least one or more genetic reference sequences, and/or an index of the one or more genetic reference sequences.

Additionally, the platform may include one or more of a second integrated circuits, such as where each second integrated circuit forms a field programmable gate array (FPGA) having a second set of physical electronic interconnects to connect with the CPU and the memory, such as via a point-to-point interconnect protocol. In such an instance, the FPGA may be programmable by firmware to configure a set of hardwired digital logic circuits that are interconnected by a plurality of physical interconnects to perform a second set of genomics analysis functions, e.g., mapping, aligning, variant calling, e.g., an HMM function, etc. Particularly, the hardwired digital logic circuits of the FPGA may be arranged as a set of processing engines to perform one or more pre-configured steps in a sequence analysis pipeline of the genomics analysis, such as where the set(s) of processing engines include one or more of a mapping and/or aligning and/or variant call module, which modules may be formed of the separate or the same subsets of processing engines.

For instance, with respect to variant calling, a pair-HMM calculation is one of the most compute-intensive steps of a haplotype-based variant calling. Hence, variant calling speed may be greatly improved by accelerating this step in one or more FPGA engines, as herein described. However, there may be additional benefit in accelerating other compute-intensive steps in additional FPGA engines, to achieve a greater speed-up of variant calling, or reduce CPU load and the number of CPU cores required, or both, as seen with respect to FIG. 30. Additional compute-intensive functions, with respect to variant calling, that may be implemented in FPGA engines include: callable-region detection, where reference genome regions covered by adequate depth and/or quality of aligned reads are selected for processing; active-region detection, where reference genome loci with non-trivial evidence of possible variants are identified, and windows of sufficient context around these loci are selected as active regions for further processing; De-Bruijn or other assembly graph construction, where reads overlapping an active region and/or K-mers from those reads are assembled into a graph; assembly graph preparation, such as trimming low-coverage or low-quality paths, repairing dangling head and tail paths by joining them onto a reference backbone in the graph, transformation from K-mer to sequence representation of the graph, merging similar branches and otherwise simplifying the graph; extracting candidate haplotypes from the assembly graph; as well as aligning candidate haplotypes to the reference genome, such as by Smith-Waterman alignment, e.g., to determine variants (SNPs and/or indels) from the reference represented by each haplotype, and synchronize its nucleotide positions with the reference.

All of these functions may be implemented as high-performance hardware engines within the FPGA. However, calling such a variety of hardware acceleration functions from many integration points in the variant calling software may become inefficient on a loosely-coupled CPU+FPGA platform, and therefore a tightly-integrated CPU+FPGA platform may be desirable. For instance, various stepwise processing methods such as: constructing, preparing, and extracting haplotypes from a De Bruijn, or other assembly graph, could strongly benefit from a tightly-integrated CPU+FPGA platform. Additionally, assembly graphs are large and complex data structures, and passing them repeatedly between the CPU and the FPGA could become resource expensive and inhibit significant acceleration. Hence, an ideal model for such graph processing, employing a tightly-integrated CPU+FPGA platform, is to retain such graphs in cache-coherent shared memory for alternating processing by CPU software and FPGA hardware functions. In such an instance, a software thread processing a given graph may iteratively command various compute-intensive graph processing steps by a hardware engine, and then the software could inspect the results and determine the next steps between the hardware calls. This processing model, may be configured to correspond to software paradigms such as a data-structure API or an object-oriented method interface, but with compute intensive functions being accelerated by custom hardware engines, which is made practical by being implemented on a tightly-integrated CPU+FPGA platform, with cache-coherent shared memory and high-bandwidth/low-latency CPU/FPGA interconnects.

Hence, in addition to mapping and aligning sequencer reads to a reference genome, reads may be assembled "de novo," e.g., without a reference genome, such as by detecting apparent overlap between reads, e.g., in a pileup, where they fully or mostly agree, and joining them into longer sequences, contigs, scaffolds, or graphs. This assembly may also be done locally, such as using all reads determined to map to a given chromosome or portion thereof. Assembly in this manner may also incorporate a reference genome, or segment of one, into the assembled structure.

In such an instance, due to the complexity of joining together read sequences that do not completely agree, a graph structure may be employed, such as where overlapping reads may agree on a single sequence in one segment, but branch into multiple sequences in an adjacent segment. Such an assembly graph, therefore, may be a sequence graph, where each edge or node represents one nucleotide or a sequence of nucleotides that is considered to adjoin contiguously to the sequences in connected edges or nodes. In particular instances, such an assembly graph may be a k-mer graph, where each node represents a k-mer, or nucleotide sequence of (typically) fixed length k, and where connected nodes are considered to overlap each other in longer observed sequences, typically overlapping by k−1 nucleotides. In various methods there may be one or more transformations performed between one or more sequence graphs and k-mer graphs.

Although assembly graphs are employed in haplotype-based variant calling, and some of the graph processing methods employed are similar, there are important differences. De novo assembly graphs are generally much larger, and employ longer k-mers. Whereas variant-calling assembly graphs are constrained to be fairly structured and simple, such as having no cycles and flowing source-to-sink along a reference sequence backbone, de novo assembly graphs tend to be more unstructured and complex, with cycles, dangling paths, and other anomalies not only permitted, but subjected to special analysis. De novo assembly graph coloring is sometimes employed, assigning "colors" to nodes and edges signifying, for example, which biological sample they came from, or matching a reference sequence. Hence, a wider variety of graph analysis and processing functions need to be employed for de novo assembly graphs, often iteratively or recursively, and especially due to the size and complexity of de novo assembly graphs, processing functions tend to be extremely compute intensive.

Hence, as set forth above, an ideal model for such graph processing, on a tightly-integrated CPU+FPGA platform, is to retain such graphs in cache-coherent shared memory for alternating processing between the CPU software and FPGA hardware functions. In such an instance, a software thread processing a given graph may iteratively command various compute-intensive graph processing steps to be performed by a hardware engine, and then inspect the results to thereby determine the next steps to be performed by the hardware, such as by making appropriate hardware calls. Like above, this processing model, is greatly benefitted by implementation on a tightly-integrated CPU+FPGA platform, with cache-coherent shared memory and high-bandwidth/low-latency CPU/FPGA interconnect.

Additionally, as described herein below, tertiary analysis includes genomic processing that may follow variant calling, which in clinical applications may include variant annotation, phenotype prediction, disease testing, and/or treatment response prediction, as described herein. Reasons it is beneficial to perform tertiary analysis on such a tightly-integrated CPU+FPGA platform are that such a platform configuration enables efficient acceleration of primary and/or secondary processing, which are very compute intensive, and it is ideal to continue with tertiary analysis on the same platform, for convenience and reduced turnaround time, and to minimize transmission and copying of large genomic data files. Hence, either a loosely or tightly-integrated CPU+FPGA platform is a good choice, but a tightly coupled platform may include additional benefits because tertiary analysis steps and methods vary widely from one application to another, and in any case where compute-intensive steps slow down tertiary analysis, custom FPGA acceleration of those steps can be implemented in an optimized fashion.

For instance, a particular benefit to tertiary analysis on a tightly-integrated CPU+FPGA platform is the ability to re-analyze the genomic data iteratively, leveraging the CPU+FPGA acceleration of secondary processing, in response to partial or intermediate tertiary results, which may benefit additionally from the tight integration configuration. For example, after tertiary analysis detects a possible phenotype or disease, but with limited confidence as to whether the detection is true or false, focused secondary re-analysis may be performed with extremely high effort on the particular reads and reference regions impacting the detection, thus improving the accuracy and confidence of relevant variant calls, and in turn improving the confidence in the detection call. Additionally, if tertiary analysis determines information about the ancestry or structural variant genotypes of the analyzed individual, secondary analysis may be repeated using a different or modified reference genome, which is more appropriate for the specific individual, thus enhancing the accuracy of variant calls and improving the accuracy of further tertiary analysis steps.

However, if tertiary analysis is done on a CPU-only platform after primary and secondary processing (possibly accelerated on a separate platform), then re-analysis with secondary processing tools is likely to be too slow to be useful on the tertiary analysis platform itself, and the alternative is transmission to a faster platform, which is also prohibitively slow. Thus, in the absence of any form of hardware acceleration on the tertiary analysis platform, primary and secondary processing must generally be completed before tertiary analysis begins, without the possibility of easy re-analysis or iterative secondary analysis. But on an FPGA-accelerated platform, and especially a tightly-integrated CPU+FPGA platform where secondary processing is maximally efficient, iterative analysis becomes practical and useful.

Accordingly, as indicated above, the modules herein disclosed may be implemented in the hardware of the chip, such as by being hardwired therein, and in such instances their implementation may be such that their functioning may take place at a faster speed, with greater accuracy, as compared to when implemented in software, such as where there are minimal instructions to be fetched, read, and/or executed. Additionally, in various instances, the functions to be performed by one or more of these modules may be distributed such that various of the functions may be configured so as to be implemented by the host CPU software, whereas in other instances, various other functions may be performed by the hardware of an associated FPGA, such as where the two devices perform their respective functions with one another such as in a seamless fashion. For such purposes, the CPU and FPGA may be tightly coupled, such as via a low latency, high bandwidth interconnect, such as a QPI.

Hence, given the unique hardware implementation, the modules of the disclosure may function directly in accordance with their operational parameters, such as without needing to fetch, read, and/or execute instructions, such as when implemented solely in software. Additionally, memory requirements and processing times may be further reduced, such as where the communications within chip is via files, e.g., stored locally in the FPGA/CPU cache, such as a cache coherent manner, rather than through extensive accessing an external memory. Of course, in some instances, the chip and/or card may be sized so as to include more memory, such as more on board memory, so as to enhance parallel processing capabilities, thereby resulting in even faster processing speeds. For instance, in certain embodiments, a chip of the disclosure may include an embedded DRAM, so that the chip does not have to rely on external memory, which would therefore result in a further increase in processing speed, such as where a Burrows-Wheeler algorithm or De Brujin Graph may be employed, instead of a hash table and hash function, which may in various instances, rely on external, e.g., host memory. In such instances, the running of a portion or an entire pipeline can be accomplished in 6 or 10 or 12 or 15 or 20 minutes or less, such as from start to finish.

As indicated above, there are various different points where any given module can be positioned on the hardware, or be positioned remotely therefrom, such as on a server accessible on the cloud. Where a given module is positioned on the chip, e.g., hardwired into the chip, its function may be performed by the hardware, however, where desired, the module may be positioned remotely from the chip, at which point the platform may include the necessary instrumentality for sending the relevant data to a remote location, such as a server accessible via the cloud, so that the particular module's functionality may be engaged for further processing of the data, in accordance with the user selected desired protocols. Accordingly, part of the platform may include a web-based interface for the performance of one or more tasks pursuant to the functioning of one or more of the modules disclosed herein. For instance, where mapping, alignment, and/or sorting are all modules that may occur on the chip, in various instances, one or more of local realignment, duplicate marking, base quality core recalibration, and/or variant calling may take place on the cloud.

Figure 32:
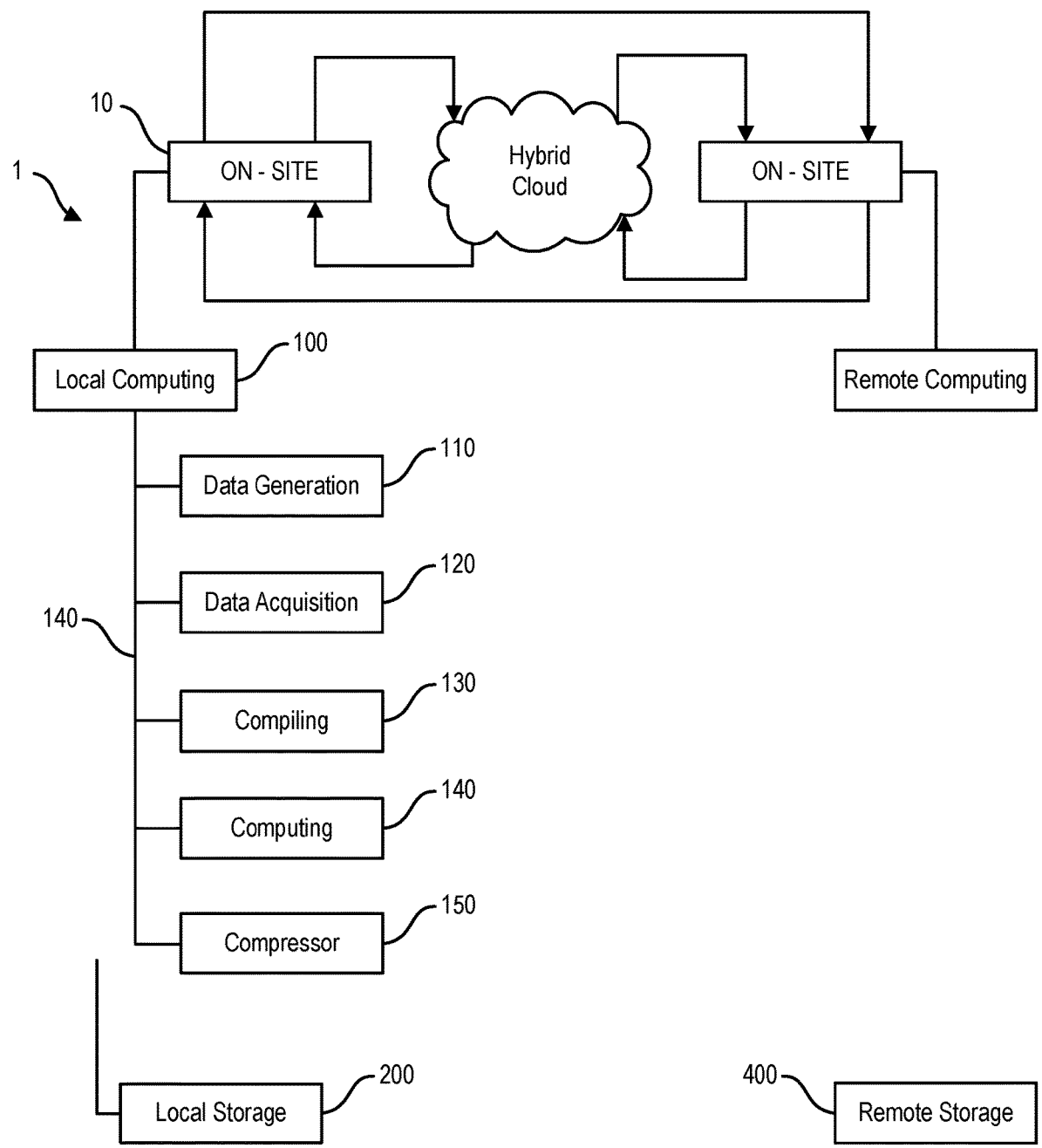
FIG. 32 depicts a block diagram for a genomic infrastructure for onsite and/or cloud based genomics processing and analysis.

Particularly, once the genetic data has been generated and/or processed, e.g., in one or more primary and/or secondary processing protocols, such as by being mapped, aligned, and/or sorted, such as to produce one or more variant call files, for instance, to determine how the genetic sequence data from a subject differs from one or more reference sequences, a further aspect of the disclosure may be directed to performing one or more other analytical functions on the generated and/or processed genetic data such as for further, e.g., tertiary, processing, as depicted in FIG. 32. For example, the system may be configured for further processing of the generated and/or secondarily processed data, such as by running it through one or more tertiary processing pipelines 700, such as one or more of a genome pipeline, an epigenome pipeline, metagenome pipeline, joint genotyping, a MuTect2 pipeline, or other tertiary processing pipeline, such as by the devices and methods disclosed herein. For instance, in various instances, an additional layer of processing 800 may be provided, such as for disease diagnostics, therapeutic treatment, and/or prophylactic prevention, such as including NIPT, NICU, Cancer, LDT, AgBio, and other such disease diagnostics, prophylaxis, and/or treatments employing the data generated by one or more of the present primary and/or secondary and/or tertiary pipelines. Hence, the devices and methods herein disclosed may be used to generate genetic sequence data, which data may then be used to generate one or more variant call files and/or other associated data that may further be subject to the execution of other tertiary processing pipelines in accordance with the devices and methods disclosed herein, such as for particular and/or general disease diagnostics as well as for prophylactic and/or therapeutic treatment and/or developmental modalities.

As described above, the system herein presented may include the generating, such as by the sequencer on a chip technology as disclosed herein, or the otherwise acquiring of genetic sequence data, and may include the performance of one or more secondary processing protocols, such as including one or more of mapping, aligning, and sorting of the generated genetic sequence data, such as to produce one or more variant call files, for instance, so as to determine how the genetic sequence data from a subject differs from one or more reference sequences or genomes. A further aspect of the disclosure may be directed to performing one or more other analytical functions on the generated and/or processed genetic data such as for further, e.g., tertiary, processing, which processing may be performed on or in association with the same chip or chipset as that hosting the aforementioned sequencer technology.

In a first instance, such as with respect to the generation, acquisition, and/or transmission of genetic sequence data, as set forth in FIG. 30, such data may be produced either locally or remotely and/or the results thereof may then be directly processed, such as by a local computing resource 100, or may be transmitted to a remote location, such as to a remote computing resource 300, for further processing. For instance, the generated genetic sequence data may be processed locally, and directly, such as where the sequencing and secondary processing functionalities are housed on the same chipset and/or within the same device. Likewise, the generated genetic sequence data may be processed locally, and indirectly, such as where the sequencing and secondary processing functionalities occur separately by distinct apparatuses that share the same facility or location but may be separated by a space albeit communicably connected, such as via a local network 10. In a further instance, the genetic sequence data may be derived remotely, such as by a NGS, and the resultant data may be transmitted over a cloud based network 50 to a remote location, such as separated geographically from the sequencer.

Specifically, as illustrated in FIG. 30, in various embodiments, a nucleotide sequencer may be provided on site, such as by a sequencer on a chip or by an NGS, wherein the sequencer is associated with a local computing resource 100 either directly or indirectly such as by a local network connection 10. The local computing resource 100 may include or otherwise be associated with one or more of a data generation 110 and/or a data acquisition 120 mechanism(s). Such mechanisms may be any mechanism configured for either generating and/or otherwise acquiring data, such as analog, digital, and/or electromagnetic data related to one or more genetic sequences of a subject or group of subjects.

For example, such a data generating mechanism 110 may be a primary processor such as a sequencer, such as a NGS, a sequencer on a chip, or other like mechanism for generating genetic sequence information. Further, such data acquisition mechanisms 120 may be any mechanism configured for receiving data, such as generated genetic sequence information, and/or together with the data generator 110 and/or computing resource 150 capable of subjecting the same to one or more secondary processing protocols, such as a secondary processing pipeline apparatus configured for running a mapper, aligner, sorter, and/or variant caller protocol on the generated and/or acquired sequence data as herein described. In various instances, the data generating 110 and/or data acquisition 120 apparatuses may be networked together such as over a local network 10, such as for local storage 200, or may be networked together over a cloud based network 30, such as for transmitting and/or receiving data, such as digital data related to the primary and/or secondary processing of genetic sequence information, such as to or from a remote location 30 such as for remote processing 300 and/or storage 400. In various embodiments, one or more of these components may be communicably coupled together by a hybrid network as herein described.

The local computing resource 100 may also include or otherwise be associated with a compiler 130 and/or a processor 150, such as a compiler 130 configured for compiling the generated and/or acquired data and/or data associated therewith, and a processor 150 configured for processing the generated and/or acquired and/or compiled data and/or controlling the system 1 and its components as herein described. Further, the local computing resource 100 may include a compressor unit 160 configured for compressing data, such as generated and/or acquired primary and/or secondary processed data, which data may be compressed, such as prior to transfer over a local 10 and/or cloud 30 and/or hybrid cloud based 50 network.

In particular instances, the system 1 may be configured for subjecting the generated and/or secondarily processed data to further processing, e.g., via a local 100 and/or a remote 300 computing resource, such as by running it through one or more tertiary processing pipelines, such as one or more of a genome pipeline, an epigenome pipeline, metagenome pipeline, joint genotyping, a MuTect2 pipeline, or other tertiary processing pipeline. Such data may then be compressed and/or stored locally 200 and/or be transferred so as to be stored remotely.

In additional instances, the system 1 may include a further tier of processing modules, such as configured for rendering additional processing such as for diagnosis, disease and/or therapeutic discovery, and/or prophylaxis thereof. For instance, in various instances, an additional layer of processing may be provided, such as for disease diagnostics, therapeutic treatment, and/or prophylactic prevention, such as including NIPT, NICU, Cancer, LDT, AgBio, and other such disease diagnostics, prophylaxis, and/or treatments employing the data generated by one or more of the present primary and/or secondary and/or tertiary pipelines.

Accordingly, herein presented is a system 1 for producing and using a global hybrid cloud network 50. For instance, presently, the cloud 30 is used primarily for storage, such as at a remote storage location 400. In such an instance, the computing of data is performed locally 100 by a local computing resource 150, and where storage needs are extensive, the cloud 30 is accessed so as to store the data generated by the local computing resource 150, such as by use of a remote storage resource 400. Hence, generated data is typically either wholly managed on site locally 100, or it is totally managed off site 300, on the cloud 30.

Particularly, in a general implementation of a bioinformatics analysis platform, the computing 150 and/or storage 200 functions are maintained locally on site, and where storage needs exceed local storage capacity, or where there is a need for stored data to be made available to other remote users, such data may be transferred via internet 30 to the cloud for remote storage 400 thereby. In such an instance, where the computing resources 150 required for performance of the computing functions are minimal, but the storage requirements extensive, the computing function 150 may be maintained locally 100, while the storage function 400 may be maintained remotely, with the fully processed data being transferred back and forth between the processing function 150, such as for local processing only, and the storage function 400, such as for the remote storage 400 of the processed data.

For instance, this may be exemplified with respect to the sequencing function, such as with a typical NGS, where the computing resource 150 is configured for performing the functions required for the sequencing of the genetic material so as to produce genetic sequenced data, e.g., reads, which data is produced onsite 100. These reads, once generated, such as by the onsite NGS, may then be transferred such as over the cloud network 30, such as for storage 400 at a remote location 300 in a manner so as to be recalled from the cloud 30 when necessary such as for further processing, such as for the performance of one or more of secondary and/or tertiary processing functions, that is at a location remote from the storage facility 400, e.g., locally. In such an instance, the local storage resource 150 serves merely as a storage cache where data is placed while waiting transfer to or from the cloud 30, such as to or from the remote storage facility 400.

Likewise, where the computing function is extensive, such as requiring one or more remote computer cluster cores 300 for processing the data, and where the storage demands for storing the processed data 200 are relatively minimal, as compared to the computing resources 300 required to process the data, the data to be processed may be sent, such as over the cloud 30, so as to be processed by a remote computing resource 300, which resource may include one or more cores or clusters of computing resources, e.g., one or more super computing resources. In such an instance, once the data has been processed by the cloud based computer core 300, the processed data may then be transferred over the cloud network 30 so as to be stored local 200 and readily available for use by the local computing resource 150, such as for local analysis and/or diagnostics.

This may be exemplified with respect to a typical secondary processing function, such as where the pre-processed sequenced, e.g., read, data that is stored locally 200 is accessed, such as by the local computing resource 100, and transmitted over the cloud internet 30 to a remote computing facility 300 so as to be further processed thereby, e.g., in a secondary processing function, to obtain processed results data that may then be sent back to the local facility 100 for storage 200 thereby. This may be the case where a local practitioner generates sequenced read data using a local data generating resource 100, e.g., automated sequencer, and then sends that data over the network 30 to a remote computing facility 300, which then runs one or more functions on that data, such as a Burrows-Wheeler transform or Needlemen-Wunsch and/or Smith-Waterman alignment function on that sequence data, so as to generate results data that may then be transmitted over the internet 30 to the local computing resource 100 so as to be examined thereby in one or more local administered processing protocols and/or stored locally 200.

What is needed, however, is a seamless integration between the engagement between local 100 and remote 300 computer processing as well as between local 200 and remote 400 storage, such as in the hybrid cloud 50 based system presented herein. In such an instance, the system can be configured such that local 100 and remote 300 computing resources are configured so as to run seamlessly together, such that data to be processed thereby can be allocated real time to either the local 200 or the remote 300 computing resource without paying an extensive penalty due to transfer rate and/or in operational efficiency. This may be the case, for instance, where the software and/or hardware to be deployed or otherwise run by the computing resources are configured so as to correspond to one another and/or are the same or functionally similar, e.g., the hardware and/or software is configured in the same manner so as to run the same algorithms in the same manner on the generated and/or received data.

Figure 33A:
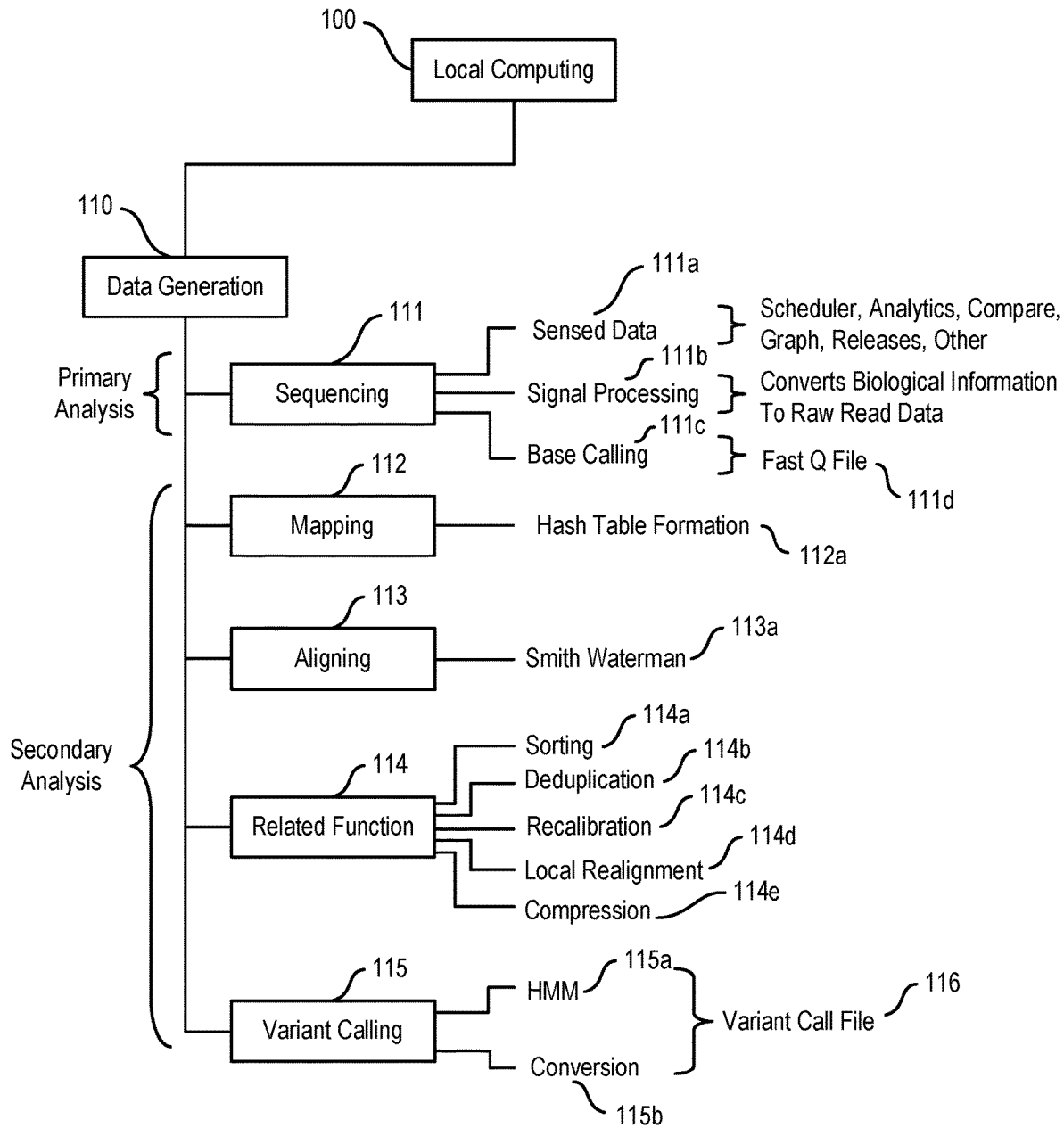
FIG. 33A depicts a block diagram of a local and/or cloud based computing function of FIG. 32 for a genomic infrastructure for onsite and/or cloud based genomics processing and analysis.

For instance, as can be seen with respect to FIG. 33A a local computing resource 100 may be configured for generating data, and therefore may include a data generating mechanism 110, such as for primary data generation and/or analysis, e.g., so as to produce a FASTQ sequence file. This data generating mechanism 110 may be a local computer, as described herein throughout, having a processor that may be configured to run one or more software applications and/or may be hardwired so as to perform one or more algorithms such as in a wired configuration on the generated and/or acquired data. For example, the data generating mechanism 110 may be configured for one or more of generating data, such as sequencing data 111, which data may be sensed data 111a, such as data that is detectable as a change in voltage, ion concentration, electromagnetic radiation, and the like; and/or the data generating mechanism 110 may be configured for generating and/or processing signal, e.g., analog or digital signal data, such as data representing one or more nucleotide identities in a sequence or chain of associated nucleotides. In such an instance, the data generating mechanism 110, e.g., sequencer 111, may further be configured for preliminarily processing the generated data so as to perform one or more base call operations 111c, such as on the data so as to produce sequence identity data, e.g., a FASTQ file.

It is to be noted, that in this instance, the data 111 so generated may be generated locally, such as by a local data generating and/or computing resource 150, e.g., a sequencer on a chip; or it may be produced remotely, e.g., by a remote computing and/or generating resource, such as a remote NGS 300, but be transferred over the cloud 30/50 to the local computing resource 100 such as for secondary processing 150 and/or storage thereby in a local storage resource 200, such as while awaiting further local processing 150. In such an instance, where the data generation resource 300 is remote from the local processing 100 and/or storage 200 resources, the corresponding resources may be configured such that the remote and/or local storage, remote and local processing, and/or communicating protocols employed by each resource may be adapted to smoothly and/or seamlessly integrate with one another, e.g., by running the same, similar, and/or equivalent software and/or by having the same, similar, and/or equivalent hardware configurations, and/or employing the same communications and/or transfer protocols, which, in some instances, may have been implemented at the time of manufacture or later thereto.

Particularly, these functions may be implemented in a hardwired configuration such as where the sequencing function and the secondary processing function are maintained upon the same or associated chip or chipset, e.g., such as where the sequencer and secondary processor are directly interconnected on a chip, as herein described, or may be implemented via software that has been optimized to allow the two remote devices to communicate seamlessly with one another. A combination of optimized hardware and software implementations for performing the recited functions may also be employed, as described herein. In various embodiments, the data generating resource, such as the sequencer 111, whether implemented in software and/or in hardware or a combination of the same, may further be configured to include an initial tier of processors 500 such as a scheduler, various analytics, comparers, graphers, releasers, and the like, so as to assist the data generator 111, e.g., sequencer, in converting biological information into raw read data, such as in a FASTQ file format 111d.

Likewise, the same may be true with respect to the performance of the other functions that may be deployed by the local 100 and/or remote 300 computing resources. For example, the local computing resource 100 may include hardware and/or software configured for performing one or more secondary tier 700 of processing functions 112-115 on remotely and/or locally generated data, such as genetic sequence data, in a manner that the processing and results thereof may be seamlessly shared with one another and/or stored thereby. Particularly, the local computing function 100 and/or the remote computing function 300 may be configured for generating and/or receiving primary data, such as genetic sequence data, e.g., in a FASTQ or other like file format, and running one or more secondary processing protocols 600 on that generated and/or acquired data, which protocols may be implemented in a software, hardware, or combinational format. For instance, the data generating and/or processing resource 110 may be configured for performing one or more of a mapping operation 112, an alignment operation 113, or other related function 114 on the acquired or generated data.

More particularly, the data generating resource 110 may include a mapping engine 112, as herein described, or may otherwise include programming for running a mapping algorithm on the genetic sequence data, such as for performing a Burrows-Wheeler transform and/or other algorithms for building a hash table and/or running a hash function 112a on said data, such as for hash seed mapping, so as to generate mapped sequence data. The data generating resource 110 may also include an alignment engine 113, as herein described, or may otherwise include programming for running an alignment algorithm on the genetic sequence data, e.g., mapped sequenced data, such as for performing a gapped and/or gapless Smith-Waterman alignment, and/or Needleman-Wunsch, or other like scoring algorithm 113a on said data, so as to generate aligned sequence data. The data generating resource 110 may also be configured to include one or more other modules 114 adapted to perform one or more other processing functions on the genetic sequence data, such as on the mapped and/or aligned sequence data, and thus may include a suitably configured engine 114 or otherwise include programming for running the one or more other processing functions such as a sorting 114a, deduplication 114b, recalibration 114c, local realignment 114d, duplicate marking 114f, Base Quality Score Recalibration 114g function(s) and/or a compression function (such as to produce a BAM, Reduced BAM, and/or a CRAM compression and/or decompression file) 114e, in accordance with the methods herein described, which processing functions may be configured as one or more pipelines of the system 1. Likewise, the system 1 may be configured to include a module 115 adapted for processing the data, e.g., the sequenced, mapped, aligned, and/or sorted data in a manner such as to produce a variant call file 116, such as in a hardware and/or software based processing functionality. More particularly, the system 1 may include a variant call module 115 for running one or more variant call functions, such as a Hidden Markov Model (HMM) and/or GATK function 115a such as in a wired configuration and/or via one or more software applications, e.g., either locally or remotely, and/or a converter 115b for the same.

In particular embodiments, as set forth in FIG. 33B, the system 1 may include a local computing function 100 that may be configured for employing a computer processing resource 150 for performing one or more further computer processing functions on data generated by the system generator 110 or acquired by the system acquisition mechanism 120 (as described below), such as by being transferred thereto, for instance, by a third party I2I, such as via a cloud 30 or hybrid cloud network 50. For instance, a third party analyzer I2I may deploy a remote computing resource 300 so as to generate relevant data in need of further processing, such as genetic sequence data or the like, which data may be communicated to the system 1 over the network 30/50 so as to be further processed. This may be useful, for instance, where the remote computing resource 300 is a NGS, configured for taking raw biological data and converting it to a digital representation thereof, such as in the form of one or more FASTQ files containing reads of genetic sequence data, and where further processing is desired, such as to determine how the generated sequence of an individual differs from that of one or more reference sequences, as herein described, and/or it is desired to subject the results thereof to furthered, e.g., tertiary, processing.

In such an instance, the system 1 may be adapted so as to allow one or more parties, e.g., a primary and/or secondary and/or third party user, to access the associated local processing resources 100, and/or a suitably configured remote processing resource 300 associated therewith, in a manner so as to allow the user to perform one or more quantitative and/or qualitative processing functions 152 on the generated and/or acquired data. For instance, in one configuration, the system 1 may include, e.g., in addition to primary 600 and/or secondary 600 processing pipelines, a third tier of processing modules 700, which processing modules may be configured for performing one or more processing functions on the generated and/or acquired primary and/or secondary processed data.

Particularly, in one embodiment, the system 1 may be configured for generating and/or receiving processed genetic sequence data 111 that has been either remotely or locally mapped 112, aligned 113, sorted 114a, and/or further processed 114 so as to generate a variant call file 116, which variant call file may then be subjected to further processing such as within the system 1, such as in response to a second and/or third party analytics requests I2I. More particularly, the system 1 may be configured to receive processing requests from a third party I2I, and further be configured for performing such requested tertiary processing 700 on the generated and/or acquired data. Specifically, the system 1 may be configured for producing and/or acquiring genetic sequence data 111, may be configured for taking that genetic sequence data and mapping 112, aligning 113, and/or sorting 114a it to produce one or more variant call files (VCFs) 116, and additionally the system 1 may be configured for performing a tertiary processing function 700 on the data, e.g., with respect to the one or more VCFs. The system 1 may be configured so as to perform any form of tertiary processing 700 on the generated and/or acquired data, such as by subjecting it to one or more pipeline processing functions 700 such as to generate genome data 122a, epigenome data 122b, metagenome data 122c, and the like, including joint genotyping 122d, GATK 122e and/or MuTect2 122f analysis pipelines. Further, the system 1 may be configured for performing an additional tier of processing on the generated and/or processed data, such as including one or more of non-invasive prenatal testing (NIPT) 123a, N/P ICU 123b, cancer related diagnostics and/or therapeutic modalities 123c, various laboratory developed tests (LDT) 123d, agricultural biological (Ag Bio) applications 123e, or other such health care related 123f processing function.

Hence, in various embodiments, where a primary user may access and/or configure the system 1 and its various components directly, such as through direct access therewith, such as through the local computing resource 100, as presented herein, the system 1 may also be adapted for being accessed by a secondary party, such as is connected to the system 1 via a local network or intranet connection 10 so as to configure and run the system 1 within the local environment. Additionally, in certain embodiments, as presented in FIG. 33B, the system may be adapted for being accessed and/or configured by a third party I2I, such as over an associated hybrid-cloud network 50 connecting the third party I2I to the system 1, such as through an application program interface (API), accessible as through one or more graphical user interface (GUI) components. Such a GUI may be configured to allow the third party user to access the system 1, and using the API configure the various components of the system, the modules, associated pipelines, and other associated data generating and/or processing functionalities so as to run only those system components necessary and/or useful to the third party and/or requested or desired to be run thereby.

Accordingly, in various instances, the system 1 as herein presented may be adapted so as to be configurable by a primary, secondary, or tertiary user of the system. In such an instance, the system 1 may be adapted to allow the user to configure the system 1 and thereby to arrange its components in such a manner as to deploy one, all, or a selection of the analytical system resources, e.g., 152, to be run on data that is either generated, acquired, or otherwise transferred to the system, e.g., by the primary, secondary, or third party user, such that the system 1 runs only those portions of the system necessary or useful for running the analytics requested by the user to obtain the desired results thereof. For example, for these and other such purposes, an API may be included within the system 1 wherein the API is configured so as to include or otherwise be operably associated with a graphical user interface (GUI) including an operable menu and/or a related list of system function calls from which the user can select and/or otherwise make so as to configure and operate the system and its components as desired.

In such an instance, the GUI menu and/or system function calls may direct the user selectable operations of one or more of a first tier of operations 600 including: sequencing 111, mapping 112, aligning 113, sorting 114a, variant calling 115, and/or other associated functions 114 in accordance with the teachings herein, such as with relation to the primary and/or secondary processing functions herein described. Further, where desired the GUI menu and/or system function calls may direct the operations of one or more of a second tier of operations 700 including: a genome pipeline 122a, epigenome pipeline 122b, metagenome pipeline 122c, a joint genotyping pipeline 122d, GATK 122e and/or MuTect2 122f analysis pipelines. Furthermore, where desired the GUI menu and system function calls may direct the user selectable operations of one or more of a third tier of operations 800 including: non-invasive prenatal testing (NIPT) 123a, N/P ICU 123b, cancer related diagnostics and/or therapeutic modalities 123c, various laboratory developed tests (LDT) 123d, agricultural biological (Ag Bio) applications 123e, or other such health care related 123f processing functions.

Accordingly, the menu and system function calls may include one or more primary, secondary, and/or tertiary processing functions, so as to allow the system and/or its component parts to be configured such as with respect to performing one or more data analysis pipelines as selected and configured by the user. In such an instance, the local computing resource 100 may be configured to correspond to and/or mirror the remote computing resource 300, and/or likewise the local storage resource 200 may be configured to correspond and/or mirror the remote storage resource 400 so that the various components of the system may be run and/or the data generated thereby may be stored either locally or remotely in a seamless distributed manner as chosen by the use of the system 1. Additionally, in particular embodiments, the system 1 may be made accessible to third parties, for running proprietary analysis protocols 121a on the generated and/or processed data, such as by running through an artificial intelligence interface designed to find correlations there between.

Figure 33B:
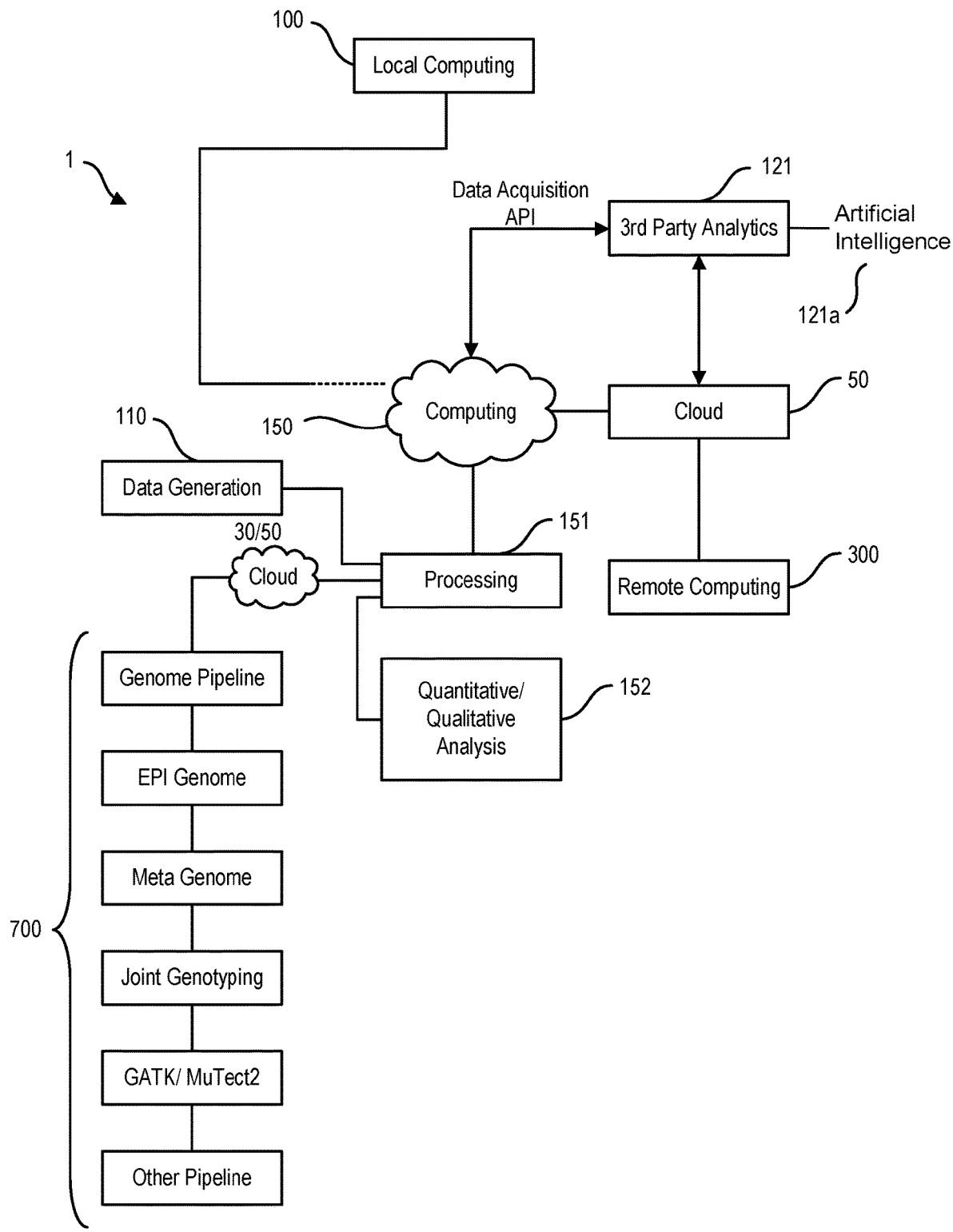
FIG. 33B depicts the block diagram of FIG. 33A illustrating greater detail regarding the computing function for a genomic infrastructure for onsite and/or cloud based genomics processing and analysis.
Figure 33C:
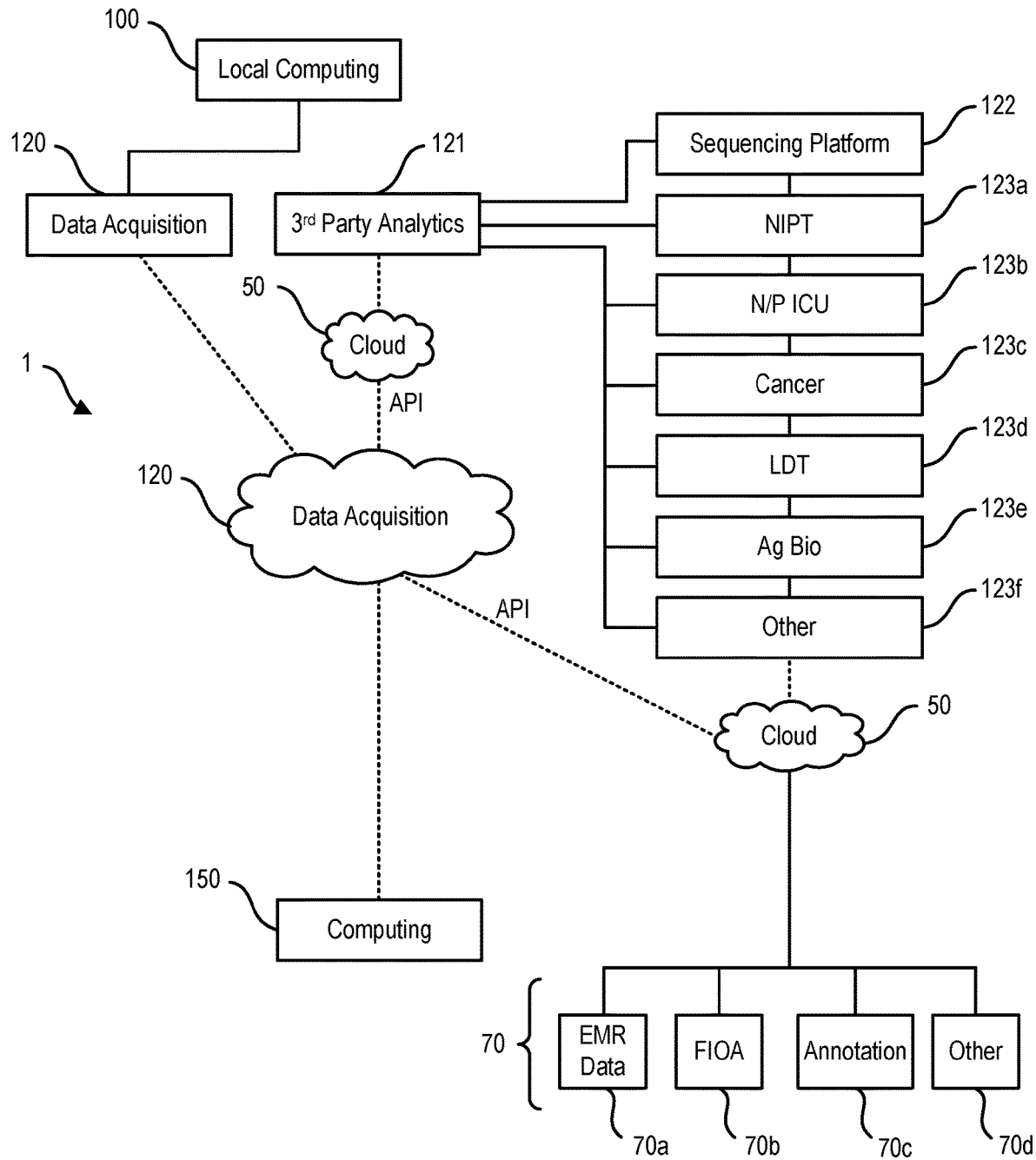
FIG. 33C depicts the block diagram of FIG. 32 illustrating greater detail regarding the $3^{rd}$-Party analytics function for a genomic infrastructure for onsite and/or cloud based genomics processing and analysis.

The system 1 may be configured so as to perform any form of tertiary processing on the generated and/or acquired data. Hence, in various embodiments, a primary, secondary, or tertiary user may access and/or configure any level of the system 1 and its various components either directly, such as through direct access with the computing resource 100, indirectly, such as via a local network connection 10, or over an associated hybrid-cloud network 50 connecting the party to the system 1, such as through an appropriately configured API having the appropriate permissions. In such an instance, the system components may be presented as a menu, such as a GUI selectable menu, where the user can select from all the various processing and storage options desired to be run on the user presented data. Further, in various instances, the user may upload their own system protocols so as to be adopted and run by the system so as to process various data in a manner designed and selected for by the user. In such an instance, the GUI and associated API will allow the user to access the system 1 and using the API add to and configure the various components of the system, the modules, associated pipelines, and other associated data generating and/or processing functionalities so as to run only those system components necessary and/or useful to the party and/or requested or desired to be run thereby.

Where the above with respect to FIGS. 33A and 33B are directed to data generation 110 such as local data generation 100, employing a local computing resource 150; as indicated above, and with respect to FIG. 33C, one or more of the above demarcated modules, and their respective functions and/or associated resources, may be configured for being performed remotely, such as by a remote computing resource 300, and further be adapted to be transmitted to the system 1, such as in a seamless transfer protocol over a cloud based internet connection 30/50, such as via a suitably configured data acquisition mechanism 120.

Accordingly, in such an instance, the local computing resource 100 may include a data acquisition mechanism 120, such as configured for transmitting and/or receiving such acquired data and/or associated information. For instance, the system 1 may include a data acquisition mechanism 120 that is configured in a manner so as to allow the continued processing and/or storage of data to take place in a seamless and steady manner, such as over a cloud or hybrid based network 30/50 where the processing functions are distributed both locally 100 and/or remotely 300, and likewise where one or more of the results of such processing may be stored locally 200 and/or remotely 400, such that the system seamlessly allocates to which local or remote resource a given job is to be sent for processing and/or storage regardless of where the resource is physically positioned. Such distributed processing, transferring, and acquisition may include one or more of sequencing 111, mapping 112, aligning 113, sorting 114a, duplicate marking 114c, deduplication, recalibration 114d, local realignment 114e, Base Quality Score Recalibration 114f function(s) and/or a compression function 114g, as well as a variant call function 116, as herein described. Where stored locally 200 or remotely 400, the processed data, in whatever state it is in the process may be made available to either the local 100 or remote processing 300 resources, such as for further processing prior to re-transmission and/or re-storage.

Specifically, the system 1 may be configured for producing and/or acquiring genetic sequence data 111, may be configured for taking that genetic sequence data 111 and processing it locally 150, or transferring the data over a suitably configured cloud 30 or hybrid cloud 50 network such as to a remote processing facility for remote processing 300. Further, once processed the system 1 may be configured for storing the processed data remotely 400 or transferring it back for local storage 200. Accordingly, the system 1 may be configured for either local or remote generation and/or processing of data, such as where the generation and/or processing steps may be from a first tier of primary and/or secondary processing functions 600, which tier may include one or more of: sequencing 111, mapping 112, aligning 113, and/or sorting 114a so as to produce one or more variant call files (VCFs) 116. Likewise, the system 1 may be configured for either local or remote generation and/or processing of data, such as where the generation and/or processing steps may be from a second tier of tertiary processing functions 700, which tier may include one or more of generating and/or acquiring data pursuant to a genome pipeline 122a, epigenome pipeline 122b, metagenome pipeline 122c, a joint genotyping pipeline 122d, GATK 122e and/or MuTect2 122f analysis pipeline. Additionally, the system 1 may be configured for either local or remote generation and/or processing of data, such as where the generation and/or processing steps may be from a third tier of tertiary processing functions 800, which tier may include one or more of generating and/or acquiring data related to and including: non-invasive prenatal testing (NIPT) 123a, N/P ICU 123b, cancer related diagnostics and/or therapeutic modalities 123c, various laboratory developed tests (LDT) 123d, agricultural biological (Ag Bio) applications 123e, or other such health care related 123f processing functions.

In particular embodiments, as set forth in FIG. 33C, the system 1 may further be configured for allowing one or more parties to access the system and transfer information to or from the associated local processing 100 and/or remote 300 processing resources as well as to store information either locally 200 or remotely 400 in a manner that allows the user to choose what information get processed and/or stored where on the system 1. In such an instance, a user can not only decide what primary, secondary, and/or tertiary processing functions get performed on generated and/or acquired data, but also how those resources get deployed, and/or where the results of such processing gets stored. For instance, in one configuration, the user may select whether data is generated either locally or remotely, or a combination thereof, whether it is subjected to secondary processing, and if so, which modules of secondary processing it is subjected to, and/or which resource runs which of those processes, and further may determine whether the then generated or acquired data is further subjected to tertiary processing, and if so, which modules and/or which tiers of tertiary processing it is subjected to, and/or which resource runs which of those processes, and likewise, where the results of those processes are stored for each step of the operations.

Particularly, in one embodiment, the user may configure the system 1 of FIG. 33A so that the generating of genetic sequence data 111 takes place remotely, such as by an NGS, but the secondary processing 600 of the data occurs locally 100. In such an instance, the user can then determine which of the secondary processing functions occur locally 100, such as by selecting the processing functions, such as mapping 112, aligning 113, sorting 111, and/or producing a VCF 116, from a menu of available processing options. The user may then select whether the locally processed data is subjected to tertiary processing, and if so which modules are activated so as to further process the data, and whether such tertiary processing occurs locally 100 or remotely 300. Likewise, the user can select various options for the various tiers of tertiary processing options, and where any generated and/or acquired data is to be stored, either locally 200 or remotely 400, at any given step or time of operation.

More particularly, a primary user may configure the system to receive processing requests from a third party, where the third party may configure the system so as for performing such requested primary, secondary, and/or tertiary processing on generated and/or acquired data. Specifically, the user or second or third party may configure the system 1 for producing and/or acquiring genetic sequence data, either locally 100 or remotely 200, may configure the system 1 for taking that genetic sequence data and mapping, aligning, and/or sorting it, either locally or remotely, so as to produce one or more variant call files (VCFs), and additionally may configure the system for performing a tertiary processing function on the data, e.g., with respect to the one or more VCFs, either locally or remotely. More particular still, the user or other party may configure the system 1 so as to perform any form of tertiary processing on the generated and/or acquired data, and where that processing is to occur in the system. Hence, in various embodiments, the first, second, and/or third party I2I user may access and/or configure the system 1 and its various components directly such as by directly accessing the local computing function 100, via a local network connection 10, or over an associated hybrid-cloud network 50 connecting the party I2I to the system 1, such as through an application program interface (API), accessible as through one or more graphical user interface (GUI) components. In such an instance, the third party user may access the system 1 and use the API to configure the various components of the system, the modules, associated pipelines, and other associated data generating and/or processing functionalities so as to run only those system components necessary and/or useful to the third party and/or requested or desired to be run thereby, and further allocate which computing resources will provide the requested processing, and where the results data will be stored.

Accordingly, in various instances, the system 1 may be configurable by a primary, secondary, or tertiary user of the system who can configure the system 1 so as to arrange its components in such a manner as to deploy one, all, or a selection of the analytical system resources to be run on data that the user either directly generates, causes to be generated by the system 1, or causes to be transferred to the system 1, such as over a network associated therewith, such as via the data acquisition mechanism 120. In such a manner, the system 1 is configurable so as to only run those portions of the system necessary or useful for the analytics desired and/or requested by the requesting party. For example, for these and other such purposes, an API may be included wherein the API is configured so as to include a GUI operable menu and/or a related list of system function calls that from which the user can select so as to configure and operate the system as desired. Additionally, in particular embodiments, the system 1 may be made accessible to third parties, such as governmental regulators, such as the Federal Drug Administration (FDA) 70b, or allow third parties to collate, compile, and/or access a data base of genetic information derived or otherwise acquired and/or compiled by the system 1 so as to form an electronic medical records (EMR) database 70a and/or to allow governmental access and/or oversight of the system, such as the FDA for Drug Development Evaluation. The system 1 may also be set up to conglomerate, compile, and/or annotate the data 70c and/or allow other high level users access thereto.

Figure 34A:
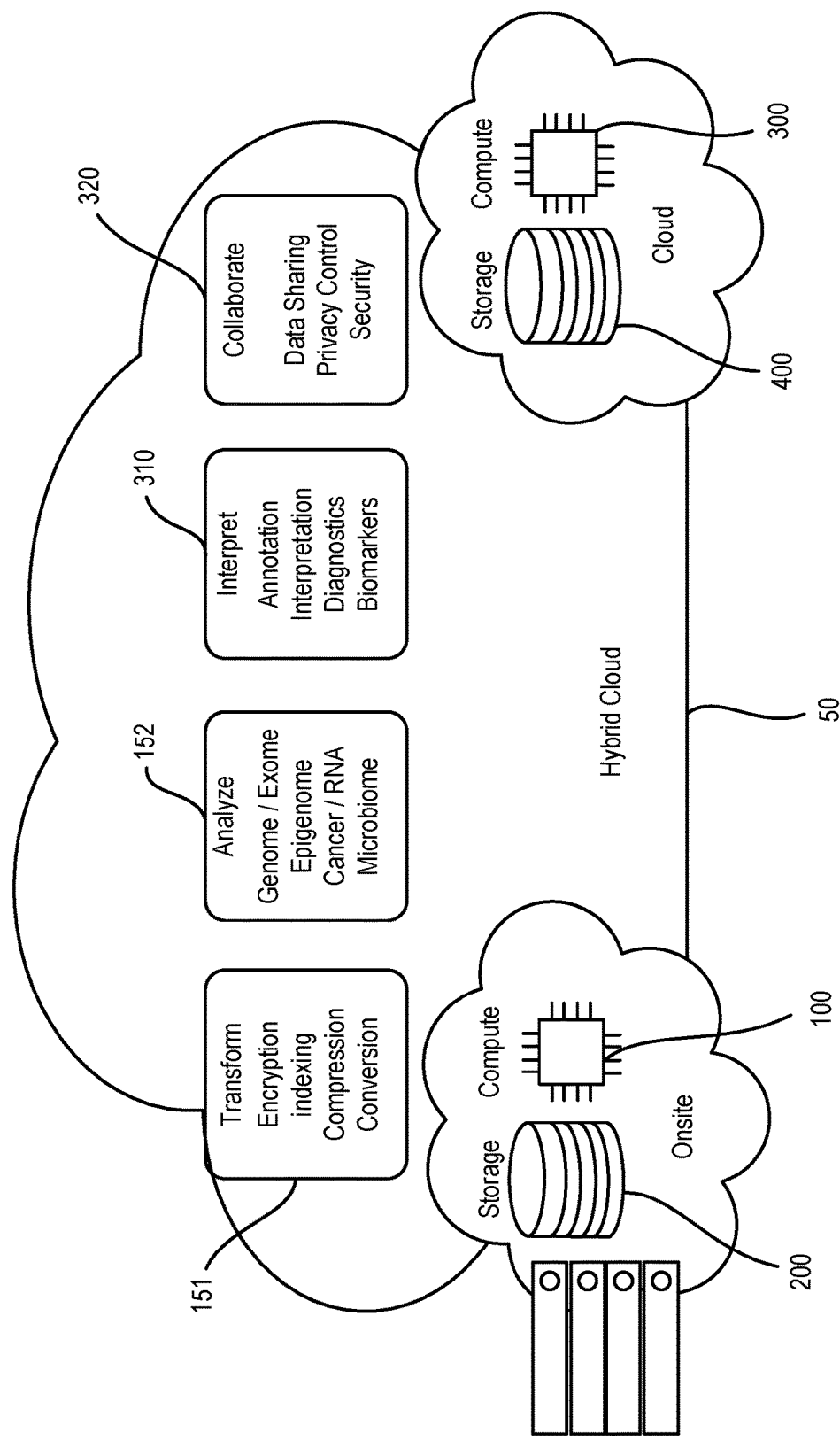
FIG. 34A depicts a block diagram illustrating a hybrid cloud configuration.

Accordingly, in various embodiments, as can be seen with respect to FIG. 34A, a hybrid cloud 50 is provided wherein the hybrid cloud is configured for connecting a local computing 100 and/or storage resource 200 with a remote computing 300 and/or storage 400 resource, such as where the local and remote resources are separated one from the other distally, spatially, geographically, and the like. In such an instance, the local and distal resources may be configured for communicating with one another in a manner so as to share information, such as digital data, seamlessly between the two. Particularly, the local resources may be configured for performing one or more types of processing on the data, such as prior to transmission across the hybrid network 50, and the remote resources may be configured for performing one or more types of further processing of the data.

For instance, in one particular configuration, the system 1 may be configured such that a generating and/or analyzing function 152 is configured for being performed locally 100 by a local computing resource, such as for the purpose of performing a primary and/or secondary processing function, so as to generate and/or process genetic sequence data, as herein described. Additionally, in various embodiments, the local resources may be configured for performing one or more tertiary processing functions on the data, such as one or more of genome, exome, and/or epigenome analysis, or a cancer, microbiome, and/or other DNA/RNA processing analysis. Further, where such processed data is meant to be transferred, such as to a remote computing 300 and/or storage 400 resource, the data may be transformed such as by a suitably configured transformer 151, which transformer 151 may be configured for indexing, converting, compressing, and/or encrypting the data, such as prior to transfer over the hybrid network 50.

In particular instances, such as where the generated and processed data is transferred to a remote computing resource 300 for further processing, such processing may be of a global nature and may include receiving data from a plurality of local computing resources 100, collating such pluralities of data, annotating the data, and comparing the same, such as to interpret the data, determine trends thereof, analyzing the same for various biomarkers, and aiding in the development of diagnostics, therapeutics, and/or prophylactics. Accordingly, in various instances, the remote computing resource 300 may be configured as a data processing hub, such as where data from a variety of sources may be transferred, processed, and/or stored while waiting to be transformed and/or transferred, such as by being accessed by the local computing resource 100. More particularly, the remote processing hub 300 may be configured for receiving data from a plurality of resources 100, processing the same, and distributing the processed data back to the variety of local resources 100 so as to allow for collaboration amongst researchers and/or resources 100. Such collaboration may include various data sharing protocols, and may additionally include preparing the data to be transferred, such as by allowing a user of the system 1 to select amongst various security protocols and/or privacy settings so as to control how the data will be prepared for transfer.

Figure 34B:
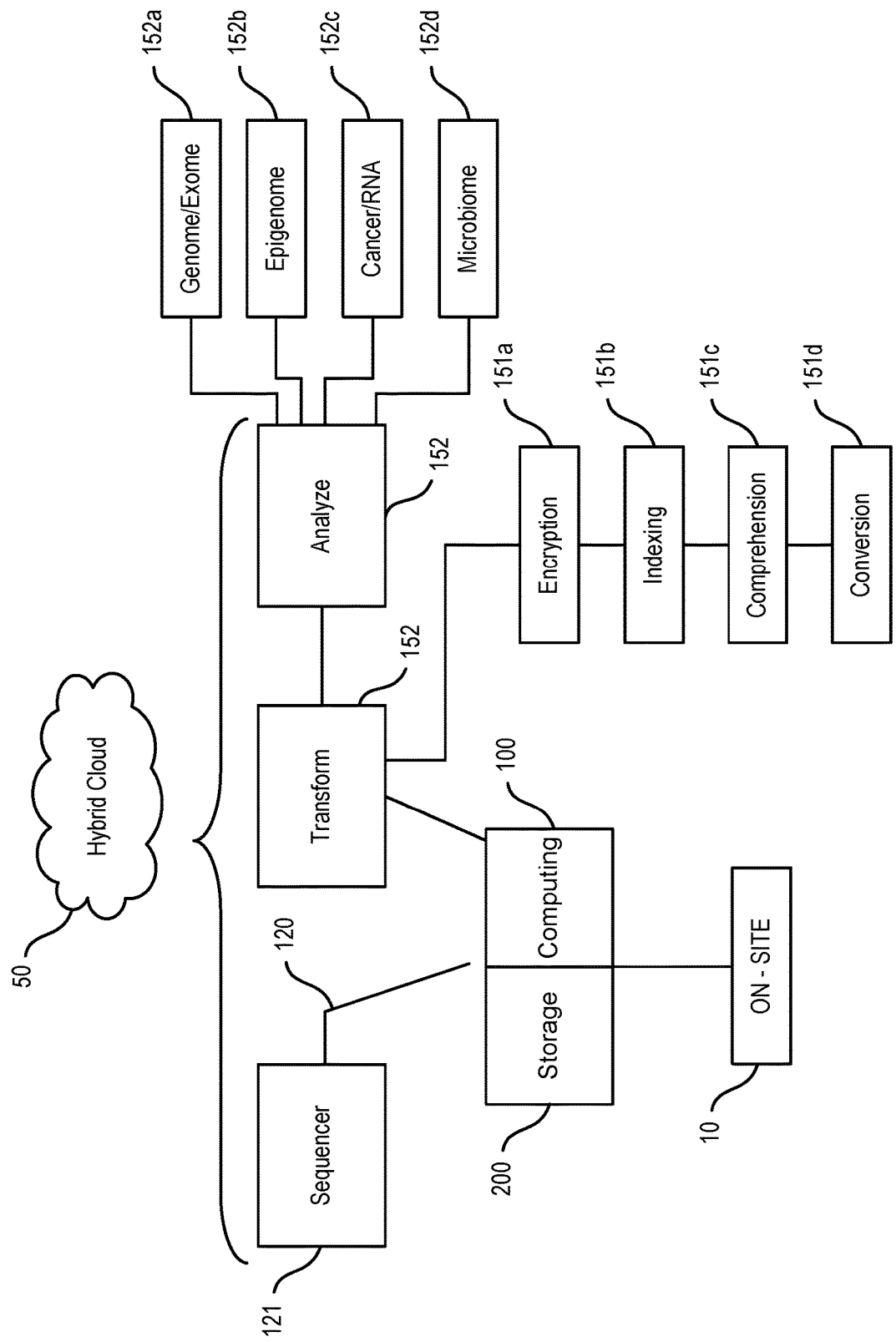
FIG. 34B depicts the block diagram of FIG. 34A in greater detail, illustrating a hybrid cloud configuration.

In one particular instance, as presented in FIG. 34B, a local computing 100 and/or storage 200 resource is provided, such as on-site at a user's location. The computing resource 100 and/or storage 200 resource may be coupled to a data generating resource I2I, such as an NGS or sequencer on a chip, as herein described, such as over a direct or an intranet connection 10, where the sequencer I2I is configured for generating genetic sequencing data, such as FASTQ files. For instance, the sequencer I2I may be part of and/or housed in the same apparatus as that of the computing resource 100 and/or storage unit 200, so as to have a direct communicable and/or operable connection therewith, or the sequencer I2I and computing resource 100 and/or storage resource 200 may be part of separate apparatuses from one another, but housed in the same facility, and thus connected over a cabled or intranet 10 connection. In some instances, the sequencer I2I may be housed in a separate facility than that of the computing 100 and/or storage 200 resource and thus may be connected over an internet 30 or hybrid cloud connection 50.

In such instances, the genetic sequence data may be processed 100 and stored locally 200, prior to being transformed, by a suitably configured transformer 151, or the generated sequence data may be transmitted directly to one or more of the transformer 151 and/or analyzer 152, such as over a suitably configured local connection 10, intranet 30, or hybrid cloud connection 50, as described above such as prior to being processed locally. Particularly, like the data generating resource I2I, the transformer 151 and/or analyzer 152 may be part of and/or housed in the same apparatus as that of the computing resource 100 and/or storage unit 200, so as to have a direct communicable and/or operable connection therewith, or the transformer 151 and/or analyzer 152 and computing resource 100 and/or storage resource 200 may be part of separate apparatuses from one another, but housed in the same facility, and thus connected over a cabled or intranet 10 connection. In some instances, the transformer 151 and/or analyzer 152 may be housed in a separate facility than that of the computing 100 and/or storage 200 resource and thus may be connected over an internet 30 or hybrid cloud connection 50.

For instance, the transformer 151 may be configured for preparing the data to be transmitted either prior to analysis or post analysis, such as by a suitably configured computing resource 100 and/or analyzer 152. For instance, the analyzer 152 may perform a secondary and/or tertiary processing function on the data, as herein described, such as for analyzing the generated sequence data with respect to determining its genomic and/or exomic characteristics 152a, its epigenomic features 152b, any various DNA and/or RNA markers of interests and/or indicators of cancer 152c, and its relationships to one or more microbiomes 152d, as well as one or more other secondary and/or tertiary processes as described herein. As indicated, the generated and/or processed data may be transformed, such as by a suitably configured transformer 151 such as prior to transmission throughout the system 1 from one component thereof to another, such as over a direct, local 10, internet 30, or hybrid cloud 50 connection. Such transformation may include one or more of conversion 151d, such as where the data is converted from one form to another; comprehension 151c, including the coding, decoding, and/or otherwise taking data from an incomprehensible form and transforming it to a comprehensible form, or from one comprehensible form to another; indexing 151b, such as including compiling and/or collating the generated data from one or more resources, and making it locatable and/or searchable, such as via a generated index; and/or encryption 151a, such as creating a lockable and unlockable, password protected dataset, such as prior to transmission over an internet 30 and/or hybrid cloud 50.

Figure 34C:
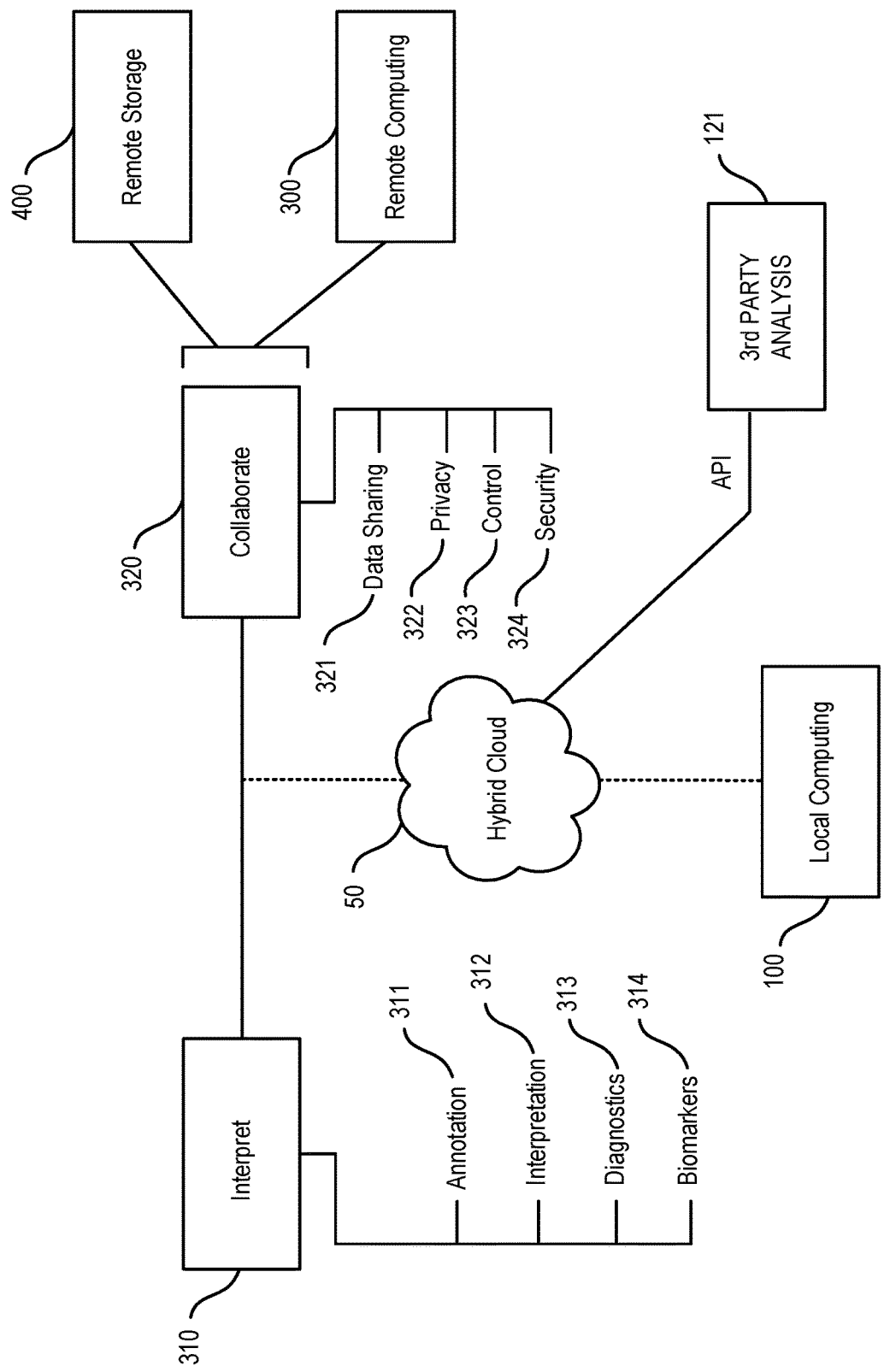
FIG. 34C depicts the block diagram of FIG. 34A in greater detail, illustrating a hybrid cloud configuration.

Hence, in these and/or other such instances, the hybrid cloud 50 may be configured for allowing seamless and protected transmission of data throughout the components of the system, such as where the hybrid cloud 50 is adapted to allow the various users of the system to configure its component parts and/or the system itself so as to meet the research, diagnostic, therapeutic and/or prophylactic discovery and/or development needs of the user. Particularly, the hybrid cloud 50 and/or the various components of the system 1 may be operably connected with compatible and/or corresponding API interfaces that are adapted to allow a user to remotely configure the various components of the system 1 so as to deploy the resources desired in the manner desired, and further to do so either locally, remotely, or a combination of the same, such as based on the demands of the system and the particulars of the analyses being performed, all the while being enabled to communicate in a secured, encryptable environment. Another exemplary embodiment of the hybrid cloud system, as herein presented, is depicted in FIG. 34C.

Figure 35:
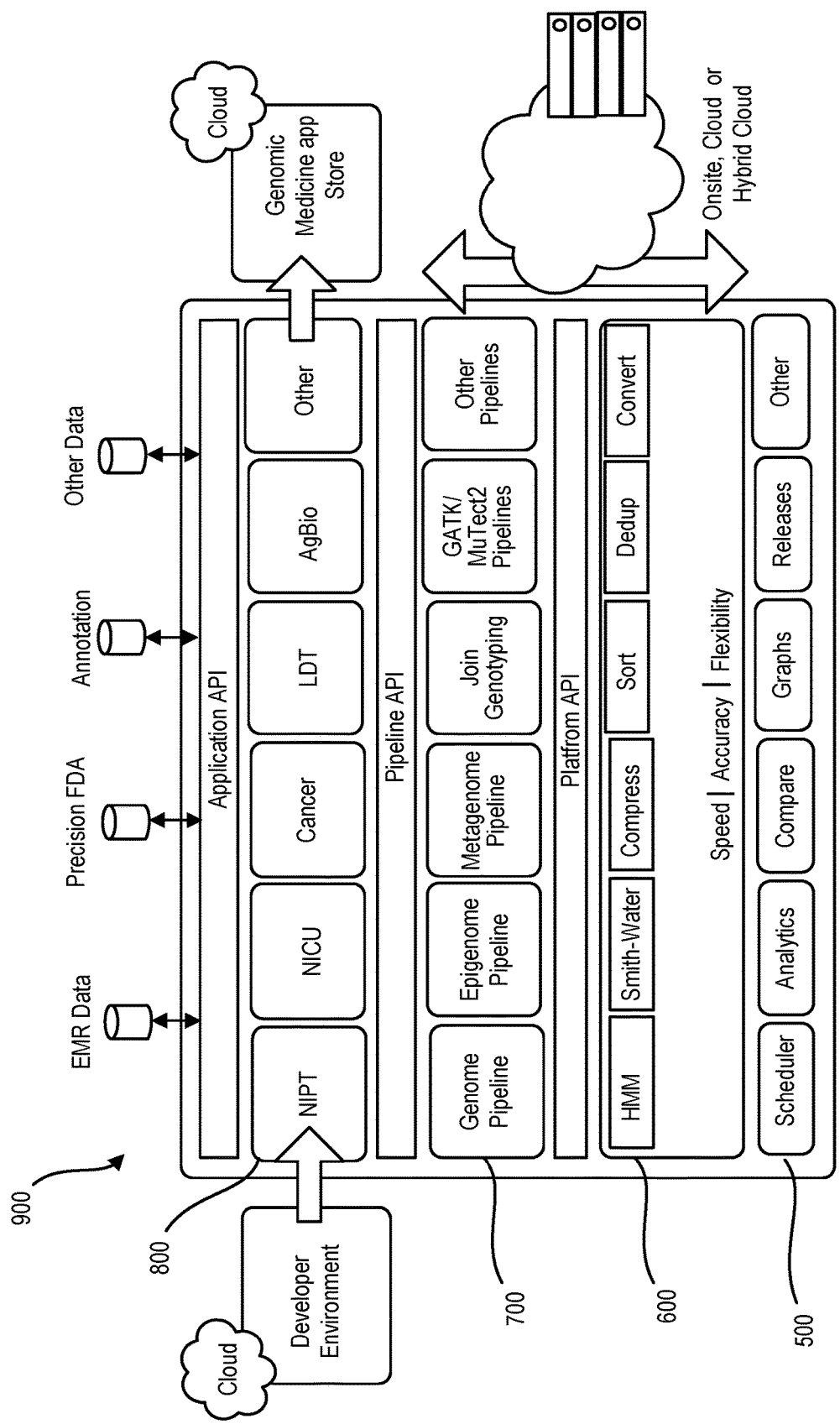
FIG. 35 depicts a block diagram illustrating a primary, secondary, and/or tertiary analysis pipeline as presented herein.

For instance, as can be seen with respect to FIG. 35, the system 1 may be a multi-tiered and/or multiplexed bioanalytical processing platform that includes layers of processing units each having one or more processing pipelines that may be deployed in a systematic and/or concurrent and/or sequential manner so as to process genetic information from its primary processing stage 400/500, so as to produce genetic sequence data, such as in one or more FASTQ files; to its secondary processing stage 600, so as to produce one or more variant call files; and further to take the one or more variant call files, or other associated processed data, and perform one or more other operations thereon such as for the purposes of performing one or more diagnostics and/or prophylactic and/or therapeutic procedures there with, such as in response to a third party request I2I and/or in response to data submitted by the third party I2I. Such further processing may include various pipeline protocols 700, such as configured so as to run analytics on the determined genetic variation data of one or more subjects, including genome, epigenome, metagenome, and/or genotyping analytics, such as in one tier, and/or various disease diagnostic and/or research protocols 800, which may include one or more of NIPT, NICU, cancer, LDT, biological, AgBio applications and the like. Particularly, the system 1 may further be adapted so as to receive and/or transmit various data 900 related to the procedures and processes herein such as related to electronic medical records (EMR) data, Federal Drug Administration testing and/or structuring data, data relevant to annotation, and the like. Such data may be useful so as to allow a user to make and/or allow access to generated medical, diagnostic, therapeutic, and/or prophylactic modalities developed through use of the system 1 and/or made accessible thereby.

Hence, one or more, e.g., all, of these functions therefore may be performed locally, e.g., on site 10, on the cloud 30, or via controlled access through the hybrid cloud 50. In such an instance, developer environment is created that allows the user to control the functionality of the system to meet his or her individual needs and/or to allow access thereto for others seeking the same or similar results. Consequently, the various components, processes, procedures, tools, tiers, and hierarchies of the system may be configurable such as via a GUI interface that allows the user to select which components to be run on which data at what time in what order in accordance with the user determined desires and protocols so as to generate relevant data and connections between data that may be securely communicated throughout the system whether locally or remotely. As indicated, these components can be made to communicate seamlessly together regardless of location and/or how connected, such as by being configurable so as to run the same or similar processes in the same or similar manner such as by employing corresponding API interfaces dispersed throughout the system the employment of which allows the various users to configure the various components to run the various procedures in like manner.

For instance, an API may be defined in a header file with respect to the processes to be run by each particular component of the system 1, wherein the header describes the functionality and determines how to call a function, such as the parameters that are passed, the inputs received and outputs transmitted, and the manner in which this occurs, what comes in and how, what goes out and how, and what gets returned, and in what manner. For example, in various embodiments, one or more of the components and/or elements thereof, which may form one or more pipelines of one or more tiers of the system may be configurable such as by instructions entered by a user and/or one or more second and/or third party applications. These instructions may be communicated to the system via the corresponding APIs which communicate with one or more of the various drivers of the system, instructing the driver(s) as to which parts of the system, e.g., which modules and/or which processes thereof are to be activated, when, and in what order, given a preselected parameter configuration, which may be determined by a user selectable interface, e.g., GUI.

As described above, the one or more DMA drivers of the system 1 may be configured to run in corresponding fashion, such as at the kernel level of each component and the system 1 as a whole. In such an instance, one or more of the provided kernel's may have their own very low level, basic API that provides access to the hardware and functions of the various components of the system 1 so as to access applicable registers and modules so as to configure and direct the processes and the manners in which they are run on the system 1. Particularly, on top of this layer, a virtual layer of service functions may be built so as to form the building blocks that are used for a multiplicity of functions that send files down to the kernel(s) and get results back, encodes, encrypts, and/or transmits the relevant data and further performs more higher level functions thereon. On top of that layer an additional layer may be built that uses those service functions, which may be an API level that a user may interface with, which may be adapted to function primarily for configuration of the system 1 as a whole or its component parts, downloading files, and uploading results, which files and/or results may be transmitted throughout the system either locally or globally.

Such configuration may include communicating with registers and also performing function calls. For example, as described herein above, one or more function calls necessary and/or useful to perform the steps, e.g., sequentially, to execute a mapping and/or aligning and/or sorting and/or variant call, or other secondary and/or tertiary function as herein described may be implemented in accordance with the hardware operations and/or related algorithms so as to generate the necessary processes and perform the required steps.

Specifically, because in certain embodiments one or more of these operations may be based on one or more structures, the various structures needed for implementing these operations may need to be constructed. There will therefore be a function call that performs this function, which function call will cause the requisite structure to be built for the performance of the operation, and because of this a call will accept a file name of where the structure parameter files are stored and will then generate one or more data files that contain and/or configure the requisite structure. Another function call may be to load the structure that was generated via the respective algorithm and transfer that down to the memory on the chip and/or system 1, and/or put it at the right spot where the hardware is expecting them to be. Of course, various data will need to be downloaded onto the chip and/or otherwise be transferred to the system generator, as well for the performance of the various other selected functions of the system 1, and the configuration manager can perform these functions, such as by loading everything that needs to be there in order for the modules of pipelines of the tiers of the platforms of the chip and/or system as a whole to perform their functions, into a memory on, attached, or otherwise associated with the chip and/or system.

Additionally, the API may be configured to allow one or more chips of the system 1 to interface with the circuit board of the sequencer 12I, the computing resource 100/300, transformer 151, analyzer 152, interpreter 310, collaborator 320, or other system component, when included therewith, so as to receive the FASTQ and/or other generated and/or processed genetic sequencing files directly from the sequencer or other processing component such as immediately once they have been generated and/or processed and then transfers that information to the configuration manager which then directs that information to the appropriate memory banks in the hardware and/or software that makes that information available to the pertinent modules of the hardware, software, and/or system as a whole so that they can perform their designated functions on that information so as to call bases, map, align, sort, etc. the sample DNA/RNA with respect to the reference genome, and or to run associated secondary and/or tertiary processing operations thereon.

Accordingly, in various embodiments, a client level interface (CLI) may be included wherein the CLI may allow the user to call one or more of these functions directly. In various embodiments, the CLI may be a software application, e.g., having a GUI, that is adapted to configure the accessibility and/or use of the hardware and/or various other software applications of the system. The CLI, therefore, may be a program that accepts instructions, e.g., arguments, and makes functionality available simply by calling an application program. As indicated above, the CLI can be command line based or GUI (graphical user interface) based. The line based commands happen at a level below the GUI, where the GUI includes a windows based file manager with click on function boxes that delineate which modules, which pipelines, which tiers, of which platforms will be used and the parameters of their use. For example, in operation, if instructed, the CLI will locate the reference, will determine if a hash table and/or index needs to be generated, or if already generated locate where it is stored, and direct the uploading of the generated hash table and/or index, etc. These types of instructions may appear as user options at the GUI that the user can select the associated chip(s)/system 1 to perform.

Furthermore, a library may be included wherein the library may include preexisting, editable, configuration files, such as files orientated to the typical user selected functioning of the hardware and/or associated software, such as with respect to a portion or whole genome and/or protein analysis, for instance, for various analyses, such as personal medical histories and ancestry analysis, or disease diagnostics, or drug discovery, therapeutics, and/or one or more of the other analytics, etc. These types of parameters may be preset, such as for performing such analyses, and may be stored in the library. For example, if the platform herein described is employed such as for NIPT, NICU, Cancer, LDT, AgBio, and related research on a collective level, the preset parameters may be configured differently than if the platform were directed simply to researching genomic and/or genealogy based research, such as on an individual level.

More particularly, for specific diagnosis of an individual, accuracy may be an important factor, therefore, the parameters of the system may be set to ensure increased accuracy albeit in exchange for possibly a decrease in speed. However, for other genomics applications, speed may be the key determinant and therefore the parameters of the system may be set to maximize speed, which however may sacrifice some accuracy. Accordingly, in various embodiments, often used parameter settings for performing different tasks can be preset into the library to facilitate ease of use. Such parameter settings may also include the necessary software applications and/or hardware configurations employed in running the system 1. For instance, the library may contain the code that executes the API, and may further include sample files, scripts, and any other ancillary information necessary for running the system 1. Hence, the library may be configured for compiling software for running the API as well as various of the executables.

Additionally, as can be seen with respect to FIG. 34C, the system may be configured such that one or more of the system components may be performed remotely, such as where the system component is adapted to run one or more comparative functions on the data, such as an interpretive function 310 and/or collaborative function 320. For instance, where an interpretive protocol is employed on the data, the interpretive protocol 312 may be configured to analyze and draw conclusions about the data and/or determine various relationships with respect thereto, one or more other analytical protocols may also be performed and include annotating the data 311, performing a diagnostic 313 on the data, and/or analyzes the data, so as to determine the presence or absence of one or more biomarkers 314. Additionally, where a collaborative protocol is performed, the system 1 may be configured for providing an electronic forum where data sharing 321 may occur, which data sharing protocol may include user selectable security 324 and/or privacy 322 settings that allow the data to be encrypted and/or password protected, so that the identity and sources of the data may be hidden from a user of the system 1. In particular instances, the system 1 may be configured so as to allow a $3^{rd}$ party analyzer I2I to run virtual simulations on the data. Further, one generated, the interpreted data and/or the data subjected to one or more collaborative analyses may be stored either remotely 400 or locally 200 so as to be made available to the remote 300 or local 100 computing resources, such as for further processing and/or analysis.

Figure 36:
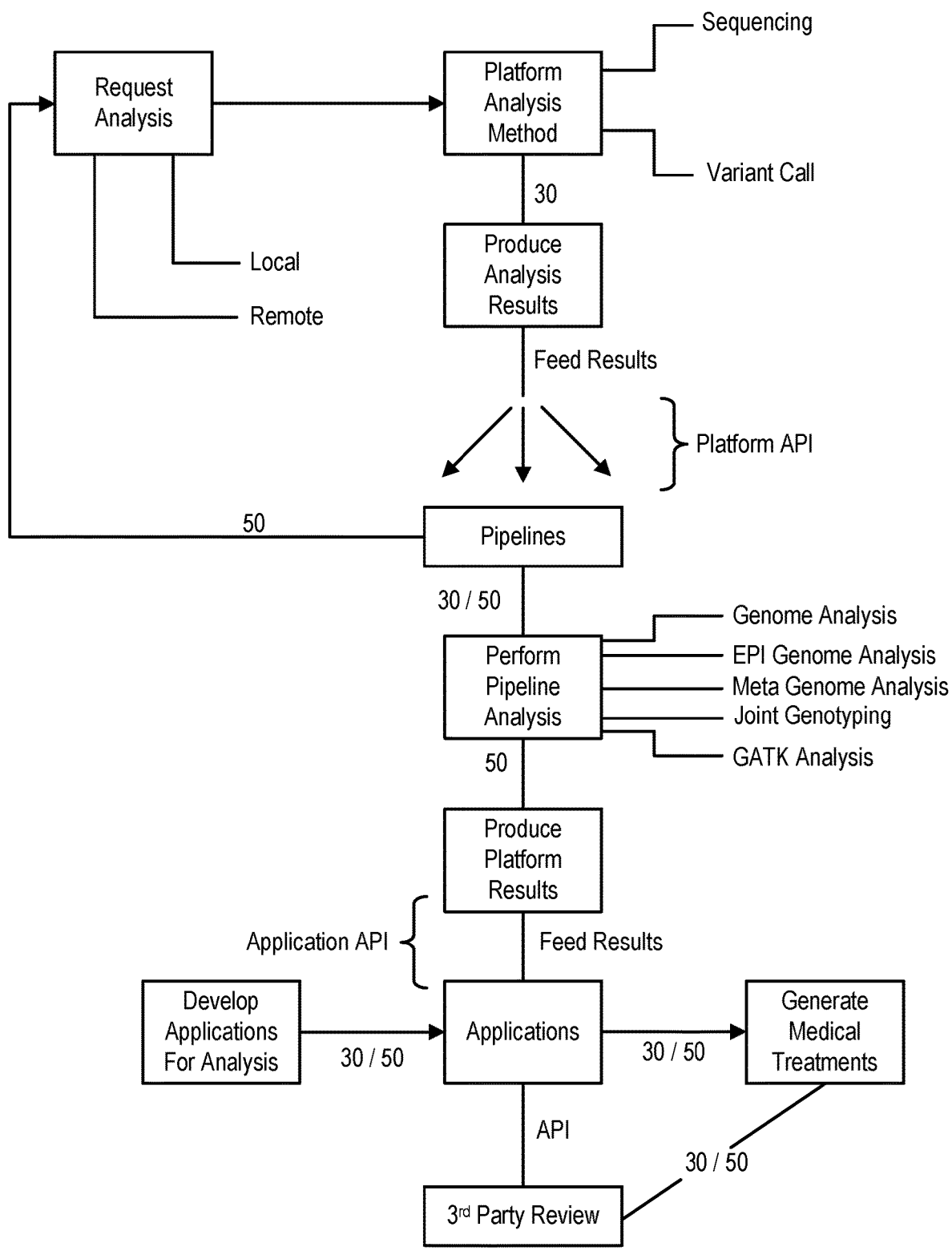
FIG. 36 depicts a flow diagram for an analysis pipeline of the disclosure.

In another aspect, as can be seen with respect to FIG. 36, a method for using the system to generate one or more data files upon which one or more secondary and/or tertiary processing protocols may be run is provided. For instance, the method may include providing a genomic infrastructure such as for one or more of onsite, cloud-based, and/or hybrid genomic and/or bioinformatics generation and/or processing and/or analysis.

In such an instance, the genomic infrastructure may include a bioinformatics processing platform having one or more memories that are configured to store one or more configurable processing structures for configuring the system so as to be able to perform one or more analytical processing functions on data, such as data including a genomic sequence of interest or processed result data pertaining thereto. The memory may include the genomic sequence of interest to be processed, e.g., once generated and/or acquired, one or more genetic reference sequences, and/or may additionally include an index of the one or more genetic reference sequences and/or a list of splice junctions pertaining thereto. The system may also include an input having a platform application programming interface (API) for selecting from a list of options one or more of the configurable processing structures, such as for configuring the system, such as by selecting which processing functions of the system will be run on the data, e.g., the pre- or processed genomic sequences of interest. A graphical user interface (GUI) may also be present, such as operably associated with the API, so as to present a menu by which a user can select which of the available options he or she desires to be run on the data.

The system may be implemented on one or more integrated circuits that may be formed of one or more sets of configurable, e.g., preconfigured and/or hardwired, digital logic circuits that may be interconnected by a plurality of physical electrical interconnects. In such an instance, the integrated circuit may have an input, such as a memory interface, for receiving one or a plurality of the configurable structure protocols, e.g., from the memory, and may further be adapted for implementing the one or more structures on the integrated circuit in accordance with the configurable processing structure protocols. The memory interface of the input may also be configured for receiving the genomic sequence data, which may be in the form of a plurality of reads of genomic data. The interface may also be adapted for accessing the one or more genetic reference sequences and the index(es).

In various instances, the digital logic circuits may be arranged as a set of processing engines that are each formed of a subset of the digital logic circuits. The digital logic circuits and/or processing engines may be configured so as to perform one or more pre-configurable steps of a primary, secondary, and/or tertiary processing protocol so as to generate the plurality of reads of genomic sequence data, and/or for processing the plurality of reads of genomic data, such as according to the genetic reference sequence(s) or other genetic sequence derived information. The integrated circuit may further have an output so as to output result data from the primary, secondary, and/or tertiary processing, such as according to the platform application programming interface (API).

Particularly, in various embodiments, the digital logic circuits and/or the sets of processing engines may form a plurality of genomic processing pipelines, such as where each pipeline may have an input that is defined according to the platform application programming interface so as to receive the result data from the primary and/or secondary processing by the bioinformatics processing platform, and for performing one or more analytic processes thereon so as to produce result data. Additionally, the plurality of genomic processing pipelines may have a common pipeline API that defines a secondary and/or tertiary processing operation to be run on the result data from the primary and/or secondary processed data, such as where each of the plurality of genomic processing pipelines is configured to perform a subset of the secondary and/or tertiary processing operations and to output result data of the secondary and/or tertiary processing according to the pipeline API.

In such instances, a plurality of the genomic analysis applications may be stored in the memory and/or an associated searchable application repository, such as where each of the plurality of genomic analysis applications are accessible via an electronic medium by a computer such as for execution by a computer processor, so as to perform a targeted analysis of the genomic pre- or post processed data from the result data of the primary, secondary, and/or tertiary processing, such as by one or more of the plurality of genomic processing pipelines. In particular instances, each of the plurality of genomic analysis applications may be defined by the API and may be configured for receiving the result data of the primary, secondary, and/or tertiary processing, and/or for performing the target analysis of the pre- or post processed genomic data, and for outputting the result data from the targeted analysis to one of one or more genomic databases.

The method may additionally include, selecting, e.g., from the menu of the GUI, one or more genomic processing pipelines from a plurality of the available genomic processing pipelines of the system; selecting one or more genomic analysis applications from the plurality of genomic analysis applications that are stored in an application repository; and executing, using a computer processor, the one or more selected genomic analysis applications to perform a targeted analysis of genomic data from the result data of the primary, secondary, and/or tertiary processing.

Additionally, in various embodiments, all of mapping, aligning, and sorting, may take place on the chip, and local realignment, duplicate marking, base quality score recalibration may, and/or one or more of the tertiary processing protocols and/or pipelines, in various embodiments, also take place on the chip, and in various instances, various compression protocols, such as BAM and CRAM, may also take place on the chip. However, once the primary, secondary, and/or tertiary processed data has been produced, it may be compressed, such as prior to being transmitted, such as by being sent across the system, being sent up to the cloud, such as for the performance of the variant calling module, a secondary, tertiary, and/or other processing platform, such as including an interpretive and/or collaborative analysis protocol. This might be useful especially given the fact that variant calling, including the tertiary processing thereof, can be a moving target, e.g., there is not one standardized agreed upon algorithm that the industry uses.

Hence, different algorithms can be employed, such as by remote users, so as to achieve a different type of result, as desired, and as such having a cloud based module for the performance of this function may be useful for allowing the flexibility to select which algorithm is useful at any particular given moment, and also as for serial and/or parallel processing. Accordingly, any one of the modules disclosed herein can be implemented as either hardware, e.g., on the chip, or software, e.g., on the cloud, but in certain embodiments, all of the modules may be configured so that their function may be performed on the chip, or all of the modules may be configured so that their function may be performed remotely, such as on the cloud, or there will be a mixture of modules wherein some are positioned on one or more chips and some are positioned on the cloud. Further, as indicated, in various embodiments, the chip(s) itself may be configured so as to function in conjunction with, and in some embodiments, in immediate operation with a genetic sequencer, such as an NGS and/or sequencer on a chip.

Figure 37:
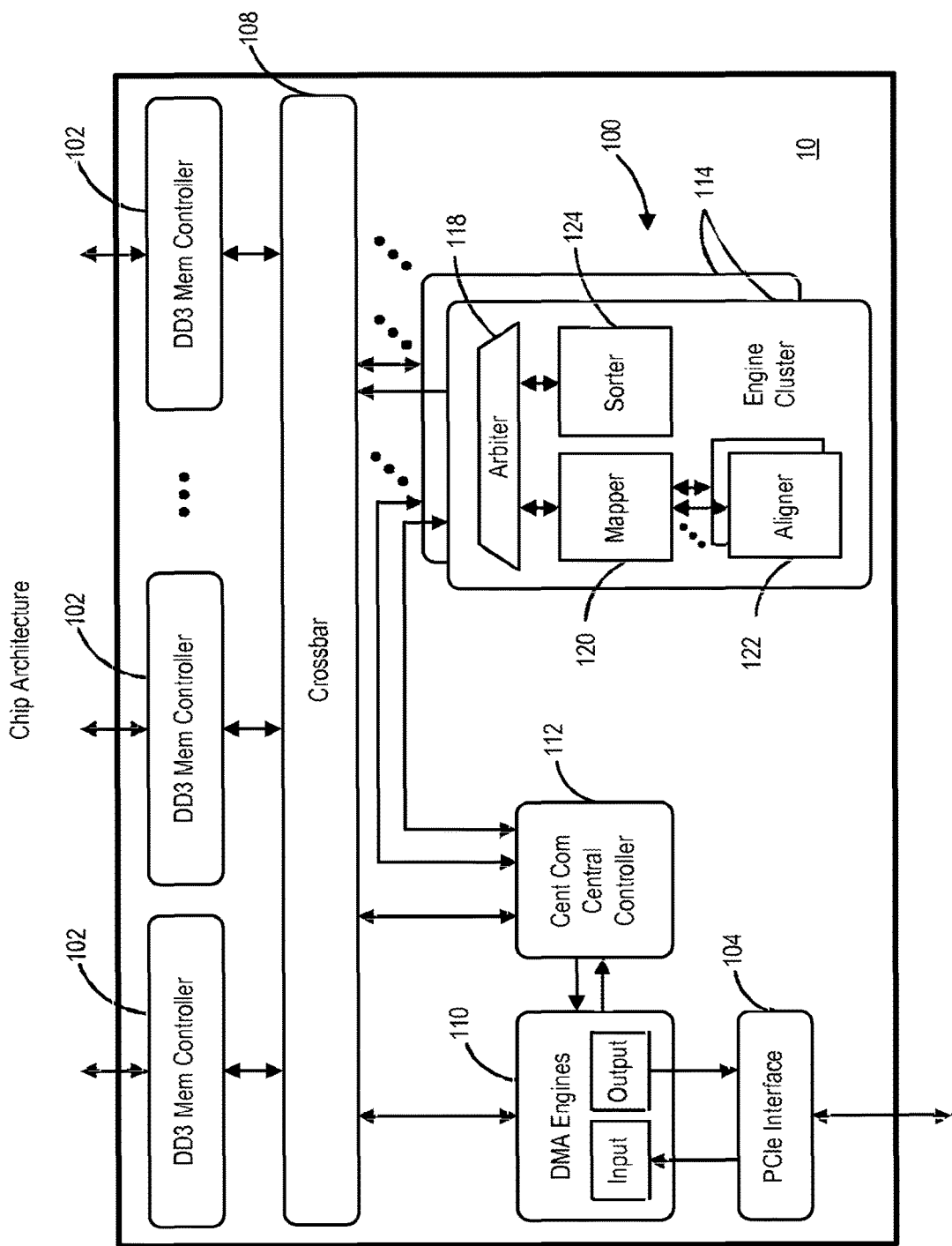
FIG. 37 is a block diagram of a hardware processor architecture in accordance with an implementation of the disclosure.

More specifically, in various embodiments, an apparatus of the disclosure may be a chip, such as a chip that is configured for processing genomics data, such as by employing a pipeline of data analysis modules. Accordingly, as can be seen with respect to FIG. 37, a genomics pipeline processor chip 100 is provided along with associated hardware of a genomics pipeline processor system 10. The chip 100 has one or more connections to external memory 102 (at "DDR3 Mem Controller"), and a connection 104 (e.g., PCIe or QPI Interface) to the outside world, such as a host computer 1000, for example. A crossbar 108 (e.g., switch) provides access to the memory interfaces to various requestors. DMA engines 110 transfer data at high speeds between the host and the processor chip's 100 external memories 102 (via the crossbar 108), and/or between the host and a central controller 112. The central controller 112 controls chip operations, especially coordinating the efforts of multiple processing engines 13. The processing engines are formed of a set of hardwired digital logic circuits that are interconnected by physical electrical interconnects, and are organized into engine clusters 11/114. In some implementations, the engines 13 in one cluster 11/114 share one crossbar port, via an arbiter 115. The central controller 112 has connections to each of the engine clusters. Each engine cluster 11/114 has a number of processing engines 13 for processing genomic data, including a mapper 120 (or mapping module), an aligner 122 (or aligning module), and a sorter 124 (or sorting module), one or more processing engines for the performance of other functions, such as variant calling, may also be provided. Hence, an engine cluster 11/114 can include other engines or modules, such as a variant caller module, as well.

In accordance with one data flow model consistent with implementations described herein, the host CPU 1000 sends commands and data via the DMA engines 110 to the central controller 112, which load-balances the data to the processing engines 13. The processing engines return processed data to the central controller 112, which streams it back to the host via the DMA engines 110. This data flow model is suited for mapping and alignment and variant calling. As indicated, in various instances, communication with the host CPU may be through a relatively loose or tight coupling, such as a low latency, high bandwidth interconnect, such as a QPI, such as to maintain cache coherency between associated memory elements of the two devices.

Hence, in accordance with an alternative data flow model consistent with implementations described herein, the host CPU 1000 streams data into the external memory 1014, either directly via DMA engines 110 and the crossbar 108, or via the central controller 112. The host CPU 1000 sends commands to the central controller 112, which sends commands to the processing engines 13, which instruct the processing engines as to what data to process. Because of the tight coupling, the processing engines 13 access input data directly from the external memory 1014 or a cache associated therewith, process it, and write results back to the external memory 1014, such as over the tightly coupled interconnect 3, reporting status to the central controller 112. The central controller 112 either streams the result data back to the host 1000 from the external memory 1014, or notifies the host to fetch the result data itself via the DMA engines 110.

Figure 38:
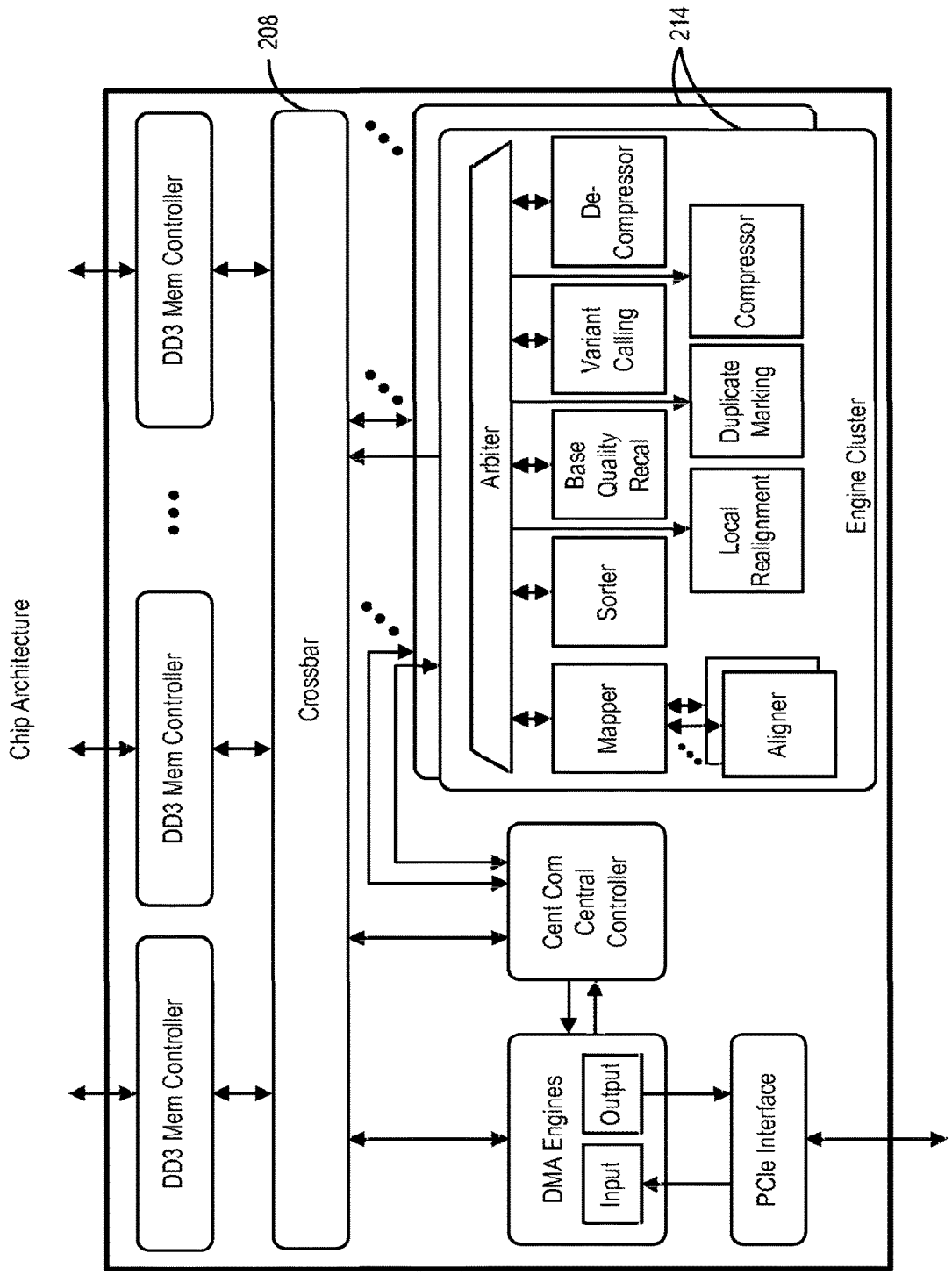
FIG. 38 is a block diagram of a hardware processor architecture in accordance with another implementation.

FIG. 38 illustrates a genomics pipeline processor system 20, showing a full complement of processing engines 13 inside an engine cluster 11/214. The pipeline processor system 20 may include one or more engine clusters 11/214. In some implementations, the pipeline processor system 20 includes four or more engine clusters 11/214. The processing engines 13 or processing engine types can include, without limitation, a mapper, an aligner, a sorter, a local realigner, a base quality recalibrater, a duplicate marker, a variant caller, a compressor and/or a decompressor. In some implementations, each engine cluster 11/214 has one of each processing engine type. Accordingly, all processing engines 13 of the same type can access the crossbar 208 simultaneously, through different crossbar ports, because they are each in a different engine cluster 11/214. Not every processing engine type needs to be formed in every engine cluster 11/214. Processing engine types that require massive parallel processing or memory bandwidth, such as the mapper (and attached aligner(s)) and sorter, may appear in every engine cluster of the pipeline processor system 20. Other engine types may appear in only one or some of the engine clusters 214, as needed to satisfy their performance requirements or the performance requirements of the pipeline processor system 20.

Figure 39:
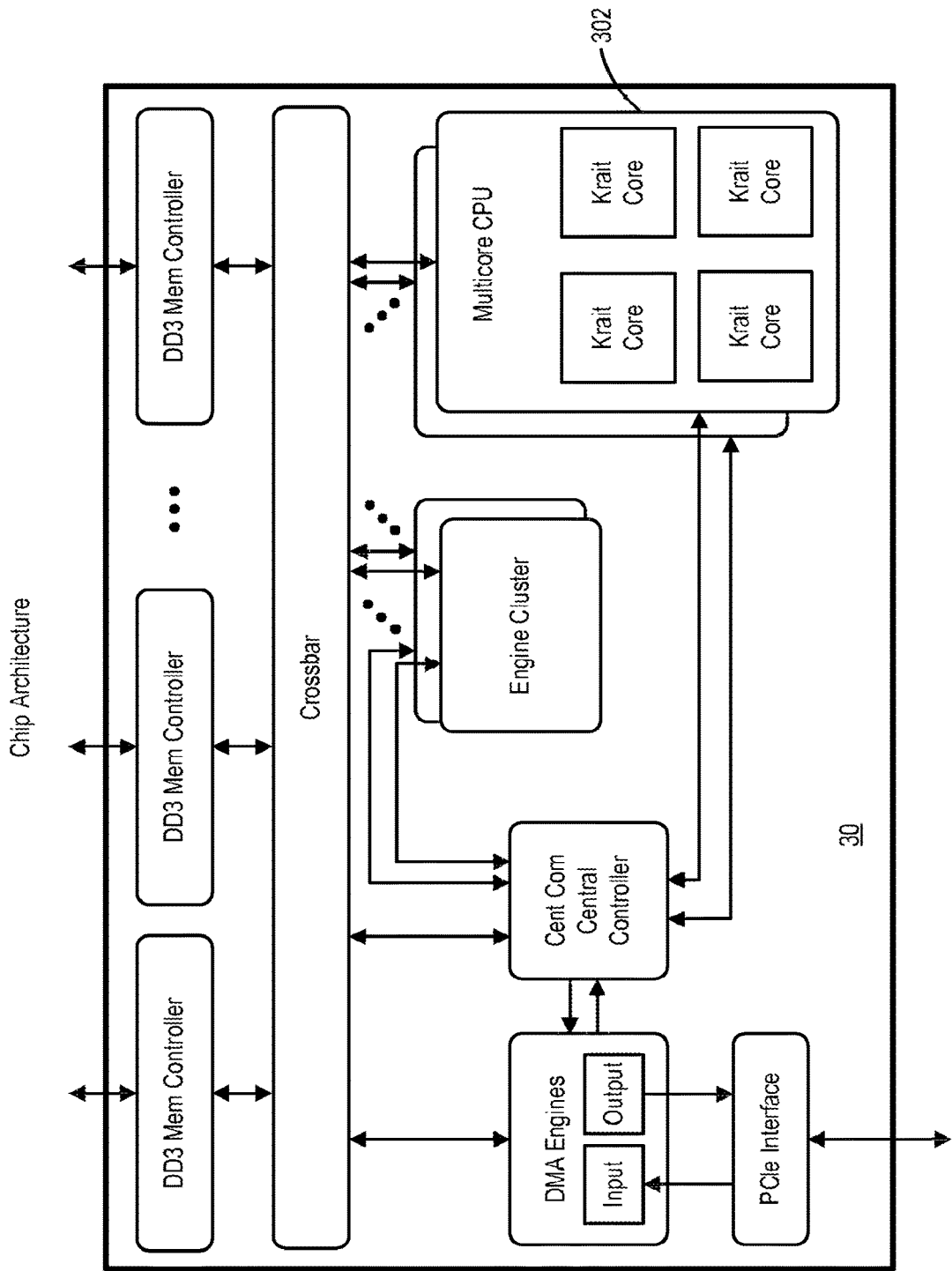
FIG. 39 is a block diagram of a hardware processor architecture in accordance with yet another implementation.

FIG. 39 illustrates a genomics pipeline processor system 30, showing, in addition to the engine clusters 11 described above, one or more embedded central processing units (CPUs) 302. Examples of such embedded CPUs include Snapdragons® or standard ARM® cores, or in other instances may be an FPGA. These CPUs execute fully programmable bio-IT algorithms, such as advanced variant calling, such as the building of a DBG or the performance of an HMM. Such processing is accelerated by computing functions in the various engine clusters 11, which can be called by the CPU cores 302 as needed. Furthermore, even engine-centric processing, such as mapping and alignment, can be managed by the CPU cores 302, giving them heightened programmability.

Figure 40:
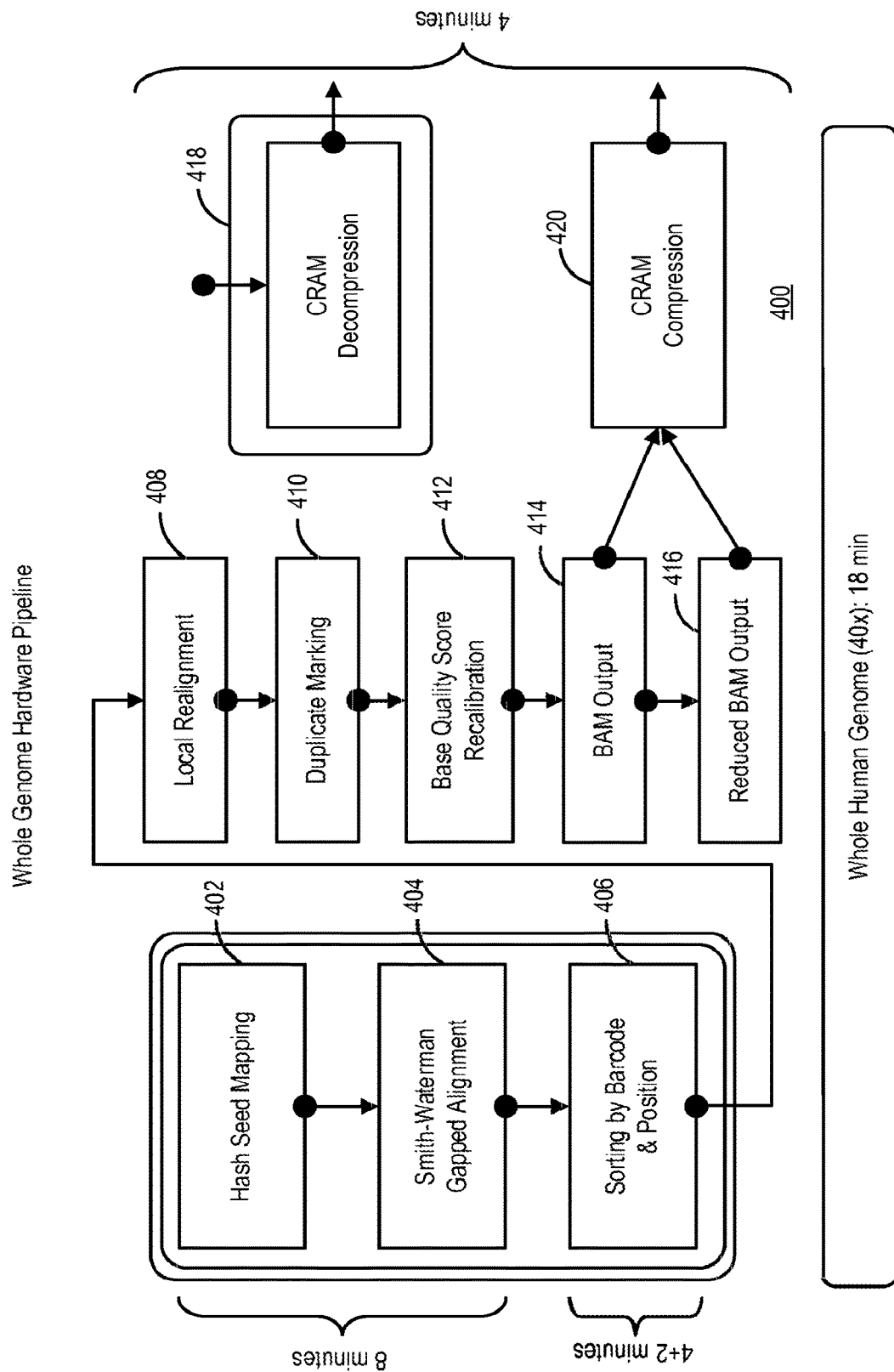
FIG. 40 illustrates a genetic sequence analysis pipeline.

FIG. 40 illustrates a processing flow for a genomics pipeline processor system and method. In some preferred implementations, there are three passes over the data. The first pass includes mapping 402 and alignment 404, with the full set of reads streamed through the engines 13. The second pass includes sorting 406, where one large block to be sorted (e.g., a substantial portion or all reads previously mapped to a single chromosome) is loaded into memory, sorted by the processing engines, and returned to the host. The third pass includes downstream stages (local realignment 408, duplicate marking 410, base quality score recalibration (BQSR) 412, BAM output 414, reduced BAM output 416, and/or CRAM compression 418). The steps and functions of the third pass may be done in any combination or subcombination, and in any order, in a single pass. Hence, in this manner data is passed relatively seamlessly from the one or more processing engines, to the host CPU, such as in accordance with one or more of the methodologies described herein. Hence, a virtual pipeline architecture, such as described above, is used to stream reads from the host into circular buffers in memory, through one processing engine after another in sequence, and back out to the host. In some implementations, CRAM decompression can be a separate streaming function. In some implementations, the BAM output 414, reduced BAM output 416, and/or CRAM compression 418 can be replaced with variant calling, compression and decompression.

Figure 41:
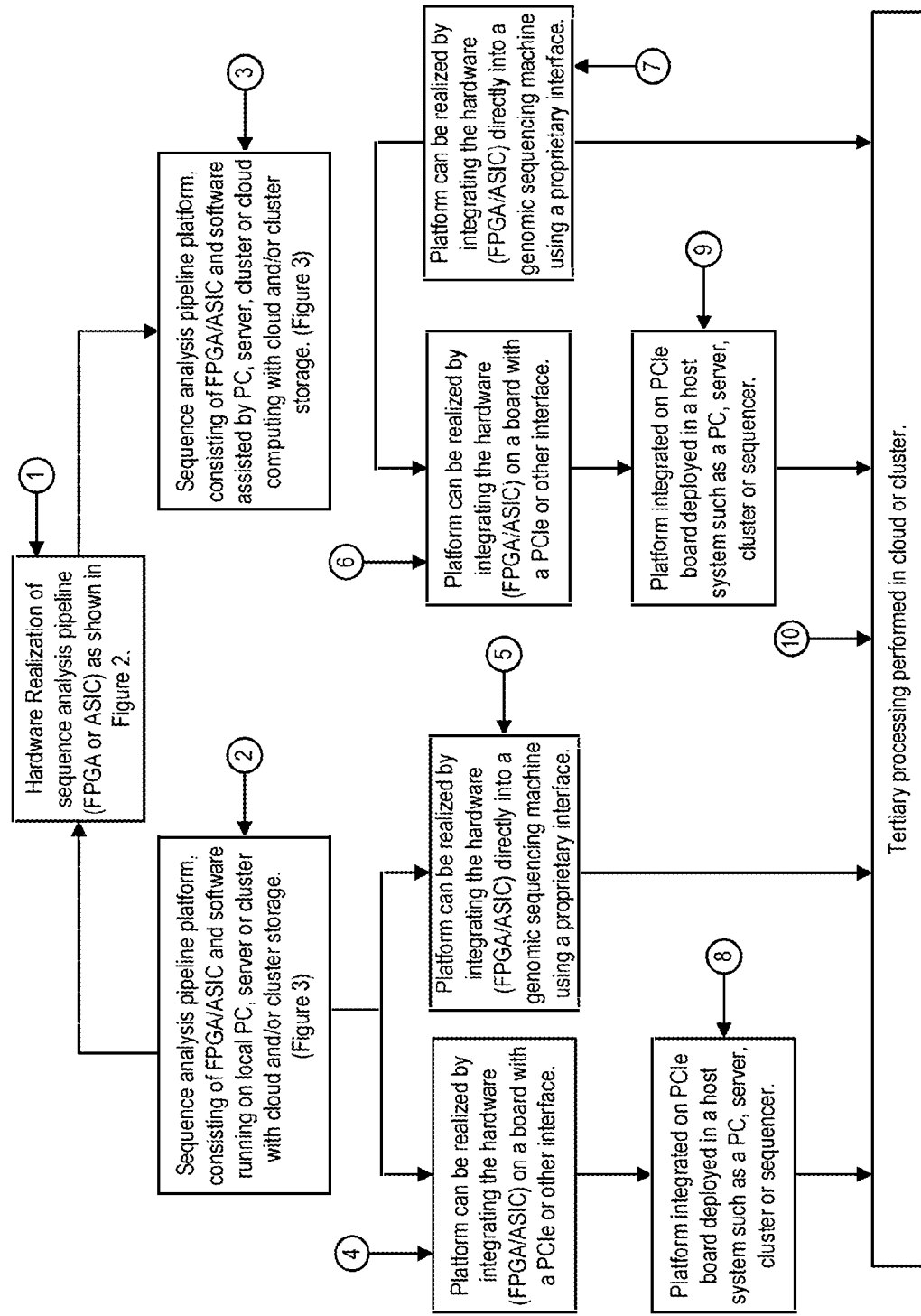
FIG. 41 illustrates processing steps using a genetic sequence analysis hardware platform.

In various instances, a hardware implementation of a sequence analysis pipeline is described. This can be done in a number of different ways such as an FPGA or ASIC or structured ASIC implementation. The functional blocks that are implemented by the FPGA or ASIC or structured ASIC are set forth in FIG. 41. Accordingly, the system includes a number of blocks or modules to do sequence analysis. The input to the hardware realization can be a FASTQ file, but is not limited to this format. In addition to the FASTQ file, the input to the FPGA or ASIC or structured ASIC consists of side information, such as Flow Space Information from technology such as from the NGS. The blocks or modules may include the following blocks: Error Control, Mapping, Alignment, Sorting, Local Realignment, Duplicate Marking, Base Quality Recalibration, BAM and Side Information reduction and/or variant calling.

These blocks or modules can be present inside, or implemented by, the hardware, but some of these blocks may be omitted or other blocks added to achieve the purpose of realizing a sequence analysis pipeline. Blocks 2 and 3 describe two alternatives of the sequence analysis pipeline platform. The sequence analysis pipeline platform comprising an FPGA or ASIC or structured ASIC and software assisted by a host (e.g., PC, server, cluster or cloud computing) with cloud and/or cluster storage. Blocks 4-7 describe different interfaces that the sequence analysis pipeline can have. In Blocks 4 and 6 the interface can be a PCIe or QPI interface, but is not limited to a PCIe or QPI interface. In Blocks 5 and 7 the hardware (FPGA or ASIC or structured ASIC) can be directly integrated into a sequencing machine. Blocks 8 and 9 describe the integration of the hardware sequence analysis pipeline integrated into a host system such as a PC, server cluster or sequencer. Surrounding the hardware FPGA or ASIC or structured ASIC are a plurality of DDR3 memory elements and a PCIe/QPI interface. The board with the FPGA/ASIC/sASIC connects to a host computer, consisting of a host CPU, that could be either a low power CPU such as an ARM®, Snapdragon®, or any other processor. Block 10 illustrates a hardware sequence analysis pipeline API that can be accessed by third party applications to perform tertiary analysis.

Figure 42A:
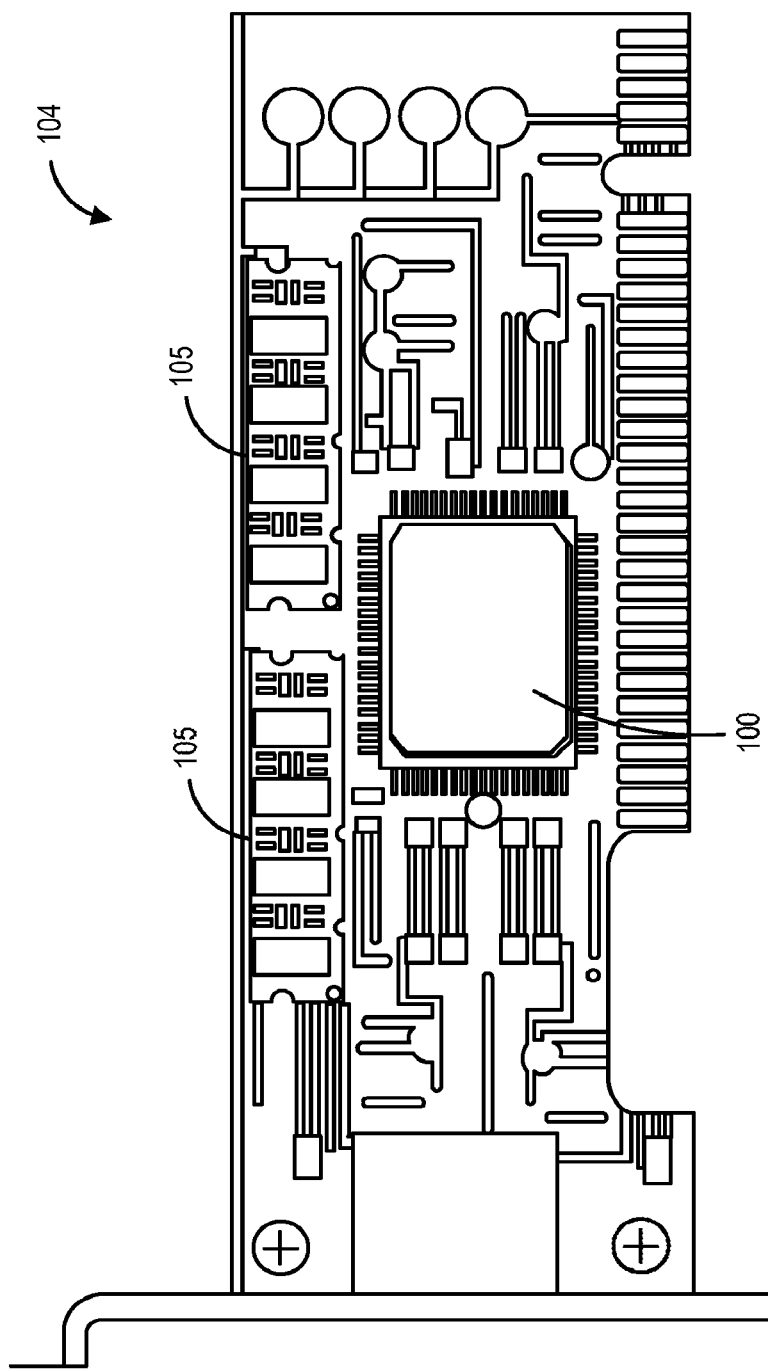
FIG. 42A illustrates an apparatus in accordance with an implementation of the disclosure.
Figure 42B:
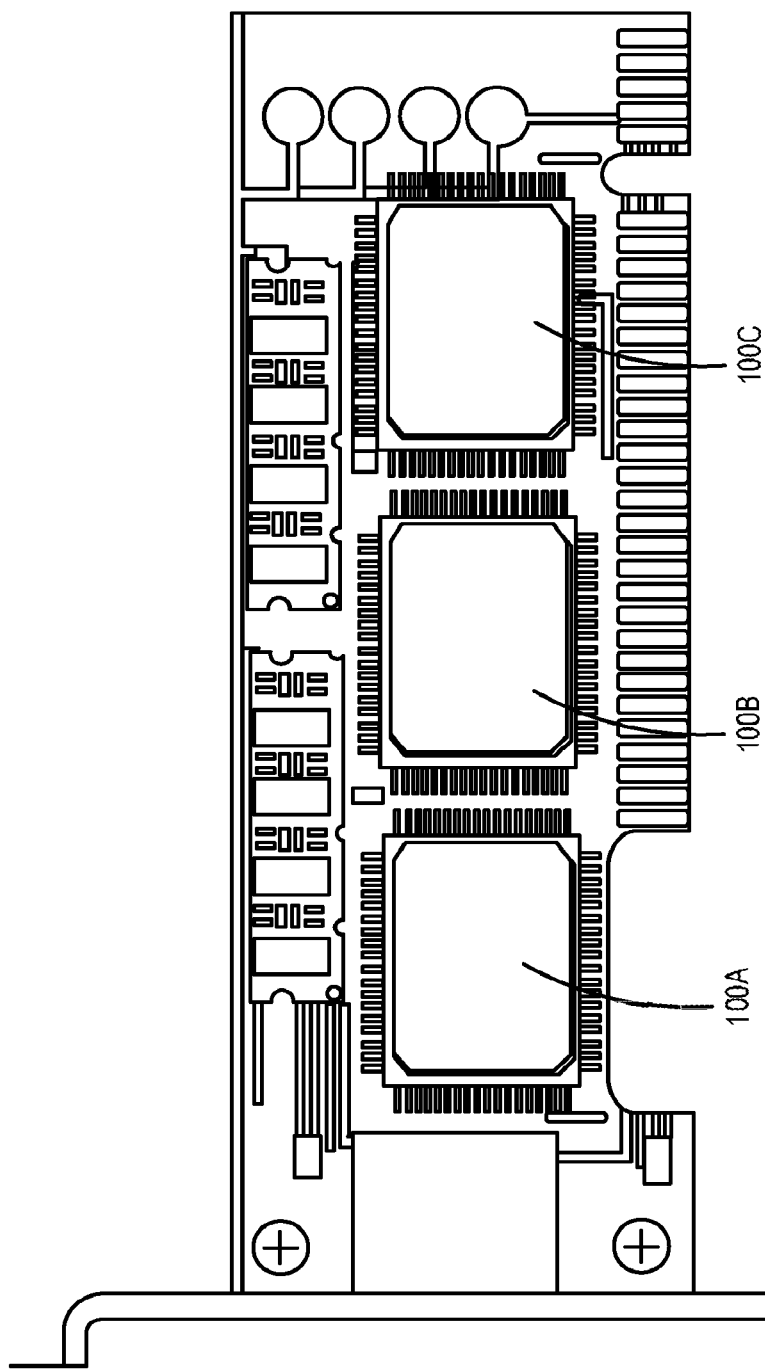
FIG. 42B illustrates another apparatus in accordance with an alternative implementation of the disclosure.

FIGS. 42A and 42B depict an expansion card 104 having a processing chip 100, e.g., an FPGA, of the disclosure, as well as one or more associated elements 105 for coupling the FPGA 100 with the host CPU, such as for the transferring of data, such as data to be processed and result data, back and forth from the CPU to the FPGA 100. FIG. 42B depicts the expansion card of FIG. 42A having a plurality, e.g., 3, slots containing a plurality, e.g., 3, processing chips of the disclosure.

Specifically, as depicted in FIGS. 42A and 42B, in various embodiments, an apparatus of the disclosure may include a computing architecture, such as embedded in a silicon field gated programmable array (FPGA) or application specific integrated circuit (ASIC) 100. The FPGA 100 can be integrated into a printed circuit board (PCB) 104, such as a Peripheral Component Interface-Express (PCIe) card, which can be plugged into a computing platform. In various instances, as shown in FIG. 42A, the PCIe card 104 may include a single FPGA 100, which FPGA may be surrounded by local memories 105, however, in various embodiments, as depicted in FIG. 42B, the PCIe card 104 may include a plurality of FPGAs 100A, 100B and 100C. In various instances, the PCI card may also include a PCIe bus. This PCIe card 104 can be added to a computing platform to execute algorithms on extremely large data sets. IN an alternative embodiment, as noted above with respect to FIG. 26, in various embodiments, the FPGA may be adapted so as to be directly associated with the CPU, such as via an interloper, and tightly coupled therewith, such as via a QPI interface. Accordingly, in various instances, the overall work flow of genomic sequencing involving the FPGA may include the following: Sample preparation, Alignment (including mapping and alignment), Variant analysis, Biological Interpretation, and/or Specific Applications.

Hence, in various embodiments, an apparatus of the disclosure may include a computing architecture that achieves the high performance execution of algorithms, such as mapping and alignment algorithms, that operate on extremely large data sets, such as where the data sets exhibit poor locality of reference (LOR). These algorithms are designed to reconstruct a whole genome from millions of short read sequences, from modern so-called next generation sequencers, require multi-gigabyte data structures that are randomly accessed. Once reconstruction is achieved, as described herein above, further algorithms with similar characteristics are used to compare one genome to libraries of others, do gene function analysis, etc.

There are two other typical architectures that in general may be constructed for the performance of one or more of the operations herein described in detail, such as including purpose multicore CPUs and general purpose Graphic Processing Units (GPGPUs). In such an instance, each CPU in a multicore system may have a classical cache based architecture, wherein instructions and data are fetched from a level 1 cache (L1 cache) that is small but has extremely fast access. Multiple L1 caches may be connected to a larger but slower shared L2 cache. The L2 cache may be connected to a large but slower DRAM (Dynamic Random Access Memory) system memory, or may be connected to an even larger but slower L3 cache which may then connected to DRAM. An advantage of this arrangement may be that applications in which programs and data exhibit locality of reference behave nearly as if they are executing on a computer with a single memory as large as the DRAM but as fast as the L1 cache. Because full custom, highly optimized CPUs operate at very high clock rates, e.g., 2 to 4 GHz, this architecture may be essential to achieving good performance. Additionally, as discussed in detail with respect to FIG. 25, in various embodiments the CPU may be tightly coupled to an FPGA, such as an FPGA configured for running one or more functions related to the various operations described herein, such as via a high bandwidth, low latency interconnect such as a QPI, so as to further enhance performance as well as the speed and coherency of the data transferred throughout the system. In such an instance, cache coherency may be maintained between the two devices, as noted above.

Further, GPGPUs may be employed to extend this architecture, such as by implementing very large numbers of small CPUs, each with their own small L1 cache, wherein each CPU executes the same instructions on different subsets of the data. This is a so called SIMD (Single Instruction stream, Multiple Data stream) architecture. Economy may be gained by sharing the instruction fetch and decode logic across a large number of CPUs. Each cache has access to multiple large external DRAMs via an interconnection network. Assuming the computation to be performed is highly parallelizable, GPGPUs have a significant advantage over general purpose CPUs due to having large numbers of computing resources. Nevertheless, they still have a caching architecture and their performance is hurt by applications that do not have a high enough degree of locality of reference. That leads to a high cache miss rate and processors that are idle while waiting for data to arrive from the external DRAM.

For instance, in various instances, Dynamic RAMs may be used for system memory because they are more economical than Static RAMs (SRAM). The rule of thumb used to be that DRAMs had 4× the capacity for the same cost as SRAMs. However, due to declining demand for SRAMs in favor of DRAMs, which difference has increased considerably due to the economies of scale that favor DRAMs which are in high demand. Independent of cost, DRAMs are 4× as dense as SRAMs laid out in the same silicon area because they only require one transistor and capacitor per bit compared to 4 transistors per bit to implement the SRAM's flip-flop. The DRAM represents a single bit of information as the presence or absence of charge on a capacitor. A problem with this arrangement is that the charge decays over time, so it has to be refreshed periodically. The need to do this has led to architectures that organize the memory into independent blocks and access mechanisms that deliver multiple words of memory per request. This compensates for times when a given block is unavailable while being refreshed. The idea is to move a lot of data while a given block is available. This is in contrast to SRAMs in which any location in memory is available in a single access in a constant amount of time. This characteristic allows memory accesses to be single word oriented rather than block oriented. DRAMs work well in a caching architecture because each cache miss leads to a block of memory being read in from the DRAM. The theory of locality of reference is that if just accessed word N, then probably going to access words N+1, N+2, N+3 and so on, soon.

Figure 43:
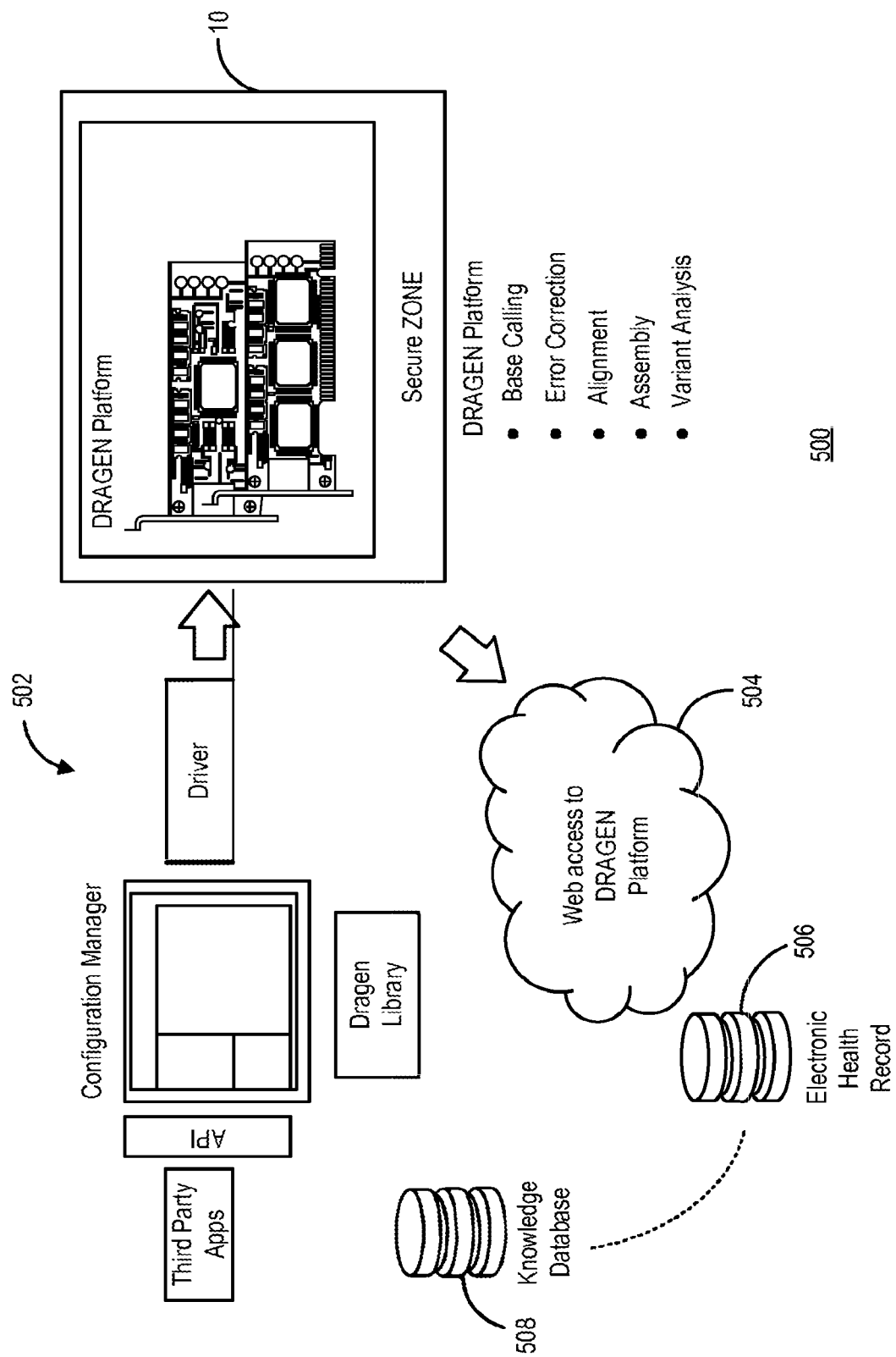
FIG. 43 illustrates a genomics processing system in accordance with an implementation.

FIG. 43 provides an exemplary implementation of a system 500 of the disclosure, including one or more of the expansions cards of FIG. 42, such as for bioinformatics processing 10. The system includes a Bio IT processing chip 100 that is configured for performing one or more functions in a processing pipeline, such as base calling, error correction, mapping, alignment, sorting, assembly, variant calling, and the like as described herein.

The system 500 further includes a configuration manager that is adapted for configuring the onboard functioning of the one or more processors 100. Specifically, in various embodiments, the configuration manager is adapted to communicate instructions to the internal controller of the FPGA, such as by a suitably configured driver over a loose or tightly coupled interconnect, so as to configure the one or more processing functions of the system 500. For instance, the configuration manager may be adapted to configure the internal processing clusters 11 and/or engines 13 associated therewith so as to perform one or more desired operations, such as mapping, aligning, sorting, variant calling, and the like, in accordance with the instructions received. In such a manner only the clusters 11 containing the processing engines 13 for performing the requested processing operations on the data provided from the host system 1000 to the chip 100 may be engaged to process the data in accordance with the received instructions. Additionally, in various embodiments, the configuration manager may further be adapted so as to itself be adapted, e.g., remotely, by a third party user, such as over an API connection, as described in greater detail herein above, such as by a user interface (GUI) presented by an App of the system 500. Additionally, the configuration manager may be connected to one or more external memories, such as a memory forming or otherwise containing a database, such as a data base including one or more reference or individually sequenced genomes and/or an index thereof, and/or one or more previously mapped, aligned, and/or sorted genomes or portions thereof. In various instances, the database may further include one or more genetic profiles characterizing a diseased state such as for the performance of one or more tertiary processing protocols, such as upon newly mapped, aligned genetic sequences or a VCF pertaining thereto.

The system 500 may also include a web-based access so as to allow remote communications such as via the internet so as to form a cloud or at least a hybrid cloud 504 communications platform. In such a manner as this, the processed information generated from the Bio IT processor, e.g., results data, may be encrypted and stored as an electronic health record, such as in an external, e.g., remote, database. In various instances, the EMR database may be searchable, such as with respect to the genetic information stored therein, so as to perform one or more statistical analyses on the data, such as to determine diseased states or trends or for the purposes of analyzing the effectiveness of one or more prophylactics or treatments pertaining thereto. Such information along with the EMR data may then be further processed and/or stored in a further database 508 in a manner so as to insure the confidentiality of the source of the genetic information.

More particularly, FIG. 43 illustrates a system 500 for executing a sequence analysis pipeline on genetic sequence data. The system 500 includes a configuration manager 502 that includes a computing system. The computing system of the configuration manager 502 can include a personal computer or other computer workstation, or can be implemented by a suite of networked computers. The configuration manager 502 can further include one or more third party applications connected with the computing system by one or more APIs, which, with one or more proprietary applications, generate a configuration for processing genomics data from a sequencer or other genomics data source. The configuration manager 502 further includes drivers that load the configuration to the genomics pipeline processor system 10. The genomics pipeline processor system 10 can output result data to, or be accessed via, the Web 504 or other network, for storage of the result data in an electronic health record 506 or other knowledge database 508.

As discussed in several places herein above, the chip implementing the genomics pipeline processor can be connected or integrated in a sequencer. The chip can also be connected or integrated, e.g., directly via an interloper, or indirectly, e.g., on an expansion card such as via a PCIe, and the expansion card can by connected or integrated in a sequencer. In other implementations, the chip can be connected or integrated in a server computer that is connected to a sequencer, to transfer genomic reads from the sequencer to the server. In yet other implementations, the chip can be connected or integrated in a server in a cloud computing cluster of computers and servers. A system can include one or more sequencers connected (e.g. via Ethernet) to a server containing the chip, where genomic reads are generated by the multiple sequencers, transmitted to the server, and then mapped and aligned in the chip.

For instance, in general next generation DNA sequencer (NGS) data pipelines, the primary analysis stage processing is generally specific to a given sequencing technology. This primary analysis stage functions to translate physical signals detected inside the sequencer into "reads" of nucleotide sequences with associated quality (confidence) scores, e.g. FASTQ format files, or other formats containing sequence and usually quality information. Primary analysis, as mentioned above, is often quite specific in nature to the sequencing technology employed. In various sequencers, nucleotides are detected by sensing changes in fluorescence and/or electrical charges, electrical currents, or radiated light. Some primary analysis pipelines often include: Signal processing to amplify, filter, separate, and measure sensor output; Data reduction, such as by quantization, decimation, averaging, transformation, etc.; Image processing or numerical processing to identify and enhance meaningful signals, and associate them with specific reads and nucleotides (e.g. image offset calculation, cluster identification); Algorithmic processing and heuristics to compensate for sequencing technology artifacts (e.g. phasing estimates, cross-talk matrices); Bayesian probability calculations; Hidden Markov models; Base calling (selecting the most likely nucleotide at each position in the sequence); Base call quality (confidence) estimation, and the like. As discussed herein above, one or more of these steps may be benefitted by implementing one or more of the necessary processing functions in hardware, such as implemented by an integrated circuit, e.g., an FPGA. Further, after such a format is achieved, secondary analysis proceeds, as described herein, to determine the content of the sequenced sample DNA (or RNA etc.), such as by mapping and aligning reads to a reference genome, sorting, duplicate marking, base quality score recalibration, local re-alignment, and variant calling. Tertiary analysis may then follow, to extract medical or research implications from the determined DNA content.

Accordingly, given the sequential nature of the above processing functions, it may be advantageous to integrate primary, secondary, and/or tertiary processing acceleration in a single integrated circuit, or multiple integrated circuits positioned on a single expansion card. This may be beneficial because sequencers produce data that typically requires both primary and secondary analysis so as to be useful and may further be used in various tertiary processing protocols, and integrating them in a single device is most efficient in terms of cost, space, power, and resource sharing. Hence, in one particular aspect, the disclosure is directed to a system, such as to a system for executing a sequence analysis pipeline on genetic sequence data. In various instances, the system may include an electronic data source, such as a data source that provides digital signals, for instance, digital signals representing a plurality of reads of genomic data, where each of the plurality of reads of genomic data include a sequence of nucleotides. The system may include one or more of a memory, such as a memory storing one or more genetic reference sequences and/or an index of the one or more genetic reference sequences; and/or the system may include a chip, such as an ASIC, FPGA, or sASIC.

One or more aspects or features of the subject matter described herein can be realized in digital electronic circuitry, integrated circuitry, specially designed application specific integrated circuits (ASICs), field programmable gate arrays (FPGAs), or structured ASIC computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT), a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A genomics analysis platform for executing a sequence analysis pipeline, the genomics analysis platform comprising:
one or more first integrated circuits, each first integrated circuit forming a processing unit that is responsive to one or more software algorithms that are configured to instruct the processing unit to perform one or more of genomic processing steps of the sequence analysis pipeline, the processing unit having a first set of physical electronic interconnects;
one or more second integrated circuits, each second integrated circuit forming a programmable logic device, the programmable logic device having one or more hardware logic circuits that are programmatically configured to arrange the hardwired digital logic circuits to perform one or more different genomic processing steps of the sequence analysis pipeline, the hardwired digital logic circuits of each programmable logic device being arranged as a set of processing engines to perform the one or more different genomic processing steps; and
a shared memory electronically connected to the one or more first integrated circuits via at least a portion of the first set of physical electronic interconnects, the shared memory storing genetic sequence data, wherein each of the one or more first integrated circuits and each of the one or more second integrated circuits are configured to access the genetic sequence data in the shared memory based on one or more cache coherency protocols.

2. The genomics analysis platform of claim 1, wherein the cache coherency protocols describe rules for alternating processing of genetic sequence data stored in the shared memory based on a level of computational-intensity ascribed to a portion of the genetic sequence data stored in the memory.

3. The genomics analysis platform of claim 2, wherein the rules for alternating processing of genetic sequence data stored in the shared memory include requiring use of the programmable logic circuit to process at least a first portion of the genetic sequence data stored in the shared memory, wherein the processing of the first portion of the genetic sequence data includes performing operations satisfying a threshold level of computational-intensity.

4. The genomics analysis platform of claim 3, wherein the operations that satisfy the threshold level of computational intensity include the operations that account for 90% of the computing load.

5. The genomics analysis platform of claim 4, wherein the operations that satisfy the threshold level of computational intensity include the operations that account for 98% of the computing load.

6. The genomics analysis platform of claim 2, wherein the rules for alternating processing of genetic sequence data stored in the shared memory include requiring use of the processing unit to perform to process at least a second portion of the genetic sequence data stored in the shared memory, wherein the processing of the second portion of the genetic sequence data includes performing operations that fail to satisfy a threshold level of computational-intensity.

7. The genomics analysis platform of claim 3, wherein the operations that fail to satisfy the threshold level of computational-intensity include the operations that account for 10% of the computing load.

8. The genomics analysis platform of claim 3, wherein the operations that fail to satisfy the threshold level of computational-intensity include the operations that account for 2% of the computing load.

9. The genomic analysis platform of claim 2, wherein the rules for alternating processing of genetic sequence data stored in the shared memory include:
identifying one or more computationally-intensive sub-routines of an operation,
using the programmable logic circuit to perform the identified one or more computationally-intensive sub-routines of the operations; and
using the processing unit to perform a balance of remaining sub-routines of the operation.

10. The genomic analysis platform of claim 2, wherein the rules for alternating processing of genetic sequence data stored in the shared memory include:
for mapping and aligning operations, determining one or more discrete operations that are to be performed during the mapping and aligning operations;
triggering an acceleration call to the programmable logic circuit that instructs the programmable logic circuit to perform a subset of the discrete operations that satisfy a threshold level of computational-intensity; and
instructing the processing unit to perform a balance of the discrete operations.

11. The genomic analysis platform of claim 10, wherein the one or more discrete operations include seed generation, mapping, seed chain formation, paired end rescue scans, gapless alignment, or gapped alignment.

12. The genomic analysis platform of claim 2, wherein the rules for alternating processing of genetic sequence data stored in the shared memory include:
for variant calling operations, determining one or more discrete operations that are to be performed during the variant calling operations;
triggering an acceleration call to the programmable logic circuit that instructs the programmable logic circuit to perform a subset of the discrete operations that satisfy a threshold level of computational-intensity; and
instructing the processing unit to perform a balance of the discrete operations.

13. The genomic analysis platform of claim 12,
wherein the subset of the discrete operations that satisfy the threshold level of computational-intensity include using a pair hidden markov model to estimate a probability of observing a particular read given the truth of a candidate haplotype.

14. The genomic analysis platform of claim 1, wherein the processing unit includes a central processing unit (CPU) or a graphical processing unit (GPU).

15. The genomic analysis platform of claim 1, wherein the programmable logic circuit includes a field-programmable gate array (FPGA) or an Application Specific Integrated Circuit (ASIC).

* * * * *

SEQUENCE LISTING

```
<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 1
acgtcacatt tc                                                          12

<210> SEQ ID NO 2
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 2
acgtcacttc                                                             10
```